United States Patent
Finke et al.

(10) Patent No.: US 6,593,346 B2
(45) Date of Patent: *Jul. 15, 2003

(54) N-CYCLOPENTYL MODULATORS OF CHEMOKINE RECEPTOR ACTIVITY

(75) Inventors: Paul E. Finke, Milltown, NJ (US); Kerry A. Hilfiker, Cranford, NJ (US); Malcolm MacCoss, Freehold, NJ (US); Kevin T. Chapman, Scotch Plains, NJ (US); Jennifer L. Loebach, Westfield, NJ (US); Sander G. Mills, Scotch Plains, NJ (US); Ravi N. Guthikonda, Edison, NJ (US); Shrenik K. Shah, Metuchen, NJ (US); Dooseop Kim, Westfield, NJ (US); Dong-Ming Shen, Edison, NJ (US); Bryan Oates, San Diego, CA (US)

(73) Assignee: Merck & Co. Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/075,163

(22) Filed: Feb. 14, 2002

(65) Prior Publication Data

US 2002/0120146 A1 Aug. 29, 2002

Related U.S. Application Data

(62) Division of application No. 09/590,750, filed on Jun. 8, 2000, now Pat. No. 6,358,979.
(60) Provisional application No. 60/138,886, filed on Jun. 11, 1999.

(51) Int. Cl.$^7$ .............................................. A61K 31/445
(52) U.S. Cl. ........................ 514/326; 514/252; 514/269; 514/300; 514/329
(58) Field of Search ................. 514/252, 269, 514/326, 300, 329

(56) References Cited

U.S. PATENT DOCUMENTS

| | | |
|---|---|---|
| 3,647,802 A | 3/1972 | Rynbrandt et al. |
| 4,105,666 A | 8/1978 | Ward |
| 4,281,132 A | 7/1981 | Ward |
| 5,169,844 A | 12/1992 | Commons et al. |
| 5,424,319 A | 6/1995 | Hanson et al. |
| 5,712,279 A | 1/1998 | Biller et al. |
| 5,750,549 A | 5/1998 | Caldwell et al. |
| 5,935,974 A | 8/1999 | Rae et al. |
| 6,054,468 A | 4/2000 | Geerts et al. |
| 6,140,349 A | 10/2000 | Caldwell et al. |
| 6,331,541 B1 | 12/2001 | Ko et al. |
| 6,358,979 B1 * | 3/2002 | Finke et al. ................. 514/326 |
| 2002/0019345 A1 | 2/2002 | Hancock |

FOREIGN PATENT DOCUMENTS

| | | |
|---|---|---|
| WO | WO 98/25617 | 6/1998 |
| WO | WO 98/31364 | 7/1998 |
| WO | WO 99/04794 | 2/1999 |
| WO | WO 99/09984 | 3/1999 |
| WO | WO 01/78707 | 10/2001 |

OTHER PUBLICATIONS

J. J. Gomez–Reino, et al., "Association of Rheumatoid Arthritis with a Functional Chemokine Receptor, CCR5", Arthritis & Rheumatism, vol. 42, No. 5, May 1999, pp. 989–992.

T. J. Schall, "Biology of the Rantes/sis Cytokine Family", Cytokine, vol. 3, No. 3, May 1991, pp. 165–183.

P. M. Murphy, "The Molecular Biology of Leukocyte Chemoattractant Receptors", Annual Review of Immunology, vol. 12, 1994, pp. 593–633.

H. Deng, et al., "Identification of a major co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

A. Ben–Baruch, et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote, et al., "Molecular Cloning, Functional Expression, and Signaling Characteristics of a C–C Chemokine Receptor", Cell, vol. 72, Feb. 1993, pp. 415–425.

C. Combadiere, et al., "Cloning and Functional Expression of a Human Eosinophil CC Chemokine Receptor", J. Biol. Chem., vol. 270, No. 27, Jul. 1995, pp. 16491–16494.

C. A. Power, et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.

M. Samson, et al., "Molecular Cloning and Functional Expression of a New Human CC–Chemokine Receptor Gene", Biochemistry, vol. 35, 1995, pp. 3362–3367.

A. Chaudhuri, et al., "Expression of the Duffy Antigen in K562 Cells", J. Biol. Chem., vol. 269, No. 11, Mar. 1994, pp. 7835–7838.

(List continued on next page.)

Primary Examiner—Bernard Dentz
(74) Attorney, Agent, or Firm—Kenneth R. Walton; Melvin Winokur

(57) ABSTRACT

The present invention is directed to compounds of the formula I:

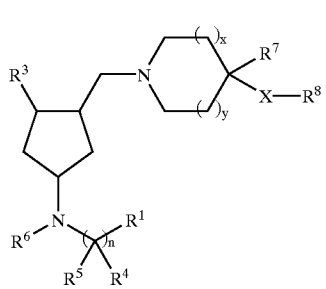

(wherein $R^1$, $R^3$, $R^4$, $R^5$, $R_6$, $R^7$, $R^8$, X, n, x and y are defined herein) which are useful as modulators of chemokine receptor activity. In particular, these compounds are useful as modulators of the chemokine receptors CCR-5 and/or CCR-3.

27 Claims, No Drawings

OTHER PUBLICATIONS

H. Kita, et al., "Chemokines Active on Eosinophils: Potential Roles in Allergic Inflammation", J. Exp. Med., vol. 183, Jun. 1996, pp. 2421–2426.

D. Smith, et al., "Blocking of HIV–1 Infectivity by a Soluble, Secreted Form of the CD4 Antigen", Science, vol. 238, 1987, pp. 1704–1707.

J. A. Levy, "Infection by Human Immunodeficiency Virus—CD4 is not Enough", N. Eng. J. Med., vol. 335, No. 20, Nov. 1996, pp. 1528–1530.

T. Dragic, et al., "HIV–1 entry into CD4+ cells is mediated by the chemokine receptor CC–CKR5", Nature, vol. 381, Jun. 1996, pp. 667–673.

L. Wu, et al., "CD4–induced interaction of primary HIV–1 gp120 glycoproteins with the chemokine receptor CCR–5", Nature, vol. 384, Nov. 1996, pp. 179–183.

A. Trkola, et al., "CD4–dependent, antibody–sensitive interactions between HIV–2 and its co–receptor CCR–5", Nature, vol. 384, Nov. 1996, pp. 184–187.

M. Samson, et al., "Resistance HIV–1 infection in caucasian individuals bearing mutant alleles if the CCR–5 chemokine receptor gene", Nature, vol. 382, Aug. 1996, pp. 722–725.

C. M. Hill, et al., "Natural resistance to HIV?", Nature, vol. 382, Aug. 1996, pp. 668–669.

Y. Huang, et al., "The role of a mutant CCR5 allele in HIV–1 transmission and disease progression", Nature Medicine, vol. 2, No. 11, Nov. 1996, pp. 1240–1243.

L. Zhang, et al., "HIV–1 subtype and second–receptor use", Nature, vol. 383, Oct. 1996, p. 768.

M. Baba, et al., "A small–molecule, nonpeptide CCR5 antagonist with highly potent and selective antiHIV–1 activity", Proc. Natl. Acad. Sci., vol. 96, May 1999, pp. 5698–5703.

Y. Zhou, et al., "Impaired Macrophage Function and Enhanced T Cell–Dependent Immune Response in Mice Lacking CCR5, the Mouse Homologue of the Major HIV–1 Coreceptor", J. Immunology, vol. 160, 1998, pp. 4018–4025.

M. Fischereder, et al., "CC chemokine receptor 5 and renal–transplant survival", Lancet, vol. 357, Jun. 2001, pp. 1758–1761.

W. Gao, et al., "Targeting of Chemokine Receptors CCR2 and CCR5 Prolongs Murine Cardiac Allograft Survival", Amer. Soc. of Transplantion Meeting (Transplant 2000), May 2000, Chicago, IL, USA.

P. J. Nelson, et al., "Chemokines, Chemokine Receptors, and Allograft Rejection", Immunity, vol. 14, Apr. 2001, pp. 377–386.

W. Gao, et al., "Beneficial Effects of Targeting CCR5 in Allograft Recipients", Transplantation, vol. 72, No. 7, Oct. 2001, pp. 1199–1205.

R. N. Pierson, et al., "CCR5 Blockade Modulates the Primate Immune Response After Cardiac Allotransplantation", Abstract #324, Amer. Journal of Transplantation, American Transplant Congress 2002, vol. 2, Suppl. 3, 2002.

* cited by examiner

N-CYCLOPENTYL MODULATORS OF CHEMOKINE RECEPTOR ACTIVITY

This application is a divisional of pending U.S. Ser. No. 09/590,750, filed Jun. 8, 2000, now U.S. Pat. No. 6,358,979, which claims the benefit of U.S. Provisional Application No. 60/138,886, filed Jun. 11, 1999.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C—X—C ($\alpha$) and C—C ($\beta$), depending on whether the first two cysteines are separated by a single amino acid (C—X—C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory proteins), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120, It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

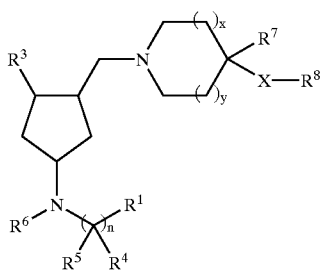

wherein:

X is selected from:
—($C_{0-6}$ alkyl)-Y—($C_{0-6}$ alkyl)-, —($C_{0-6}$ alkyl)-$C_{3-8}$ cycloalkyl-($C_{0-6}$ alkyl)-, $C_{2-10}$ alkenyl, and $C_{2-10}$ alkynyl,
where the alkyl is unsubstituted or substituted with 1–7 substituents where the substituents are independently selected from:
(a) halo,
(b) hydroxy,
(c) —O—$C_{1-3}$ alkyl, and
(d) trifluoromethyl, and where Y is selected from:
a single bond, —O—, —$SO_2$—, —$NR^{10}$—, —$NR^{10}$—$SO_2$—, —$SO_2$—$NR^{10}$—, —S—, and —SO—,
and where $R^{10}$ is independently selected from: hydrogen, $C_{1-6}$ alkyl, benzyl, phenyl, and $C_{1-6}$ alkyl-$C_{3-6}$ cycloalkyl,
which is unsubstituted or substituted with 1–3 substituents where the substituents are independently selected from: halo, $C_{1-3}$ alkyl, $C_{1-3}$ alkoxy and trifluoromethyl;

$R^1$ is selected from:
(1) —$CO_2H$,
(2) —$NO_2$,
(3) -tetrazolyl,
(4) -hydroxyisoxazole,
(5) —$SO_2NHCO$—($C_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) —P(O)(OH)$_2$;

$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$, $R^5$ and $R^6$ are independently selected from:
hydrogen, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)-$C_{3-8}$ cycloalkyl, naphthyl, biphenyl, and heterocycle,
which is unsubstituted or substituted with 1–7 of $R^{11}$
where $R^{11}$ is independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a 3–8 membered saturated ring which may be unsubstituted or substituted with 1–7 of $R^{11}$,
or where $R^5$ and $R^6$ may be joined together to form a 3–8 membered saturated ring which may be unsubstituted or substituted with 1–7 of $R^{11}$;

$R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy, and
(4) halo;

$R^8$ is selected from:
hydrogen, $C_{3-8}$ cycloalkyl, phenyl, naphthyl, biphenyl, and heterocycle, which is unsubstituted or substituted with 1–7 of $R^{12}$
where $R^{12}$ is independently selected from:
- (a) halo,
- (b) cyano,
- (c) hydroxy,
- (d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), trifluoromethyl, and —$NR^9R^{10}$,
- (e) —O—$C_{1-6}$ alkyl, which is unsubstituted or substituted with 1–5 of $R^{13}$,
- (f) —$CF_3$,
- (g) —$CHF_2$,
- (h) —$CH_2F$,
- (i) —$NO_2$,
- (j) $C_{0-6}$ alkyl-phenyl or $C_{0-6}$ alkyl-heterocycle, which is unsubstituted or substituted with 1–7 substituents where the substituents are independently selected from:
  - (i) halo,
  - (ii) hydroxy,
  - (iii) $C_{1-6}$ alkyl, unsubstituted or substituted with 1–5 substituents, each of which is independently selected from halo, cyano, hydroxy, $C_{1-6}$ alkoxy, —$CO_2H$, —$CO_2(C_{1-6}$ alkyl), trifluoromethyl, and —$NR^9R^{10}$,
  - (iv) —O—$C_{1-6}$ alkyl,
  - (v) —$CF_3$,
  - (vi) —$OCF_3$,
  - (vii) —$NO_2$,
  - (viii) —CN,
  - (ix) —$SO_2$—$C_{1-6}$ alkyl,
  - (x) —$CO_2R^9$,
  - (xi) —$NR^9R^{10}$,
  - (xii) —$CONR^9R^{10}$,
  - (xiii) —$SO_2$—$NR^9R^{10}$,
  - (xiv) —$NR_9$—$SO_2$—$R^{10}$,
  - (xv) —$C_{3-8}$ cycloalkyl,
  - (xvi) —$OC_{3-8}$ cycloalkyl, and
  - (xvii) phenyl;
- (k) —$CO_2R^9$,
- (l) tetrazolyl,
- (m) —$NR^9R^{10}$,
- (n) —$NR^9$—$COR^{10}$,
- (o) —$NR^9$—$CO_2R^{10}$,
- (p) —$CO$—$NR^9R^{10}$,
- (q) —$OCO$—$NR^9R^{10}$,
- (r) —$NR^9CO$—$NR^9R^{10}$,
- (s) —$S(O)_m$—$R^9$, wherein m is an integer selected from 0, 1 and 2,
- (t) —$S(O)_2$—$NR^9R^{10}$,
- (u) —$NR^9S(O)_2$—$R^{10}$,
- (v) —$NR^9S(O)_2$—$NR^9R^{10}$,
- (w) $C_{1-6}$ alkyl substituted with —$C_{3-8}$ cycloalkyl, and
- (x) —$C_{3-8}$ cycloalkyl;

n is an integer selected from 1, 2, 3 and 4;
x is an integer selected from 0, 1 and 2, and y is an integer selected from 0, 1 and 2, with the proviso that the sum of x and y is 2;
and pharmaceutically acceptable salts thereof and individual diastereomers thereof.

In one embodiment, the present invention is directed to compounds of Formula I, and pharmaceutically acceptable salts thereof and individual diastereomers thereof, wherein $R^1$ is selected from:
- (1) —$CO_2H$,
- (2) —$NO_2$,
- (3) -tetrazolyl,
- (4) -hydroxyisoxazole, and
- (5) —$P(O)(OH)_2$;

$R^8$ is selected from:

hydrogen, $C_{3-8}$ cycloalkyl, phenyl, naphthyl, biphenyl, and heterocycle,
which is unsubstituted or substituted with 1–7 of $R^{12}$
where $R^{12}$ is independently selected from:
- (a) halo,
- (b) cyano,
- (c) hydroxy,
- (d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), trifluoromethyl, and —$NR^9R^{10}$,
- (e) —O—$C_{1-6}$ alkyl, which is unsubstituted or substituted with 1–5 of $R^{13}$,
- (f) —$CF_3$,
- (g) —$CHF_2$,
- (h) —$CH_2F$,
- (i) —$NO_2$,
- (j) $C_{0-6}$ alkyl-phenyl or $C_{0-6}$ alkyl-heterocycle, which is unsubstituted or substituted with 1–7 substituents where the substituents are independently selected from:
  - (i) halo,
  - (ii) hydroxy,
  - (iii) $C_{1-6}$ alkyl,
  - (iv) —O—$C_{1-6}$ alkyl,
  - (v) —$CF_3$,
  - (vi) —$OCF_3$,
  - (vii) —$NO_2$,
  - (viii) —CN,
  - (ix) —$SO_2$—$C_{1-6}$ alkyl,
  - (x) —$CO_2R^9$,
  - (xi) —$NR^9R^{10}$,
  - (xii) —$CONR^9R^{10}$,
  - (xiii) —$SO_2$—$NR^9R^{10}$, and
  - (xiv) —$NR^9$—$SO_2$—$R^{10}$;
- (k) —$CO_2R^9$,
- (l) tetrazolyl,
- (m) —$NR^9R^{10}$,
- (n) —$NR^9$—$COR^{10}$,
- (o) —$NR^9$—$CO_2R^{10}$,
- (p) —$CO$—$NR^9R^{10}$,
- (q) —$OCO$—$NR^9R^{10}$,
- (r) —$NR^9CO$—$NR^9R^{10}$,
- (s) —$S(O)_m$—$R^9$, wherein m is an integer selected from 0, 1 and 2,
- (t) —$S(O)_2$—$NR^9R^{10}$,
- (u) —$NR^9S(O)_2$—$R^{10}$, and
- (v) —$NR^9S(O)_2$—$NR^9R^{10}$;

and all else is as defined above.

Preferred compounds of the present invention include those of formula Ia:

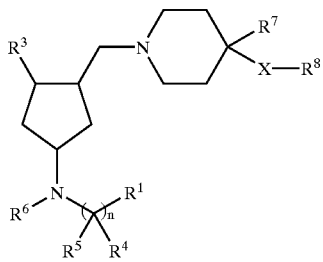

Ia wherein $R^1$, $R^3$, $R^4$, $R^5$, $R^6$, $R^7$, $R^8$, X and n are defined herein;

and pharmaceutically acceptable salts and individual diastereomers thereof.

More preferred compounds of the present invention include those of formula Ic:

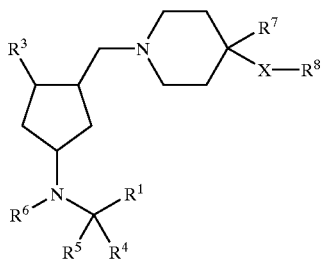

Ic wherein $R^1$, $R^3$, $R^4$, $R^5$, $R^6$, $R^7$, $R^8$ and X are defined herein;

and pharmaceutically acceptable salts and individual diastereomers thereof.

Highly preferred compounds of the present invention include those of formula Id:

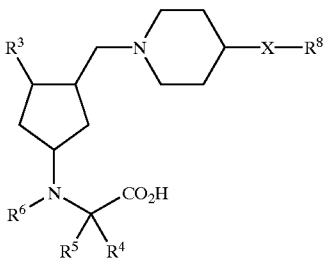

Id wherein $R^3$, $R^4$, $R^5$, $R^6$, $R^8$ and X are defined herein;

and pharmaceutically acceptable salts and individual diastereomers thereof.

More highly preferred compounds of the present invention include those of formula Ie:

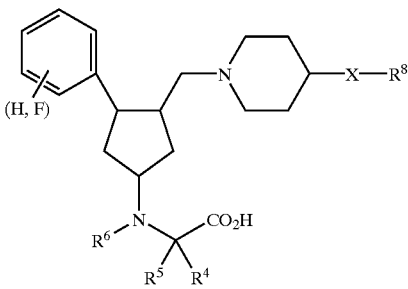

Ie wherein $R^4$, $R^5$, $R^6$, $R^8$ and X are defined herein;
and pharmaceutically acceptable salts and individual diastereomers thereof.

In the present invention it is preferred that $R^1$ is selected from:
(1) —$CO_2H$,
(2) —$P(O)(OH)_2$, and
(3) -tetrazolyl.

In the present invention it is more preferred that $R^1$ is selected from:
(1) —$CO_2H$, and
(2) -tetrazolyl.

In the present invention it is even more preferred that $R^1$ is —$CO_2H$.

In the present invention it is preferred that $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is still more preferred that $R^3$ is unsubstituted phenyl, (3-fluoro)phenyl or 3-thienyl.

In the present invention it is preferred that $R^4$ is hydrogen or $C_{1-6}$ alkyl.

In the present invention it is more preferred that $R^4$ is hydrogen.

In the present invention it is preferred that $R^5$ is selected from: hydrogen, $C_{1-6}$ alkyl, $C_{3-8}$ cycloalkyl, $C_{1-6}$ alkyl-$C_{3-8}$ cycloalkyl, and phenyl.

In the present invention it is more preferred that $R^5$ is selected from: hydrogen, methyl, n-propyl, isopropyl, n-butyl, t-butyl, isobutyl, sec-butyl, cyclohexyl, —CH$_2$-cyclopropyl, —CH$_2$-cyclobutyl, and phenyl.

In the present invention it is still more preferred that $R^5$ is selected from: isopropyl, isobutyl, sec-butyl, and cyclohexyl.

In the present invention it is preferred that $R^6$ is selected from: hydrogen, $C_{1-6}$ alkyl, $C_{3-8}$ cycloalkyl, $C_{1-6}$ alkyl-$C_{3-8}$ cycloalkyl, and phenyl.

In the present invention it is more preferred that $R^6$ is selected from: hydrogen, methyl, n-butyl, t-butyl, isobutyl, sec-butyl, —CH$_2$-cyclopropyl, —CH$_2$-cyclobutyl, and cyclohexyl.

In the present invention it is still more preferred that $R^6$ is selected from: hydrogen, methyl, —CH$_2$-cyclopropyl, —CH$_2$-cyclobutyl, and cyclohexyl.

In an alternate embodiment of the present invention it is preferred that $R^5$ and $R^6$ are joined together to form a $C_{3-8}$ cycloalkyl ring.

In an alternate embodiment of the present invention it is more preferred that $R^5$ and $R^6$ are joined together to form a pyrrolidine ring.

In another alternate embodiment of the present invention it is more preferred that $R^4$ and $R^5$ are joined together to form a $C_{3-8}$ cycloalkyl ring. In an aspect of this embodiment, the ring formed by joining $R^4$ and $R^5$ is cyclopentyl.

In the present invention it is preferred that $R^7$ is hydrogen, fluoro, hydroxy or $C_{1-6}$ alkyl.

In the present invention it is more preferred that $R^7$ is hydrogen or fluoro.

In the present invention it is even more preferred that $R^7$ is hydrogen.

In the present invention it is preferred that X is:

—(C$_{0-4}$ alkyl)-Y—(C$_{0-4}$ alkyl)—, where the alkyl is unsubstituted or substituted with 1–4 substituents where the substituents are independently selected from:
(a) halo,
(b) hydroxy,
(c) —O—C$_{1-3}$ alkyl, and
(d) trifluoromethyl,
and where Y is selected from:
a single bond, —O—, —SO$_2$—, —NR$^{10}$—, —S—, and —SO—,
and where R$^{10}$ is independently selected from:
hydrogen, C$_{1-6}$ alkyl, C$_{2-6}$ alkenyl, C$_{2-6}$ alkynyl, benzyl, phenyl, and C$_{1-6}$ alkyl-C$_{3-6}$ cycloalkyl, which is unsubstituted or substituted with 1–3 substituents where the substituents are independently selected from: halo, C$_{1-3}$ alkyl, C$_{1-3}$ alkoxy and trifluoromethyl.

In the present invention it is more preferred that X is:

—(C$_{0-2}$ alkyl)-Y—(C$_{0-2}$ alkyl)-, where the alkyl is unsubstituted or substituted with 1–4 substituents where the substituents are independently selected from:
(a) halo,
(b) hydroxy,
(c) —O—C$_{1-3}$ alkyl, and
(d) trifluoromethyl,
and where Y is selected from:
a single bond, —O—, —SO$_2$—, —NR$^{10}$—, —S—, and —SO—,
where R$^{10}$ is independently selected from:
hydrogen, C$_{1-6}$ alkyl, C$_{2-6}$ alkenyl, C$_{2-6}$ alkynyl, benzyl, phenyl, and C$_{1-6}$ alkyl-C$_{3-6}$ cycloalkyl,
which is unsubstituted or substituted with 1–3 substituents where the substituents are independently selected from:
halo, C$_{1-3}$ alkyl, C$_{1-3}$ alkoxy and trifluoromethyl.

In the present invention it is even more preferred that X is selected from:
—(C$_{0-2}$ alkyl)-Y—(C$_{0-2}$ alkyl)-, where the alkyl is unsubstituted or substituted with fluoro,
and where Y is selected from:
a single bond, —SO$_2$—, —SO—, and —NR$^{10}$—,
where R$^{10}$ is independently selected from: hydrogen, C$_{1-3}$ alkyl, C$_{2-3}$ alkenyl, and C$_{2-3}$ alkynyl.

In the present invention it is still more preferred that X is selected from:
(1) a single bond,
(2) —CH$_2$CH$_2$—,
(3) —CH$_2$CH$_2$CH$_2$—,
(4) —CH$_2$CH$_2$—CF$_2$—,
(5) —CH$_2$CH$_2$—SO$_2$—, and
(6) —CH$_2$CH$_2$—SO—.

In the present invention it is preferred that $R^8$ is selected from:
phenyl, naphthyl, cyclohexyl, benzoimidazolyl, benzofurazanyl, imidazopyridyl, imidazolyl, isoxazolyl, oxazolyl, pyrazinyl, pyridazinyl, pyridyl, pyrimidyl, thiazolyl, tetrazolopyridyl, pyrazolyl, tetrahydroindazolyl, tetrahydroimidazopyridyl, and tetrahydropyrazolopyridyl;
which is unsubstituted or substituted with 1–7 substituents where the substituents are independently selected from:
(a) halo,
(b) cyano,
(c) hydroxy,
(d) C$_{1-6}$ alkyl, which is unsubstituted or substituted with 1–5 of R$^{13}$ where R$^{13}$ is independently selected from: halo, cyano, hydroxy, C$_{1-6}$ alkoxy, —CO$_2$H, —CO$_2$(C$_{1-6}$ alkyl), trifluoromethyl, and —NR$^9$R$^{10}$, wherein R$^9$ and R$^{10}$ are independently selected from: hydrogen, C$_{1-6}$ alkyl, C$_{5-6}$ cycloalkyl, benzyl or phenyl, which is unsubstituted or substituted with 1–3 substituents where the substituents are independently selected from: halo, C$_{1-3}$ alkyl, C$_{1-3}$ alkoxy and trifluoromethyl;
(e) —O—C$_{1-6}$ alkyl, which is unsubstituted or substituted with 1–5 of R$^{13}$,
(f) —CF$_3$,
(g) —CHF$_2$,
(h) —CH$_2$F,
(i) —NO$_2$,
(j) C$_{0-6}$ alkyl-phenyl or C$_{0-6}$ alkyl-heterocycle, which is unsubstituted or substituted with 1–7 substituents where the substituents are independently selected from:
(i) halo,
(ii) hydroxy,
(iii) C$_{1-6}$ alkyl,
(iv) —O—C$_{1-6}$ alkyl,
(v) —CF$_3$,
(vi) —OCF$_3$,
(vii) —NO$_2$,
(viii) —CN, (ix) —$SO_2$—$C_{1-6}$ alkyl,
(x) —$CO_2R^9$,
(xi) —$NR^9R^{10}$,
(xii) —$CONR^9R^{10}$,
(xiii) —$SO_2$—$NR^9R^{10}$, and
(xiv) —$NR^9$—$SO_2$—$R^{10}$;
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —$CO$—$NR^9R^{10}$,
(q) —$OCO$—$NR^9R^{10}$,
(r) —$NR^9CO$—$NR^9R^{10}$,
(s) —$S(O)_m$—$R^9$, wherein m is an integer selected from 0, 1 and
(t) —$S(O)_2$—$NR^9R^{10}$,
(u) —$NR^9S(O)_2$—$R^{10}$, and
(v) —$NR_9S(O)_2$—$NR^9R^{10}$.

In an aspect of the preceding embodiment, in the present invention it is preferred that $R^8$ is selected from: phenyl, naphthyl, cyclohexyl, benzoimidazolyl, benzofurazanyl, imidazopyridyl, imidazolyl, isoxazolyl, oxazolyl, pyrazinyl, pyridazinyl, pyridyl, pyrimidyl, thiazolyl, and tetrazolopyridyl; which is unsubstituted or substituted with 1–7 substituents as set forth in the preceding paragraph.

In the present invention it is more preferred that $R^8$ is selected from:

phenyl, imidazopyridyl, imidazolyl, oxazolyl, pyrazolyl, pyridyl, thiazolyl, tetrahydroindazolyl, tetrahydroimidazopyridyl, and tetrahydropyrazolopyridyl;

which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(h) $C_{1-6}$ alkyl,
(i) $C_{1-3}$ alkyl-phenyl or $C_{1-3}$ alkyl-pyridyl, which is unsubstituted or substituted with 1–4 substituents where the substituents are independently selected from:
(i) halo,
(ii) $C_{1-6}$ alkyl,
(iii) —O—$C_{1-6}$ alkyl,
(iv) —$CF_3$,
(vi) —$OCF_3$,
(vii) —CN, and
(j) —O—$C_{1-6}$ alkyl.

In an aspect of the preceding embodiment, in the present invention it is preferred that $R^8$ is selected from: phenyl, imidazopyridyl, imidazolyl, oxazolyl, pyrazolyl, pyridyl, and thiazolyl; which is unsubstituted or substituted with 1–5 substituents as set forth in the preceding paragraph.

In the present invention it is even more preferred that $R^8$ is selected from:

imidazolyl, oxazolyl, pyrazolyl, thiazolyl, tetrahydroindazolyl, tetrahydroimidazopyridyl, and tetrahydropyrazolopyridyl;
which is unsubstituted or substituted with 1–3 substituents where the substituents are independently selected from:

(a) fluoro,
(b) cyano,
(c) $C_{1-3}$ alkyl,
(d) —$CH_2$-phenyl, which is unsubstituted or substituted with 1–4 substituents where the substituents are independently selected from:
(i) fluoro,
(ii) chloro,
(iii) —O—$CH_3$,
(iv) —$CF_3$,
(v) —CN, and
(e) —$CF_3$.

In an aspect of the preceding embodiment, in the present invention it is preferred that $R^8$ is selected from: imidazolyl, oxazolyl, pyrazolyl, and thiazolyl; which is unsubstituted or substituted with 1–3 substituents as set forth in the preceding paragraph.

In the present invention it is still more preferred that $R^8$ is selected from: 5-(3-benzyl)pyrazolyl, 5-(1-methyl-3-benzyl)pyrazolyl, 5-(1-ethyl-3-benzyl)pyrazolyl, 5-(2-benzyl)thiazolyl, 5-(2-benzyl-4-methyl)thiazolyl, and 5-(2-benzyl4-ethyl)thiazolyl).

In the present invention it is preferred that n is an integer selected from 1, 2 and 3.

In the present invention it is more preferred that n is an integer which is 1.

In the present invention it is preferred that x is an integer which is 1 and y is an integer which is 1.

It is to be understood that embodiments of the present invention include, but are not limited to, compounds of formula I wherein $R^1$, $R^3$, $R^4$, $R^5$, $R^6$, $R^7$, $R^8$, x, y and n are defined in accordance with one of the embodiments or aspects thereof as set forth above. Any and all possible combinations of preferred, more preferred, even more preferred, highly preferred, more highly preferred, and most preferred definitions of these variables in formulas I are within the scope of the present invention.

The compounds of the instant invention have at least two asymmetric centers at the ring junction of the substitutents bearing the piperidine and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

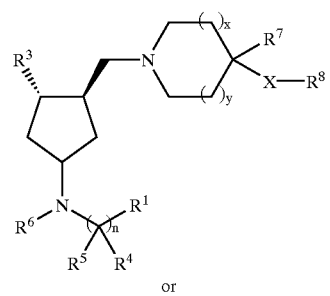

or

-continued

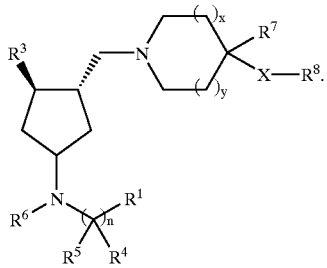

The relative configurations of the even more preferred compounds of this invention wherein $R^6$ is hydrogen, methyl or wherein $R^5$ and $R^6$ form a pyrrolidine ring with respect to the configuration of the nitrogen substituent on the cyclopentane ring is cis to the orientation of $R^3$ as depicted:

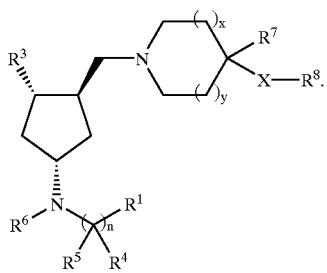

The relative configurations of the most preferred compounds of this invention wherein $R^6$ is hydrogen or methyl with respect to the configuration of the nitrogen substituent on the cyclopentane ring is is cis to the orientation of $R^3$ and with the (R)-stereochemistry of the nitrogen side chain of the orientation as depicted:

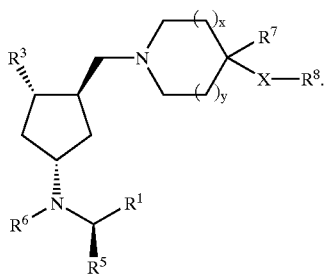

The relative configurations of the even more preferred compounds of this invention wherein $R^6$ is other than hydrogen or methyl with respect to the configuration of the nitrogen substituent on the cyclopentane ring is 1,3-cis of the orientation as depicted:

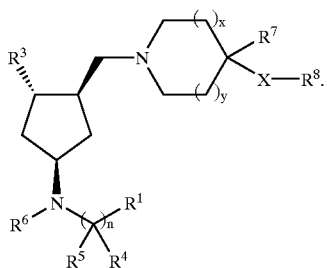

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

In a preferred aspect the present invention is a compound of formula (II);

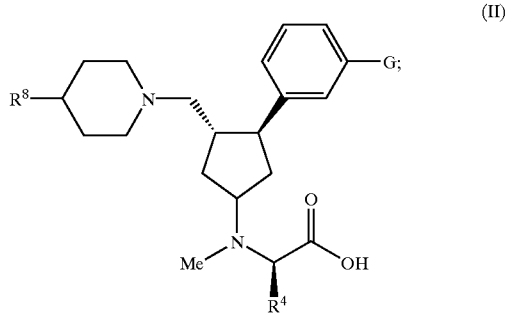

(II)

wherein $R^4$ is

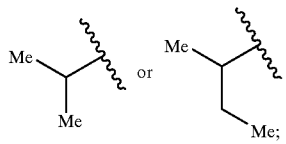

$R^8$ is selected from the group consisting of

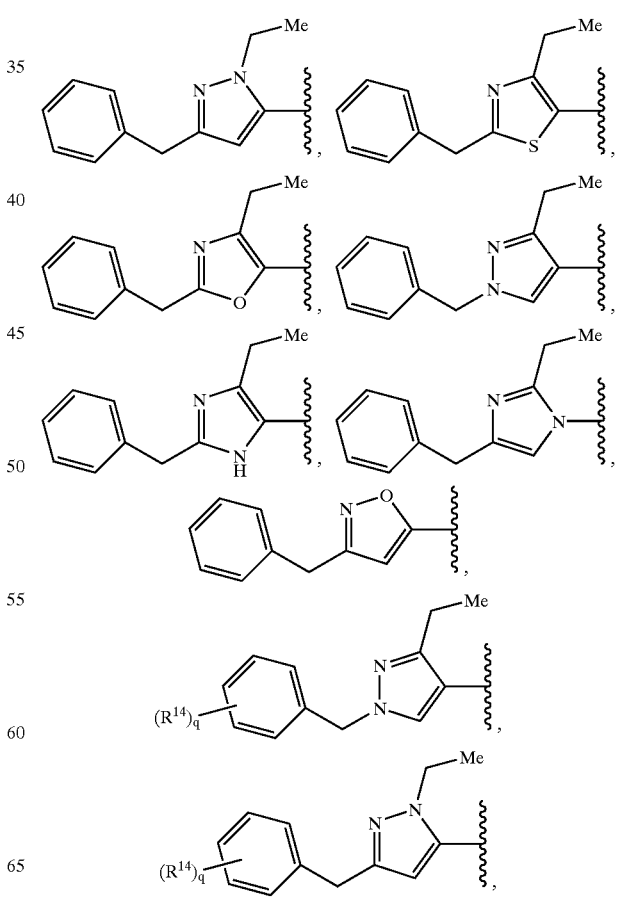

-continued

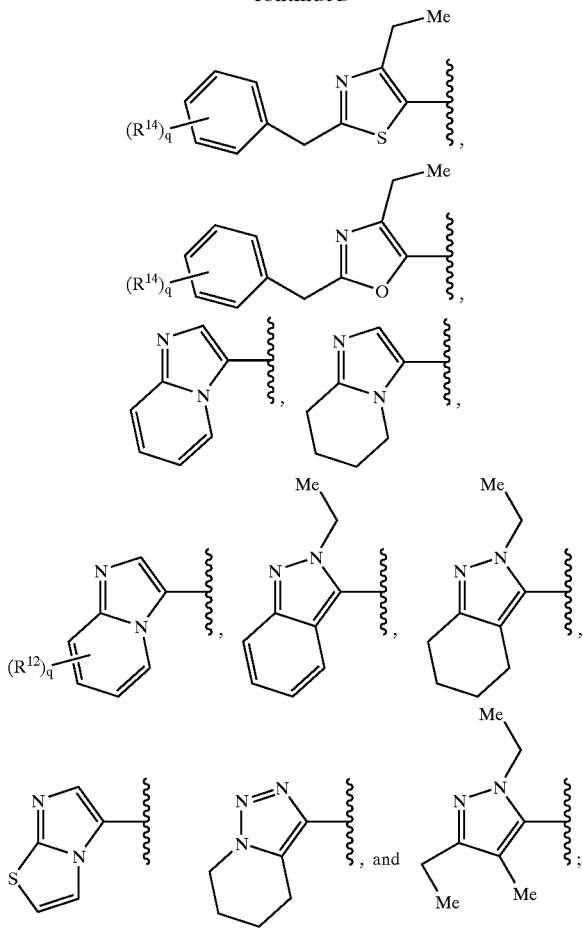

$R^{12}$ and $R^{14}$ are each independently selected from the group consisting of F, Cl, $CF_3$, $OCH_3$, $OCH_2CH_3$, $OCF_3$, O-cyclobutyl, CN, O-cyclopropyl, $CH_3$, $CH_2CH_3$, $CH(CH_3)_2$, $C(CH_3)_3$, and $SO_2CH_3$;

G is hydrogen or fluoro; and q is an integer equal to 1 or 2;

and pharmaceutically acceptable salts thereof and individual diastereomers thereof.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1-3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.
Exemplifying the invention is the use of the compounds disclosed in the Examples and herein.
Specific compounds within the present invention include a compound which is selected from the group consisting of:
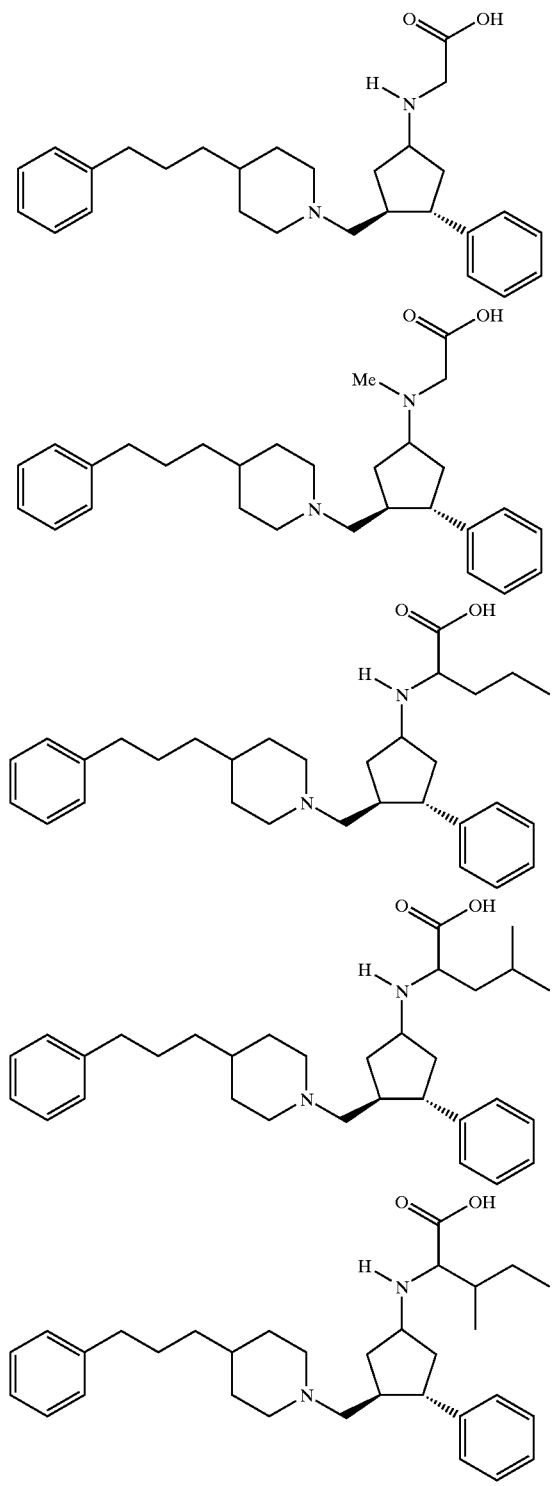
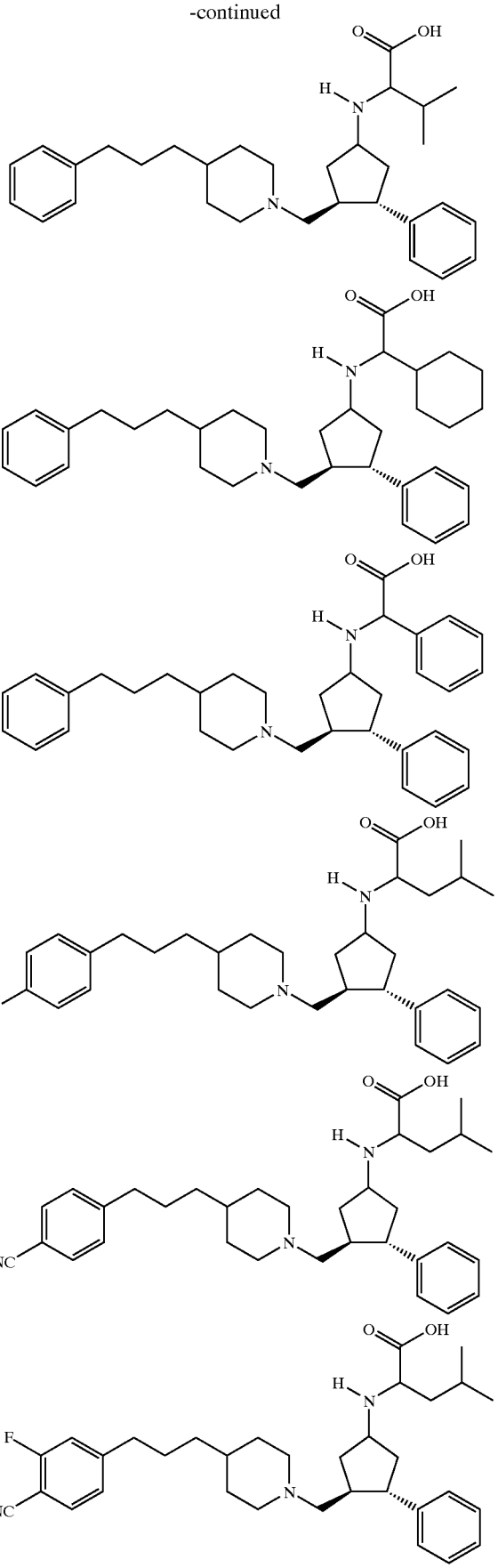
-continued

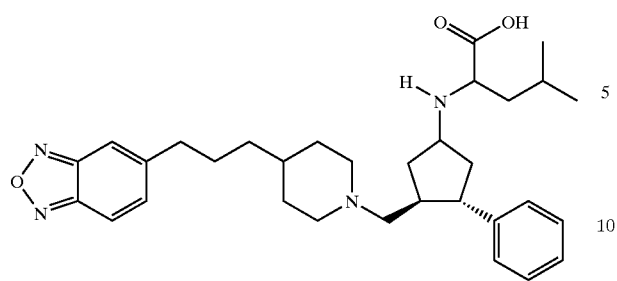
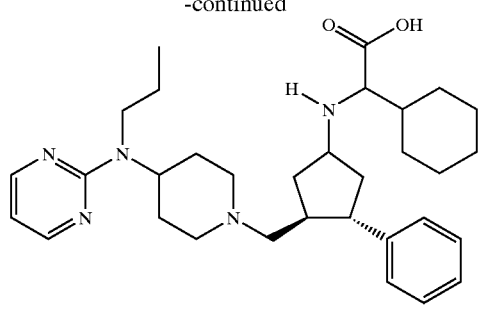
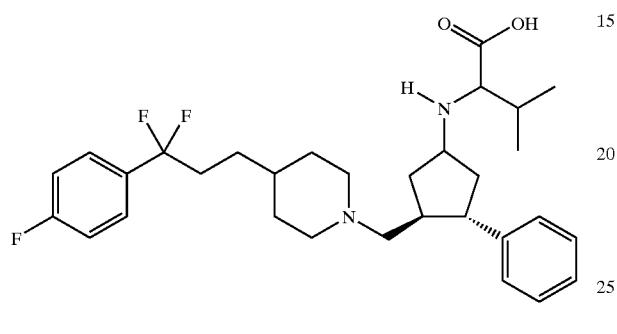
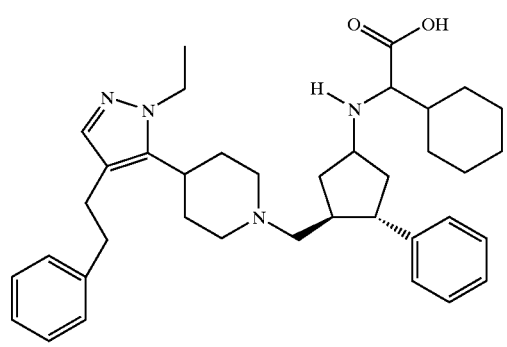
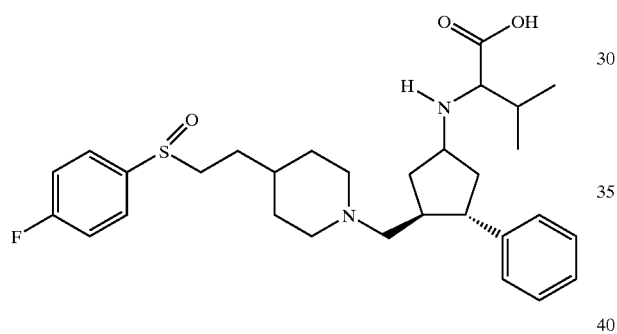
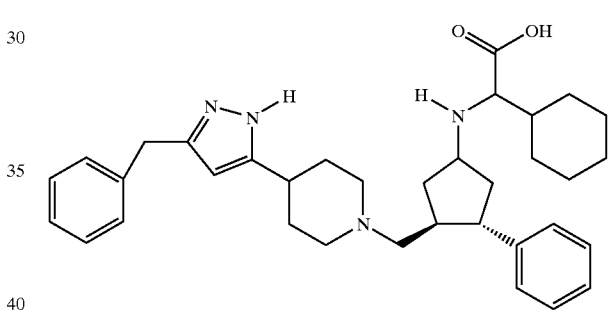
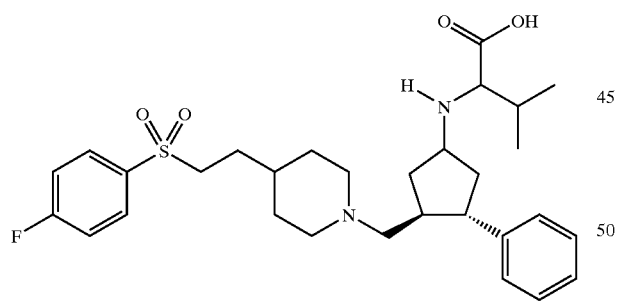
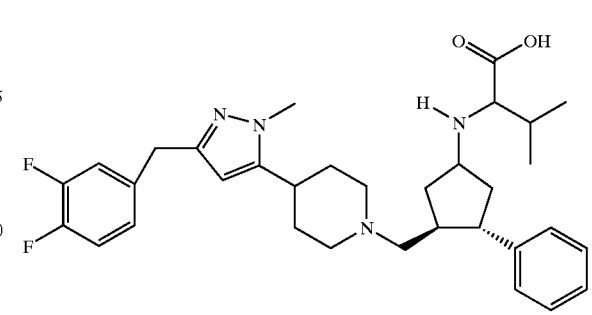
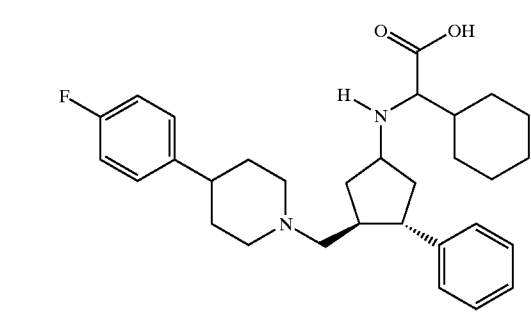
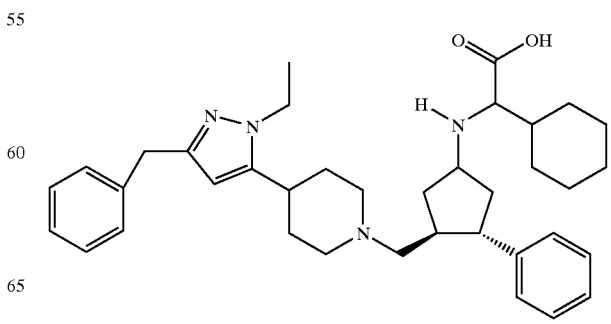

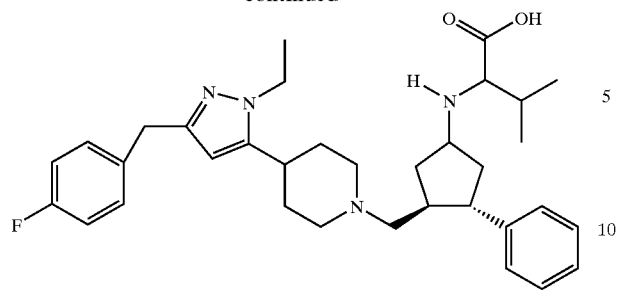
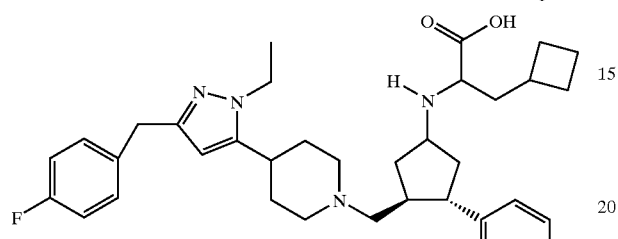
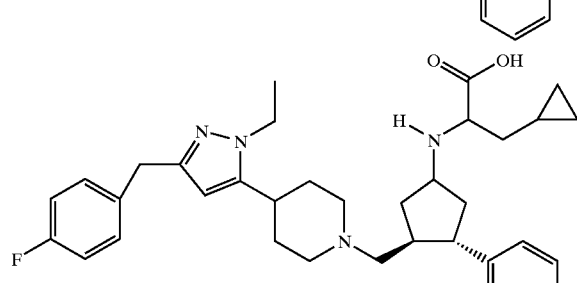
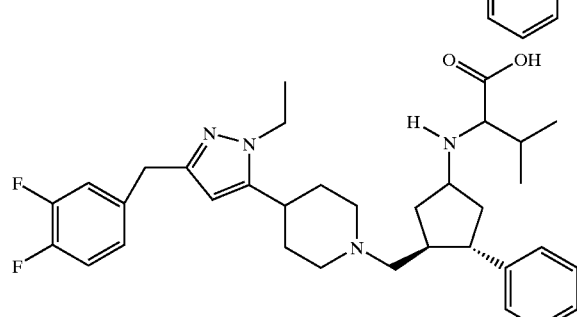
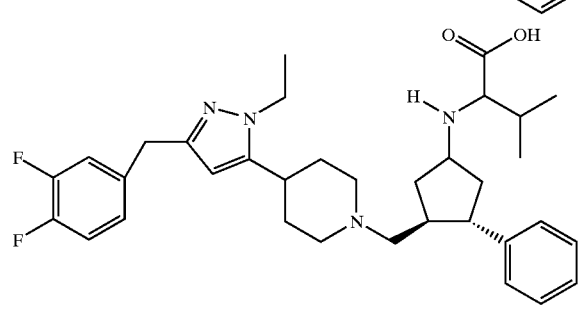
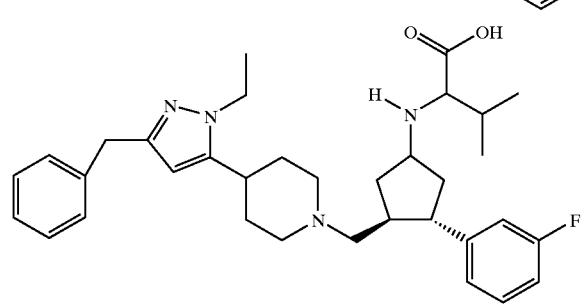
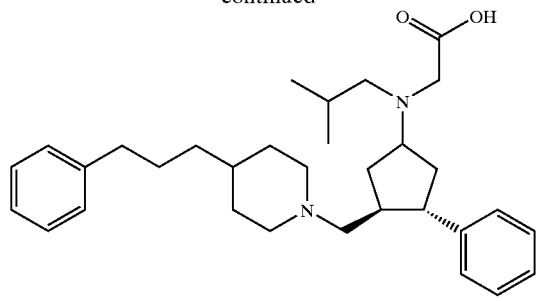
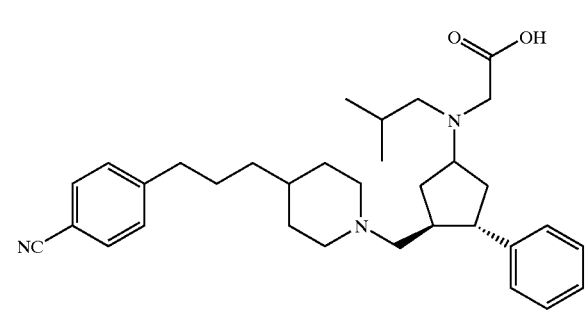
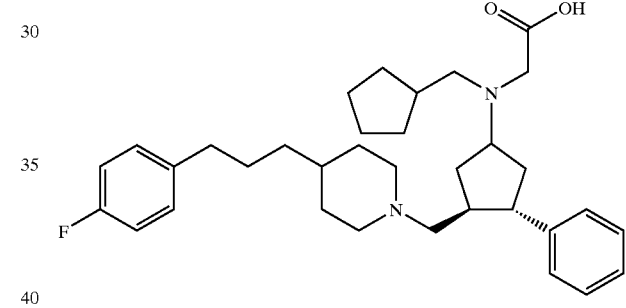
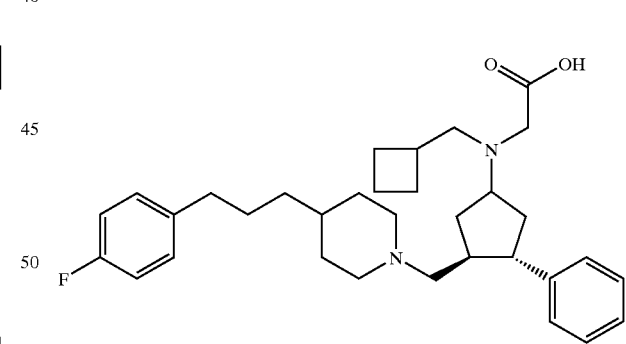
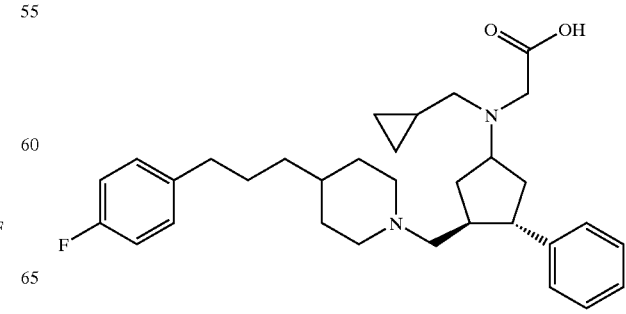

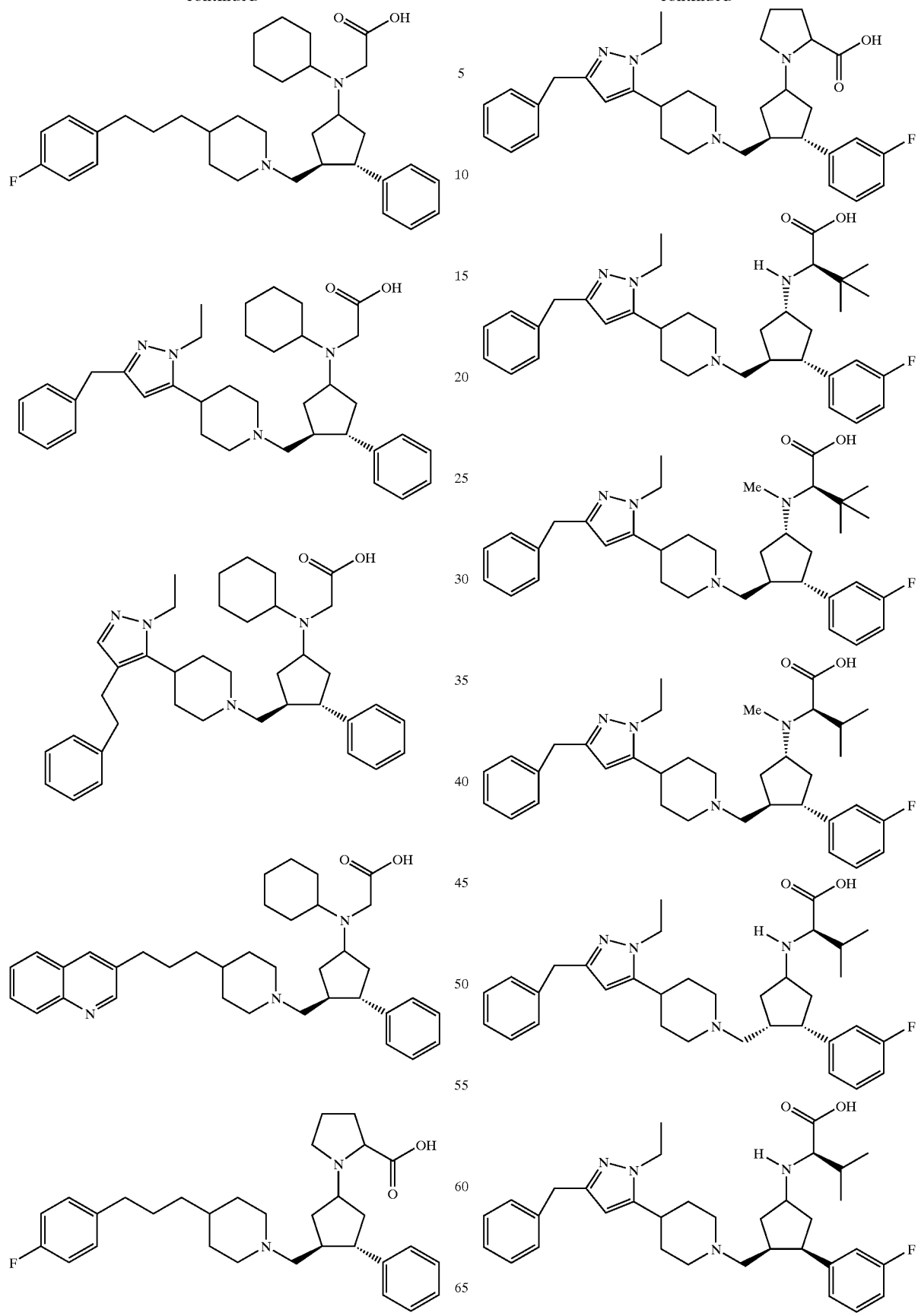

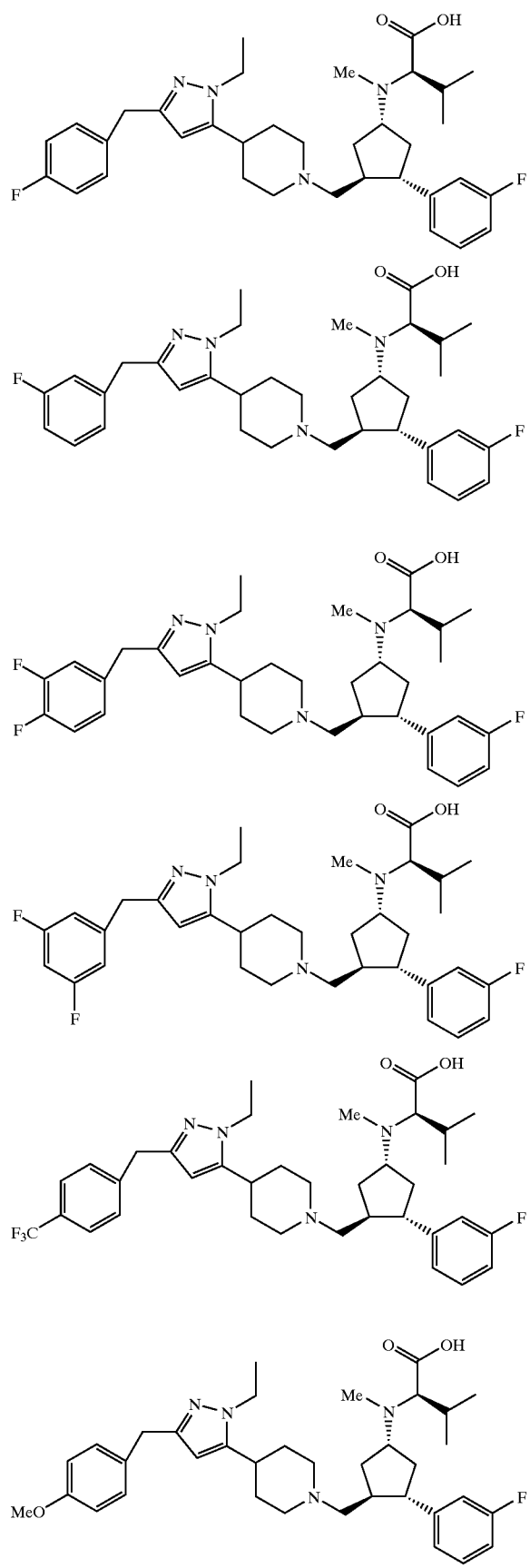
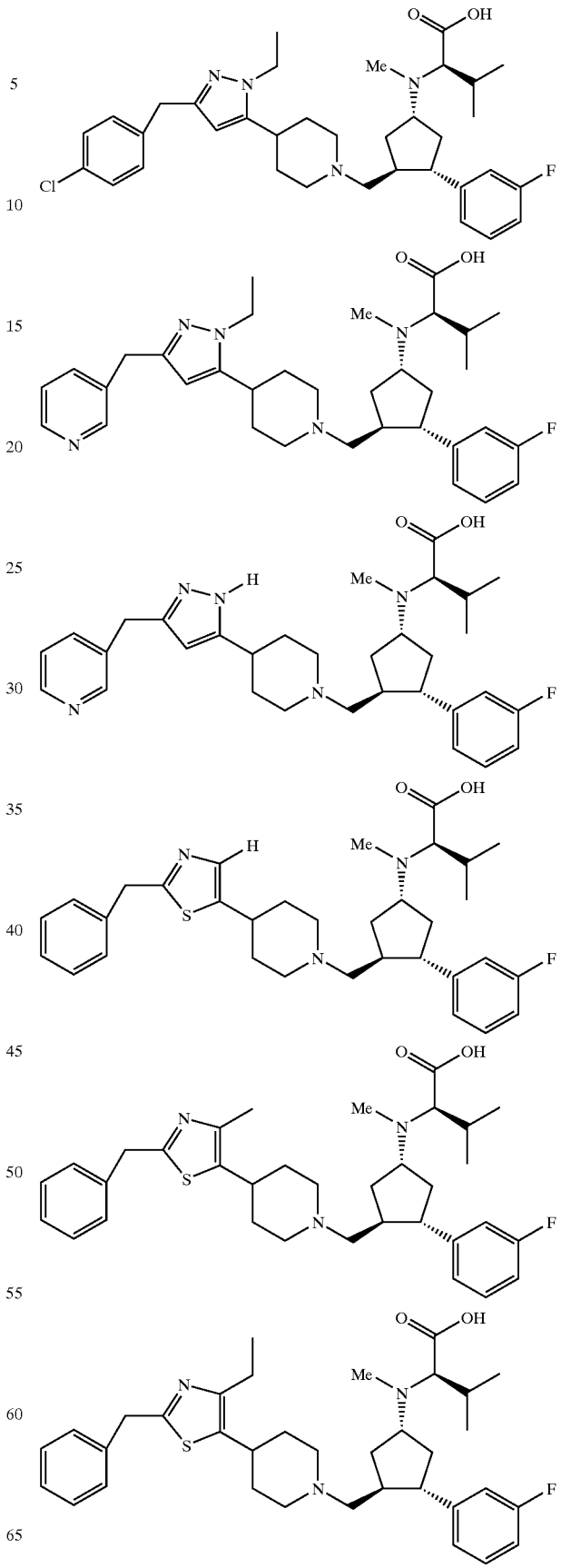

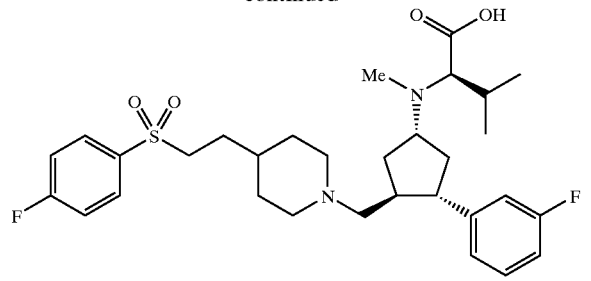
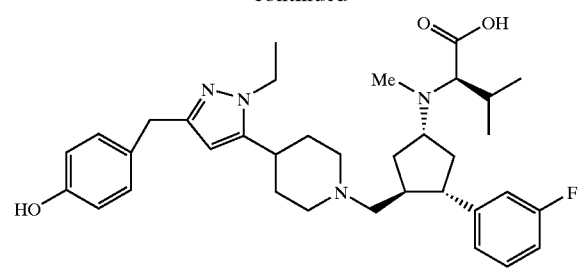
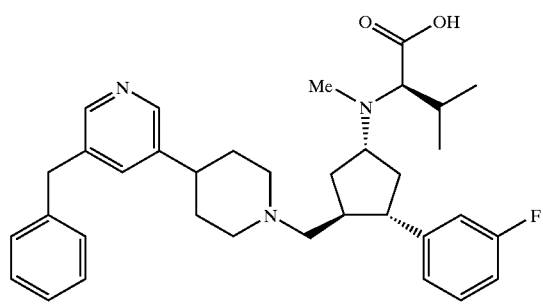
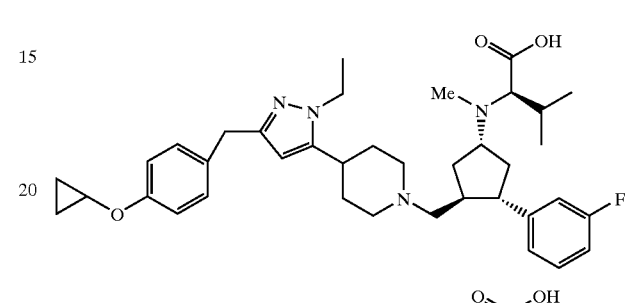
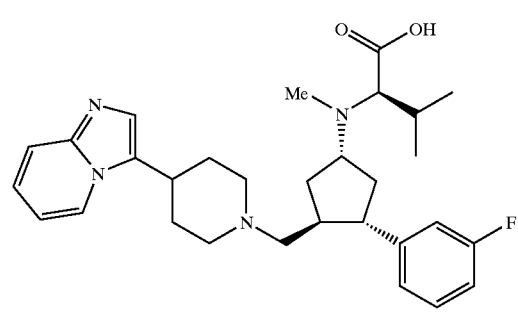
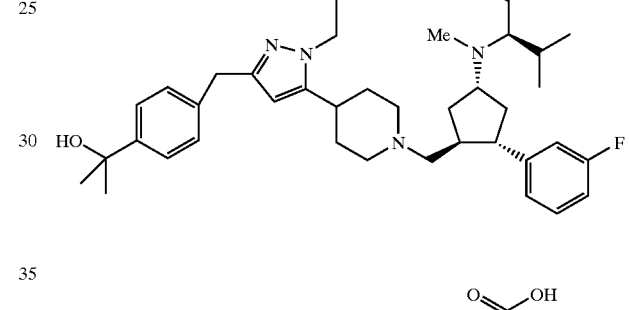
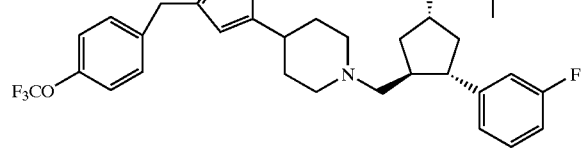
and pharmaceutically acceptable salts thereof and individual diastereomers thereof.
Specific compounds within the present invention also include compounds selected from the group consisting of:
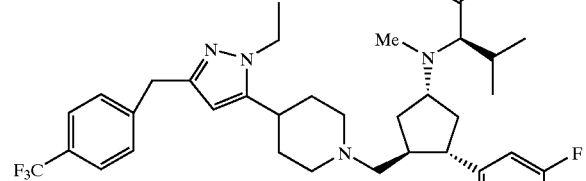
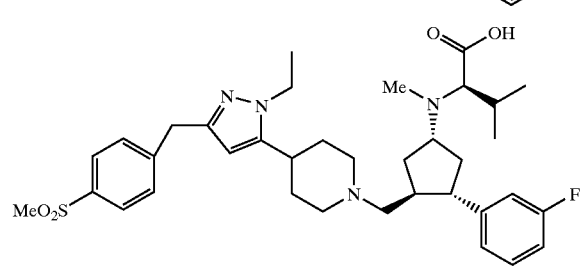
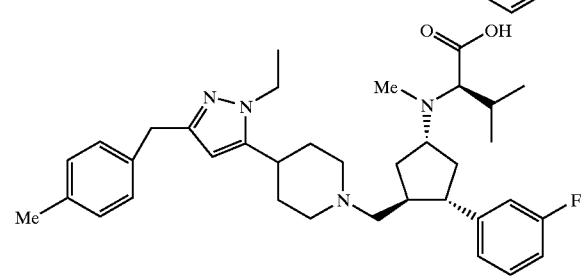
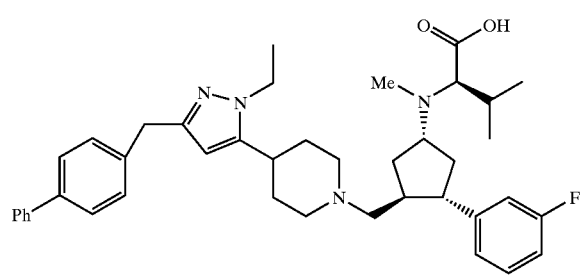

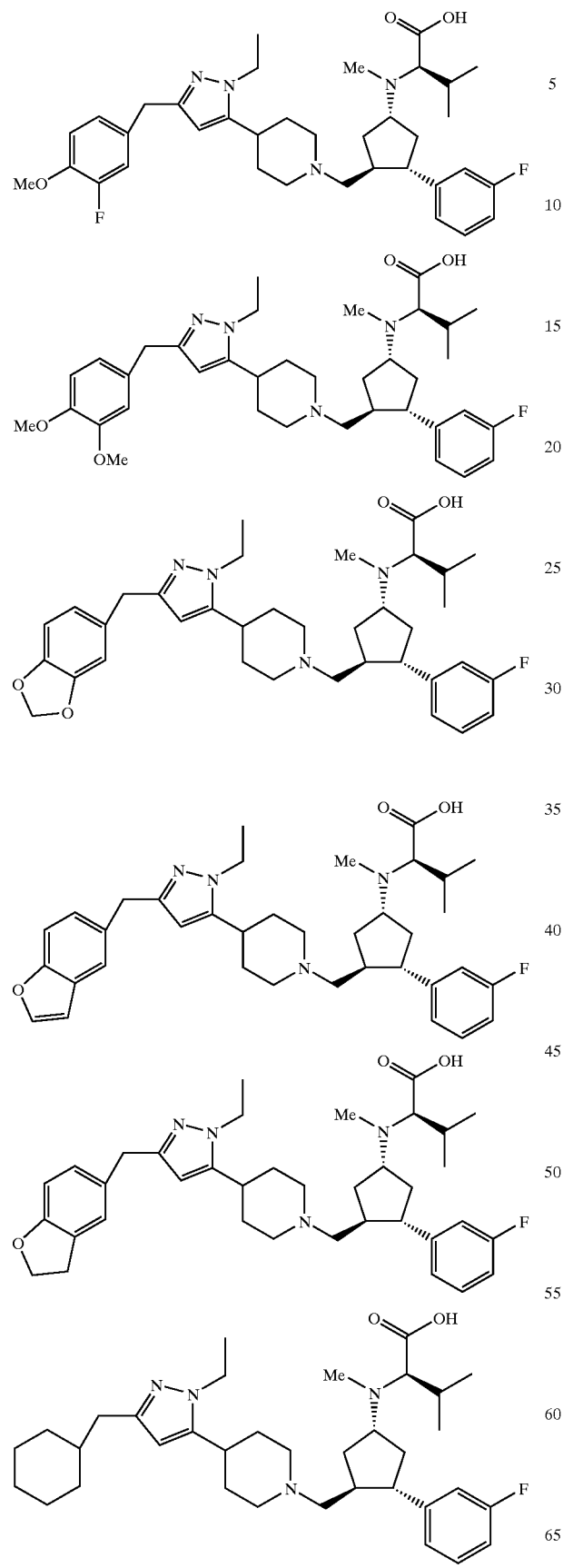
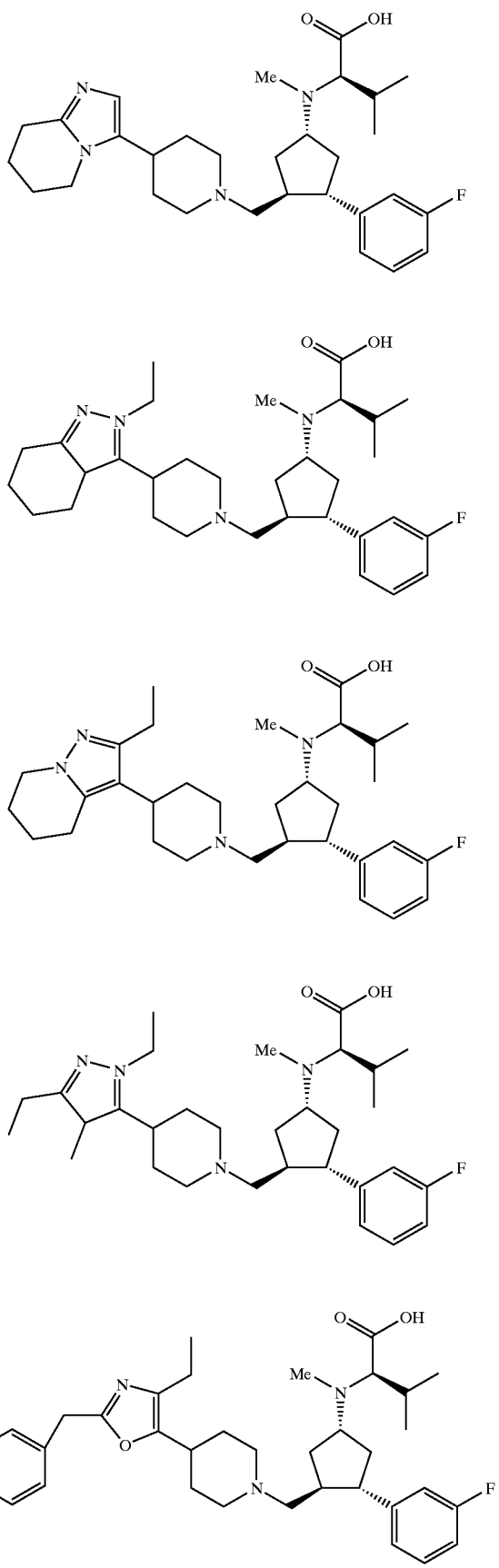

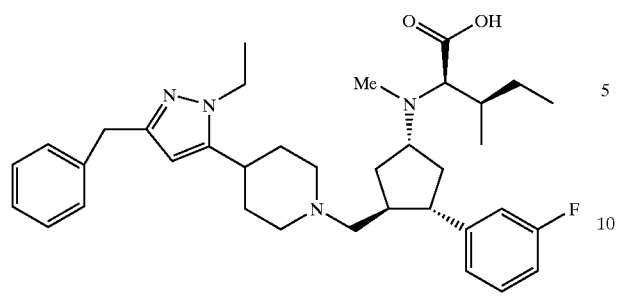
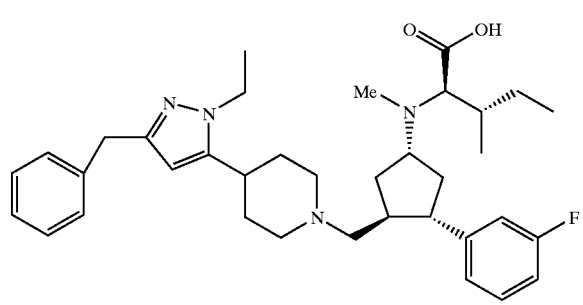
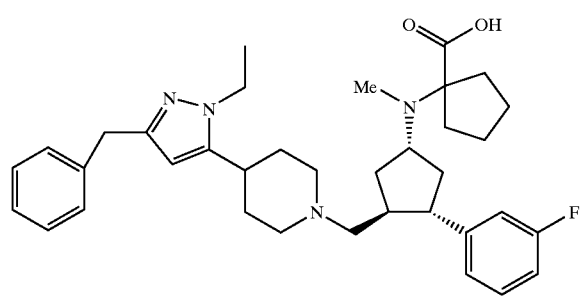
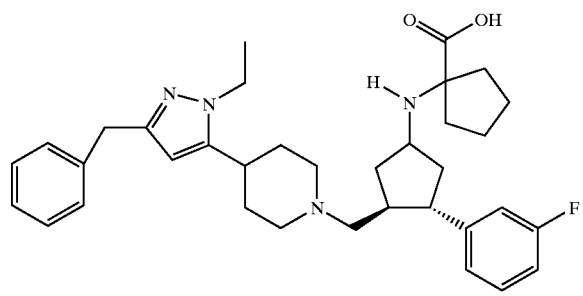
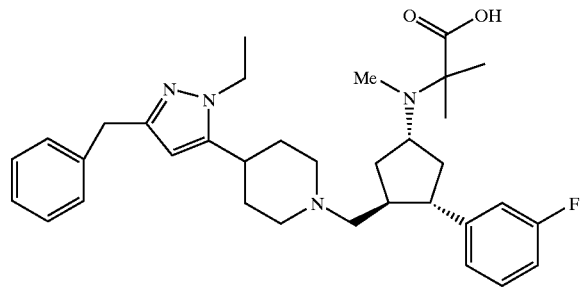
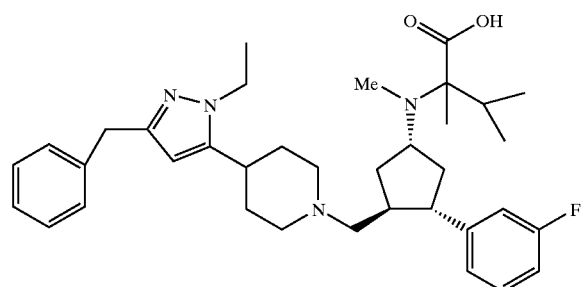
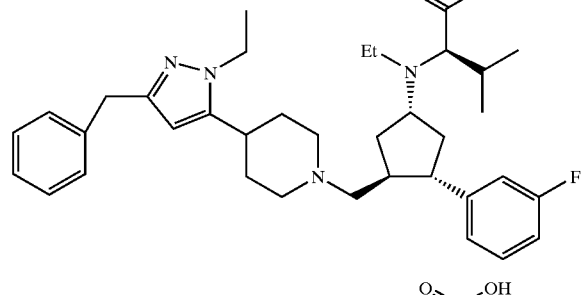
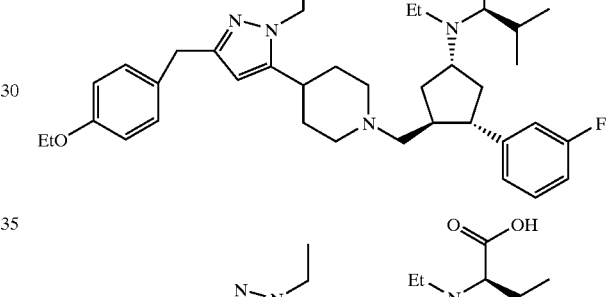
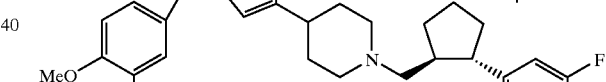
and pharmaceutically acceptable salts thereof and individual diastereomers thereof.
An aspect of the present invention is a compound selected from the group consisting of:
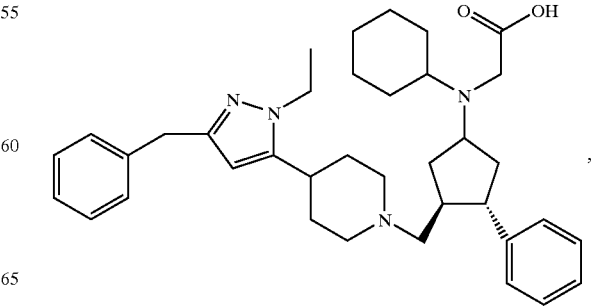

-continued
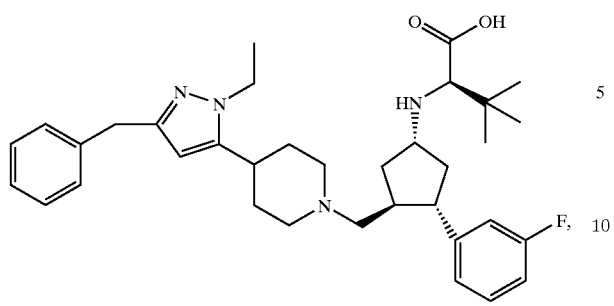
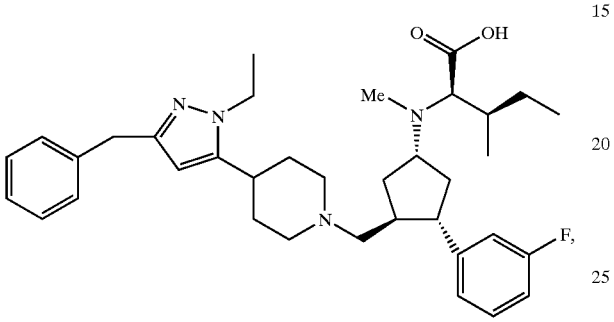
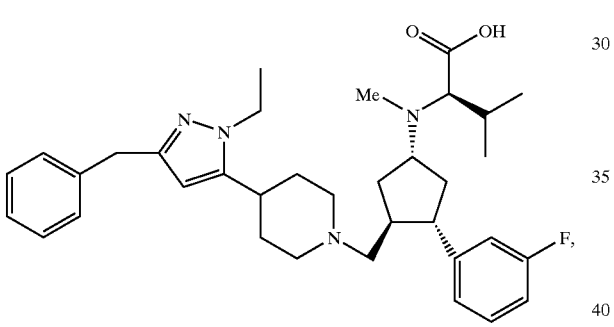
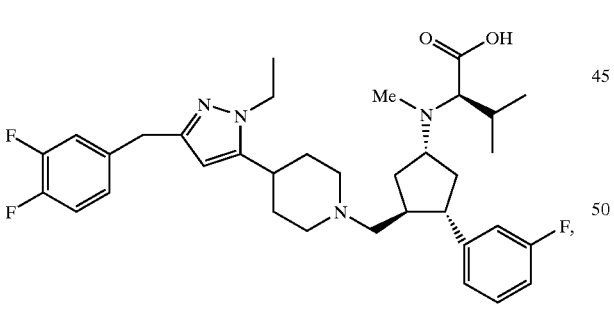
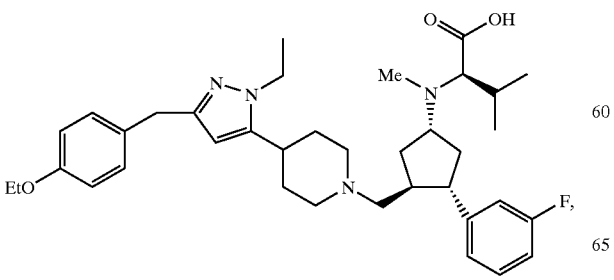
-continued
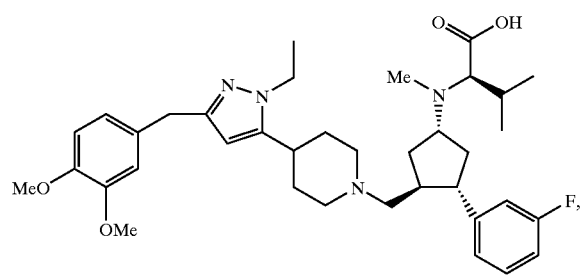
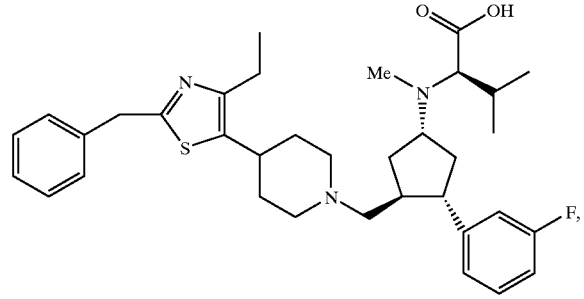
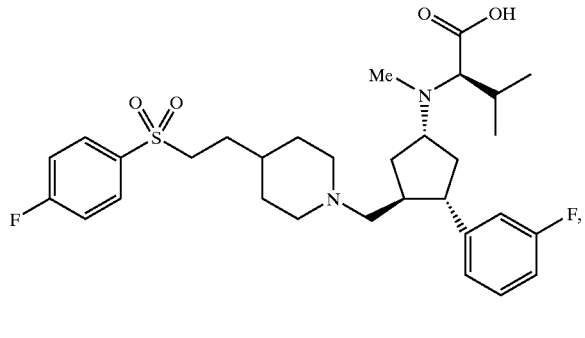
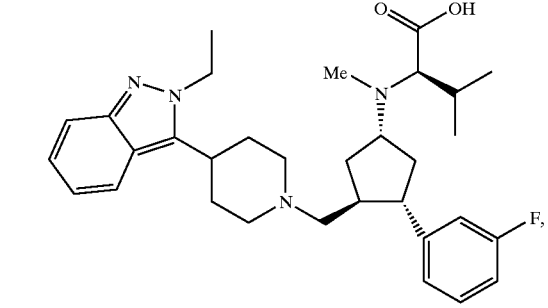
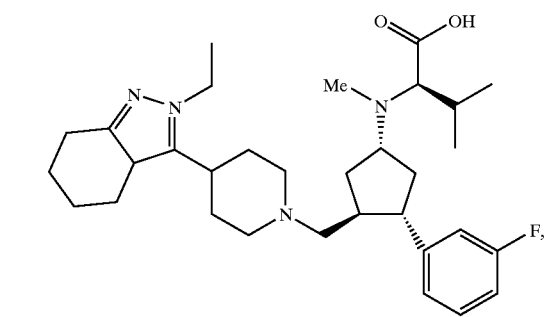

-continued

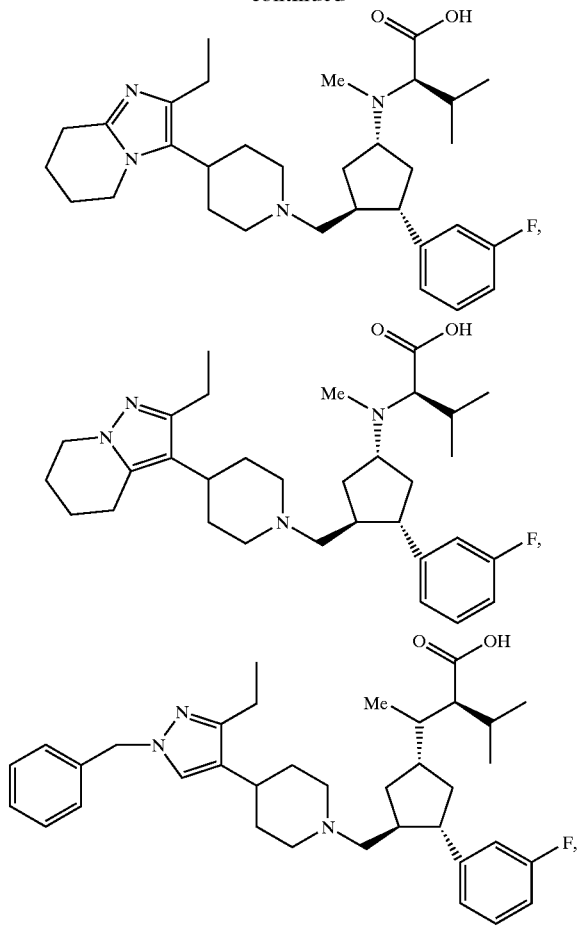

and pharmaceutically acceptable salts thereof and individual diastereomers thereof.

Another aspect of the present invention is

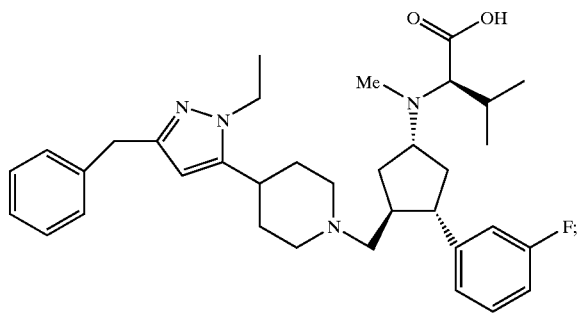

or a pharmaceutically acceptable salt thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR3.

The utility of the compounds in accordance with the present invention as modulators of chemokine receptor activity may be demonstrated by methodology known in the art, such as the assay for chemokine binding as disclosed by Van Riper, et al., *J. Exp. Med* 177 851–856 (1993) which may be readily adapted for measurement of CCR-5 binding, and the assay for CCR-3 binding as disclosed by Daugherty, et al., *J. Exp. Med.* 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |

| Drug Name | Manufacturer | Indication |
|---|---|---|
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (-)6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) | DuPont (SUSTIVA ®), Merck (STOCRIN ®) | HIV infection, AIDS, ARC |
| (-)6-Chloro-4(S)-cyclopropylethynyl-4(S)-trifluoro-methyl-1,4-dihydro-2H-3,1-benzoxazin-2-one, | | (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Rousell | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |

-continued

| Drug Name | Manufacturer | Indication |
|---|---|---|
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2 (R)-phenylmethyl-4-(S)-hydroxy-5-(1-(4-(2-benzo[b] furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

SCHEME 1

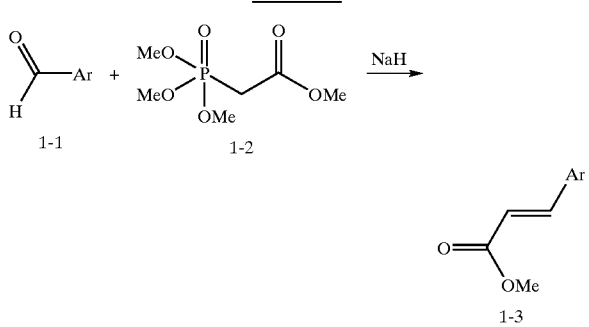

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

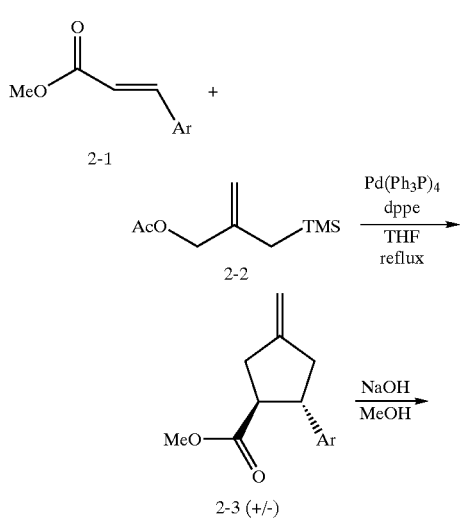

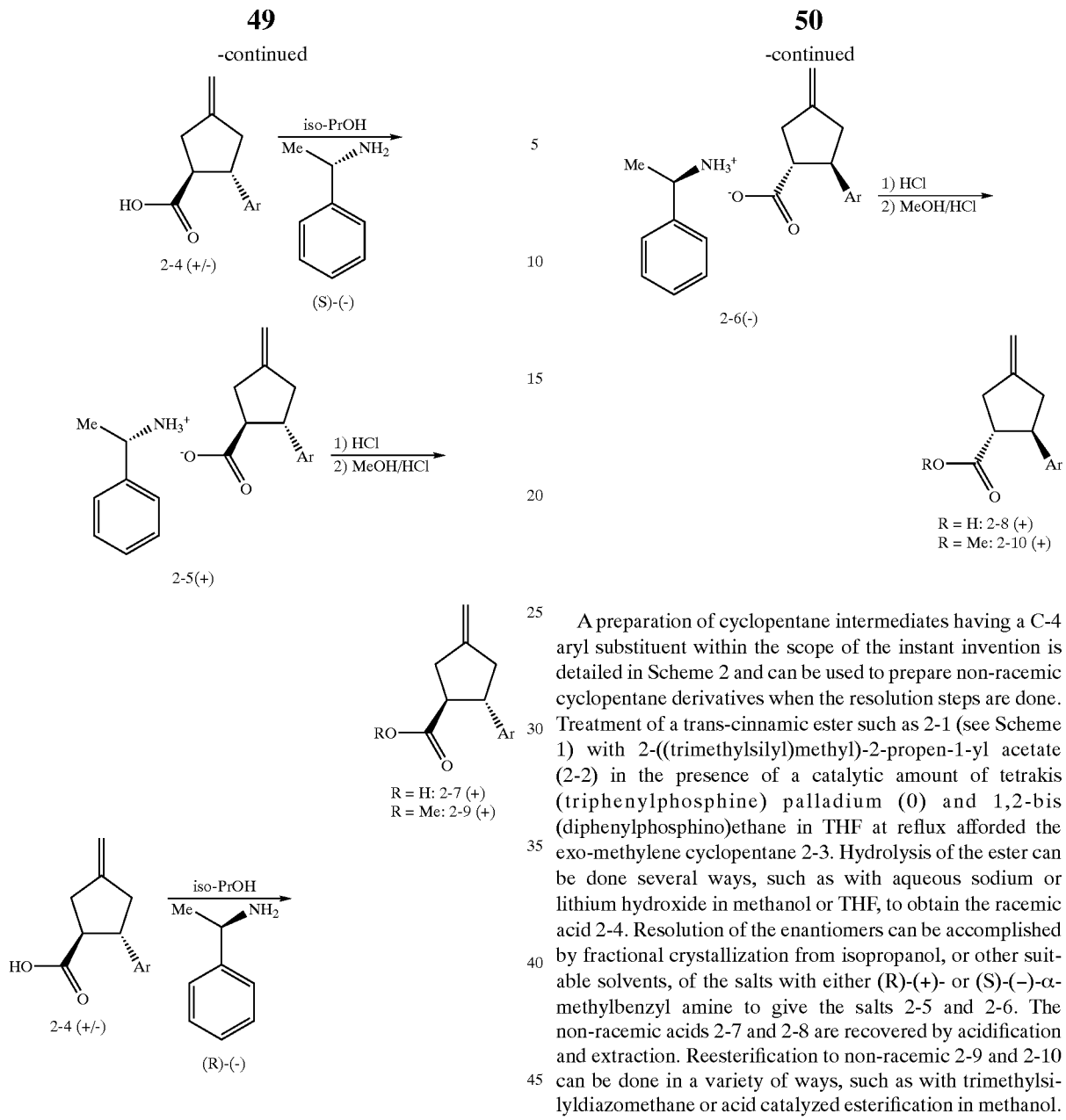

A preparation of cyclopentane intermediates having a C-4 aryl substituent within the scope of the instant invention is detailed in Scheme 2 and can be used to prepare non-racemic cyclopentane derivatives when the resolution steps are done. Treatment of a trans-cinnamic ester such as 2-1 (see Scheme 1) with 2-((trimethylsilyl)methyl)-2-propen-1-yl acetate (2-2) in the presence of a catalytic amount of tetrakis (triphenylphosphine) palladium (0) and 1,2-bis (diphenylphosphino)ethane in THF at reflux afforded the exo-methylene cyclopentane 2-3. Hydrolysis of the ester can be done several ways, such as with aqueous sodium or lithium hydroxide in methanol or THF, to obtain the racemic acid 2-4. Resolution of the enantiomers can be accomplished by fractional crystallization from isopropanol, or other suitable solvents, of the salts with either (R)-(+)- or (S)-(−)-α-methylbenzyl amine to give the salts 2-5 and 2-6. The non-racemic acids 2-7 and 2-8 are recovered by acidification and extraction. Reesterification to non-racemic 2-9 and 2-10 can be done in a variety of ways, such as with trimethylsilyldiazomethane or acid catalyzed esterification in methanol.

SCHEME 2A

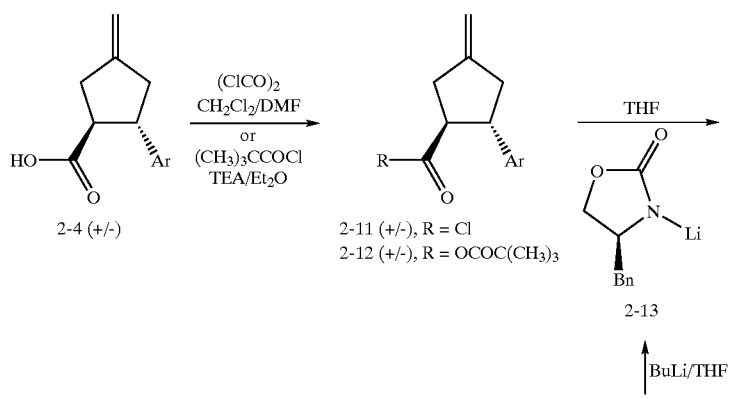

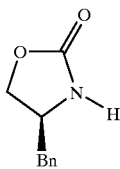

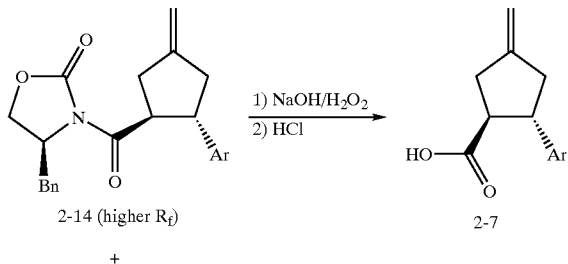

2-14 (higher R$_f$)

+

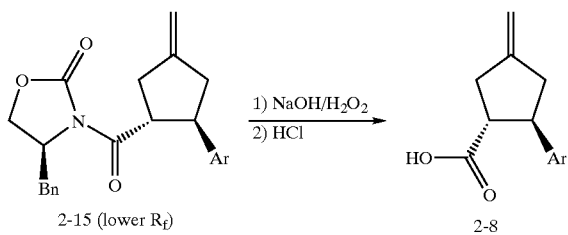

2-15 (lower R$_f$)

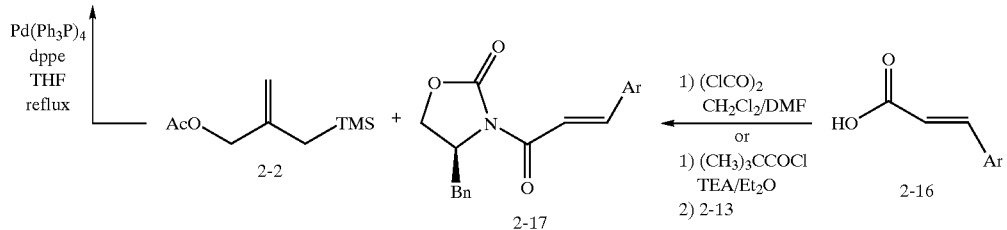

An alternative preparation of non-racemic cyclopentane intermediates having a C-4 aryl substituent within the scope of the instant invention is detailed in Scheme 2A. Conversion of the cyclopentane acid 2-4 to the acid chloride 2-11 under standard conditions, such as with oxalyl chloride in methylene chloride with a catalytic amount of DMF, or to the mixed anhydride 2-12, prepared in situ with trimethylacetyl chloride in ether with TEA as base, followed by reaction with the preformed lithium salt of (S)-(−)-4-benzyl-2-oxazolidinone 2-13, afforded the two non-racemic diastereomeric products 2-14 and 2-15, which are then separable by chromatography. Hydrolysis of each diastereomer under standard conditions, such as with lithium hydroxide and hydrogen peroxide or trimethylamine-N-oxide, affords the two non-racemic acids 2-7 and 2-8. Alternatively, in order to obtain an enhanced amount of the desired diastereomer 2-14 before separation, similar conversion of the starting trans-cinnamic acid 2-16 (Scheme 1) to the chiral trans-cinnamate 2-17 followed by the ring formation reaction with 2-((trimethylsilyl)methyl)-2-propen-1-yl acetate (2-2) as detailed in Scheme 2 affords a 60:40 product mixture of 2-14:2-15.

SCHEME 3

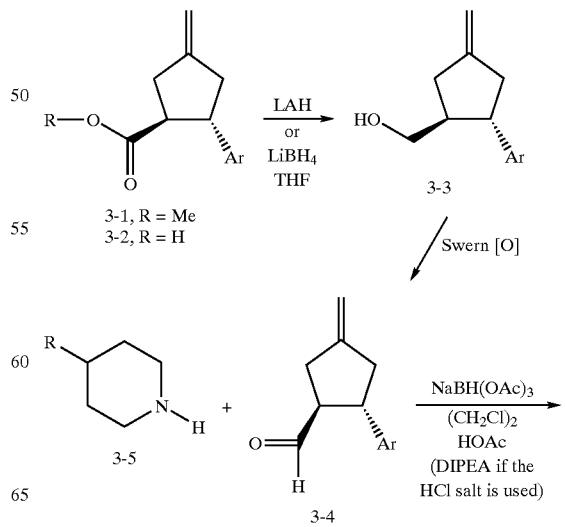

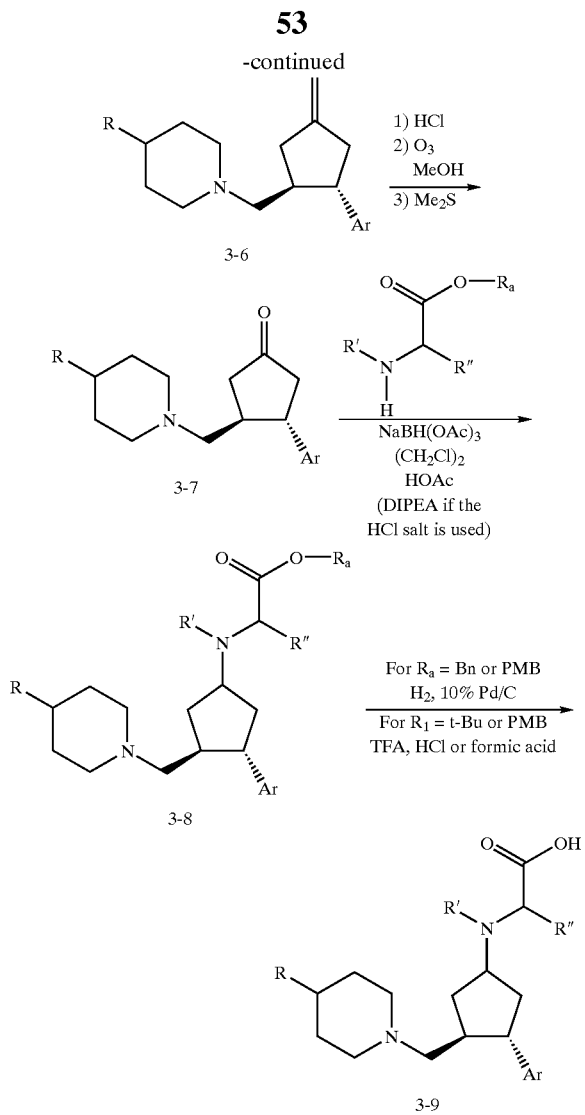

chloride, 1,2-dichloroethane, THF, acetonitrile or methanol, with 3-4 then provides a 3-((4-substitutedpiperidin-1-yl)methyl)cyclopentane derivative 3-6. In the cases where the R group of the piperidine is stable to ozone, ozonolysis of the exo-methylene followed by a reductive work-up with dimethyl sulfide affords the ketone 3-7. Alternatively, 3-7 can be obtained from 3-6 through a stepwise oxidation using catalytic osmium tetroxide in the presence of N-methylmorpholine-N-oxide followed by sodium periodate cleavage of the intermediate diol. A second reductive alkylation of a D- and/or L-amino-acid ester, such as the methyl, ethyl, t-butyl, benzyl or 4-methoxybenzyl ester of glycine (R"=H), alanine (R"=Me), valine (R"=iso-Pr), leucine (R"=iso-Bu), isoleucine (R'=sec-Bu), cyclopropylalanine (R"=CH$_2$cycPr), cyclobutylalanine (R"=CH$_2$cycBu), cyclohexylglycine (R"=cycHex) or a N-alkyl amino-acid, such as N-methyl glycine (R'=Me), or a cyclic amino-acid, such as proline (R'R"=—(CH$_2$)$_3$—), with 3-7 as described above with sodium triacetoxyborohydride or sodium cyanoborohydride affords 3-8. Final deprotection of the ester under conditions to which the R group is stable, such as HCl in ether, TFA or formic acid for t-butyl and 4-methoxybenzyl esters, hydrogenation for benzyl esters or standard hydrolysis for alkyl or benzyl esters, affords the final product(s) 3-9 which are within the scope of the instant invention and which can be chemokine receptor modulators. The two individual C-1 isomers (four diastereomers when either the cyclopentyl scaffold or the amino-acid are racemic) can be separated by flash chromatography, Prep TLC or HPLC methods as either the penultimate esters 3-8 and/or the final compounds 3-9.

SCHEME 4

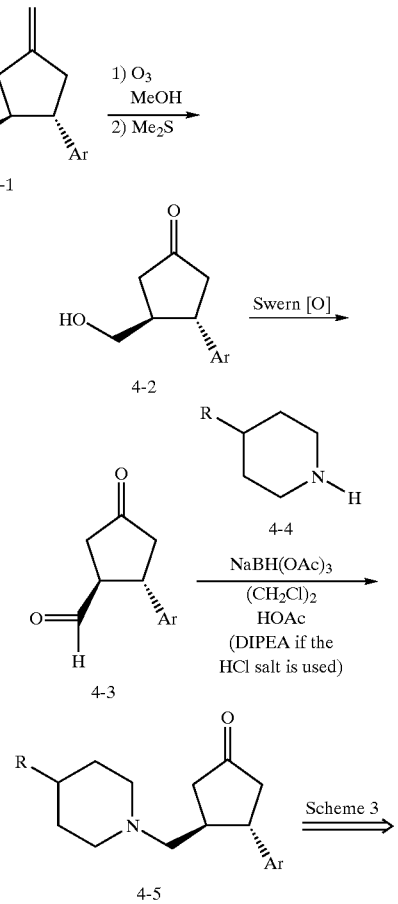

Preparation of some 1,3,4-trisubstituted cyclopentanes within the scope of the instant invention is given in Scheme 3. Reduction of ester 3-1 (either racemic or non-racemic) (Scheme 2), for example, with lithium borohydride, diisobutylaluminum hydride, lithium aluminium hydride, or sodium bis(2-methoxyethoxy)aluminum hydride in a suitable solvent, such as ether or THF, provides the primary alcohol 3-3. Alternatively, reduction of the acid 3-2 (either racemic or non-racemic) (Scheme 2 or 2A), for example with lithium aluminium hydride in THF, will also afford the alcohol 3-3. In cases where the Ar moiety is not amenable to salt resolution as detailed in Scheme 2, an alternative resolution can often be achieved using chiral HPLC methods to separate the enantiomers of 3-3. Oxidation of 3-3 to the aldehyde 3-4 can be carried out under numerous conditions, such as with DMSO and oxalyl chloride at low temperature, followed by triethylamine (Swern oxidation), with the Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Reductive alkylation of a cyclic amine, such as piperidine 3-5 (see Schemes 12 to 29), using for example sodium triacetoxyborohydride or sodium cyanoborohydride in a suitable solvent such as methylene

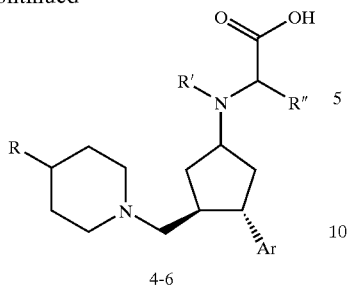

4-6

An alternative route for the preparation of some 1,3,4-tri substituted cyclopentanes within the scope of the instant invention is given in Scheme 4. In the cases where the R group of the piperidine in Scheme 3 is not stable to ozone or the osmium tetroxide/sodium periodate sequence, oxidation of the exo-methylene can be done prior to the reductive alkylation of the piperidine. Thus, ozonolysis of the alcohol 4-1 (Scheme 3) followed by a reductive work-up with dimethyl sulfide affords the ketone-alcohol 4-2. Oxidation to the ketone-aldehyde 4-3 can be done as described for Scheme 3 with N-methylmorpholine/TPAP or under Swern conditions. Selective reductive alkylation of the 4-substituted piperidine 4-4 (see Schemes 12 to 29) with the aldehyde of 4-3, using for example sodium triacetoxyborohydride or sodium cyanoborohydride in a suitable solvent such as methylene chloride, 1,2-dichloroethane, THF, acetonitrile or methanol, then provides the 3-((4-substitutedpiperidin-1-yl)methyl)cyclopentane derivative 4-5 (same as 3-7). This can then be converted to the final product(s) 4-6 as described in Scheme 3.

SCHEME 5

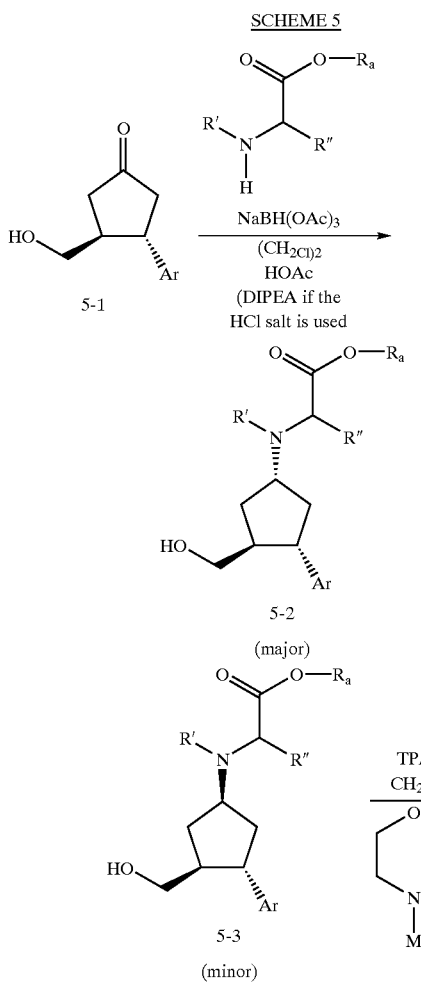

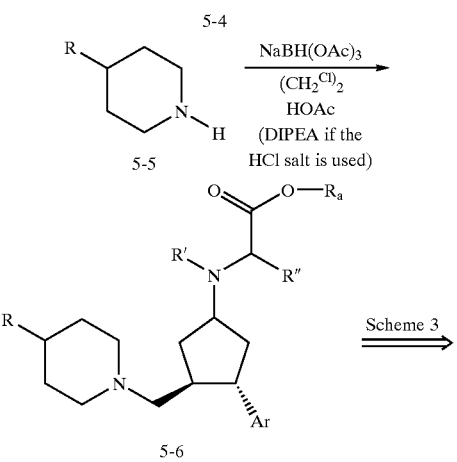

An alternative route for the preparation of some 1,3,4-trisubstituted cyclopentanes within the scope of the instant invention is given in Scheme 5. Reductive alkylation with ketone alcohol 5-1 (Scheme 4) of a variety of amino-acid esters (See Scheme 3) affords the alcohols 5-2 and 5-3, of which 5-2 is the major product (lower $R_f$ when R" is (S), higher $R_f$ when R" is (R)) and 5-3 is the minor product (higher $R_f$ when R" is (S), lower $R_f$ when R" is (R)). Separation of the individual diastereomers (2 when both reactants are non-racemic, 4 when only one is non-racemic) can be done at this intermediate or at a later step. Oxidation of 5-2 and/or 5-3 to the aldehyde(s) 5-4 can be done as described in Scheme 3, preferably now with N-methylmorpholine/TPAP due to the presence of the secondary N—H. Reductive alkylation of a 4-substitutedpiperidine 5-5 (see Schemes 12 to 29) with the aldehyde of 5-4, using for example sodium triacetoxyborohydride or sodium cyanoborohydride in a suitable solvent such as methylene chloride, 1,2-dichloroethane, THF, acetonitrile or methanol, then provides the 3-((4-substitutedpiperidin-1-yl)methyl)cyclopentane derivative 5-6. The intermediate ester(s) 5-6 can then be converted to the final product(s) 5-7 as described in Scheme 3.

SCHEME 5A

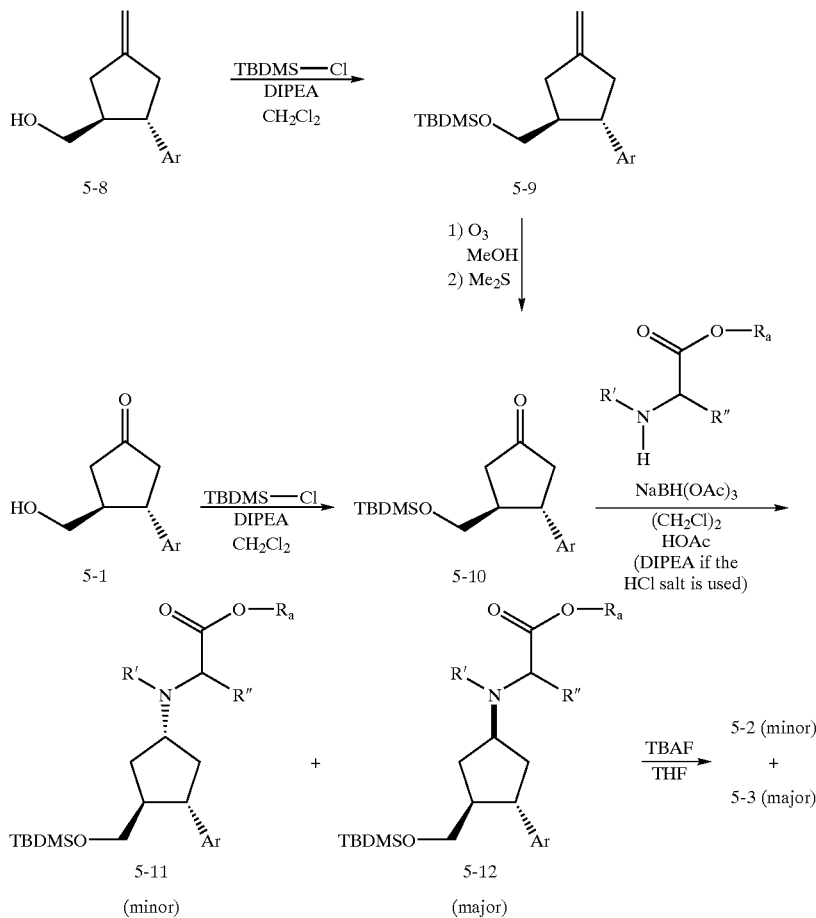

An alternative preparation of the intermediates 5-2 and 5-3 in Scheme which reverses the C-1 isomeric selectivity is shown in Scheme 5A. Silylation of the alcohol moiety of 5-1 (Scheme 4) gives the silyl ether 5-10. Alternatively, silylation of the alcohol 5-8 (Scheme 3) gives 5-9 which on ozonolysis can also afford the silyl ether 5-10. Reductive alkylation of the aforementioned amino-acid esters now using the silyl ether 5-10 affords the products 5-11 and 5-12 in an essentially opposite ratio as is obtained in Scheme 5 for 5-2 and 5-3. TBAF desilylation then affords primarily 5-3. Thus, the preferred C-1 orientation can be selected for depending on the requirements of the desired final compounds.

SCHEME 5B

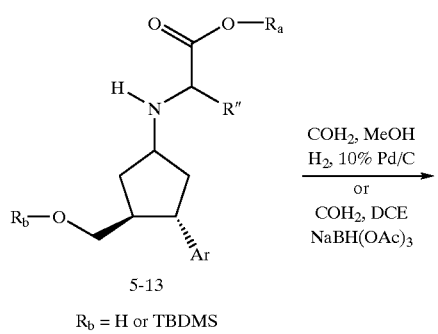

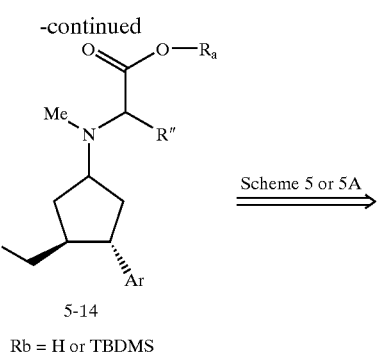

An alternative preparation of the intermediates 5-2 or 5-3 in Scheme 5 and intermediates 5-11 and 5-12 in Scheme 5A when R' is Me is shown in Scheme 5B. When 5-13 is formed in the reductive amination with ketones 5-1 ($R_b$=H) or 5-10 ($R_b$=TBDMS), a second reductive amination of 5-13 with formaldehyde, either in the presence of hydrogen and a suitable catalyst, such as 10% Pd/C or Pearlman's catalyst, in methanol or standard reaction with sodium triacetoxyborohydride in 1,2-dichloroehthane, affords the methylated intermediates 5-14. These intermediates can be further elaborated to the final products as described in Scheme 5 and/or 5A.

SCHEME 6
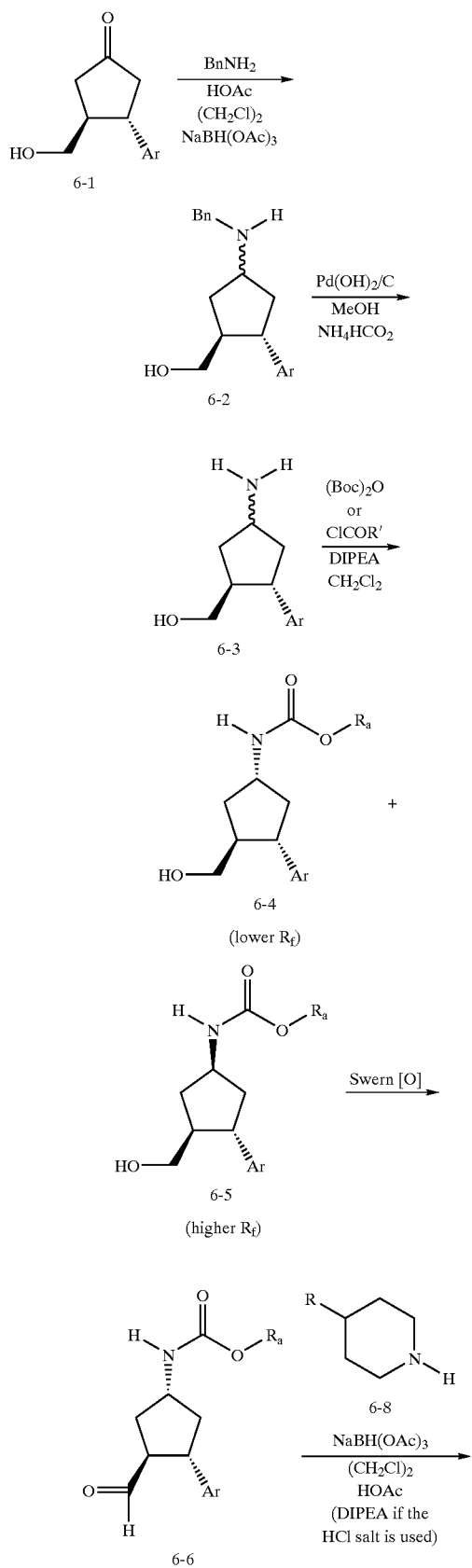
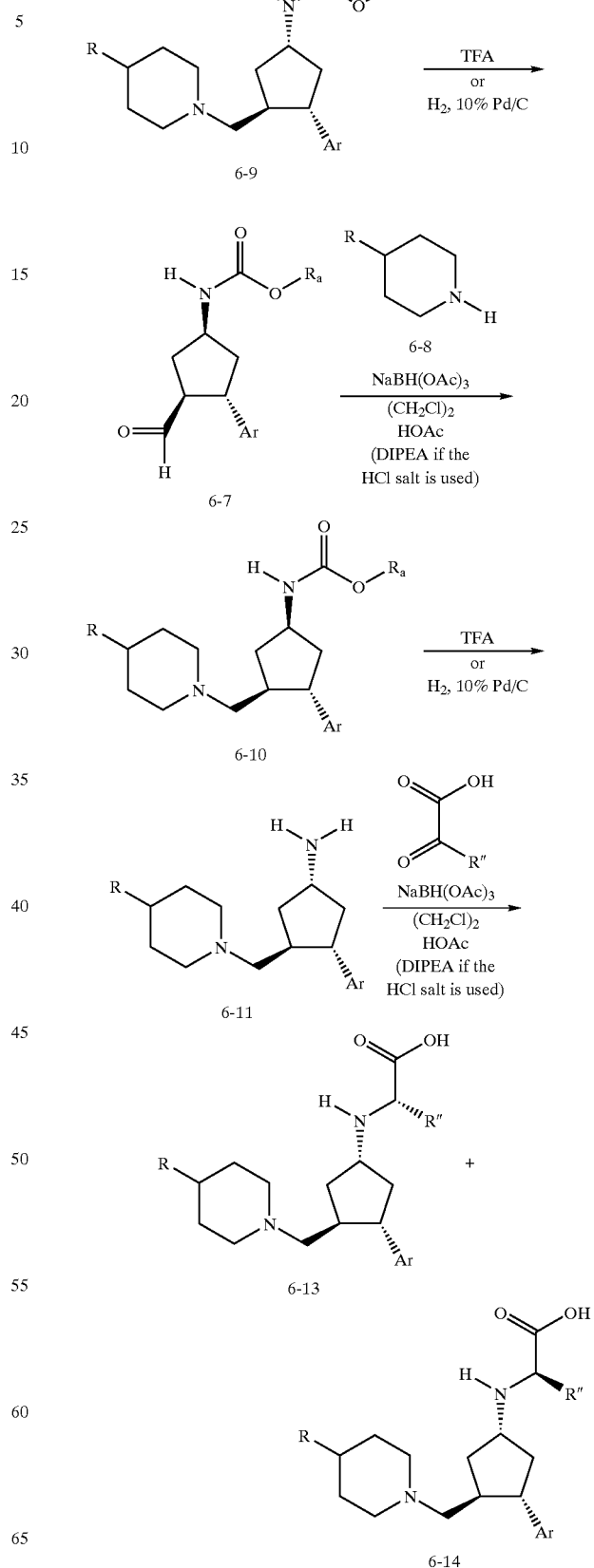

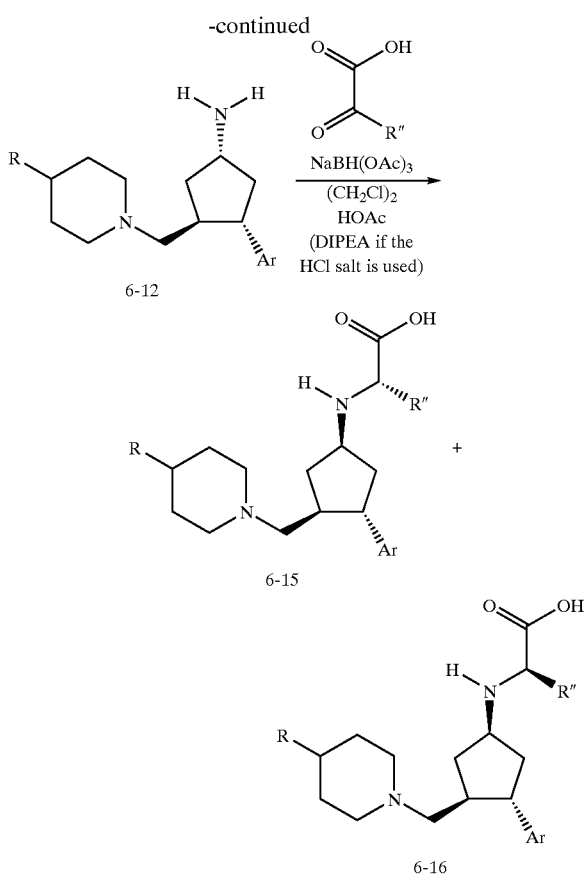

An alternative route for the preparation of some 1,3,4-trisubstituted cyclopentanes within the scope of the instant invention is given in Scheme 6. Reductive alkylation of benzylamine with ketone-alcohol 6-1 (Scheme 4, either racemic or non-racemic), using for example sodium triacetoxyborohydride or sodium cyanoborohydride, gives 6-2 which can be hydrogenated under standard conditions in methanol in the presence of a palladium catalyst, for example Pd/C or Pearlman's catalyst and using either hydrogen under pressure or ammonium formate at reflux, to afford the primary amine 6-3. Reaction of the amine with CBZ chloride or Boc anhydride gives the amine protected carbamates 6-4 and 6-5 as a mixture of C-1 isomers which can be separated. Oxidation to the aldehydes 6-6 and 6-7 is carried out under Swern conditions or with N-methylmorpholine/TPAP. The relative stereochemistry of the C-1 to the C-3 and C-4 substituents was determined by NMR Noe experiments on either the alcohols 6-4 and 6-5 or the aldehydes 6-6 and 6-7. Reductive alkylation of a 4-substitutedpiperidine 6-8 with the individual aldehydes 6-6 and 6-7, using for example sodium triacetoxyborohydride or sodium cyanoborohydride in a suitable solvent such as methylene chloride, 1,2-dichloroethane, THF, acetonitrile or methanol, then provides each of the C-1 amino-protected isomeric 3-((4-substituted piperidin-1-yl)methyl)cyclopentane derivatives 6-9 and 6-10. Deprotection of the C-1 amino with either TFA (for $R_a$=t-butyl) or standard hydrogenation (for $R_a$=Bn) depending on the stability of the piperidine R group affords the amines 6-11 and 6-12. These amines can then be individually reductively alkylated as above with 2-oxo-acetic acids, such as 2-oxovaleric (R"=n-Pr), 4-methyl-2-oxovaleric (R"=iso-Bu), 2-oxophenylacetic (R"=Ph), to afford the final compounds 6-13 and 6-14 and 6-15 and 6-16 as mixtures of the R" isomers. In the case of R"=iso-Bu and non-racemic cyclopentyl scaffold, comparison of the HPLC of these products with those obtained in Scheme 5 allowed the stereochemical assignments of all the final products and intermediates.

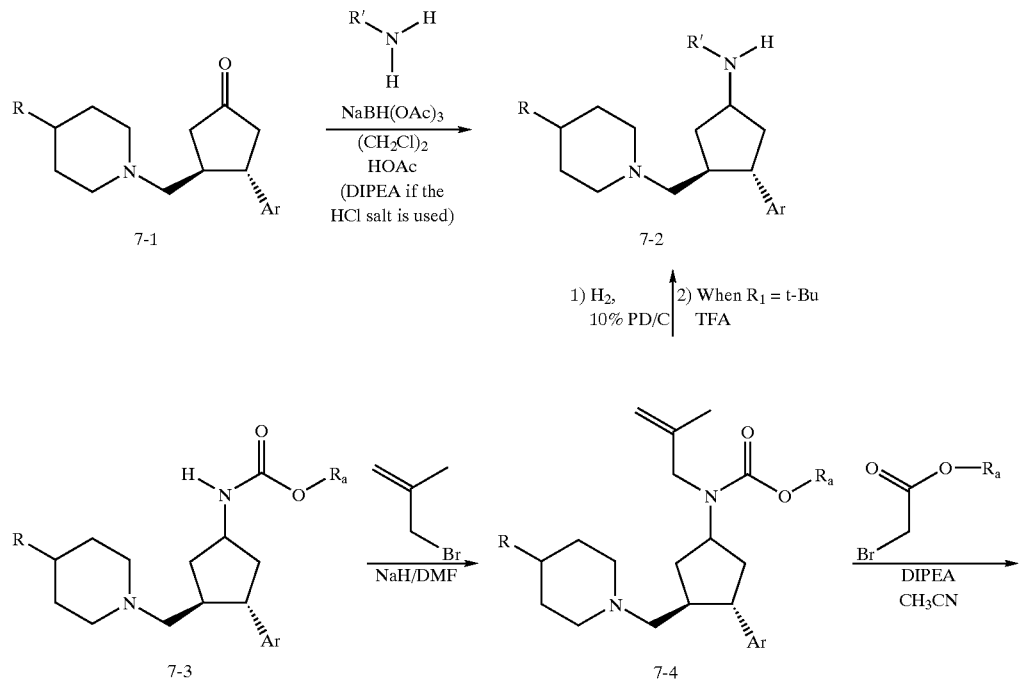

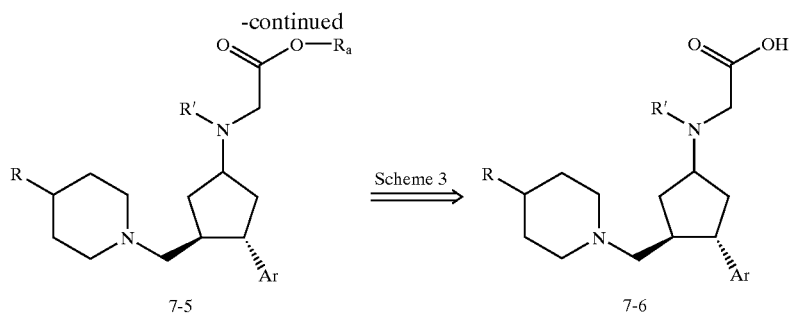

An alternative route for the preparation of some 1,3,4-trisubstituted cyclopentanes within the scope of the instant invention is given in Scheme 7. Reductive alkylation, using for example sodium triacetoxyborohydride or sodium cyanoborohydride, of an alkyl amine with the ketone 7-1 (Schemes 3 or 4) gives 7-2 as a mixture of C-1 isomers which may be separated. Alternatively, carbamate 7-3 (see Scheme 6) can be alkylated with an alkyl or allyl halide, such as 1-bromo-2-methylprop-2-ene, and a strong base, such as sodium hydride in DMF, followed by hydrogenation under standard conditions to reduce the allyl. When $R_a$ is Bn, removal the CBZ can occur simultaneously to give the same amine intermediate 7-2. When $R_a$ is t-butyl, a subsequent reaction with TFA is required to give 7-2. Alkylation of the amine with t-butyl or benzyl bromoacetate affords 7-5 which can be converted to the desired final compound(s) 7-6 as described in Scheme 3.

SCHEME 8

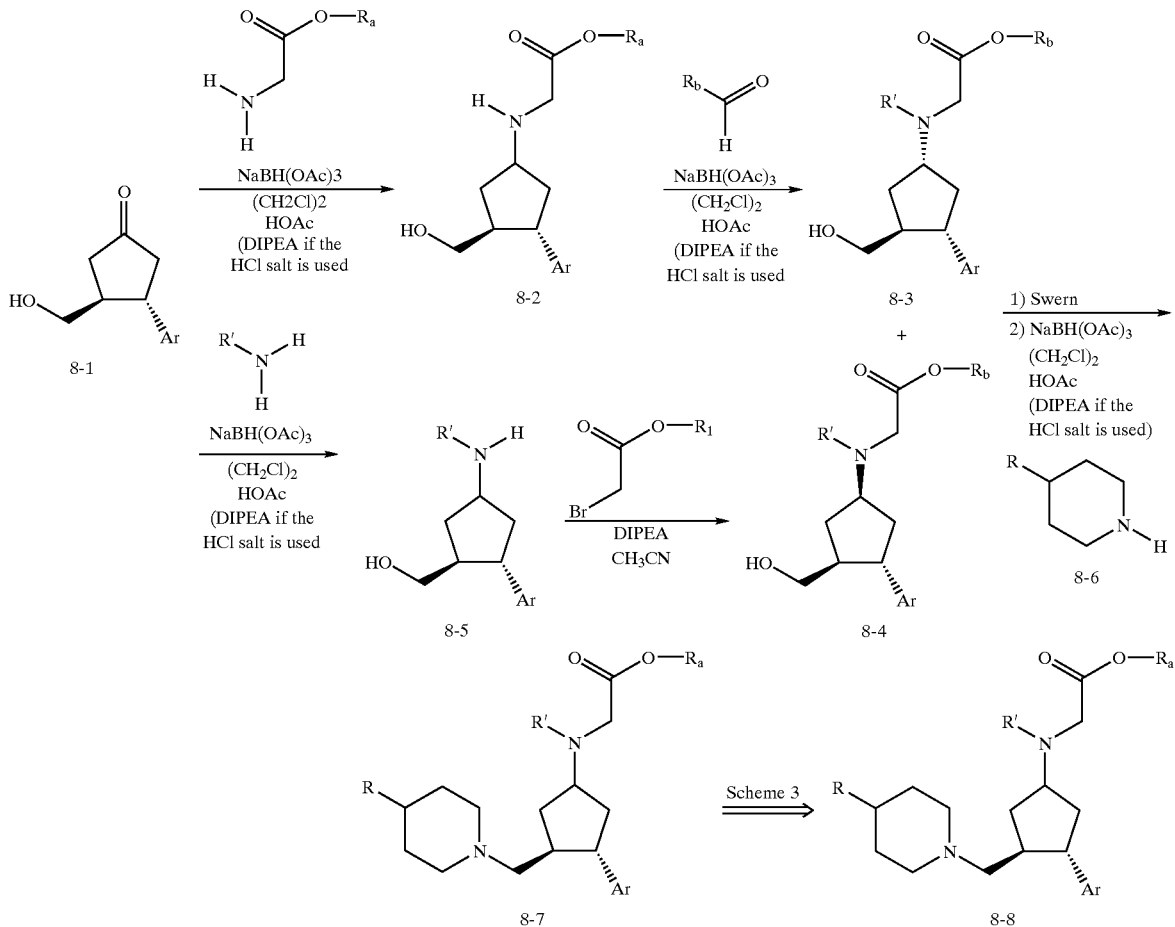

An alternative route for the preparation of some 1,3,4-trisubstituted cyclopentanes within the scope of the instant invention is given in Scheme 8. Reductive alkylation, using for example sodium triacetoxyborohydride or sodium cyanoborohydride, of glycine t-butyl, benzyl or PMB ester with the ketone-alcohol 8-1 (Scheme 4) gives 8-2 as a mixture of C-1 isomers. A second reductive alkylation with a ketone or aldehyde affords the N-alkyl glycine derivatives 8-3 and 8-4 which can be separated chromatographically either before and/or after the second alkylation. Also, the order of the steps can be reversed such that reductive alkylation of an amine with 8-1 first to give 8-5, followed by alkylation with an alkyl or benzyl bromoacetate as in Scheme 7, affords 8-3 and 8-4. These reactions generally give 8-3 as the predominate product. Individual oxidation of the alcohols 8-3 and 8-4 can be done either under Swern conditions or using the N-methylmorpholine/TPAP method to give the aldehyde intermediate(s) followed by a second or third reductive alkylation of a 4-substitutedpiperidine 8-6, using for example sodium triacetoxyborohydride or sodium cyanoborohydride in a suitable solvent such as methylene chloride, 1,2-dichloroethane, THF, acetonitrile or methanol, which then provides the 3-((4-substitutedpiperidin-1-yl)methyl)cyclopentane derivative 8-7. This intermediate can then be converted to the final product(s) 8-8 as described in Scheme 3.

An alternative preparation of the intermediates 8-3 and 84 in Scheme 8 which again reverses the C-1 isomeric selectivity is shown in Scheme 8A. Silylation of the alcohol moiety of 8-1 (Scheme 4) gives the silyl ether 8-9. Alternatively, silylation of the alcohol 8-10 (Scheme 3)

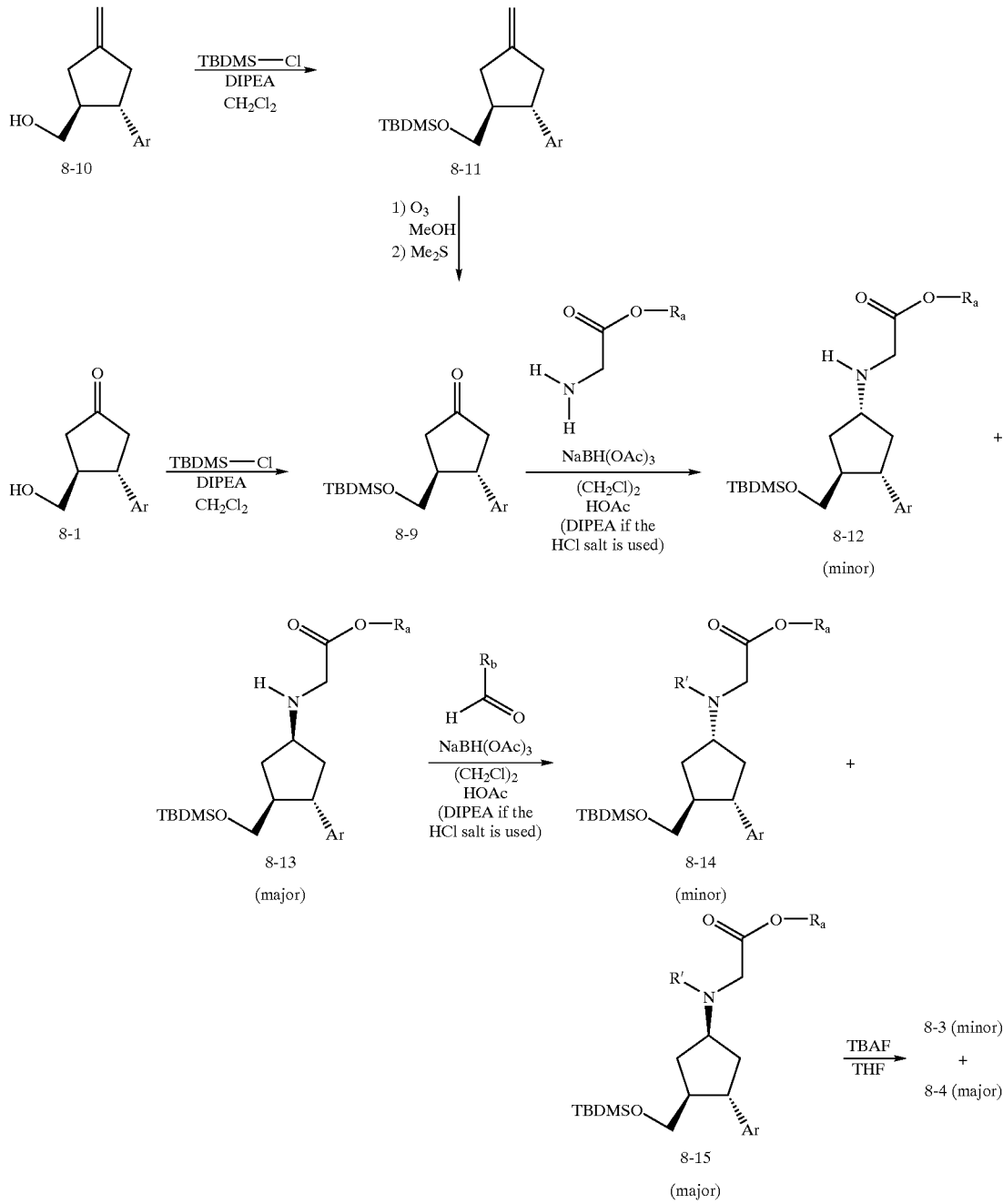

SCHEME 8A gives 8-11, which on ozonolysis can also afford the silyl ether 8-9. Reductive alkylation now using the silyl ether 8-9 gives 8-12 and 8-13 followed by the second reductive alkylation with an aldehyde or ketone affords the products 8-14 and 8-15 in an essentially opposite ratio as is obtained in Scheme 8 for 8-3 and 8-4. TBAF desilylation then affords primarily 8-4. Separation of the C-1 isomers can usually be achieved at one or more of the intermediate steps. Thus, the preferred C-1 orientation can be selected for depending on the requirements of the desired final compounds.

SCHEME 9

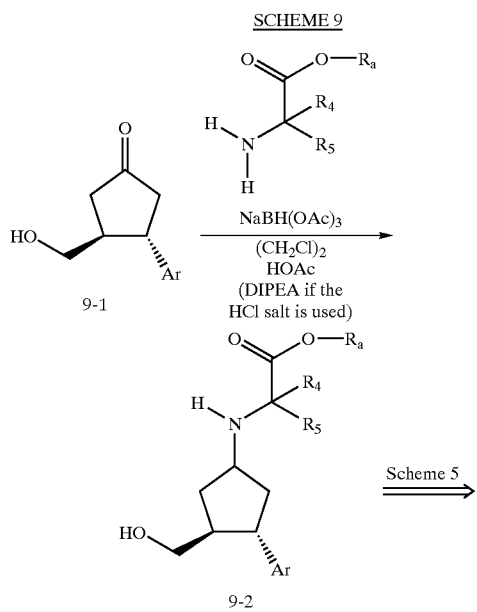

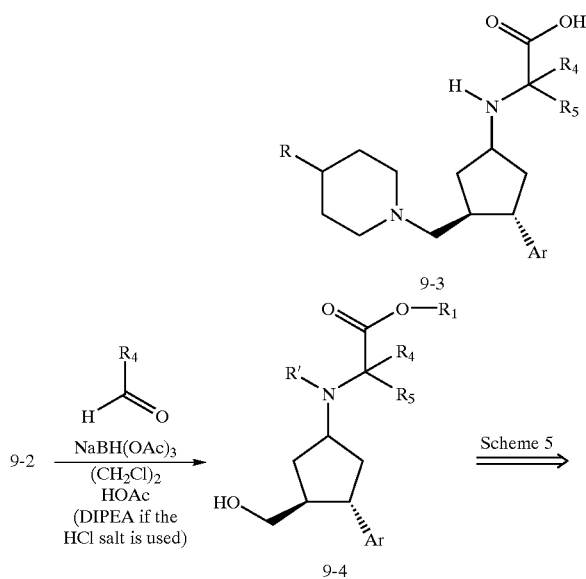

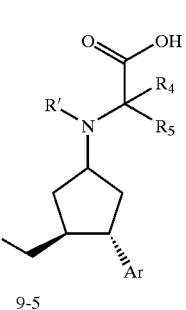

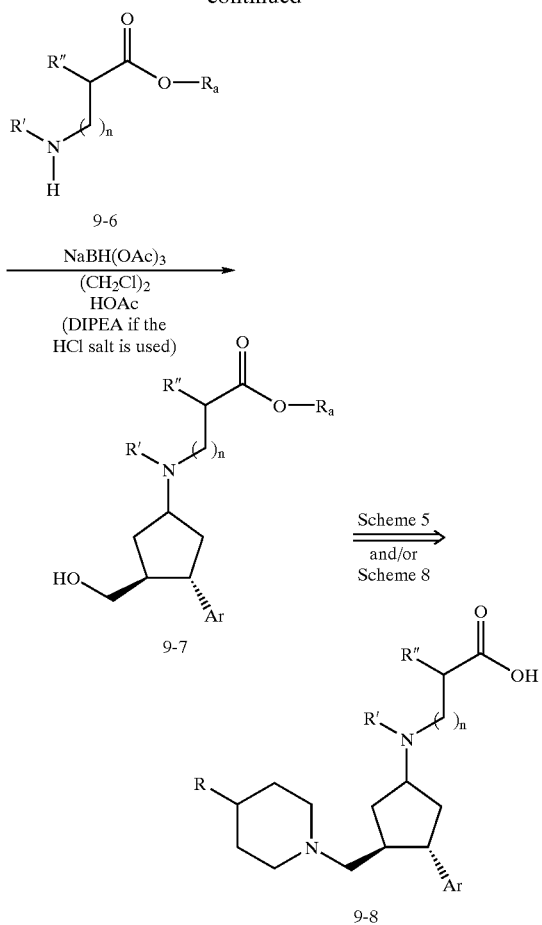

Several other alternative routes for the preparation of some 1,3,4-trisubstituted cyclopentanes within the scope of the instant invention are given in Scheme 9. Reductive alkylation, using for example sodium triacetoxyborohydride or sodium cyanoborohydride, of an amino-acid ester having dialkyl substitution with the ketone-alcohol 9-1 (Scheme 4) gives 9-2 as a mixture of C-1 isomers which may be separated and carried on to the final product(s) 9-3 individually or as a mixture as detailed in Scheme 5. Alternatively, a second reductive alkylation of 9-2 as in Scheme 8 affords 9-4 which may be separable or used as a mixture to give final product(s) 9-5. Also, more extended amino-acid esters, such as β-alanine ester (9-6, n=1) or 4-aminobutyrate (9-6, n=2), which may also be substituted on the chain or on N, can be employed to give 9-7. These intermediates can then be converted to final product(s) 9-8 as described in Scheme 5 and/or 8.

SCHEME 10

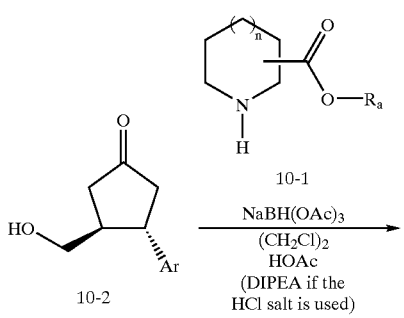

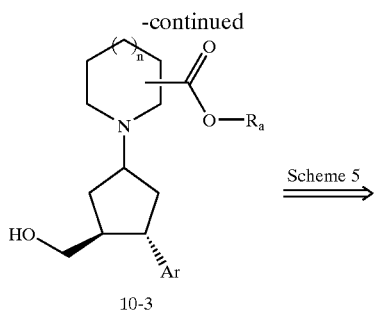

10-3

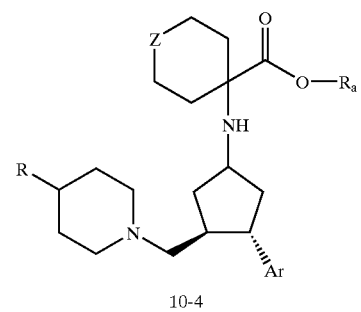

10-4

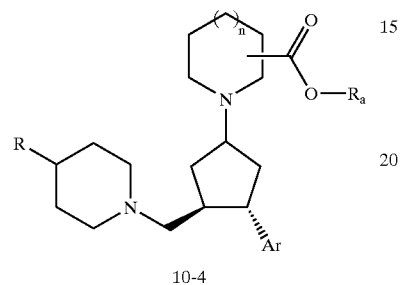

10-4

An alternative route for the preparation of some 1,3,4-trisubstituted cyclopentanes within the scope of the instant invention is given in Scheme 10. Reductive alkylation, using for example sodium triacetoxyborohydride or sodium cyanoborohydride, of a cyclic secondary amino-acid 10-1, such as D- or L-proline t-butyl ester (n=0), β-proline t-butyl ester (n=0), 2-, 3-, and 4-t-butylcarboxypiperidine (n=1), with the ketone-alcohol 10-2 (Scheme 4) gives 10-3 and 10-4 as a mixture of C-1 isomers which may be separated. These intermediates can then be converted to the final product(s) as described in Scheme 5.

An alternative route for the preparation of some 1,3,4-trisubstituted cyclopentanes within the scope of the instant invention is given in Scheme 11. Reductive alkylation, using for example sodium triacetoxyborohydride or sodium cyanoborohydride, of a cycloalkyl amino-acid 11-1, such as 1-aminocyclopentane carboxylic acid t-butyl ester (Z=single bond) or a heterocyclic amino-acid, such as 4-aminomorpholin-2-yl carboxylic acid t-butyl ester (Z=O) with the ketone-alcohol 11-2 (Scheme 4) gives 11-3 and 11-4 as a mixture of C-1 isomers which may be separated. These intermediates can then be converted to the final product(s) as described in Scheme 5.

SCHEME 11

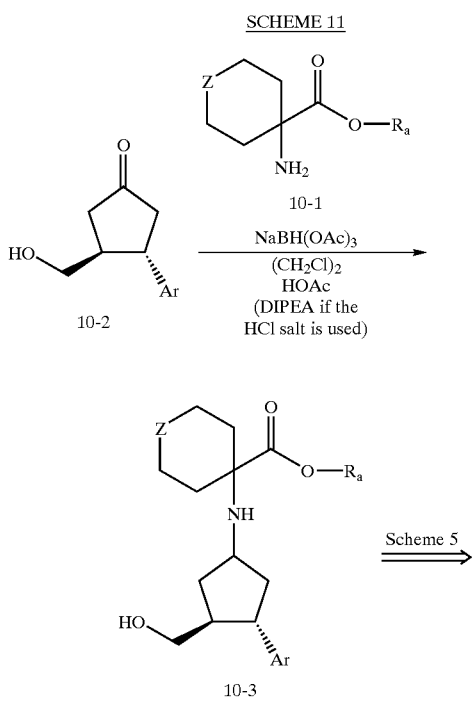

SCHEME 12

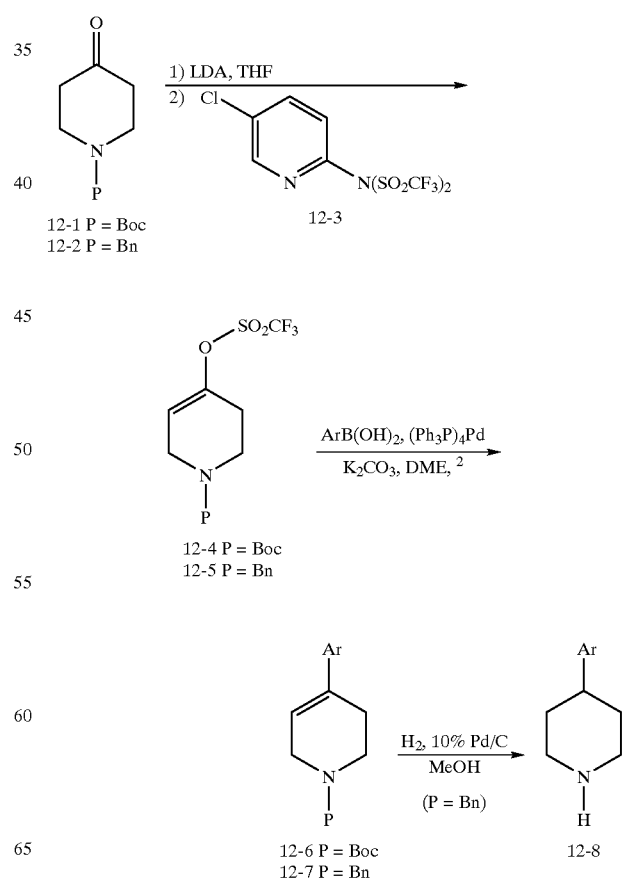

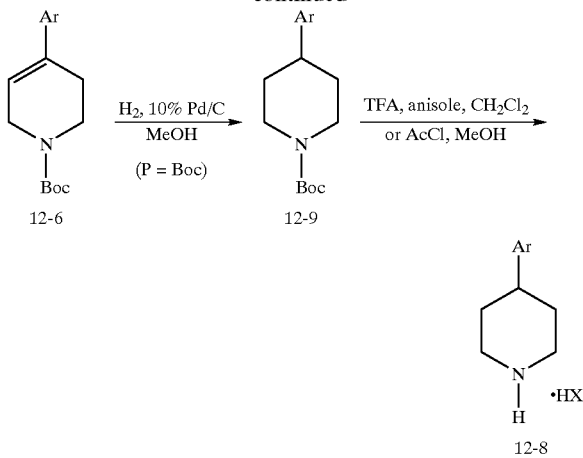

One method of generating 4-aryl piperidines as intermediates is given in Scheme 12. Reaction of commercially available 12-1 or 12-2 with a strong base, such as LDA, LHDMS, NaHMDS, KHMDS, or NaH followed by treating with a suitable triflating agent, such as 5-chloropyrid-2-yl triflimide (12-3), N-phenyl triflimide or triflic anhydride, provides enol triflates 12-4 or 12-5. Heating with commercially available aryl boronic acids in the presence of a suitable palladium(0) catalyst such as tetrakis triphenylphosphine palladium, a base (such as potassium carbonate or sodium carbonate), in a solvent such as DME, THF, dioxane or toluene/ethanol, effects coupling to provide the unsaturated products 12-6 or 12-7. In the case of 12-7, treatment with a heterogeneous palladium catalyst in methanol or ethanol in an atmosphere of hydrogen provides the desired intermediate 12-8. Alternatively, the Boc protected derivative 12-6 is hydrogenated under standard conditions to provided the saturated piperidine 12-9, which is then deprotected under acidic conditions (such as trifluoroacetic acid and anisole in methylene chloride or HCl in methanol), to provide 12-8 as a salt, which is then utilized as the cyclic secondary amine component as shown above in Schemes 3, 4, 5, 6, 8, 9, 10 and 11.

SCHEME 13

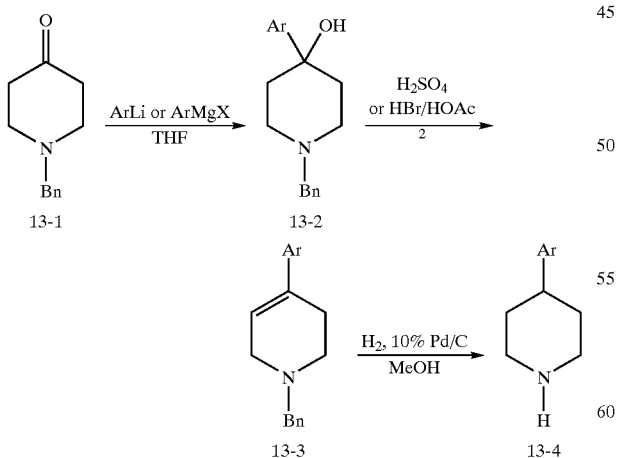

An alternative method of generating 4-aryl piperidines as intermediates is given in Scheme 13. Reaction of commercially available 13-1 with an aryl magnesium halide or with an aryllithium (in the presence or absence of anhydrous cerium trichloride) provides tertiary alcohol 13-2, which upon treatment under acidic conditions (such as sulfuric acid, HBr in acetic acid, HCl in acetic acid) or under dehydrating conditions (such as with thionyl chloride in pyridine or with phosphorus oxychloride) provides olefin 13-3. Hydrogenation under standard conditions using either hydrogen gas or a hydrogen donor (such as ammonium formate or cyclohexene) effects reduction of the double bond and cleavage of the N-benzyl group to provide the desired intermediate 13-4. Under some circumstances it may be preferable to reduce the double bond under non-hydrogenolytic conditions, for example with triethylsilane and trifluoroacetic acid or under dissolving metal conditions (for example, sodium or lithium metal in ammonia or a lower alkyl amine). If the N-benzyl group is not removed under these conditions, it may be cleaved by treatment with either vinyl chloroformate and then hydrogen chloride or by treatment with 2-chloroethyl chloroformate followed by heating in methanol. The product 13-4 is then utilized as the cyclic secondary amine component as shown above in Schemes 3, 4, 5, 6, 8, 9, 10 and 11.

SCHEME 14

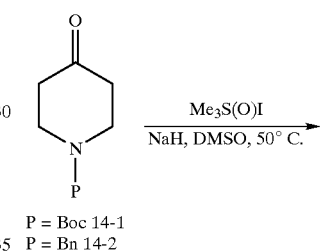

P = Boc 14-1
P = Bn 14-2

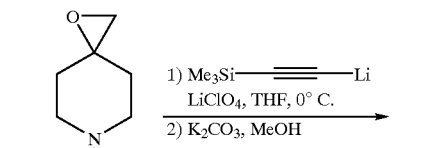

P = Boc 14-3
P = Bn 14-4

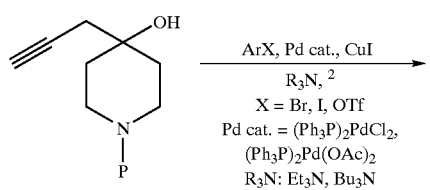

P = Boc 14-5
P = Bn 14-6

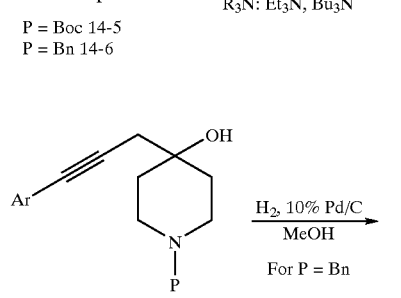

P = Boc 14-7
P = Bn 14-8

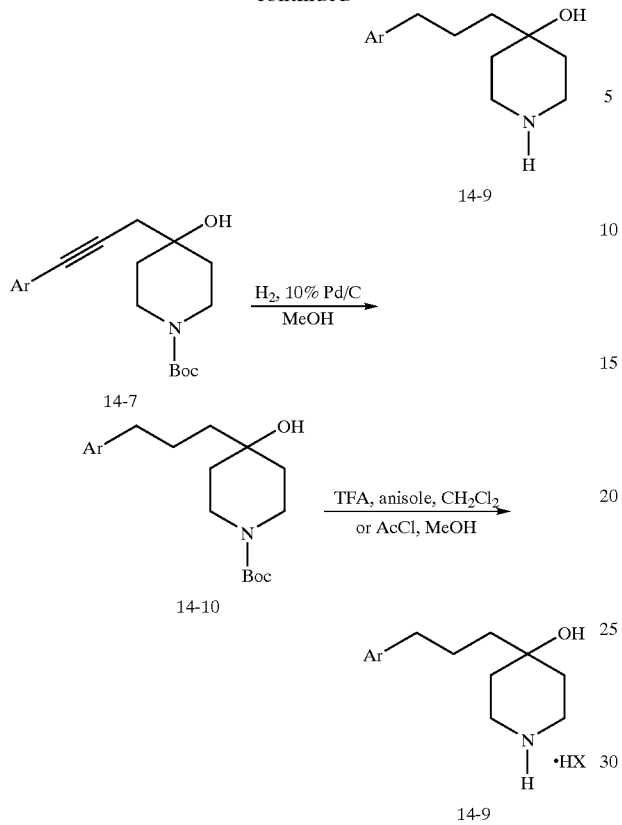

SCHEME 15

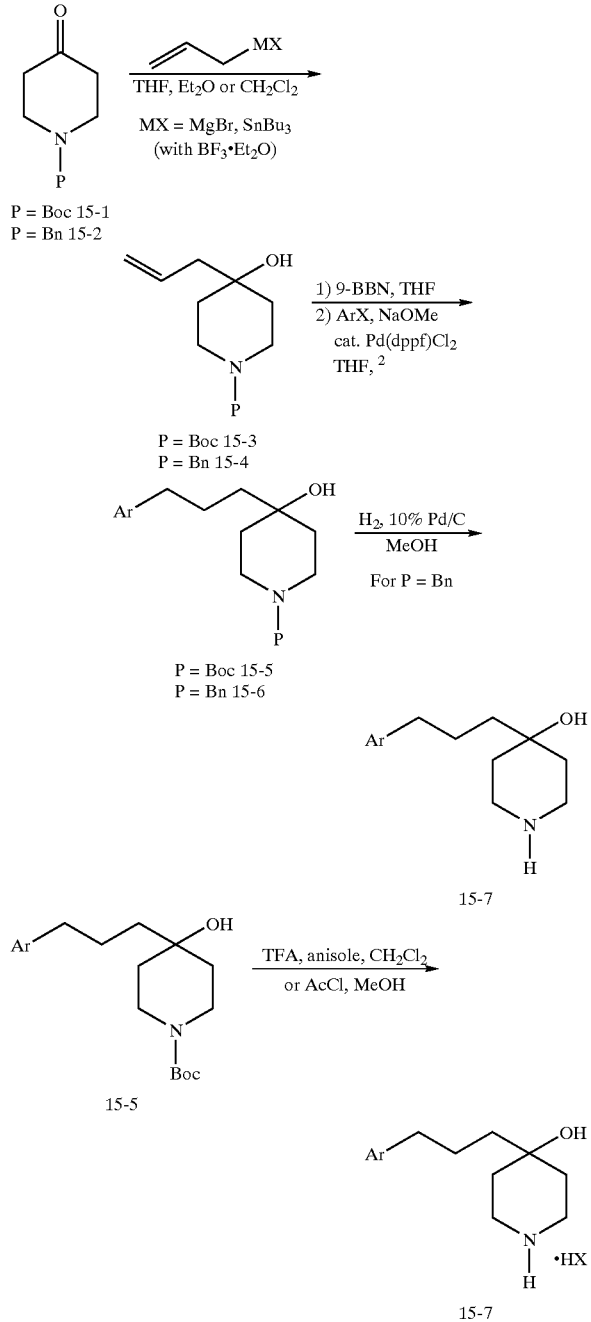

One route for the preparation of 4-hydroxy-4-(3-arylpropyl)piperidines is given in Scheme 14. Treatment of commercially available 4-piperidones 14-1 or 14-2 with trimethylsulfonium iodide and sodium hydride in dimethyl sulfoxide at or above room temperature provides Spiro epoxides 14-3 or 14-4. Addition of the lithium salt of trimethylsilylacetylene to these epoxides in the presence of lithium perchlorate in THF at 0 degrees C., followed by treatment of the crude intermediate with potassium carbonate in methanol, affords the acetylenic alcohols 14-5 or 14-6. Heating of these alkynes with an aromatic halide or triflate in the presence of copper(I) iodide, a palladium catalyst such as bis(triphenylphosphine)palladium dichloride or bis(triphenylphosphine)palladium diacetate in the presence of a tertiary amine base such as triethylamine or tributylamine, then provides coupling products 14-7 or 14-8. In the case of the N-benzyl protected intermediate 14-8, hydrogenation/hydrogenolysis under standard conditions (for example 10% Pd/C in an atmosphere of hydrogen) provides desired intermediate 14-9. For the Boc protected species 14-7, hydrogenation as above provides the saturated piperidine 14-10, and treatment of this compound under anhydrous acidic conditions (for example, trifluoroacetic acid and anisole in methylene chloride, or acetyl chloride in methanol) then yields the salt of intermediate 14-9. This compound is then utilized as the cyclic secondary amine component as shown above in Schemes 3, 4, 5, 6, 8, 9, 10 and 11. Alternatively, if 4-piperidone is attached directly to the functionalized alkylcyclopentane framework described above and no functionality in the alkylcyclopentane would be affected, then the chemistry described herein can be carried out treating the aforementioned alkylcyclopentane segment as 'P' given in Scheme 14.

An alternative route for the preparation of 4-hydroxy-4-(3-arylpropyl)piperidines is given in Scheme 15. Treatment of commercially available 4-piperidones 15-1 or 15-2 with a suitable allyl metal compound (such as allylmagnesium bromide or allyltributylstannane (in the presence of boron trifluoride etherate) in THF, ether or dichloromethane, provides adducts 15-3 or 15-4. Hydroboration with a dialkylborane, such as 9-borabicyclo[3.3.1]nonane (9-BBN), followed by treatment with an aryl halide (the halides preferably being bromide or iodide) or aryl triflate and sodium methoxide in the presence of a suitable soluble palladium catalyst, for example Pd(dppf)Cl$_2$, in warm to refluxing THF, provides the 3-arylpropyl derivatives 15-5 and 15-6. For benzylamine 15-6, hydrogenolysis under standard conditions provides the desired intermediate 15-7. For Boc substituted piperidine 15-5, exposure to suitable anhydrous acidic conditions (for example trifluoroacetic acid and anisole in methylene chloride or HC in methanol at temperatures from 0–25 degrees C.) affords the salt of 15-7. This compound is then utilized as the cyclic secondary amine component as shown above in Schemes 3, 4, 5, 6, 8, 9, 10 and 11. Alternatively, if no functionality are present in the alkylcyclopentane framework that would be adversely effected by the above mentioned chemistry, then 4-piperidone may be attached directly to the alkylcyclopentane framework described above, and the chemistry described in this paragraph can be carried out equating the alkylcyclopentane segment to the group 'P' given in Scheme 15, structures 1 through 6.

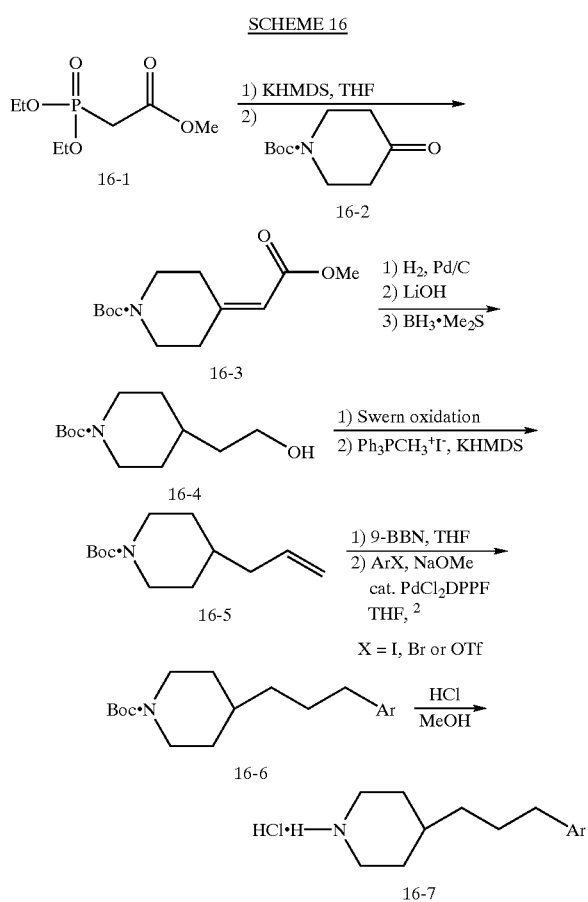

A route for the preparation of 4-(3-arylpropyl)piperidines is given in Scheme 16. Treatment of phosphonoacetate 16-1 with KHMDS followed by addition of commercially available N-Boc 4-piperidone 16-2 provides unsaturated ester 16-3. Hydrogenation of 16-3 followed by hydrolysis to the acid and then reduction with borane.ethyl sulfide then affords primary alcohol 16-4. Mild oxidation of 16-4 under Swern conditions provides the corresponding aldehyde, which upon treatment with the Wittig reagent prepared from methyltriphenylphosphonium iodide and KHMDS yields olefin 16-5. Hydroboration with a dialkylborane, such as 9-borabicyclo[3.3.1]nonane (9-BBN), followed by treatment with an aryl halide (the halides preferably being bromide or iodide) or aryl triflate in the presence of a suitable soluble palladium catalyst, for example PdCl$_2$DPPF, in warm to refluxing THF, provides the 3-arylpropyl derivative 16-6. Removal of the Boc group under acidic conditions, for example with HCl in methanol or with trifluoroacetic acid in methylene chloride, then affords the 1-unsubstituted piperidine 16-7, which can then be employed as the secondary amine component in the syntheses described above in Schemes 3, 4, 5, 6, 8, 9, 10 and 11.

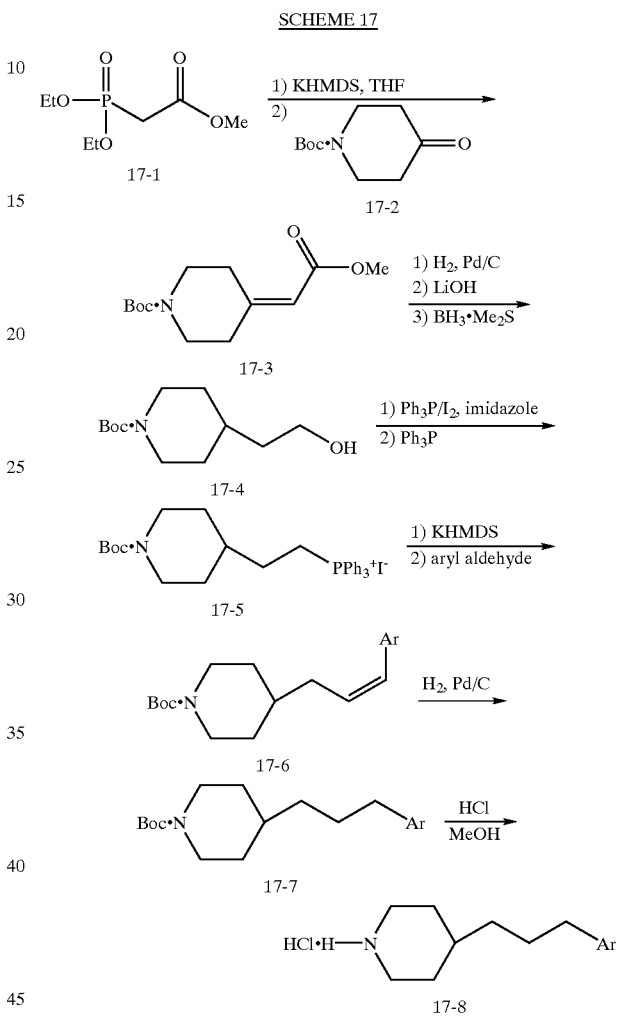

Another route for the preparation of 4-(3-arylpropyl) piperidines is given in Scheme 17. Treatment of phosphonoacetate 17-1 with KHMDS followed by addition of commercially available N-Boc-4-piperidone 17-2 provides unsaturated ester 17-3. Hydrogenation of 17-3 followed by hydrolysis to the acid and then reduction with borane.methyl sulfide then affords primary alcohol 17-4. Formation of the alkyl iodide with triphenylphosphine and iodine in the presence of imidazole followed by treatment with triphenylphosphine provides phosphonium salt 17-5. Deprotonation with a suitable base, for example, KHMDS, LiHMDS, NaHMDS, NaH, LDA, or KH affords the Wittig agent in situ, which upon treatment with a suitable aromatic aldehyde yields the unsaturated derivative 17-6. Hydrogenation under standard conditions provides 17-7, and removal of the Boc group with HCl in methanol or with other acidic conditions then provides the 1-unsubstituted piperidine 17-8, which can then be employed as the secondary amine component in the syntheses described above in Schemes 3, 4, 5, 6, 8, 9, 10 and 11.

SCHEME 18

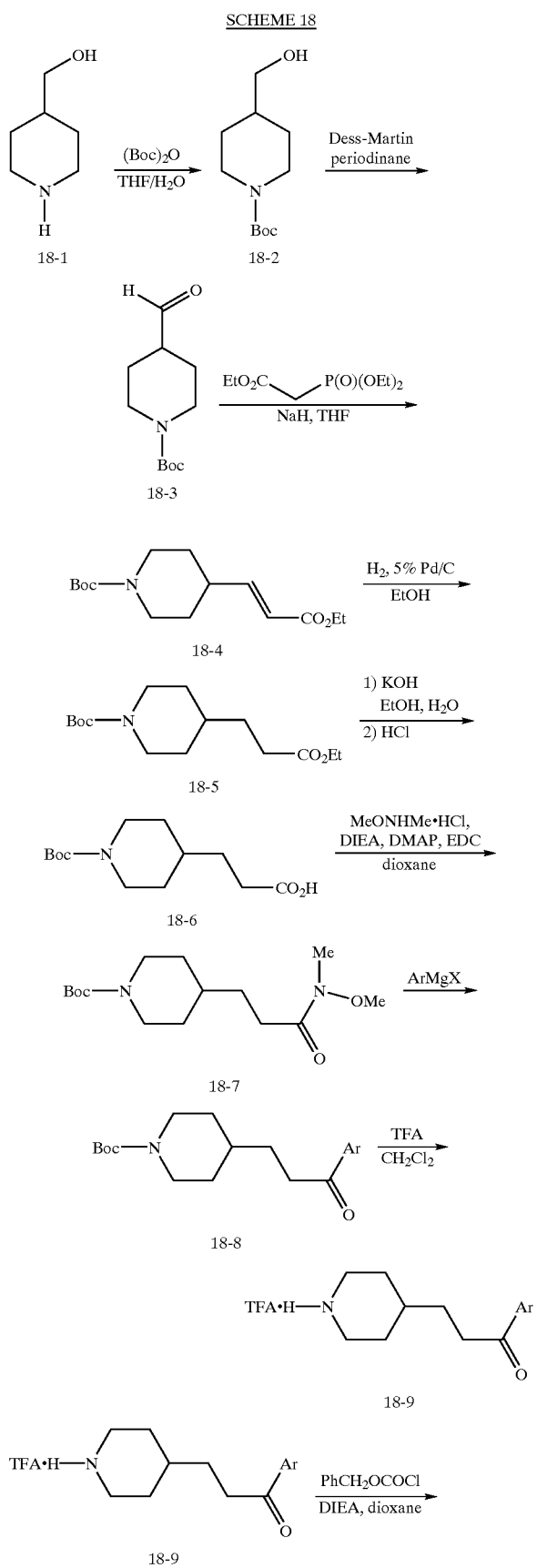

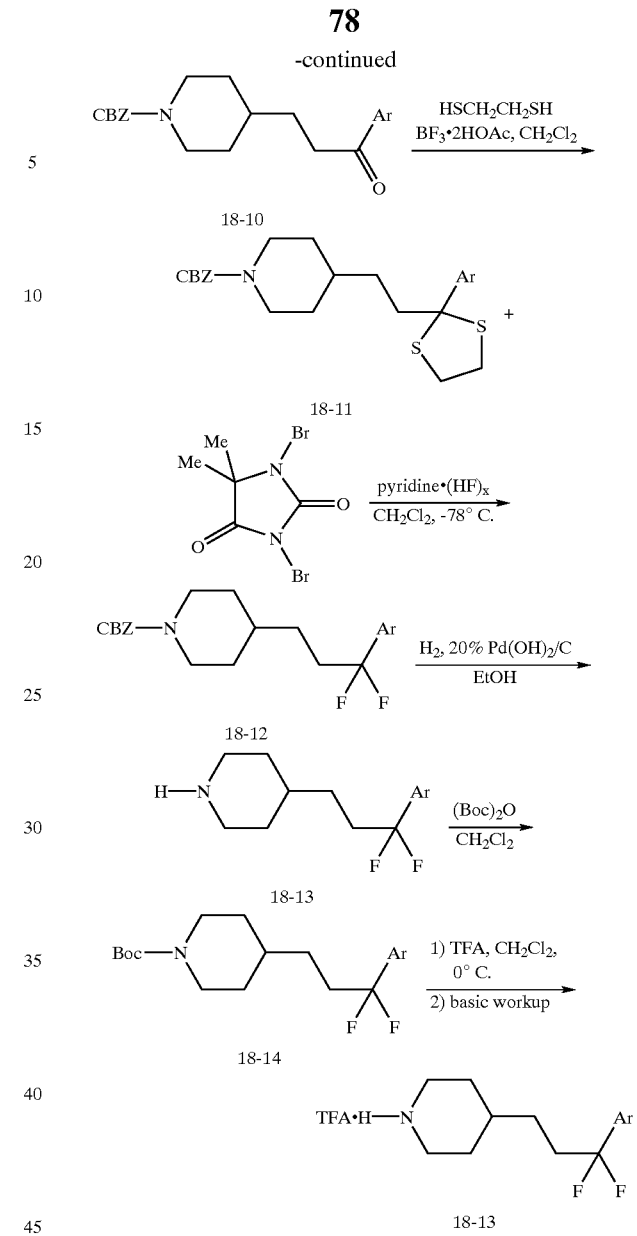

Preparation of piperidines with a 4-(3-aryl-3,3,-difluoropropyl) side chain is given in Scheme 18. Treatment of commercially available 18-1 with Boc anhydride provides protected piperidine 18-2. Oxidation, for example with the Dess-Martin reagent, by a Swern oxidation, or other known methods provides aldehyde 18-3. Condensation under Homer-Wadsworth-Emmons conditions affords unsaturated ester 18-4, which is hydrogenated to ester 18-5 and then hydrolysed to acid 18-6. Formation of the N-methyl-N-methoxy amide 18-7 is carried out employing standard activating agents such as EDC. Weinreb amide 18-7 is then allowed to react with an arylmetal reagent, such as an aryl magnesium halide or an aryllithium, to provide ketone 18-8. Cleavage of the protecting Boc group under acidic conditions yields 18-9, which is reprotected with a carbobenzyloxy group under standard conditions, to afford 18-10. Formation of dithiolane 18-11 with ethanedithiol and boron trifluoride is followed by treatment with 1,3-dibromo-3,3-dimethylhydantoin and pyridine-hydrogen fluoride complex at or around −78 degrees C., to provide gem-difluoro derivative 18-12. Removal of the CBZ group under reductive conditions provides piperidine 18-13, which may be employed directly as the secondary amine in chemistry described above. Alternatively, if additional purification is desired, 18-13 may be protected with a Boc group to afford 18-14. After suitable purification, the Boc group is removed under acidic conditions at or near 0 degrees C. A controlled, basic work-up then provides 18-13, suitable for use as described above in Schemes 3, 4, 5, 6, 8, 9, 10 and 11.

nitrogen protecting group under acidic conditions, for example, hydrochloric acid in methanol, affords cyclopropyl piperidine 19-8, which can then be employed as the secondary amine component in the syntheses described above in Schemes 3, 4, 5, 6, 8, 9, 10 and 11.

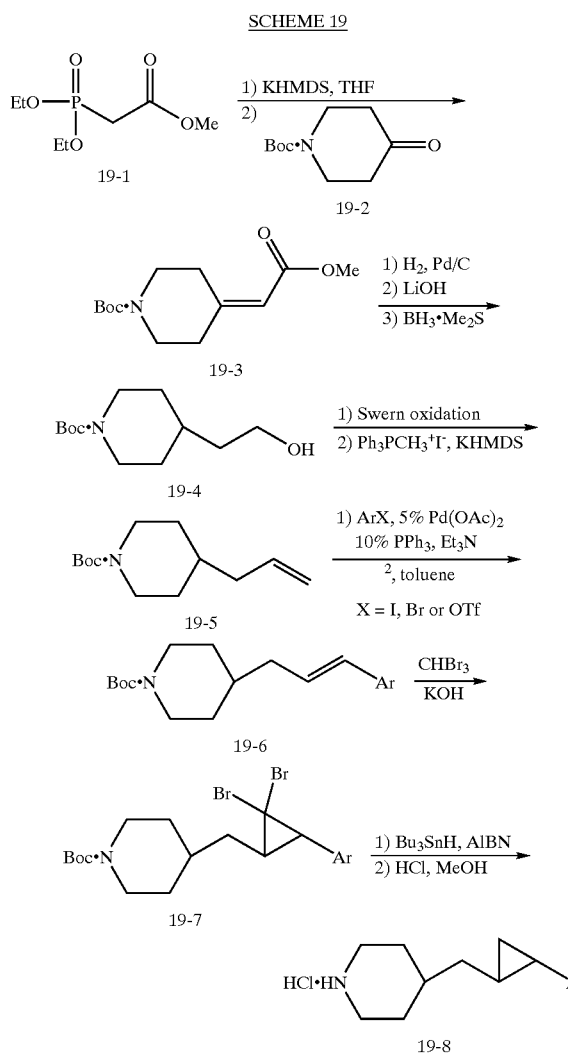

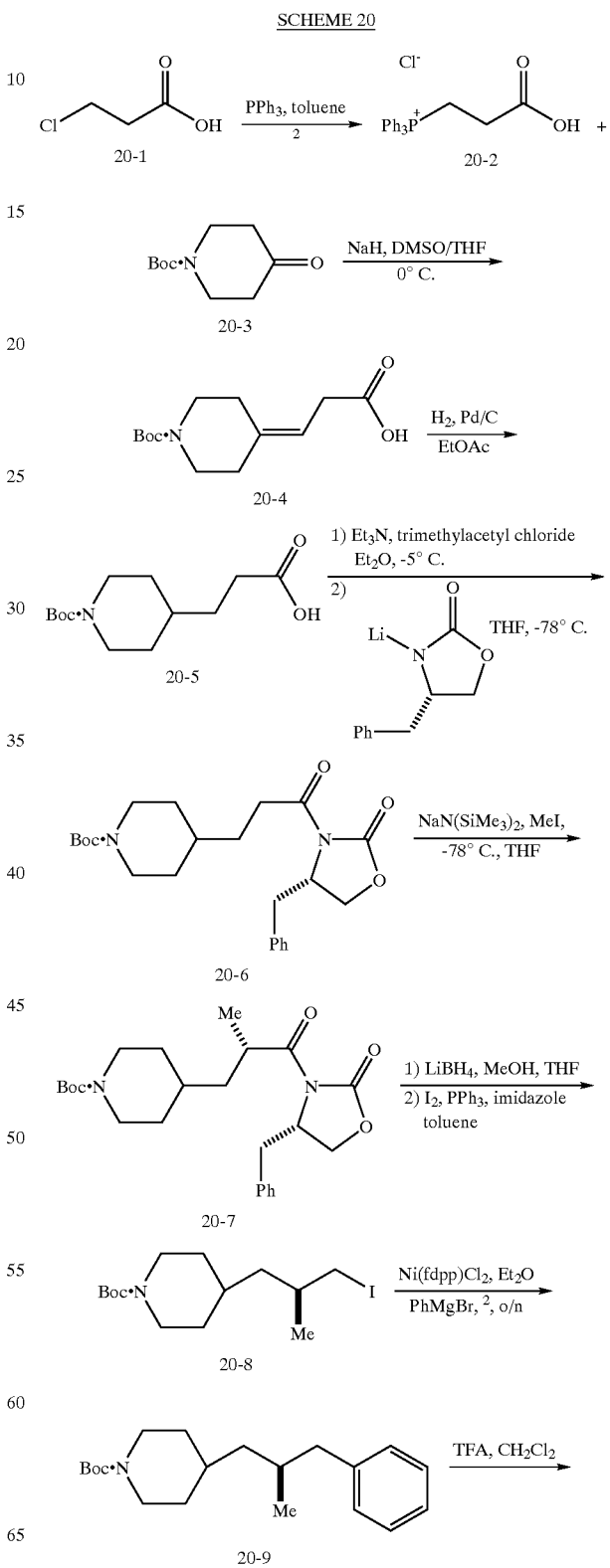

A route for the preparation of 4-(3-arylpropyl)piperidines is given in Scheme 19. Treatment of phosphonoacetate 19-1 with KHMDS followed by addition of commercially available N-Boc-4-piperidone 19-2 provides unsaturated ester 19-3. Hydrogenation of 19-3 followed by hydrolysis to the acid and then reduction with borane-methyl sulfide then affords primary alcohol 19-4. Mild oxidation of 19-4 under Swern conditions provides the corresponding aldehyde, which upon treatment with the Wittig reagent prepared from methyltriphenylphosphonium iodide and KHMDS yields olefin 19-5. Palladium-catalyzed arylation of 19-5 then affords unsaturated derivative 19-6. Addition of dibromocarbene (generated in situ from bromoform and potassium hydroxide) provides cyclopropyl derivative 19-7. Debromination is carried out by slow addition of tributyltin hydride in the presence of the radical initiator AIBN. Removal of the

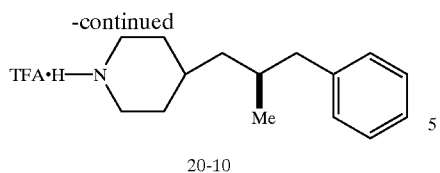

20-10

A route for the preparation of 4-(3-aryl-2-methylpropyl) piperidines is given in Scheme 20. Treatment of commercially available 3-chloropropionic acid (20-1) with triphenylphosphine in refluxing toluene provides phosphonium salt 20-2. Treatment with sodium hydride in DMSO/THF provides the ylide in situ, which upon addition of piperidone 20-3 affords the adduct 20-4. Reduction of the double bond, for example with hydrogen gas in the presence of a palladium catalyst, gives acid 20-5. Treatment of 20-5 with trimethylacetyl chloride and triethylamine generates the mixed anhydride in situ, which upon treatment with the lithium salt of 4-(S)-benzyl-2-oxazolidone yields 20-6. Deprotonation of 20-6 with sodium hexamethyldisilazide, followed by addition of methyl iodide, provides alpha-methyl derivative 20-7. Reduction of acyl-oxazolidone 20-7 with lithium borohydride produces the corresponding primary alcohol, which is converted to primary iodide 20-8 with iodine, triphenylphosphine and imidazole in toluene. Coupling with phenyl magnesium bromide in the presence of Ni(fdpp)Cl₂ affords aralkyl derivative 20-9, which is then deprotected under acidic conditions to provide piperidine 20-10. Piperidine 20-10 can then be employed as the secondary amine component in the syntheses described above in Schemes 3, 4, 5, 6, 8, 9, 10 and 11.

Scheme 21

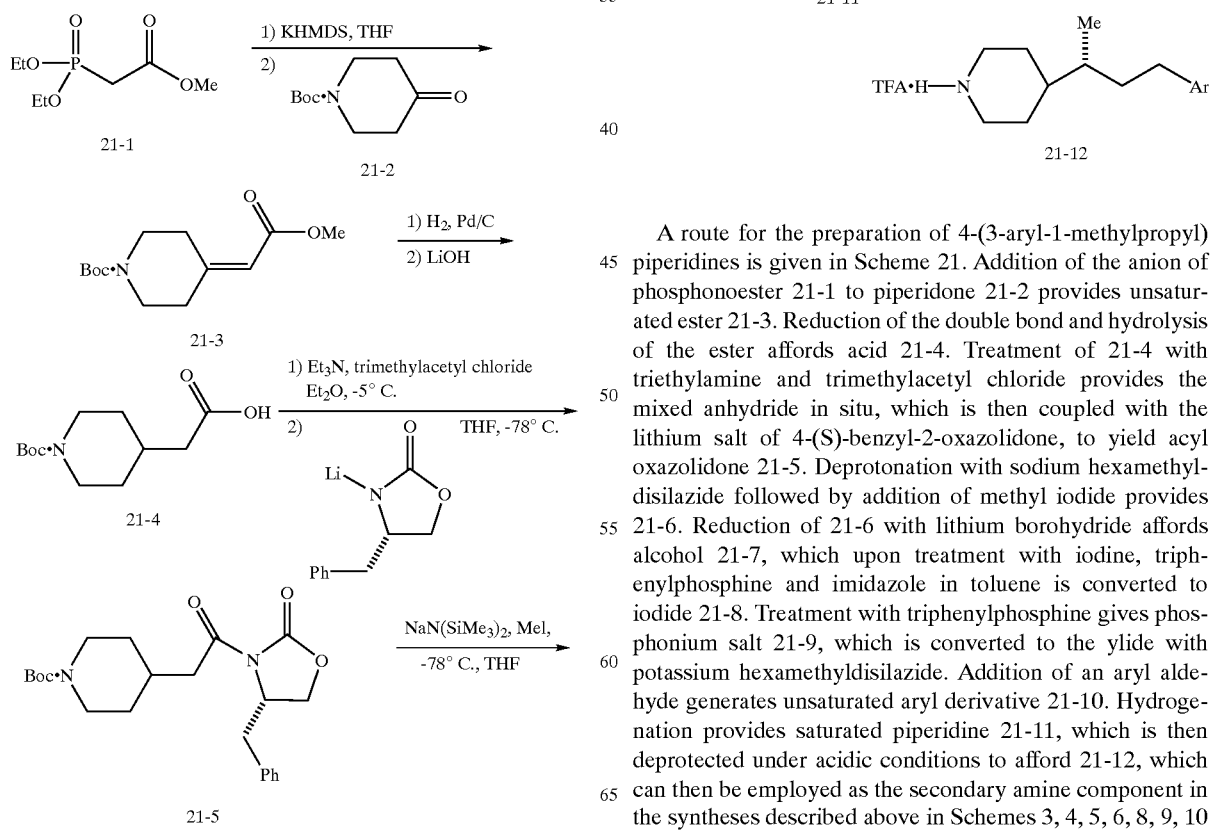

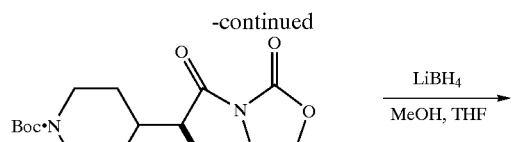

A route for the preparation of 4-(3-aryl-1-methylpropyl) piperidines is given in Scheme 21. Addition of the anion of phosphonoester 21-1 to piperidone 21-2 provides unsaturated ester 21-3. Reduction of the double bond and hydrolysis of the ester affords acid 21-4. Treatment of 21-4 with triethylamine and trimethylacetyl chloride provides the mixed anhydride in situ, which is then coupled with the lithium salt of 4-(S)-benzyl-2-oxazolidone, to yield acyl oxazolidone 21-5. Deprotonation with sodium hexamethyldisilazide followed by addition of methyl iodide provides 21-6. Reduction of 21-6 with lithium borohydride affords alcohol 21-7, which upon treatment with iodine, triphenylphosphine and imidazole in toluene is converted to iodide 21-8. Treatment with triphenylphosphine gives phosphonium salt 21-9, which is converted to the ylide with potassium hexamethyldisilazide. Addition of an aryl aldehyde generates unsaturated aryl derivative 21-10. Hydrogenation provides saturated piperidine 21-11, which is then deprotected under acidic conditions to afford 21-12, which can then be employed as the secondary amine component in the syntheses described above in Schemes 3, 4, 5, 6, 8, 9, 10 and 11.

SCHEME 22

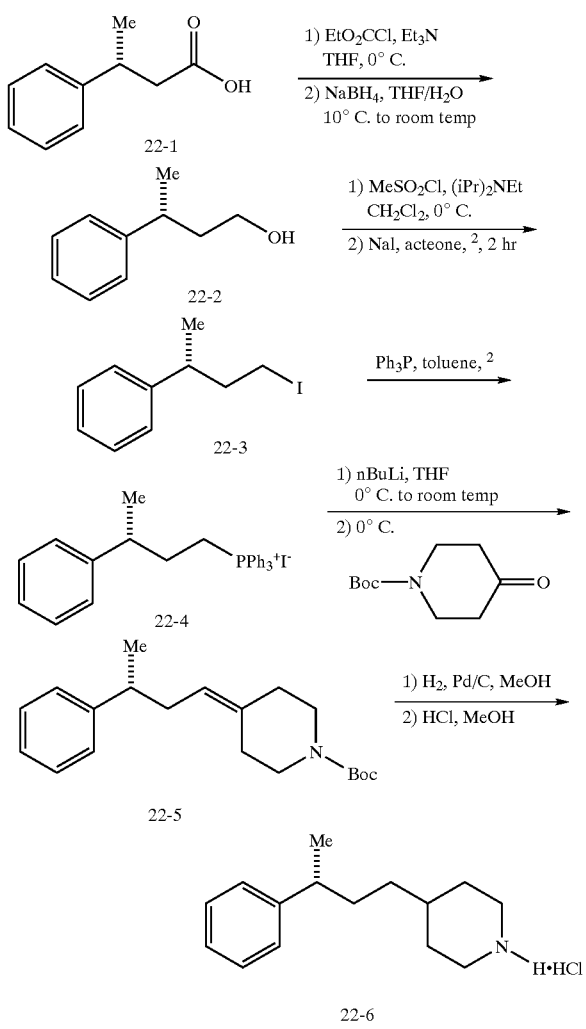

SCHEME 23

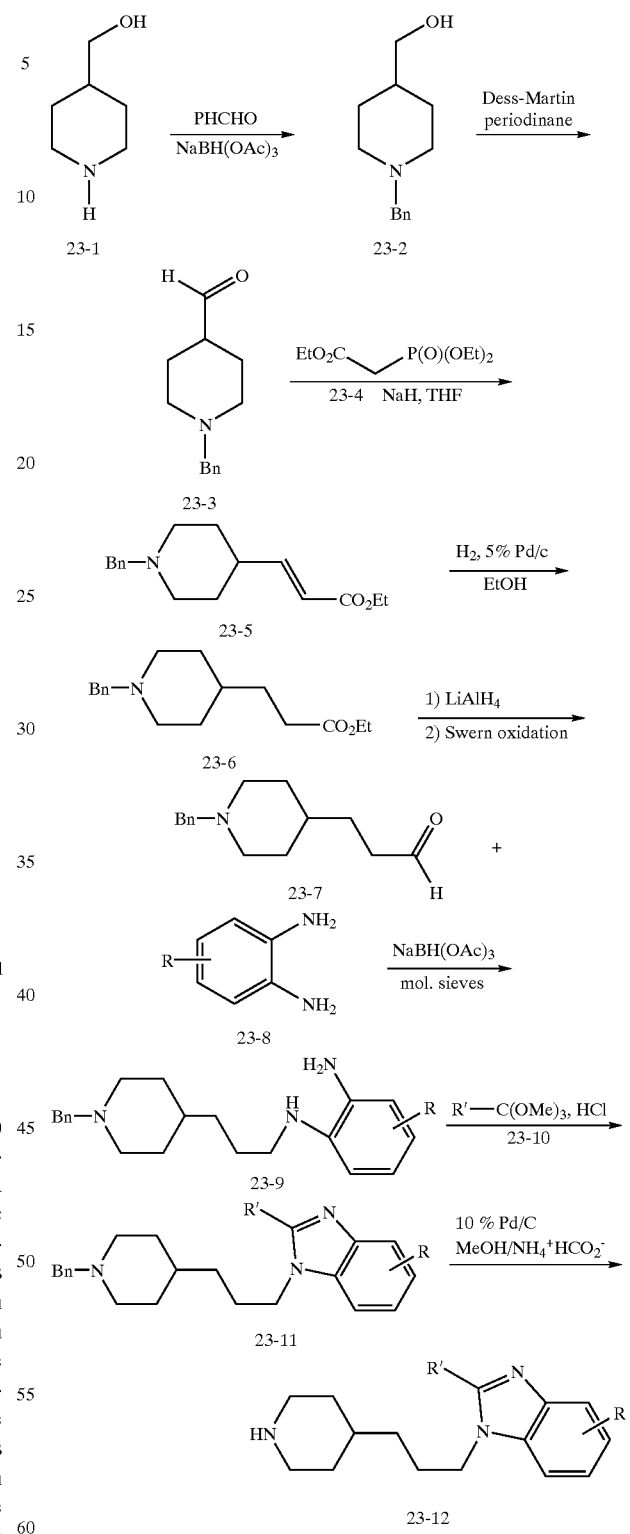

A route for the preparation of 4-(3-aryl-3-methylpropyl) piperidines is given in Scheme 22. Treatment of commercially available 4-(R)-phenylbutyric acid (22-1) with ethyl chloroformate and triethylamine forms the asymmetric anhydride in situ, which upon treatment with sodium borohydride provides primary alcohol 22-1. Alternatively, this conversion can be carried out by treatment of 22-1 with borane-THF. Activation of the hydroxy group of 22-2 with methanesulfonyl chloride in the presence of a hindered base such as N,N-(diisopropyl)ethylamine, followed by displacement with sodium iodide in refluxing acetone affords iodide 22-3. Heating with triphenylphosphine in toluene provides the phosphonium salt 22-4. Deprotonation of this salt with a strong base, for example n-butyl lithium generates the Wittig reagent in situ, which is then allowed to react with N-Boc-4-piperidone, to yield olefin 22-5. Hydrogenation of the double bond followed by treatment with acid, for example HCl in methanol, then provides the secondary amine salt 22-6, which can then be employed as the secondary amine component in the syntheses described above in Schemes 3, 4, 5, 6, 8, 9, 10 and 11.

A route for the preparation of 4-(3-(benzimidazol-2-yl) propyl)piperidines is given in Scheme 23. Protection of piperidine 23-1 under reductive amination conditions provides benzylamine 23-2. Oxidation to aldehyde 23-3 is carried out under standard conditions, for example with the Dess-Martin periodinane. Addition of ester 23-4 provides unsaturated olefin 23-5, which upon reduction affords ester 23-6. Reduction with lithium aluminum hydride or other strong hydride reducing agents followed by mild oxidation provides aldehyde 23-7. Upon combination with diamine 23-8 under reductive alkylation conditions affords the N-alkylated derivative 23-9. Treatment with orthoformate derivative 23-10 in the presence of acid yields benzimidazole 23-11, which upon hydrogenation with palladium on carbon under transfer hydrogenation conditions generates piperidine 23-12, which can then be employed as the secondary amine component in the syntheses described above in Schemes 3, 4, 5, 6, 8, 9, 10 and 11.

SCHEME 24

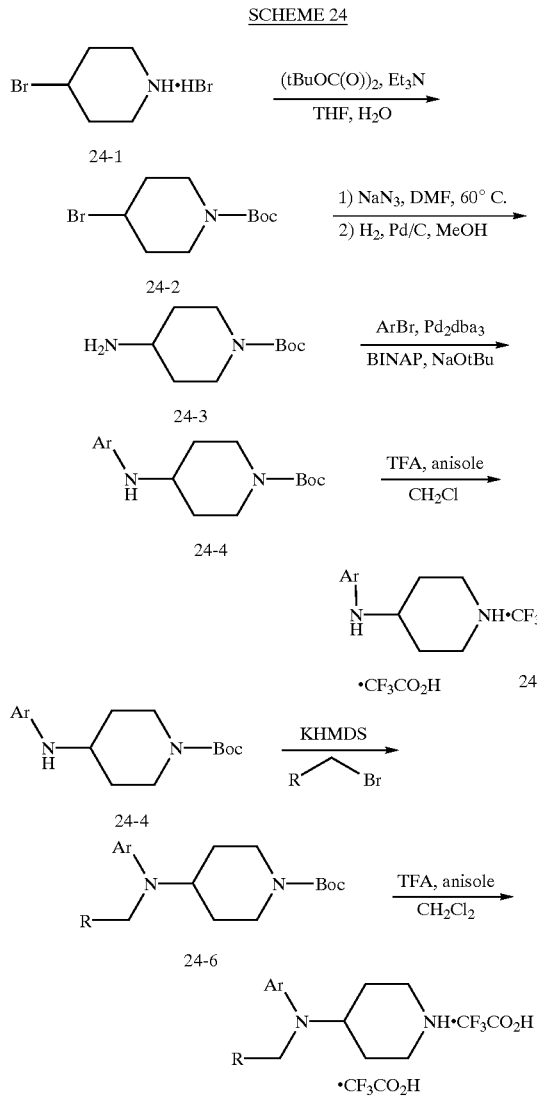

Procedures for synthesizing certain CCR5 receptor modulators containing 4-(heteroarylamino)piperidine functionality are shown in Scheme 24. After protecting commercially available 4-bromopiperidine, the bromide is displaced with sodium azide, and the azide is reduced, for example by catalytic reduction, to provide aminopiperidine 24-3. Treatment of 24-3 with an aryl or heteroaryl halide (the halide preferably being bromide) in the presence of a palladium catalyst, sodium t-butoxide and a suitable bidentate ligand (such as BINAP), according to the conditions of Buchwald et al, provides arylamine 24-4. Direct acidic deprotection of 24-4 may be carried out to provide secondary amine 24-5. Alternatively, amine 24-4 may be alkylated with a suitable alkyl, alkenyl or alkynyl halide (wherein the halide is bromo or iodo in the case of an alkyl group and chloro or bromo in the case of allylic or propargylic functionality) in the presence of a strong base, such as potassium hexamethyldisilazide, to provide trisubstituted amine 24-6. Acidic deprotection, for example, trifluoroacetic acid and anisole in dichloromethane, or methanolic hydrochloric acid, then provides the bis ammonium salt, which in the case of trifluoroacetic acid deprotection, is compound 24-7. The secondary piperidines 24-5 and 24-7 are then utilized as the cyclic secondary amine component as shown above in Schemes 3, 4, 5, 6, 8, 9, 10 and 11.

SCHEME 25

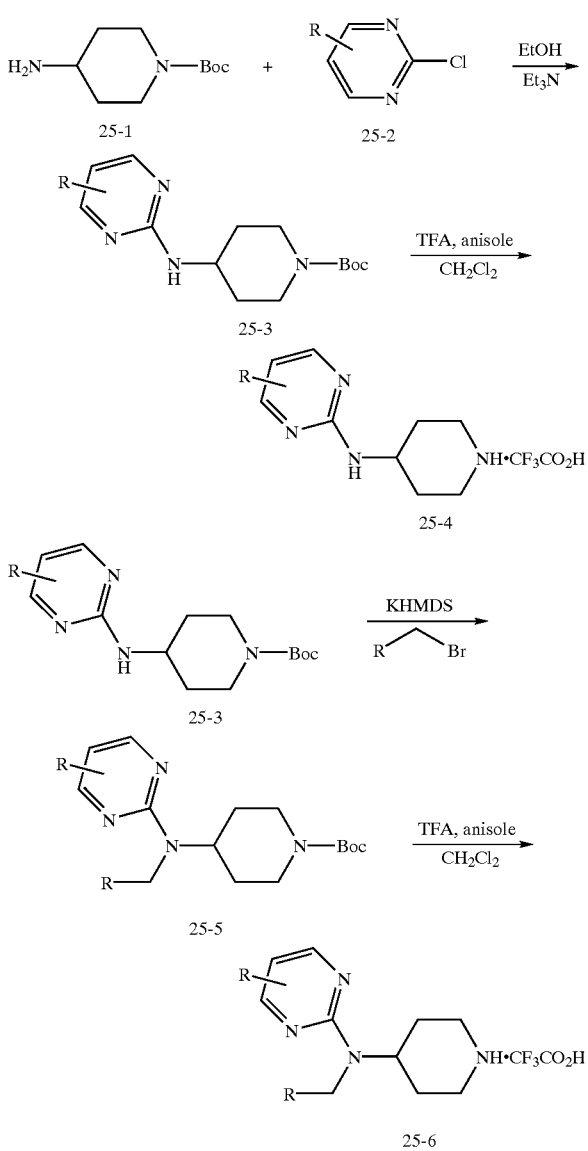

For certain aminoheterocycles, direct displacement of a halogen may provide improved access to the desired intermediates. For example, as shown in Scheme 25, unsubstituted and substituted 2-chloropyrimidines 25-2 may be coupled directly to amine 25-1 in the presence of a suitable base, such as triethylamine, to provide aminopyrimidine 25-3. Acidic deprotection then affords 25-4. Alternatively, 25-3 may be alkylated in the presence of a strong base to provide 25-5, which upon deprotection gives intermediate 25-6. The secondary piperidines 25-4 and 25-6 are then utilized as the cyclic secondary amine component as shown in Schemes 3, 4, 5, 6, 8, 9, 10 and 11.

SCHEME 26

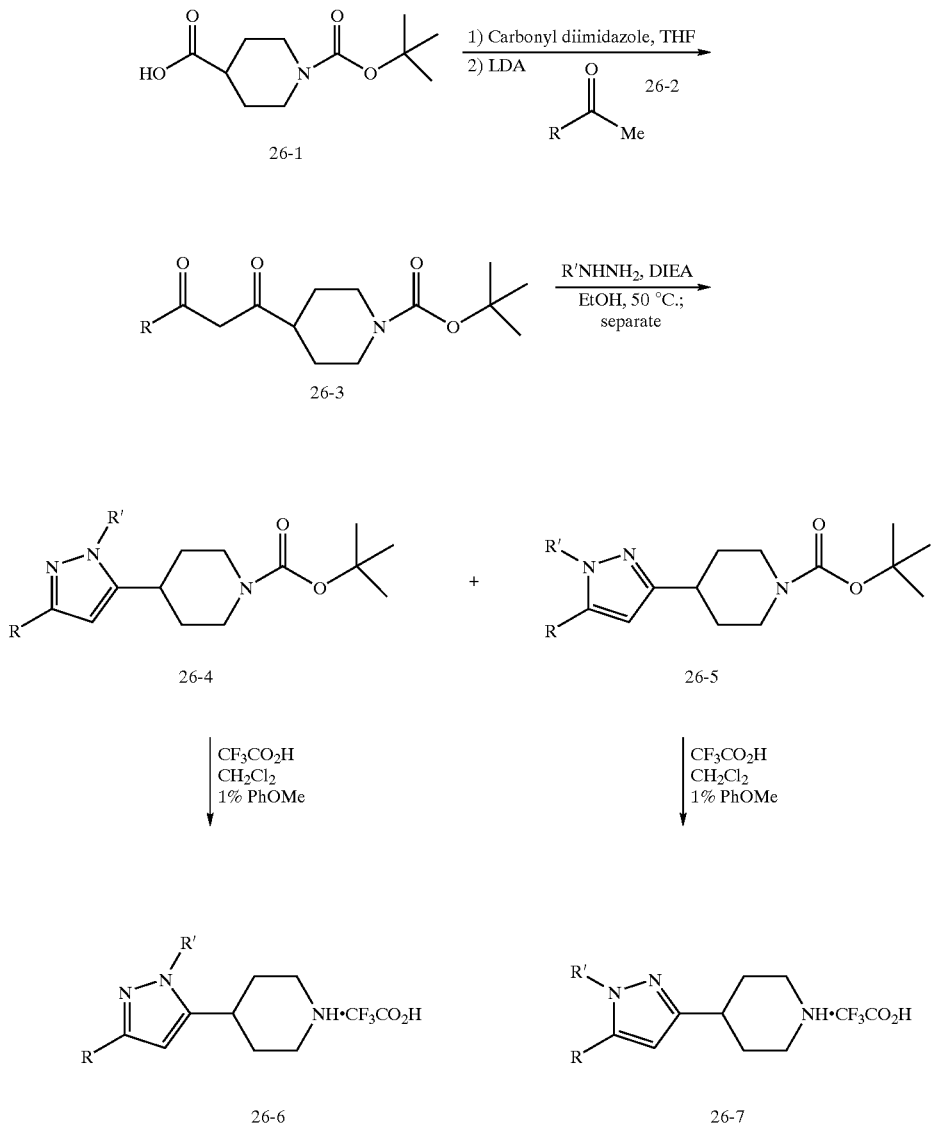

One preparation of piperidine subunits containing functionalized pyrazoles at C4 of the piperidine is given in Scheme 26. Treatment of piperidine 26-1 with carbonyldiimidazole to form the acyl imidazole, followed by addition of a dialkyl or alkyl-aryl ketone (26-2) in the presence of lithium diisopropylamide (LDA) gives the diketone 26-3. Treatment with a monoalkyhydrazine in an alcohol solvent at temperatures between 0 to 100 degrees C. (preferably about 50 degrees C.) in the presence of a hindered base such as DIPEA then provides a mixture of the isomeric pyrazoles 26-4 and 26-5. After separation of these compounds by chromatography or crystallization, the individual products are deblocked under acidic conditions (for example trifluoroacetic acid and anisole with or without methylene chloride as a co-solvent) to provide the piperidine salts 26-6 and 26-7, which are then used as the cyclic secondary amine component as shown above in Scheme 2 and in Schemes 3, 4, 5, 6, 8, 9, 10 and 11.

SCHEME 27

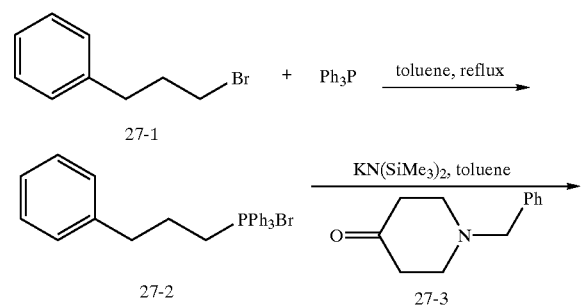

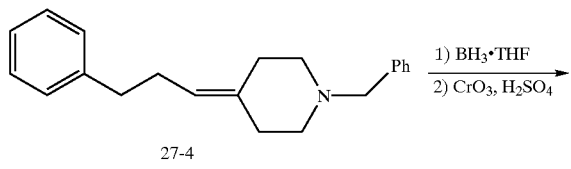

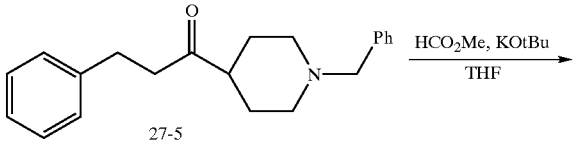

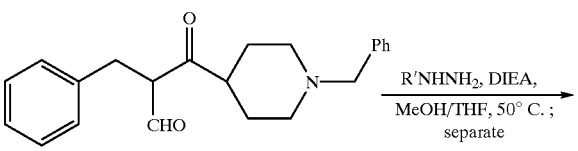

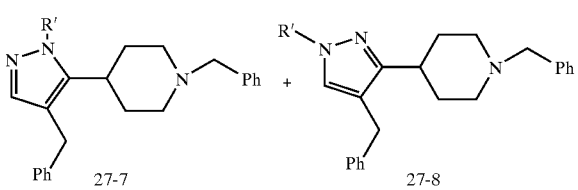

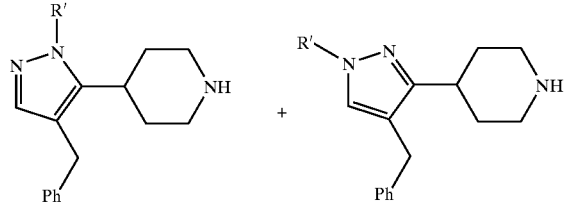

Another preparation of piperidine subunits containing functionalized pyrazoles at C4 of the piperidine is given in Scheme 27. Treatment of commercially available bromide 27-1 with triphenylphosphine in refluxing toluene provides phosphonium salt 27-2, which after treatment with a strong anhydrous base such as potassium hexamethyldisilazide in toluene and the piperidine ketone 27-3 provides the olefin 27-4. Hydroboration followed by an oxidative work-up with chromic acid then affords ketone 27-5. Selective formylation of 27-5 with methyl formate in the presence of potassium t-butoxide selectively affords ketoaldehyde 27-6. Heating of 27-6 with a monoalkylhydrazine in methanol in the presence of a hindered (or insoluble) base such as DIPEA then provides a mixture of the 1,4-disubstituted pyrazoles 27-7 and 27-8. After separation by chromatography, crystallization or fractional distillation, the purified isomers are deprotected under transfer hydrogenation conditions to provide the piperidines 27-9 and 27-10, which are then utilized as the cyclic secondary amine component as shown above in Schemes 3, 4, 5, 6, 8, 9, 10 and 11.

Scheme 28

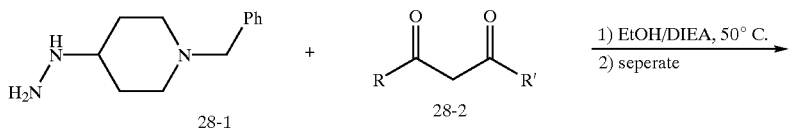

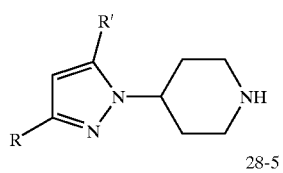

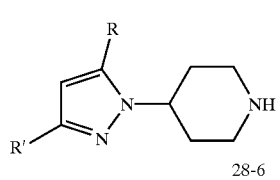

A preparation of piperidine subunits containing 3,5-difunctionalized pyrazoles linked through N-1 to C-4 of the piperidine is given in Scheme 28. Treatment of commercially available hydrazine 28-1 with diketone 28-2 in ethanol at 0 to 90 degrees C. (preferably 50 degrees C.) in the presence of DIPEA provides a mixture of pyrazoles 28-3 and 28-4, which are separated under standard conditions, for example HPLC. Removal of the benzyl groups by transfer hydrogenation provides the secondary piperidines 28-5 and 28-6, which are then utilized as the cyclic secondary amine component as shown above in Schemes 3, 4, 5, 6, 8, 9, 10 and 11.

SCHEME 29

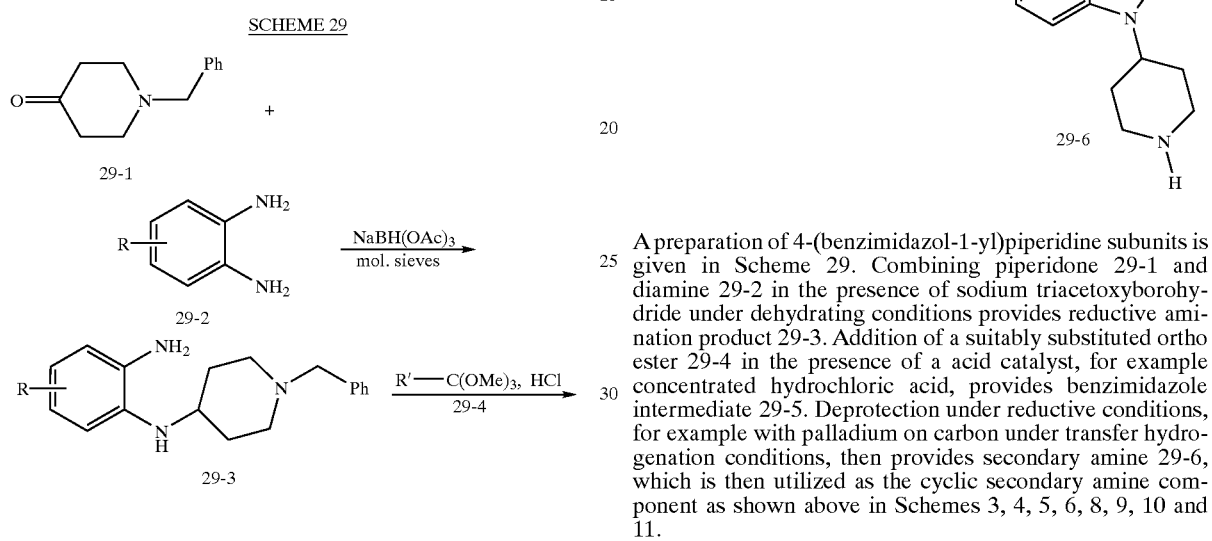

A preparation of 4-(benzimidazol-1-yl)piperidine subunits is given in Scheme 29. Combining piperidone 29-1 and diamine 29-2 in the presence of sodium triacetoxyborohydride under dehydrating conditions provides reductive amination product 29-3. Addition of a suitably substituted ortho ester 29-4 in the presence of a acid catalyst, for example concentrated hydrochloric acid, provides benzimidazole intermediate 29-5. Deprotection under reductive conditions, for example with palladium on carbon under transfer hydrogenation conditions, then provides secondary amine 29-6, which is then utilized as the cyclic secondary amine component as shown above in Schemes 3, 4, 5, 6, 8, 9, 10 and 11.

SCHEME 30

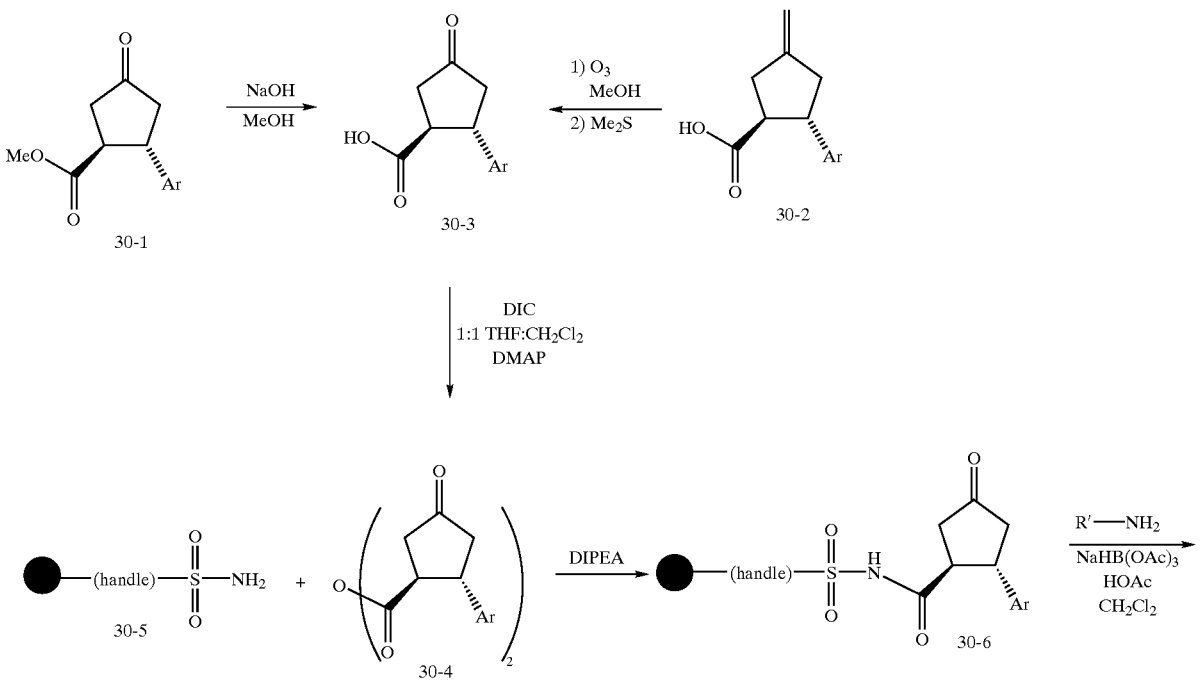

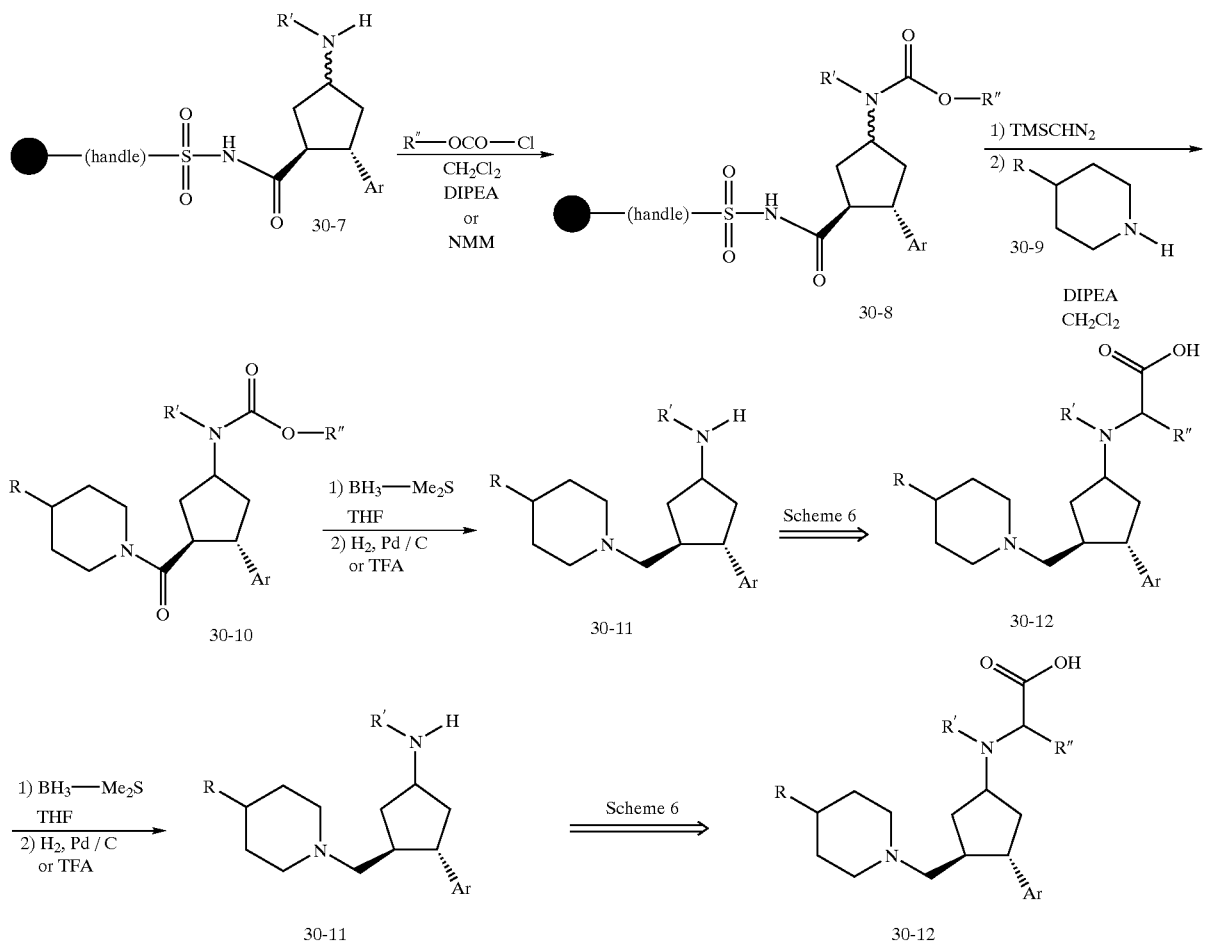

Another method of preparing compounds within the scope of the instant invention is given in Scheme 30 in which most of the chemistry is done on a resin and thus simplifies the isolations. Thus, the keto-acid 30-3, prepared either by standard hydrolysis of the ester 30-1 or oxidation of the exo-methylene of 30-2 with ozone in methanol at −70° C. followed by treatment with dimethyl sulfide, is first activated as its anhydride 30-4 by treatment with a dehydrating agent, such as dicyclohexylcarbodiimide or diisopropylcarbodiimde, in a suitable solvent, such as THF or methylene chloride or a mixture of these, with a catalytic amount of DMAP. Reaction of 30-4 with a suitable sulfonamide linker 30-5 affords the resin-bound cyclopentanone 30-6. Reductive amination of various amines with 30-6 affords the resin-bound amino derivative 30-7. Acylation can be done under standard conditions, such as with chloroformates, usually in the presence of an amine base, such as triethylamine, diisopropylethylamine, N-methylmorpholine, or pyridine, to afford the resin-bound amine derivative 30-8. Activation of the resin sulfonamide linker with trimethylsilyldiazomethane and displacement with an amine, such as the piperidine 30-9 (see Schemes 12–29) in which R must be stable to borane-dimethyl sulfide reduction, gives the corresponding amide 30-10. Subsequent reduction of the amide 30-10 with borane-dimethyl sulfide and removal of the carbamate, such as with TFA for a Boc derivative or standard hydrogenation for a CBZ derivative, affords the amine 30-11, which can be converted to the desired final compound as detailed in Scheme 6.

In some cases the order of carrying out the foregoing reaction schemes may be varied to facilitate the reaction or to avoid unwanted reaction products. The following examples are provided for the purpose of further-illustration only and are not intended to be limitations on the disclosed invention.

General

Concentration of solutions was carried out on a rotary evaporator under reduced pressure. Flash chromatography was carried out on silica gel (230–400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC Conditions

HPLC A. Retention time using the following conditions: Column: YMC ODS A, 5 μ, 4.6×50 mm; Gradient Eluant: 10:90 to 90:10 v/v CH$_3$CN/H$_2$O+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5μ 4.6×100 mm column; Gradient Eluant: 10:90 to 90:10 v/v CH$_3$CN/H$_2$O+0.5% TFA over 10 min, hold 2 min; Detection: PDA, 200–400 nm; Flow Rate: 2.25 mL/min.

The following are representative Procedures for the preparation of the piperidines used in the following Examples or which can be substituted for the piperidines used in the following Examples which may not be commercially available.

HPLC Conditions

HPLC A. Retention time using the following conditions: Column: YMC ODS A, 5 μ 4.6×50 mm; Gradient Eluent: 10:90 to 90:10 v/v acetonitrile/water+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5 μ 4.6×100-mm column; Gradient Eluent: 10:90 to 90:10 v/v acetonitrile/water+0.5% TFA over 10 min, hold 2 min; Detection: PDA, 200–400 nm; Flow Rate: 2.25 mL/min.

The following are representative Procedures for the preparation of the piperidines used in the following Examples or which can be substituted for the piperidines used in the following Examples and which are not commercially available.

Procedure 1

4-(3-Benzyl-1-ethyl-(1H)-pyrazol-5-yl)piperidine di-Trifluoroacetic acid salt

Step A: 1-(1-(t-Butoxycarbonyl)piperidin-4-yl)4-phenylbutane-1,3-dione
Method A:
n-Butyl lithium (100 mL, 0.16 mole) was added to a stirred solution of diisopropylamine (16.16 g, 22.4 mL, 0.16 mole, distilled) in THF (450 mL) at 0° C. over 45 min under nitrogen. Stirring was continued for 10 min at 0° C. after the addition was complete. After cooling to −78° C., phenylacetone (21.45 g, 21.13 mL, 0.16 mole) in THF (100 mL) was added dropwise over 15 min with stirring. This solution was stirred at −78° C. for 1 h. Meanwhile, a solution of N-Boc isonipecotic acid (18.32 g, 0.080 mole) and carbonyl diimidazole (12.98 g, 0.080 mole) in THF (150 mL) was prepared. After stirring for 15 min, this solution was canulated into the enolate solution dropwise over 15 min. The reaction was stirred at <−70° C. for 1 h and then allowed to warm to rt over 3 h. The reaction was quenched with 1M citric acid (250 mL) and stirred for 16 h. The organic layer was separated and washed with 250 mL each of saturated sodium bicarbonate solution, water and brine. After drying over sodium sulfate, the organic layer was concentrated to give an oil. The residue was purified by FC on silica gel (10% ethyl acetate in 60–80° C. petroleum ether) to give separation of the two isomers. The first higher $R_f$ fractions afforded pure title compound as the minor product (3.5 g) as an oil.

$^1$H NMR (500 MHz, CDCl$_3$): δ7.34–7.37 (m, 2 H), 7.25–7.31 (m, 3 H), 5.46 (s, 1 H), 4.11–4.17 (m, 2 H), 3.63 (s, 2 H), 2.70–2.76 (m, 2 H), 2.29 (tt, J=11.7 and 3.7 Hz, 1 H), 1.75–1.80 (m, 2 H), 1.47–1.61 (m, 2 H), 1.47 (s, 9 H). MS (ESI): m/z 346 (M+1).

The lower $R_f$ fractions contained phenylacetone and major product 1-(1-(t-butoxycarbonyl)piperidin-4-yl)-2-phenylbutane-1,3-dione from which the latter crystallized on standing to give 7 g white solid (m.p. 105–106° C.).

$^1$H NMR (360 MHz, CDCl$_3$): δ15.23 (s, 1 H), 7.3–7.45 (m, 3H), 7.15–7.2 (m, 2 H), 4–4.1 (m, 2 H), 2.35–2.50 (m, 2 H), 2.2–2.3 (m, 1 H), 1.87 (s, 3 H), 1.5–1.75 (m, 4 ), 1.43 (s, 9 H). MS (ESI): m/z 346 (M+1).

Method B:
Step B1: 1-(t-Butoxycarbonyl)piperidine-4-N-methyl-N-methoxycarboxamide
N-Boc isonipecotic acid (13.56 g, 59.2 mmol), N,O-dimethyl hydroxylamine hydrochloride (8.65 g, 88.7 mmol), and 1-hydroxybenzotriazole hydrate (15.9 g, 118 mmol) were dissolved in DMF (225 mL) in a 500 mL round-bottom flask and diisopropylethylamine (15.3 g, 20.6 mL, 118.3 mmol) was then added with stirring at rt. 1-Ethyl-3-(3-dimethylaminopropyl)carbodiimide (17.01 g, 88.74 mmol) was added in several portions over 10 min with stirring. After 22 h, the reaction mixture was poured into a water and ice mixture (600 mL) and was extracted with ethyl acetate (5×125 mL). The combined organic layers were washed with 1N HCl (2×200 mL), 5% sodium bicarbonate (2×200 mL), water and brine, dried over sodium sulfate and concentrated to give the title compound (15.58 g) as a yellowish oil.

$^1$H NMR (500 MHz, CDCl$_3$): δ4.11–4.20 (m, 2 H), 3.72 (br s, 3 H), 3.20 (br s, 3 H), 2.75–2.86 (m, 3 H), 1.63–1.76 (m, 4 H), 1.47 (s, 9 H).

Step B2: 4-Acetyl-1-(t-butoxycarbonyl)piperidine
After dissolving the Weinreb amide from Step B1 in anhydrous ether (400 mL) under nitrogen and cooling the solution in an ice bath, 1.4M methyl magnesium bromide (55 mL) in 3:1 toluene and THF was added with stirring and cooling over 30 min. After stirring at 0° C. for 1 h, the reaction was poured into a mixture of ice water (400 mL) and acetic acid (8 mL, 150 mmol). The layers were separated and the aqueous layer was extracted twice with ether. The combined organic layers were washed with 0.1N HCl (200 mL), 3% sodium bicarbonate (200 mL), water (200 mL) and brine (200 mL), dried over sodium sulfate, and concentrated to give the crude product (14.322 g). FC (20–80% ethyl acetate in hexanes) gave the title compound (9.440 g) as a yellowish oil. $R_f$: 0.27 (25% ethyl acetate in hexanes). Some starting Weinreb amide was also recovered (3.212 g). $R_f$: 0.10 (25% ethyl acetate in hexanes).

$^1$H NMR (500 MHz, CDCl$_3$): δ4.07–4.14 (m, 2 H), 2.75–2.83 (m, 2 H), 2.46 (tt, J=11.3 and 3.8 Hz, 1 H), 2.17 (s, 3 H), 1.82–1.87 (m, 2 H), 1.48–1.57 (m, 2 H), 1.46 (s, 9 H).

Step B3: 1-(1-(t-Butoxycarbonyl)piperidin-4-yl)-4-phenylbutane-1,3-dione
To a suspension of 60% sodium hydride (1.07 g) in THF (15 mL) at 0° C. was added a solution of 4-acetyl-1-(t-butoxycarbonyl)piperidine from Step B2 (3.03 g, 13.3 mmol) and methyl phenylacetate (6.01 g, 39.9 mmol) in THF (6 mL) over 20 min. The reaction was stirred for another 4 h as it was allowed to warm to rt. The mixture was diluted with ether (30 mL) and poured into 1N HCl. The layers were separated and the aqueous layer was extracted three times with ether. The combined organic layers were washed with brine (150 mL), dried over sodium sulfate and concentrated. The crude product was purified by FC (20% ethyl acetate in hexanes) to give the title compound (3.02 g). $R_f$: 0.30 (20% ethyl acetate in hexane). The $^1$H NMR data was the same as that obtained from the product of Method A.

Step B: 4-(5-Benzyl-1-ethyl-(1H)-pyrazol-3-yl)-1-(t-butoxycarbonyl)piperidine (Higher $R_f$ isomer) and 4-(3-benzyl-1-ethyl-(1H)-pyrazol-5-yl)-1-(t-butoxycarbonyl) piperidine (Lower $R_f$ isomer)
Method A:
1-(1-(t-Butoxycarbonyl)piperidin-4-yl)-4-phenylbutane-1,3-dione from Step A, from Method A or Method B, Step B3, (0.851 g, 2.46 mmol) in methanol (25 mL) was added over 10 min to a suspension of ethylhydrazine oxalate (0.444 g, 2.96 mmol) in methanol (5 mL) in a 60° C. oil bath. After 15 h, the reaction was concentrated in vacuo and the residue was purified by repeated FC using a gradient of 50–100% ethyl acetate in hexanes to give first 4-(5-benzyl-1-ethyl-(1H)-pyrazol-3-yl)-1-(t-butoxycarbonyl)piperidine (0.148 g total) as the higher $R_f$ product isomer and then the title compound (0.373 g total) as the lower $R_f$.

Higher $R_f$ isomer: $^1$H NMR (500 MHz, CDCl$_3$): δ7.2–7.3 (m, 2 H), 7.3–7.4 (m, 1 H), 7.17 (d, J=7.5 Hz, 2 H), 5.77 (s, 1 H), 4.0–4.25 (m, 2 H), 3.97 (q, J=7.3 Hz, 2 H), 3.95 (s, 2 H), 2.7–2.9 (m, 2H), 2.76 (tt, J=11.3 and 3.8 Hz, 1 H), 1.92 (b rd, J=13 Hz, 1H), 1.5–1.65 (m, 2 H), 1.47 (s, 9 H), 1.29 (t, J=7.3 Hz, 3 H). Lower $R_f$ isomer: $^1$H NMR (500 MHz, CDCl$_3$): δ7.25–7.4 (m, 3 H), 7.2 (m, 2 H), 5.72 (s, 1 H), 4.1–4.3 (m, 2 H), 4.08 (q, J=7.1 Hz, 2 H), 3.95 (s, 2 H), 2.7–2.9 (m, 2H), 2.66 (tt, J=11.3 and 3.8 Hz, 1 H), 1.82 (br d, J=12.8 Hz, 1 H), 1.4–1.6 (m, 2 H), 1.48 (s, 9 H), 1.47 (t, J=7.1 Hz, 3 H).

Method B:

Step B1: 1-(t-Butoxycarbonyl)4-hydroxymethylpiperidine

A solution of 25.03 g (109.2 mmole) N-Boc isonipecotic acid was dissolved in 200 mL THF and treated with 200 mL 1 M borane-tetrahydrofuran complex in THF, and the mixture was stirred overnight. The mixture was concentrated under vacuum, diluted with 750 mL ethyl acetate, and washed with 150 ML 1 N HCl (6×) and then saturated brine. The organic layer was dried over sodium sulfate and concentrated to give 24.3 g of crude product as a white solid. This was used as is in the next step.

$^1$H NMR (500 MHz) δ4.15 (br d, J=13.7 Hz, 2H), 3.52 (d, J=6.2 Hz, 2H), 2.69~2.75 (m, 2H), 1.71~1.75 (m, 2H), 1.62~1.70 (m, 1H), 1.47 (s, 9H), 1.12~1.21 (m, 2H),

Step B2: 1-(t-Butoxycarbonyl)-4-formylpiperidine

A mixture of 17.62 g (135.6 mmole) oxalyl chloride and 250 mL methylene chloride in a dry ice acetone bath. was treated with a solution of 21.19 g (271.2 mmole) DMSO in 150 mL methylene chloride over 20 minutes. After stirring for 20 minutes, a solution of 24.327 g 1-(t-butoxycarbonyl)-4-hydroxymethylpiperidine (from Step B1 above) in 150 mL methylene chloride was added over 1 h. After an additional 15 minutes, 57.17 (565 mmole) triethylamine in 150 mL methylene chloride was added over half an hour. The reaction mixture was allowed to warn up over night in the cooling bath. The reaction mixture was concentrated under vacuum to remove about 400 mL methylene chloride, and the residue was partitioned between 1 L ether and 300 mL water. To this was added 200 mL 1 N NaOH, the layers were separated, and the organic layer was washed with 150 mL 1 N NaOH (2×), water (3×), and saturated brine, dried over sodium sulfate, and concentrated to give 22.562 g crude product. FC (10~60% ethyl acetate in hexanes) gave 20.58 g title compound as slightly yellowish oil.

$R_F$: 0.29 (3:1 v/v hexanes/ethyl acetate). $^1$H NMR (500 MHz) δ9.68 (d, J=0.7 Hz, 1H), 3.96~4.02 (m, 2H), 2.92~2.97 (m, 2H), 2.40~2.45 (m, 1H), 1.88~1.94 (m, 2H), 1.53~1.64 (m, 2H), 1.47 (s, 9H).

Step B3: 1-(t-Butoxycarbonyl)-4-(2,2-dibromoethen-1-yl) piperidine

A solution of 48.615 g (146.6 mmole) carbon tetrabromide in 150 mL methylene chloride was added dropwise with stirring to a solution of 76.895 g (293.2 mmole) triphenyiphosphine in 150 mL methylene chloride in a 1-L rb flask with ice bath cooling over 1.75 h. After 40 minutes, a solution of 15.631 g (73.29 mmole) 1-(t-butoxycarbonyl)-4-formylpiperidine (from Step B2 above) in 100 mL methylene chloride was added to the resulting brown suspension with stirring and cooling over 40 minutes. After one hour, 200 mL ether and 400 mL hexanes was added. The top suspension was filtered through Celite, and the residue was resuspended in 150 mL methylene chloride and treated with 300 mL ether. The mixture was filtered, and the solid was washed with hexanes until the total filtrate was 2 L. The filtrate was filtered again through Celite and washed with hexanes. The filtrate was washed with 100 mL 5% sodium bicarbonate, 300 mL water (2×), and 150 mL brine. The organic layer was dried over sodium sulfate and concentrated under vacuum to give 53.5 g crude product as a yellowish solid. Flash chromatography (FC) on 250 g silica gel (0~15% ethyl acetate in hexanes) gave 21.595 g title compound as a white solid.

$R_f$: 0.57 (15% ethyl acetate in hexanes). $^1$H NMR (500 MHz) δ6.25 (d, J=8.9 Hz, 1H), 4.04~4.12 (m, 2H), 2.75~2.83 (m, 2H), 2.42~2.50 (m, 1H), 1.69~1.75 (m, 2H), 1.47 (s, 9H), 1.29~1.37 (m, 2H).

Step B4: 1-(t-Butoxycarbonyl)-4-(2-tributylstannylethyn-1-yl)piperidine

A mixture of 23.199 g (62.85 mmole) 1-(t-butoxycarbonyl)-4-(2,2-dibromoethen-1-yl)piperidine (prepared as in Step B3 above) and 600 mL anhydrous THF was cooled with dry ice acetone bath under nitrogen. To this mixture was added 88 mL of a 1.6 M butyl lithium solution in hexanes dropwise with stirring and cooling over 50 minutes. After one hour, the flask was transferred into an ice bath. After another hour, a solution of 28.64 g (87.99 mmole) tributyltin chloride in 100 mL THF was added with stirring and cooling over 35 minutes. After three h, the mixture was concentrated under vacuum to remove some THF, and the residue was partitioned between 600 mL ice water and 800 mL ether. The organic layer was washed with 200 mL of water (1×), 2% sodium bicarbonate (1×), water (2×), and saturated brine (1×), dried over sodium sulfate and concentrated under vacuum to give 30.104 g crude product as a green-yellowish liquid. FC on 275 g silica gel using cold 2.5~15% ethyl acetate in hexanes as quickly as possible to give 27.115 g title compound as a colorless liquid.

$R_f$: 0.45 (10% ethyl acetate in hexanes). $^1$H NMR (500 MHz) δ3.63~3.67 (m, 2H), 3.25~3.30 (m, 2H), 2.64~2.69 (m, 1H), 1.74~1.79 (m, 2H), 1.54~1.64 (m, 8H), 1.47 (s, 9H), 1.32~1.39 (m, 6H), 0.96~0.99 (m, 6H), 0.92 (t, J=7.3 Hz, 9H).

Step B5: 4-(1-(t-Butoxycarbonyl)piperidin-4-yl)-1-phenylbutan-2-on-3-yne

To a mixture of 1.727 g (3.466 mmole) 1-(t-butoxycarbonyl)-4-(2-tributyl-stannylethyn-1-yl)piperidine (prepared in Step B4 above) in 18 mL 1,2-dichloroethane was added 0.536 g (3.466 mmole) phenylacetyl chloride and 50 mg dichlorobis-(triphenylphosphine)palladium (II). The mixture was refluxed under nitrogen for 2 h, then concentrated under vacuum. Purification of the residue on silica gel (5~35% ethyl acetate in hexanes) gave 0.784 g title compound as a yellow oil.

$R_f$: 0.27 (20% ethyl acetate in hexanes). $^1$H NMR (500 MHz) δ7.34~7.38 (m, 2H), 7.28~7.32 (m, 1H), 7.24~7.27 (m, 2H), 3.82 (s, 2H), 3.49~3.54 (m, 2H), 3.17~3.23 (m, 2H), 2.68~2.73 (m, 1H), 1.72~1.77 (m, 2H), 1.51~1.57 (m, 2H), 1.47 (s, 9H).

Tetrakis(triphenylphosphine)palladium gave a similar result.

Step B6: 4-(3-Benzyl-1-ethyl-(1H)-pyrazol-5-yl)-1-(tert-butoxycarbonyl)piperidine Heating 1.204 g (3.677 mmole) 4-(1-(t-butoxycarbonyl) piperidin-4-yl)-1-phenylbutan-2-on-3-yne (prepared in Step B5 above) with 0.662 g (4.413 mmole) ethylhydrazine oxalate and 1.252 g (9.687 mmole) DIEA in 20 mL ethanol over night gave an 8:1 ratio of the title compound and its isomer 4-(5-benzyl-1-ethyl-(1H)-pyrazol-3-yl)-1-(tert-butoxycarbonyl)piperidine. Use of ethylhydrazine free base gave even more favorable ratios of the desired title compound. The desired isomer can be isolated by recrystallization using hexanes or by silica gel chromatography using 5~10% acetonitrile in methylene chloride in addition to the procedure described in Method A above.

Step C: 4-(3-Benzyl-1-ethyl-(1H)-pyrazol-5-yl)piperidine di-TFA salt

To a solution of 4-(3-benzyl-1-ethyl-(1H)-pyrazol-5-yl)-1-(t-butoxycarbonyl)piperidine from Step B (lower $R_f$ isomer) (0.373 g, 1.01 mmol) and anisole (0.219 mL, 2.02 mmol) in methylene chloride (15 mL) was added trifluoroacetic acid (1.555 mL, 20.2 mmol). The reaction was stirred at rt for 2.5 h and then concentrated. The residue was purified on preparative reverse-phase HPLC using 9.4×250 mm Semi-preparative Zorbax SB-C18 column with 17.5–35% acetonitrile gradient in water having 0.5% (v/v) TFA over 15 min at 6.05 mL per minute to give the title di-TFA salt compound as an oil. When a mixture of isomers from Step B is used, separation is also possible at this step with the above Prep HPLC conditions in which the title isomer elutes prior to 4-(5-benzyl-1-ethyl-(1H)-pyrazol-3-yl)piperidine.

Procedure 2

4-(3-Benzyl-(1H)-pyrazol-5-yl)piperidine di-trifluoroacetic acid salt

Step A: 4-(3-Benzyl-(1H)-pyrazol-5-yl)-1-(t-butoxycarbonyl)piperidine TFA salt

A solution of 1-(1-(t-butoxycarbonyl)piperidin-4-yl)-4-phenyl-butane-1,3-dione from Procedure 1, Step A (30 mg, 0.087 mmol), hydrazine di-hydrochloride (10.9 mg, 0.1 mmol) and DIPEA (0.045 mL, 0.25 mmol) in methanol (1 mL) was heated at 50° C. for 16 h. The volatiles were then removed under reduced pressure. Purification of the residue was done on preparative reverse-phase HPLC using a 9.4× 250 mm Semi-preparative Zorbax SB-C18 column with 35–50% acetonitrile gradient in water having 0.5% (v/v) TFA over 15 min to give the title compound (45.2 mg) as a gel.

Step B: 4-(3-Benzyl-(1H)-pyrazol-5-yl)piperidine di-TFA salt

To a solution of 4-(3-benzyl-(1H-pyrazol-5-yl))-1-(t-butoxycarbonyl)piperidine TFA salt (from Step A) in methylene chloride (1.5 mL) was added anisole (0.017 mL) and TFA (0.230 mL). After several h at rt, volatiles were removed under reduced pressure. Purification of the residue was done by preparative reverse-phase HPLC using a 9.4× 250 mm Semi-preparative Zorbax SB-C18 column with a 15–25% acetonitrile gradient in water having 0.5% (v/v) TFA over 15 min at 6.0 mL per minute to give the title compound (40.7 mg) as a gel.

Procedure 3

4-(4-(2-Phenyleth-1-yl)-1-ethyl-(1H)-pyrazol-5-yl) piperidine di-TFA salt

Step A: 4-Phenylbutyl Bromide

To a solution of 4-phenyl-1-butanol (21.75 g) in acetonitrile (300 mL) was added triphenylphosphine dibromide (67.23 g) in portions with stirring over 10 min. After stirring over night under nitrogen, methanol (4 mL) was added and after 1.5 h, the solvent was removed under reduced pressure. Hexanes (200 mL) and ~75 g silica gel were added to the residue and the mixture was filtered and the filter cake was eluted with hexanes. The clear filtrate was concentrated to give 32.8 g of clear colorless liquid. This product was again eluted through silica gel using 1.5 L hexanes to give the title compound (24.7 g) as a colorless liquid.

$^1$H NMR (500 MHz, CDCl$_3$): δ7.28–7.32 (m, 2 H), 7.20–7.23 (m, 3 H), 3.44 (t, J=6.8 Hz, 2 H), 2.67 (t, J=7.6 Hz, 2 H), 1.93–1.89 (m, 2H), 1.77–1.84 (m, 2 H).

Step B: (4-Phenylbut-1-yl)triphenylphosphonium bromide

A solution of 4-phenylbutyl bromide from the Step A (24.7 g) and triphenylphosphine (19.00 g) in toluene (100 mL) was heated at 120–130° C. for 3 days. The reaction was cooled to rt and the solid precipitate was collected by filtration, washed with toluene and air dried. The solid was dissolved in a 2:1 mixture of water and acetonitrile and gave the title compound (30.6 g) as a white solid after lyophilization.

$^1$H NMR (500 MHz, CD$_3$OD): δ7.84–7.89 (m, 2 H), 7.71–7.81 (m, 15 H), 7.20–7.23 (m, 1 H), 7.11–7.15 (m, 2 H), 3.37–3.43 (m, 2 H), 2.66 (t, J=7.5 Hz, 2 H), 1.87 (tt, J=7.5 and 7.3 Hz, 2 H), 1.63–1.70 (m, 2 H).

Step C: 1-Benzyl-4-(4-phenylbutylidene)piperidine

A 0.62M solution of potassium bis(trimethylsilyl)amide in THF (180 mL, 112 mmol) in toluene (250 mL) was added to a mixture of (4-phenylbut-1-yl)triphenylphosphonium bromide from Step B (53 g) in toluene (250 mL) in an ice bath over 15 min with stirring under nitrogen. After stirring for a further 15 min, a solution of 1-benzyl-4-piperidone (16.9 g) in toluene (100 mL) was added over 30 min with stirring. The reaction mixture was allowed to warm to rt over 15 h. The reaction mixture was then poured into cold 1N HCl (400 mL) and the layers were separated. The organic layer was extracted with two more portions of 1N HCl. The combined cloudy HCl solution and an oil layer in between were washed with toluene (200 mL) before the aqueous layer was basified by the addition of potassium hydroxide (30 g). The aqueous layer was extracted with ether (3×150 mL) and the combined organic layers were washed with water and brine, dried over sodium sulfate and concentrated. The crude product was purified by FC (10–15% ethyl acetate in hexanes having 4% (v/v) TEA) to give the title compound (16 g) as a colorless oil.

$R_f$: 0.47 (20% ethyl acetate in hexanes having 4% (v/v) TEA). $^1$H NMR (500 MHz, CDCl$_3$): δ7.26–7.38 (m, 7 H), 7.18–7.21 (m, 3 H), 5.18 (t, J=7.4 Hz, 1 H), 3.54 (s, 2 H), 2.61–2.64 (m, 2 H), 2.42–2.49 (m, 4 H), 2.22–2.27 (m, 4 H), 2.02–2.07 (m, 2 H), 1.65–1.71 (m, 2 H).

Step D: 1-(1-Benzylpiperidin-4-yl)-4-phenylbutan-1-one

To a solution of 4-(4-phenylbutylidene)-1-benzylpiperidine from Step C (4.37 g) in anhydrous ether (150 mL) under nitrogen with stirring was add 1M borane solution in THF (45 mL). The reaction was stirred for 3 h when water (2 mL) was added dropwise. The mixture was stirred a further 30 min and was then cooled in an ice bath. A solution of chromic anhydride (2.5 g), concentrated sulfuric acid (5.44 mL) and water (125 mL) was added dropwise with vigorous magnetic stirring over 5 min. After another 5 min, the ice bath was removed. After 1.5 h at rt, 0.5N sodium hydroxide and ether (400 mL each) were added and the mixture was stirred until the residue dissolved. The layers were separated and the aqueous layer was extracted twice with ether. The combined ether layers were washed with an aqueous EDTA solution, water and brine (100 mL each), dried over sodium sulfate and concentrated under reduced-pressure to give a colorless gel. Flash chromatography on silica gel with 30–50% ethyl acetate in hexanes with 3% (v/v) TEA gave the title compound (1 g) as a colorless gel. $R_f$: 0.43 (30% ethyl acetate in hexanes with 3% (v/v) TEA).

$^1$H NMR (500 MHz, CDCl$_3$): δ7.25–7.33 (m, 7 H), 7.16–7.22 (m, 3 H), 3.51 (s, 2 H), 2.89–2.93 (m, 2 H), 2.63 (t, J=7.6 Hz, 2 H), 2.46 (t, J=7.2 Hz, 2 H), 2.38 (tt, J=11.5 and 3.9 Hz, 1 H), 1.99–2.03 (m, 2 H), 1.92 (tt, J=7.2 and 7.6 Hz, 2 H), 1.76–1.81 (m, 2 H), 1.65–1.72 (m, 2 H).

Step E: 1-(1-Benzylpiperidin-4-yl)-2-formyl-4-phenylbutan-1-one

To a solution of potassium t-butoxide (0.673 g) in THF (20 mL) under nitrogen and cooled in an ice bath was added a solution of 1-(1-benzylpiperidin-4-yl)-4-phenylbutan-1-one from Step D (0.71 g) and methyl formate (3.76 mL) in THF (12 mL) over 5 minute. The reaction was stirred for 15 min before being allowed to warm to rt for 2 h. The reaction was poured into water and extracted with ether (4×100 mL), methylene chloride (100 mL), and THF (100 mL). The combined organic layers were washed with water and brine, dried over sodium sulfate and concentrate under reduced pressure. The crude product was purified by FC on silica gel eluting with 5 and 20% methanol in ethyl acetate with 4% TEA to afford the title compound (0.8 g). $^1$H NMR (500 MHz, CDCl$_3$) showed a 3:1 ratio of enol (δ8.54 ppm) and aldehyde (δ9.54 ppm) forms. Other signals from the two forms were only partially resolved. The title compound had a retention time of 9.47 min on a Zorbax SB-C18 column (4.6×75 mm) eluting with 20–100% gradient of acetonitrile in water with 0.1% TFA over 10 min at 1 mL per min.

Step F: 4-(4-(2-Phenyleth-1-yl)-1-ethyl-(1H)-pyrazol-5-yl)-1-benzylpiperidine di-TFA salt A solution of 1-(1-benzylpiperidin-4-yl)-2-formyl-4-phenyl-1-butanone from Step E (76.5 mg) and ethylhydrazine oxalate (45 mg) in methanol (4 mL) was heated at 45° C. for 15.5 h. The solvent was removed under reduced pressure. The residue was purified by preparative reverse-phase IHPLC using a 9.4×250 mm Semi-preparative Zorbax SB-C18 column with 30–50% acetonitrile gradient in water having 0.5% (v/v) TFA over 15 min at 7.1 mL per min to give the title compound (45 mg) as the faster-eluting, minor isomer.

$^1$H NMR (500 MHz, CD$_3$OD): δ7.46–7.52 (m, 5 H), 7.37 (s, 1 H), 7.21–7.24 (m, 2 H), 7.12–7.15 (m, 3 H), 4.32 (s, 2 H), 4.17 (q, J=7.2 Hz, 2 H), 3.53 (br d, J=12.4 Hz, 2 H), 3.06–3.12 (m, 3 H), 2.79–2.88 (m, 4 H), 2.10–2.20 (m, 2 H), 1.78 (br d, J=14.2 Hz, 2 H), 1.34 (t, J=7.2 Hz, 3 H). The isomeric assignment was confirmed by a NOESY spectrum. HPLC/MS (ESI): m/z 374.3 (M+1), 2.51 min.

Step G: 4-(4-(2-Phenyleth-1-yl)-1-ethyl-(1H)-pyrazol-5-yl) piperidine di-TFA salt A mixture of ammonium formate (119 mg), 20% Pd(OH)$_2$/C (5 mg) and 4-(4-(2-phenylethyl)-1-ethyl-(1H-pyrazol-5-yl))-1-benzylpiperidine di-TFA salt from Step F in methanol (2 mL) was heated at 60° C. for 1.5 h. The solvent was removed under reduced pressure and the residue was purified by preparative reverse-phase HPLC using a 9.4×250 mm Semi-preparative Zorbax SB-C18 column with 20–35% acetonitrile gradient in water having 0.5% (v/v) TFA over 15 min at 6.25 mL per min to give the title compound as the di-TFA salt (25 mg) as a gel.

$^1$H NMR (500 MHz, CD$_3$OD): δ7.40 (s, 1 H), 7.22–7.25 (m, 2 H), 7.13–7.17 (m, 3 H), 4.20 (q, J=7.3 Hz, 2 H), 3.42–3.46 (m, 2 H), 3.05–3.15 (m, 3 H), 2.83–2.90 (m, 4 H), 2.04–2.14 (m, 2 H), 1.74–1.79 (m, 2 H), 1.36 (t, J=7.4 Hz, 3 H). The isomer assignment was confirmed by an NOE difference spectrum.

Procedure 4A 4-(3-(4-Fluorobenzyl)-1-ethyl-(1H)-pyrazol-5-yl) piperidine di-TFA

The title compound was prepared using essentially the same procedure as that described in Procedure 1, but substituting methyl 4-fluorophenylacetate for methyl phenylacetate in Step A, Method B, Step B3.

Procedure 4B 4-(3-(3,4-Difluorobenzyl)-1-ethyl-(1H)-pyrazol-5-yl)piperidine di-TFA The title compound was prepared using essentially the same procedure as that described in Procedure 1, but substituting methyl 3,4-difluorophenylacetate for methyl phenylacetate in Step A, Method B.

Procedure 5

4-(3-(Benzofurazan-4-yl)prop-1-yl)piperidine Hydrochloride

Step A: (1-t-Butoxycarbonylpiperidin-4-yl)acetaldehyde

A solution of oxalyl chloride (1.23 mL, 14.1 mmol) in methylene chloride (50 mL) was cooled to −78° C. DMSO (2.0 mL, 28.3 mmol), was added slowly via syringe. After 10 min, 4-(2-hydroxyeth-1-yl)-1-t-butoxycarbonylpiperidine (2.7 g, 11.8 mmol) in methylene chloride (15 mL) was added. The cold mixture was stirred for an additional 20 min then TEA (8.2 mL, 59 mmol) was added. The mixture was warmed to rt and stirred for 1.5 h, then diluted with methylene chloride (300 mL). The organic phase was washed with 1M sodium hydroxide, dried over sodium sulfate and concentrated. FC (125 g silica, 2.5/1 hexanes/ethyl acetate) afforded the title compound (2.25 g).

$^1$H NMR (300 MHz, CDCl$_3$): δ1.1–1.2 (m, 2 H), 1.45 (s, 9 H), 1.65–1.75 (m, 2 H), 1.99–2.13 (m, 1 H), 2.38–2.4 (d, 2 H), 2.65–2.8 (m, 2 H), 4.03–4.15 (m, 2H), 9.78 (s, 1 H)

Step B: 4-(Prop-2-en-1-yl)-1-t-butoxycarbonylpiperidine

A solution of methyltriphenylphosphonium bromide (5.3 g, 14.8 mmol) in THF (50 mL) was cooled to 0° C. under nitrogen. Potassium hexamethyl disilazide (27.7 mL, 0.5M toluene solution, 13.9 mmol) was added and the mixture was stirred for 30 min. A solution of (1-t-butoxycarbonylpiperidin-4-yl)acetaldehyde from Step A (2.25 g, 9.9 mmol) in THF (10 mL) was added and the mixture was warmed to rt. After 30 min, the reaction was complete by tlc analysis. The mixture was diluted with ethyl acetate (200 mL) and washed with water and brine (100 mL each). The organic phase was dried over sodium sulfate and concentrated to give an oil which was purified by FC (75 g silica, 10/1 hexane/ethyl acetate) to afford the title compound (1.61 g).

$^1$H NMR (300 MHz, CDCl$_3$): δ1.03–1.18 (m, 2 H), 1.45 (s, 9 H), 1.4–1.5 (m, 1 H), 1.6–1.7 (m, 2 H), 1.99–2.13 (t, 1 H), 2.62–2.75 (m, 2 H), 4.03–4.15 (m, 2H), 4.98–5.12 (m, 2 H), 5.7–5.83 (m, 1 H).

Step C: 4-Bromobenzofurazan

To a solution of 2,6-dibromoaniline (10 g, 40 mmol) in glacial acetic acid (160 mL) was added 30% hydrogen peroxide (30 mL). The mixture was left for 48 h at which point crystals had precipitated. The crystals were collected by filtration, washed with acetic acid and water then dried under high vacuum to give 2,6-dibromonitrosobenzene (6.24 g). This material (2.6 g, 10 mmol) was dissolved in DMSO (25 mL) along with sodium azide (650 mg, 10 mmol). The mixture was heated to 100° C. for 1 h then cooled to rt and diluted with ethyl acetate and water. The layers were separated and the organic phase was washed with water and brine, then dried over sodium sulfate and concentrated. FC (75 g silica, 10/1 hexane/ethyl acetate) afforded the title compound (1.7 g).

$^1$H NMR (300 MHz, CDCl$_3$): δ7.25–7.35 (dd, 1 H), 7.6–7.65 (d, 1 H), 7.78–7.82 (d, 1 H)

Step D: 4-(3-(Benzofurazan-4-yl)prop-1-yl)piperidine hydrochloride

A solution of 4-(prop-2-en-1-yl)-1-t-butoxycarbonylpiperidine from Step B (330 mg, 1.46 mmol) in dry THF (0.5 mL) was cooled to 0° C. and a solution of 9-BBN (3.2 mL, 0.5 M in THF, 1.61 mmol) was added. The mixture was warmed to rt and stirred for 5 h. Potassium carbonate (405 mg, 2.93 mmol), 1,2-bis(diphenylphosphino)-ferrocenyl palladium dichloride (60 mg, 0.073 mmol) and 4-bromobenzofurazan (from Step C) (292 mg, 1.46 mmol) were added followed by dry DMF (5 mL). The resulting mixture was heated to 55° C. overnight then diluted with ethyl acetate. The solution was washed with water (3×) and brine, then dried over sodium sulfate and concentrated. FC (15 g silica, 5/1 hexane/ethyl acetate) afforded the title Boc derivative. Heating in 1% conc. HCl/methanol at 50° C. for 2 h followed by removal of solvent and drying under vacuum afforded the title compound as the hydrochloride (155 mg).

$^1$H NMR (300 MHz, CD$_3$OD): δ1.31–1.42 (m, 4 H), 1.6–1.75 (m, 1 H), 1.84–2.0 (m, 4 H), 2.9–3.1 (m, 4 H), 3.3–3.4 (m, 2 H), 7.25–7.3 (d, 1 H), 7.4–7.5 (dd, 1 H), 7.7–7.75 (d, 1 H).

Procedure 6

4-(3-(Benzofurazan-5-yl)prop-1-yl)piperidine hydrochloride

Using essentially the same methods as in Procedure 5, but substituting 2,5-dibromoaniline for 2,6-dibromoaniline in Step C, the title compound was prepared.

Procedure 7

4-(3-(4-Cyanophenyl)prop-1-yl)piperidine hydrochloride

Starting with 4-(prop-2-en-1-yl)-1-t-butoxycarbonylpiperidine from Procedure 5, Step B (475 mg, 2.1 mmol) and using essentially the same methods as in Procedure 5, Step D, but substituting 4-bromobenzonitrile (382 mg, 2.1 mmol), the title compound (337 mg) was obtained as the hydrochloride.

$^1$H NMR (300 MHz, CD$_3$OD). δ1.31–1.42 (m, 4 H), 1.58–1.75 (m, 5 H), 1.9–2.1 (m, 2 H), 2.67–2.77 (t, 2 H), 2.9–3.0 (m, 2 H), 3.3–3.4 (m, 2 H), 7.35–7.4 (d, 2 H), 7.6–7.63 (d, 2 H).

Procedure 8

4-(3-(4-Cyano-3-fluorophenyl)prop-1-yl)piperidine hydrochloride

Starting with 4-(prop-2-en-1-yl)-1-t-butoxycarbonylpiperidine from Procedure 5, Step B and using essentially the same methods as in Procedure 5, Step D, but substituting 4-bromo-2-fluorobenzonitrile, the title compound was obtained as the hydrochloride.

Procedure 9

4-(3-(4-Fluorophenyl)prop-1-yl)piperidine hydrochloride

Starting with 4-(prop-2-en-1-yl)-1-t-butoxycarbonylpiperidine (from Procedure 5, Step B) and using essentially the same methods as in Procedure 5, Step D, but substituting 4-bromofluorobenzene, the title compound was obtained as the hydrochloride.

Procedure 10

4-(3-(Quinolin-3-yl)propyl)piperidine di-hydrochloride salt

Step A: 1-(t-Butoxycarbonyl)-4-(3-(quinolin-3-yl)propyl)piperidine

A solution of 1-(t-butoxycarbonyl)-4-(prop-2-en-1-yl)piperidine (from Procedure 5, Step B) (260 mg, 1.15 mmol) in THF (3 mL) under argon was treated with 0.5M 9-BBN solution in THF (2.30 mL, 1.15 mmol). The resulting mixture was stirred at rt for 2 h, then treated with sodium methoxide (68 mg, 1.25 mmol). The resulting mixture was stirred until it was homogeneous (~15 min) and then was treated with 3-(bromo) quinoline (0.155 mL, 1.15 mmol) and [1,1'-bis(triphenylphosphino)ferrocene)dichloropalladium.methylene chloride (41 mg, 0.05 mmol). The resulting mixture was heated at reflux for 30 min, cooled and quenched with 1N NaOH (20 mL). The quenched reaction was extracted with 2×50 mL of ether; the extracts were dried over magnesium sulfate, combined and concentrated. FC (15 g of silica gel, 4:1 v/v hexanes/ethyl acetate) afforded the title compound (240 mg).

$^1$H NMR (300 MHz, CDCl$_3$): δ1.00–1.16 (m, 2 H), 1.25–1.40 (m, 2 H), 1.45 (s, 9 H), 1.60–1.80 (m, 5 H), 2.62–2.72 (m, 2 H), 2.79 (t, J=7.8, 2 H), 4.06 (br s, 2 H), 7.52 (m, 1 H), 7.66 (m, 1 H), 7.76 (dd, J=8.0, 1.6, 1 H), 7.91 (d, J=1.6, 1 H), 8.77 (d, J=2.2, 1 H).

Step B: 4-(3-(Quinolin-3-yl)propyl)piperidine di-hydrochloride salt

A solution of 1-(t-butoxycarbonyl)-4-(3-(quinolin-3-yl)propyl)piperidine from Step A (240 mg, 0.68 mmol) in 1M HCl solution (8 mL) in methanol was stirred at rt for 48 h. The solution was concentrated and the residue crystallized from ethyl acetate to afford the title compound (182 mg), $^1$H NMR (500 MHz, CD$_3$OD): δ1.37–1.49 (m, 4 H), 1.67–1.74 (m, 2 H), 1.85–1.91 (m, 2H), 1.99 (app d, J=13.5 Hz, 2 H), 2.99 (app t, J=11.5 Hz, 2 H), 3.05 (t, J=8.0 Hz, 2H), 3.38 (app d, J=12.5 Hz, 1 H), 7.97 (t, J=7.0 Hz, 1 H), 8.13 (dt. J=1.0 and 7.0 Hz, 1H), 8.24 (d, J=8.5 Hz, 1 H), 8.31 (d, J=8.0 Hz, 1 H), 9.10 (s, 1 H), 9.21 (d, J=1.0 Hz, 1 H).

Procedure 11

4-(3-(2-Pyridyl)propyl)piperidine di-TFA salt

Step A: 1-(t-Butoxycarbonyl)-4-(3-(2-pyridyl)propyl)piperidine

The title compound was prepared using a procedure analogous to that described in Procedure 10, Step A, substituting (2-bromo)pyridine for (3-bromo)quinoline. FC (4:1 v/v hexanes/ethyl acetate followed by 3:2 v/v hexanes/ethyl acetate) provided the title compound (135 mg, 48%).

$^1$H NMR (500 MHz, CDCl$_3$): δ1.05–1.81 (m, 10 H), 1.46 (s, 9 H), 2.67–2.82 (m, 2 H), 3.65 (m, 1 H), 4.08–4.16 (m, 2 H), 7.14–7.18 (m, 2 H), 7.63 (m, 1 H), 8.54 (d, J=4.4 Hz, 1 H). HPLC/MS (ESI): m/z 304 (M+1).

Step B: 4-(3-(2-Pyridyl)propyl)piperidine di-TFA salt

To a solution of 1-(t-butoxycarbonyl)-4-(3-(2-pyridyl)propyl)piperidine (from Step A) (128 mg, 0.42 mmol) in methylene chloride (1 mL) was added TFA (1 mL). After stirring for 2 h at rt, the reaction was concentrated to give the title compound (36 mg).

$^1$H NMR (500 MHz, CDCl$_3$): δ1.22–1.46 (m, 5 H), 1.73–1.79 (m, 4 H), 2.68 (t, J=11.8 Hz, 2 H), 2.78 (t, J=7.8

Hz, 2 H), 3.19 (d, J=11.8 Hz, 2 H), 5.32 (br s, 1 H), 7.09–7.15 (m, 2 H), 7.59 (t, J 7.7 Hz, 2 H), 8.52 (d, J=4.6 Hz, 1 H).

Procedure 12

4-(3-(4-(Trifluoromethyl)pyrimidin-2-yl)propyl) piperidine

Step A: 1-(t-Butoxycarbonyl)-4-(3,3-dibromoprop-2-en-1-yl)piperidine

To a solution of carbon tetrabromide (286 mg, 0.86 mmol) in methylene chloride (4 mL) at −10° C. was added triphenylphosphine (339 mg, 1.29 mmol). After 10 min, a solution of ((1-t-butoxycarbonyl)piperidin-4-yl)acetaldehyde (from Procedure 5, Step A) (98 mg, 0.43 mmol) and TEA (0.060 mL, 0.43 mmol) in methylene chloride (2 mL) was added. After stirring at rt for 2 h, the reaction mixture was concentrated. The residue was purified by FC (9:1 v/v hexanes/ethyl acetate followed by 1:1 v/v hexanes/ethyl acetate) to give the title compound (118 mg).

$^1$H NMR (500 MHz, CDCl$_3$): δ1.14–1.22 (m, 2 H), 1.47 (s, 9 H), 1.57–1.60 (m, 1 H), 1.67 (br d, J=12.6 Hz, 2H), 2.08 (t, J=7.1 Hz, 2 H), 2.70 (t, J=12.7 Hz, 2 H), 4.10 (br d, J=12.6 Hz, 2 H), 6.42 (t, J=7.4 Hz, 1 H).

Step B: 1-(t-Butoxycarbonyl)-4-(prop-2-yn-1-yl)piperidine

To a solution of 118 mg (0.31 mmol) of 1-(t-butoxycarbonyl)-4-(3,3-dibromoprop-2-en-1-yl)piperidine from Step A in THF (4 mL) at −78° C. was added a 2.5M solution of n-butyl lithium (0.370 mL, 0.92 mmol). After stirring at −78° C. for 45 min, the reaction mixture was quenched with sat'd ammonium chloride (4 mL) and diluted with ether (25 mL). After separating the phases, the aqueous layer was extracted with ether. The combined organic phases were washed with brine, dried over magnesium sulfate and concentrated. The residue was purified by FC (4:1 v/v hexanes/ether) to give the title compound (55 mg).

$^1$H NMR (500 MHz, CDCl$_3$): δ1.18–1.26 (m, 2 H), 1.47 (s, 9 H), 1.60–1.67 (m, 1 H), 1.77 (br d, J=13.2 Hz, 2 H), 1.99 (t, J=2.6 Hz, 1 H), 2.16 (dd, J=6.6 Hz, 2.5, 2 H), 2.68–2.74 (m, 2 H), 4.12 (br d, J=13.0 Hz, 2 H).

Step C: 1-(t-Butoxycarbonyl)-4-(3-((4-trifluoromethyl) pyrimidin-2-yl)prop-2-yn-1-yl)piperidine To a solution of 1-(t-butoxycarbonyl)-4-(prop-2-yn-1-yl) piperidine from Step B (86 mg, 0.39 mmol) in TEA (4 mL) under argon at 0° C. was added 2-chloro-4-(trifluoromethyl) pyrimidine (0.070 mL, 0.58 mmol). After stirring at 0° C. for 5 min, dichlorobis(triphenylphosphine)palladium(II) (27 mg, 0.04 mmol), and copper iodide (4 mg, 0.02 mmol) was added and the reaction vessel was flushed with argon. After 3 h at 60° C., the reaction mixture was cooled to rt and quenched with 1N sodium hydroxide (5 mL) and diluted with ether (25 mL). After separating the phases, the aqueous layer was extracted again with ether. The combined organic phases were washed with brine, dried over magnesium sulfate and concentrated. The residue was purified by FC (9:1 v/v hexanes/ethyl acetate followed by 2:1 v/v hexanes/ ethyl acetate) to give the title compound (132 mg).

$^1$H NMR (400 MHz, CDCl$_3$): δ1.26–1.33 (m, 2 H), 1.46 (s, 9 H), 1.80–1.88 (m, 3 H), 2.46 (d, J=6.4 Hz, 2 H), 1.99 (br t, J=11.2 Hz, 1 H), 4.10–4.40 (m, 2 H), 7.54 (d, J=5.0 Hz, 1 H), 8.94 (d, J=5.0 Hz, 1 H).

Step D: 1-(t-Butoxycarbonyl)-4-(3-((4-trifluoromethyl) pyrimidin-2-yl)prop-1-yl)piperidine To a solution of 1-(t-butoxycarbonyl)-4-(3-((4-trifluoromethyl)pyrimidin-2-yl)prop-2-yn-1-yl)piperidine from Step C (130 mg) in methanol (4 mL) was added 10% palladium on carbon (15 mg). The mixture was hydrogenated using a Parr shaker set at 40 psi. After TLC indicated the absence of the starting material, the reaction was filtered through a 0.45 micron nylon membrane polypropylene filter and concentrated. FC (9:1 v/v hexanes/ethyl acetate followed by 2:1 v/v hexanes/ethyl acetate) of the residue afforded the title compound.

$^1$H NMR (400 MHz, CDCl$_3$): δ1.04–1.15 (m, 2 H), 1.27–1.49 (m, 3 H), 1.46 (s, 9 H), 1.68 (br d, J=12.7 Hz, 2 H), 1.85–1.93 (m, 2 H), 2.68 (br t, J=12.1 Hz, 2 H), 3.05 (t, J=7.7 Hz, 2 H), 4.08(br d, J=11.5 Hz, 2 H), 7.47(d, J=5.0 Hz, 1 H), 8.92 (d, J=5.0 Hz, 1 H).

Step E: 4-(3-((4-Trifluoromethyl)pyrimidin-2-yl)prop-1-yl) piperidine

The title compound was prepared from 1-(t-butoxycarbonyl)-4-(3-((4-trifluoromethyl)pyrimidin-2-yl) prop-1-yl)piperidine (from Step D) (17 mg, 0.046 mmol) using a procedure analogous to that described in Procedure 10, Step B. FC (95:5:0.5 v/v/v methylene chloride/methanol/ NH$_4$OH) afforded the title compound (22 mg).

$^1$H NMR (300 MHz, CDCl$_3$): δ1.21–3.45 (m, 15 H), 7.52 (d, J=5.0 Hz, 1 H), 8.95 (d, J=5.0 Hz, 1 H).

Procedure 13

4-(N-(Pyrimidin-2-yl)-N-(prop-1-yl)amino) piperidine di-hydrochloride salt

Step A: 4-Amino-1-t-butoxycarbonylpiperidine 1-t-Butoxycarbonylpiperidin-4-one (20 g, 100 mmol), benzylamine (11 mL, 100 mmol) and sodium triacetoxyborohydride (32 g, 150 mmol) were stirred together in 1,2-dichloroethane (400 mL) for 3 h. The resulting mixture was diluted with ethyl acetate (1 L) and washed with 1M aqueous sodium hydroxide (500 mL) followed by brine (500 mL). The organic phase was dried over sodium sulfate and concentrated to afford 4-N-benzylamino-1-t-butoxycarbonyl piperidine (30.1 g) as a viscous oil. The oil was dissolved in methanol (400 mL) and ammonium formate (39 g, 600 mmol) was added. The vessel was purged with nitrogen and 10% palladium-on carbon (6.5 g, 6 mmol) was added. The mixture was refluxed for 1 h and then filtered through celite and concentrated. Drying under vacuum afforded the title compound (20 g).

$^1$H NMR (300 MHz, CDCl$_3$): δ1.15–1.3 (m, 2 H), 1.43 (s, 9 H), 1.7–1.9 (m, 4 H), 2.65–2.72 (m, 3 H), 3.95–4.1 (m, 2 H).

Step B: 4-(N-(Pyrimidin-2-yl)amino)-1-t-butoxycarbonylpiperidine

4-Amino-1-t-butoxycarbonylpiperidine from Step A, (1.9 g, 9.5 mmol), 2-chloropyrimidine (1.1 g, 9.5 mmol) and DIPEA (3.3 mL, 19 mmol) were combined in isopropanol (10 mL) and the mixture was refluxed for 24 h. The mixture was cooled, diluted with methylene chloride (100 mL) and washed with water and brine. The organic phase was dried over sodium sulfate and concentrated. FC (60 g silica, 1/1 hexanes/ethyl acetate) afforded the title compound (0.97 g).

$^1$H NMR (300 MHz, CDCl$_3$): δ1.31–1.45 (m, 2 H), 1.44 (s, 9 H), 2.0–2.1 (m, 2 H), 2.9–3.0 (m, 2 H), 3.9–4.1 (m, 3 H), 5.0–5.05 (m, 1 H), 6.5–6.58, (t, 1 H), 8.15–8.2 (d, 2 H).

Step C: 4-(N-(Pyrimidin-2-yl)-N-(allyl)amino)-1-t-butoxycarbonyl-piperidine

A solution of 4-(N-(pyrimidin-2-yl)amino)-1-t-butoxycarbonylpiperidine from Step B (528 mg, 1.9 mmol) in dry THF (5 mL) was cooled to −78° C. and a solution of sodium hexamethyldisilazide (2.8 mL, 1.0 M in THF, 2.8 mmol) was added via syringe. The mixture was stirred cold for 20 min then allyl bromide (0.23 mL, 2.7 mmol) was added. The mixture was then warmed to rt and stirred for 1.5 h at which time TLC showed very little starting material. The solution was poured into sat'd ammonium chloride and methylene chloride. The layers were separated and the organic phase was dried over sodium sulfate and concentrated. FC (25 g silica, 4/1 hexanes/ethyl acetate) afforded the title compound (367 mg).

$^1$H NMR (300 MHz, CDCl$_3$): δ1.45 (s, 9 H), 1.6–1.8 (m, 4 H), 2.75–2.85 (m, 2 H), 4.1–4.3 (m, 4 H), 4.74.8 (m, 1 H), 5.05–5.17 (m, 2 H), 5.92–5.98 (m, 1 H), 6.4–6.5 (t, 1 H), 8.3–8.35 (d, 2 H).

Step D: 4-(N-(Pyrimidin-2-yl)-N-(prop-1-yl)amino) piperidine di-hydrochloride salt In a round bottom flask purged with nitrogen 4-(N-(pyrimidin-2-yl)-4-N-(allyl)amino)-1-t-butoxylcarbonylpiperidine from Step C (461 mg, 1.45 mmol) was dissolved in methanol (4 mL) and 10% palladium on carbon (150 mg, 0.14 mmol) was added. The mixture was stirred under 1 atm of hydrogen using a balloon for 1.5 h. The mixture was filtered through celite and concentrated. FC (20 g silica, 3/1 hexanes/ethyl acetate) afforded 4-(N-(pyrimidin-2-yl)4-N-(prop-1-yl)amino)-1-t-butoxylcarbonylpiperidine.

$^1$H NMR (400 MHz, CDCl$_3$). δ0.9–1.0 (t, 3H, J=7 Hz), 1.5 (s, 9 H), 1.6–1.8 (m, 6 H), 2.8–2.9 (m, 2 H), 3.33–3.4 (m, 2 H), 4.2–4.27 (m, 2 H), 4.7–4.8 (m, 1 H), 6.42–6.45 (t, 1 H), 8.3–8.35 (d, 2 H).

This material was dissolved in 2% conc. HCl/methanol and heated to 50° C. for 2 h. Removal of solvent and drying under vacuum afforded the title compound as a white solid.

Procedure 14

4-(3-(3,4-Difluorophenyl)prop-1-yl)piperidine hydrochloride salt

Starting with 4-(prop-2-en-1-yl)-1-t-butoxycarbonylpiperidine from Procedure 5, Step B and using essentially the same methods as in Procedure 5, Step D, but substituting 3,4-difluorobromobenzene, the title compound was obtained as the hydrochloride.

Procedure 15

4-(5-Benzyl-1-(prop-1-yl)-(1H)-pyrazol-3-yl)piperidine di-hydrochloride salt (Higher R$_f$ isomer) and 4-(3-benzyl-1-(prop-1-yl)-(1H)-pyrazol-5-yl)piperidine di-hydrochloride salt (Lower R$_f$ isomer)

Using essentially the same methods as in Procedure 1, Step B–C, but substituting propylhydrazine for ethylhydrazine in Step B, the title compounds were prepared.

Procedure 16

4-(3,3-Difluoro-3-phenylprop-1-yl)piperidine

Step A: 1-(Benzyloxycarbonyl)-4-(3-oxo-3-phenylprop-1-en-1-yl)piperidine

DIPEA (4.6 mL, 3.4 g, 26 mmol) was added to a solution of 4-(hydroxymethyl)piperidine (2.00 g, 17.4 mmol) dissolved in methylene chloride (20 mL). The solution was cooled in an ice bath and benzyl chloroformate (2.5 mL, 3.0 g, 18 mmol) was added dropwise over 10 min. After warming to rt and stirring for 96 h, the mixture was diluted with ethyl acetate (50 mL) and washed in succession with 25 mL each of saturated aq. sodium bicarbonate, 2N aq. HCl, saturated aq. sodium bicarbonate, and saturated aq. brine. The organic layer was dried (sodium sulfate), decanted, and evaporated to give 4.14 g of 1-(benzyloxycarbonyl)-4-(hydroxymethyl)piperidine.

1,1,1-Triacetoxy-1,1-dihydro-1,2-benzoiodoxol-3(1H)-one (1.92 g, 4.53 mmol) was added to a solution of 1-(benzyloxycarbonyl)-4-(hydroxymethyl)piperidine (1.00 g, 4.01 mmol) in methylene chloride (20 mL) and the mixture was stirred at rt for 45 min. Ether (75 mL) and 1.3 N aq. NaOH (25 mL) were added and stirring was continued for 15 min. The mixture was transferred to a separatory funnel with additional ether (30 mL) and 1.3 N aq. NaOH (20 mL). The organic layer was separated, washed with saturated aq. brine (20 mL), dried (sodium sulfate), decanted, and evaporated to give 846 mg of 1-(benzyloxycarbonyl)4-piperidine carboxaldehyde as a colorless syrup.

Diethyl (2-oxo-2-phenylethyl)phosphonate (0.96 mL, 1.1 g, 4.4 mmol) was added in one portion to a stirred suspension of sodium hydride (60% oil dispersion, 158 mg, 3.95 mmol) in THF (20 mL). After 15 min. at rt, the clear solution was cooled in an ice bath and 1-(benzyloxycarbonyl)-4-piperidinecarboxaldehyde (840 mg, 3.40 mmol) was added in THF (1.0 mL) with additional THF (2×1.0 mL) for rinsing. Stirring was continued for a total of 2 h, with slow warming to rt. The mixture was then partitioned between ether (120 mL) and 2.5 N aq. NaOH (60 mL). The organic layer was washed with saturated aq. brine (60 mL), dried (sodium sulfate), decanted, and evaporated. The crude product was purified by FC, eluting with 15–20% ethyl acetate in hexane, to give 0.95 g of the title compound as a colorless syrup.

$^1$H NMR (400 MHz, CDCl$_3$): δ7.82 (d, J=8 Hz, 2 H), 7.57 (t, J=8 Hz, 1 H), 7.48 (t, J=8 Hz, 2 H), 7.39–7.29 (m, 5 H), 6.99 (dd, J=15, 6 Hz, 1 H), 6.87 (dd, J=15 and 1 Hz, 1 H), 5.15 (s, 2 H), 2.97–2.82 (m, 2 H), 2.50–2.39 (m, 1 H), 1.89–1.77 (m, 2 H), 1.54–1.39 (m, 2 H). MS (ESI): m/z 367 (M+NH$_3$+H).

Step B: 2-(2-(1-(Benzyloxycarbonyl)piperidin-4-yl)ethyl)-2-phenyl-1,3-dithiolane 1-(Benzyloxycarbonyl)-4-(3-oxo-3-phenylprop-1-en-1-yl)piperidine from Step A (0.95 g, 2.7 mmol) was hydrogenated using 5% Pd/C (10 mg) in 95% ethanol (20 mL) at atmospheric pressure. After 3.5 h, the mixture was filtered and the catalyst was washed with 95% ethanol. Evaporation of the filtrate gave 0.95 g of 1-(benzyloxycarbonyl)-4-(3-oxo-3-phenylprop-1-yl)piperidine as a colorless syrup.

Boron trifluoride-acetic acid complex (BF$_3$.2-CH$_3$CO$_2$H, 0.370 mL, 501 mg, 2.67 mmol) was added to a solution of 1,2-ethanedithiol (0.440 mL, 494 mg, 5.25 mmol) and (1-(benzyloxycarbonyl)-4-(3-oxo-3-phenylprop-1-yl) piperidine (930 mg, 2.65 mmol) in methylene chloride (4.0 mL) at rt. After 6 h, the mixture was diluted with ether (50 mL) and washed with saturated aq. sodium bicarbonate (2×25 mL), 2.5 N aq. NaOH (25 mL), and saturated aq. brine (25 mL). The organic layer was dried (sodium sulfate), decanted, and evaporated. The crude product was purified by FC, eluting with 10% ethyl acetate in hexane, to give 1.05 g of the title compound as a colorless liquid.

$^1$H NMR (400 MHz, CDCl$_3$): δ7.66 (d, J=8 Hz, 2 H), 7.38–7.26 (m, 7 H), 7.22 (t, J=8 Hz, 1 H), 5.10 (s, 2 H), 4.18–4.02 (m, 2 H), 3.41–3.32 (m, 2 H), 3.29–3.20 (m, 2 H), 2.79–2.62 (m, 2 H), 2.40–2.32 (m, 2 H), 1.65–1.54 (m, 2 H), 1.40–1.27 (m, 1 H), 1.24–1.16 (m, 2 H), 1.10–0.97 (m, 2 H); HPLC/MS (ESI): m/z 428 (M+H); HPLC: 4.21 min.

Step C: 1-(t-Butoxycarbonyl)-4-(3,3-difluoro-3-phenylprop-1-yl)piperidine 1,3-Dibromo-5,5-dimethylhydantoin (74 mg, 0.26 mmol) was stirred with methylene chloride (0.50 mL) at rt, and the suspension was then cooled in a dry ice/isopropanol bath. After 5 min., hydrogen fluoride.pyridine (70% HF, 0.18 mL) was added over 1 min. After 5 min., a solution of 2-(2-(1-(benzyloxycarbonyl)piperidin-4-yl)ethyl)-2-phenyl-1,3- dithiolane from Step B (100 mg, 0.234 mmol) in methylene chloride (0.20 mL) was added over 1 min. After 10 min, the reaction mixture was diluted into methylene chloride (25 mL) and washed with water (10 mL) containing sodium bisulfite (0.5 g). The organic layer was washed with saturated aq. sodium bicarbonate (2×10 mL) followed by saturated aq. brine (10 mL), dried (sodium sulfate), decanted, and evaporated to give 98 mg of colorless syrup. This material was combined with 195 mg of crude product from two similar reactions and purified by FC, eluting with 8% ethyl acetate in hexane, to give 247 mg of 1-(benzyloxycarbonyl)-4-(3,3-difluoro-3-phenylprop-1-yl) piperidine ($R_f$: 0.3 using 10% ethyl acetate in hexane) containing some residual impurity.

The partially purified 1-(benzyloxycarbonyl)-4-(3,3-difluoro-3-phenylprop-1-yl)piperidine (247 mg) was hydrogenated at atmospheric pressure in 95% ethanol (4.0 mL) containing 20% $Pd(OH)_2$/C (60 mg). After 6 h, additional 20% $Pd(OH)_2$/C (32 mg) was added and the hydrogenation was continued for another 16 h. The mixture was filtered and the catalyst was washed with 95% ethanol. Evaporation of the filtrate gave 164 mg of crude 4-(3,3-difluoro-3-phenylprop-1-yl)piperidine as a colorless syrup.

Di-t-butyl dicarbonate (178 mg, 0.816 mmol) was transferred with methylene chloride (2×0.5 mL) to a solution of crude 4-(3,3-difluoro-3-phenylprop-1-yl)piperidine (164 mg) in methylene chloride (2.0 mL). After stirring at rt for 1 h, the solution was stored at −20° C. for 48 h. The mixture was then diluted into ethyl acetate (25 mL) and washed with saturated aqueous sodium bicarbonate (10 mL) followed by saturated aqueous brine (10 mL). The organic layer was dried (sodium sulfate), decanted, and evaporated. The crude product was purified by FC, eluting with 4–5% ethyl acetate in hexane to give the title compound as 112 mg of colorless syrup. $R_f$: 0.25 (5% ethyl acetate in hexane).

$^1$H NMR (400 MHz, $CDCl_3$): δ7.50–7.40 (m, 5 H), 4.24–3.99 (m, 2 H), 2.64 (bt, J=12 Hz, 2 H), 2.14 (tm, J=16 Hz, 2 H), 1.62 (bd, J=12 Hz, 2 H), 1.45 (s, 9 H), 1.42–1.33 (m, 3 H), 1.13–1.00 (m, 2 H).

Step D: 4-(3,3-Difluoro-3-phenylprop-1-yl)piperidine

Trifluoroacetic acid (2.5 mL, 3.7 g, 32 mmol) was added dropwise to a solution of 1-(t-butoxycarbonyl)4-(3,3-difluoro-3-phenylprop-1-yl)piperidine from Step C (42 mg, 0.12 mmol) in methylene chloride (2.5 mL) at 0° C. After 80 min., the solution was transferred using a double-ended needle to a rapidly stirred solution of sodium bicarbonate (5.0 g, 60 mmol) in water (50 mL). Ether (50 mL) and 2.5 N aq. NaOH (20 mL) were added, followed by solid brine to saturate the aqueous layer. The aqueous layer was separated and extracted with ether (50 mL). The organic layers were washed in succession with saturated aq. brine (20 mL), combined, dried (sodium sulfate), decanted, and evaporated to give the title compound as 27 mg of colorless oil.

$^1$H NMR (400 MHz, $CD_3OD$): δ7.51–7.40 (m, 5 H), 2.98 (dm, J=12 Hz, 2 H), 2.53 (td, J=12 and 3 Hz, 2 H), 2.24–2.10 (m, 2 H), 1.65 (bd, J=12 Hz, 2 H), 1.42–1.26 (m, 3 H), 1.06 (qd, J=12 and 4 Hz, 2 H). HPLC/MS (ESI): m/z 240 (M+H); HPLC: 2.25 min.

Procedure 17

4-(3,3-Difluoro-3-(4-fluorophenyl)prop-1-yl) piperidine

Step A: 1-(t-Butoxycarbonyl)-4-(hydroxymethyl)piperidine

Di-t-butyl dicarbonate (4.69 g, 21.5 mmol) was transferred in methylene chloride (9 mL) over 10 min. to a solution of 4-(hydroxymethyl)piperidine (2.47 g, 21.4 mmol) in methylene chloride (16 mL). After stirring at rt for 1 h, the solution was diluted with ether (50 mL) and washed with 2 N aq. HCl, saturated aq. sodium bicarbonate, and saturated aq. brine (25 mL of each). The organic layer was dried (sodium sulfate), decanted, and evaporated to give 4.57 g of the title compound as a crystalline solid.

$^1$H NMR (500 MHz, $CD_3OD$): δ4.08 (d, J=14 Hz, 2 H), 3.40 (d, J=6 Hz, 2 H), 2.81–2.67 (m, 2 H), 1.71 (d, J=13 Hz, 2 H), 1.67–1.58 (m, 1 H), 1.44 (s, 9 H), 1.09 (qd, J=12 and 4 Hz, 2 H).

Step B: 1-(t-Butoxycarbonyl)-4-(iodomethyl)piperidine

Methanesulfonyl chloride (4.10 mL, 6.07 g, 52.9 mmol) was added dropwise to a solution of 1-(t-butoxycarbonyl)-4-(hydroxymethyl)piperidine from Step A (10.0 g, 46.4 mmol) and triethylamine (9.80 mL, 7.11 g, 70.3 mmol) in methylene chloride (140 mL) at 5–8° C. After 1 h, the mixture was diluted with ethyl acetate (400 mL) and washed with water (200 mL). The aqueous layer was extracted with ethyl acetate (2×150 mL) and the combined organic layers were washed with 1 N aq. HCl (200 mL), saturated aq. sodium bicarbonate (200 mL), and saturated aq. brine (200 mL). The organic layer was dried (sodium sulfate), decanted, and evaporated to give 13.58 g of 1-(t-butoxycarbonyl)piperidin-4-yl methanesulfonate as a pale yellow solid.

A mixture of 1-(t-butoxycarbonyl)piperidin-4-yl methanesulfonate (13.58 g, 46.4 mmol) and sodium iodide (34.68 g, 232 mmol) in acetone (80 mL) was heated to reflux for 3 h. The mixture was partitioned between ether (350 mL) and water (350 mL). The organic layer was washed with saturated aq. brine (250 mL), and the aqueous layers were extracted in succession with ether (250 mL). The combined organic layers were dried (sodium sulfate), decanted, and evaporated to give the title compound (14.8 g) as a pale yellow oil.

$^1$H NMR (500 MHz, $CDCl_3$): δ4.25–4.00 (m, 2 H), 3.12 (d, J=4 Hz, 2 H), 2.78–2.52 (m, 2 H), 1.85 (d, J=13 Hz, 2 H), 1.68–1.56 (m, 1 H), 1.48 (s, 9 H), 1.15 (qd, J=12 and 4 Hz, 2 H).

Step C: ((1-(t-Butoxycarbonyl)piperidin-4-yl)methyl) triphenylphosphonium iodide A solution of triphenylphosphine (6.63 g, 25.3 mmol) and 1-(t-butoxycarbonyl)-4-(iodomethyl)piperidine from Step B (7.96 g, 24.5 mmol) in acetonitrile (40 mL) was heated to reflux for 72 h. The solution was evaporated to give 13.35 g of white solid. A portion (12.34 g) of this material was dissolved in acetonitrile (25 mL) at 65° C. Ethyl acetate (35 mL) was added and the mixture was allowed to cool slowly to rt and then to −20° C. The supernatant was decanted, and the colorless crystals were washed with ethyl acetate (5×5 mL) and dried under vacuum to give 9.25 g of the title compound.

$^1$H NMR (500 MHz, $CD_3OD$): δ7.89 (t, J=8 Hz, 3 H), 7.86 (dd, J=12 and 8 Hz, 6 H), 7.76 (td, J=8 and 4 Hz, 6 H), 3.91 (bd, J=13 Hz, 2 H), 3.44 (dd, J=14 and 6 Hz, 2 H), 2.72–2.58 (m, 2 H), 2.08–1.96 (m, 1 H), 1.49 (bd, J=12 Hz, 2 H), 1.41 (s, 9 H), 1.43 (qd, J=13 and 4 Hz, 2 H).

Step D: Methyl (4-fluorobenzoyl)formate

Dimethyl oxalate (5.90 g, 50 mmol) was dissolved in THF (50 mL) and ether (50 mL) in a 3-neck round bottom flask fitted with a mechanical stirrer. The solution was stirred vigorously at −65° C. as a 1.0 M THF solution of 4-fluorophenylmagnesium bromide (60 mL, 60 mmol) was added dropwise over 40 min. The mixture was stirred 30 min at −65° C. and allowed to warm to −20° C. over 30 min before being poured into 2N aq. HCl (50 mL) with stirring. The layers were separated and the aq. layer was extracted with ether (3×50 mL). The combined organic layers were washed with saturated aq. brine (2×50 mL), dried (sodium sulfate), decanted, and evaporated. The residue was dissolved in ethyl acetate, dried (sodium sulfate), filtered, and evaporated to give a yellow solid. The crude product was dissolved in warm hexane (25 mL), filtered, and cooled to −20° C. Filtration followed by washing with cold hexane (15 mL) gave 4.95 g of the title compound as light tan crystals.

$^1$H NMR (500 MHz, CDCl$_3$): δ8.11 (dd, J=9 and 5, Hz, 2 H), 7.21 (t, J=9 Hz, 2 H), 4.00 (s, 3 H).

Step E: Methyl difluoro(4-fluorophenyl)acetate

Methyl (4-fluorobenzoyl)formate from Step D (4.75 g, 26.1 mmol) was added to (diethylamino)sulfur trifluoride (7.0 mL, 8.5 g, 53 mmol). The mixture was stirred rapidly and an ice bath was used briefly to reduce the temperature to 15° C. After the ice bath was removed, the reaction temperature rose to 48° C. over 10 min and then slowly returned to rt. After a total of 2.75 h, the solution was carefully poured onto crushed ice (30 g) and the mixture was extracted with methylene chloride (2×25 mL). The organic layers were washed in succession with saturated aq. sodium bicarbonate (2×25 mL) and saturated aq. brine (10 mL), combined, dried (sodium sulfate) decanted, and evaporated. The residue was distilled to give the title compound as 4.16 g of light yellow liquid, B.P. 46–48° C. (0.5 mm Hg).

$^1$H NMR (500 MHz, CDCl$_3$): δ7.63 (dd, J=9, 5 Hz, 2 H), 7.16 (d, J=9 Hz, 2 H), 3.88 (s, 3 H).

Step F: 1-(t-Butoxycarbonyl)-4-(3,3-difluoro-3-(4-fluorophenyl)prop-1-en-1-yl)piperidine A solution of methyl difluoro(4-fluorophenyl)acetate (2.04 g, 10.0 mmol) from Step E in methanol (10.0 mL) was cooled to −60° C. Sodium borohydride (380 mg, 10.0 mmol) was added in 5 portions at 10 to 15 min. intervals. The mixture was cooled to −60 to −55° C. prior to each addition and allowed to warm to −45° C. following each addition. After the last addition, the mixture was stirred 1.25 h at −50 to −45° C. The mixture was cooled to −60° C. and quenched with 1 N aq. HCl (30 mL), with the temperature rising to −20° C. near the end of the addition. After warming to 0° C., the mixture was extracted with ether (3×20 mL). The combined ether layers were washed with water (2×20 mL), dried (sodium sulfate), decanted, and evaporated to give 1.95 g of crude 2,2-difluoro-2-(4-fluorophenyl)-1-methoxyethanol as a pale yellow oil.

A suspension of ((1-(t-butoxycarbonyl)piperidin-4-yl)methyl)triphenylphosphonium iodide (500 mg, 0,92 mmol) from Step C in THF (7.2 mL) was stirred at rt for 30 min. A 0.5 M toluene solution of potassium bis(trimethylsilyl)amide (1.8 mL, 0.90 mmol) was added over 3 min., giving an orange suspension. After 30 min., crude 2,2-difluoro-2-(4-fluorophenyl)-1-methoxyethanol (95 mg, 0.46 mmol) was added in THF (1.0 mL). After an additional 30 min, the mixture was quenched by the addition of saturated aq. NH$_4$Cl (2 mL). The mixture was partitioned between ethyl acetate (50 mL) and water (75 mL), and the aqueous layer was extracted with ethyl acetate (50 mL). The organic layers were washed in succession with saturated aq. brine (25 mL), dried (sodium sulfate), decanted, and evaporated. The crude product was purified by FC, eluting with 10% ether in hexane to give 117 mg of the title compound as a 95:5 mixture of cis and trans isomers, respectively.

$^1$H NMR (500 MHz, CDCl$_3$): δ7.55 (dd, J=9 and 5 Hz, 2 H), 7.13 (t, J=9 Hz, 2 H), 5.76 (q, J=12 Hz, 1 H), 5.64 (dd, J=12 and 10 Hz, 1 H), 4.20–3.95 (m, 2 H), 2.80–2.54 (m, 3 H), 1.54 (bd, J=12 Hz, 2 H), 1.47 (s, 9 H), 1.26 (qd, J=12 and 4 Hz, 2 H).

Step G: 1-(t-Butoxycarbonyl)-4-(3,3-difluoro-3-(4-fluorophenyl)propyl)piperidine Potassium azodicarboxylate (695 mg, 3.58 mmol) was added to a solution of 1-(t-butoxycarbonyl)-4-(3,3-difluoro-3-(4-fluorophenyl)prop-1-en-1-yl)piperidine from Step F (424 mg, 1.19 mmol) in methanol (3.3 mL). The mixture was stirred at rt as a 9.0 M solution of acetic acid in methanol (0.80 mL, 7.2 mmol) was added over 3 h using a syringe pump. After 30 min., a second portion of potassium azodicarboxylate (695 mg, 3.58 mmol) was added followed by the addition of 9.0 M acetic acid in methanol (0.80 mL, 7.2 mmol) over 3 h. After 20 min, a third portion of potassium azodicarboxylate (695 mg, 3.58 mmol) was added followed by the addition of 9.0 M acetic acid in methanol (0.80 mL, 7.2 mmol) over 3 h. After stirring for 20 h at rt, the mixture was diluted with ethyl acetate (80 mL), and washed with 2 N aq. HCl (40 mL), saturated aq. sodium bicarbonate (40 mL), and saturated aq. brine (40 mL). The organic layer was dried (sodium sulfate), decanted, and evaporated to give 417 mg of a mixture containing the title compound and 20–25% of unreduced 1-(t-butoxycarbonyl)-4-(3,3-difluoro-3-(4-fluorophenyl)prop-1-en-1-yl)piperidine.

A portion (365 mg) of the crude mixture containing residual olefin was hydrogenated at atmospheric pressure for 16 h using iridium black (30 mg) in a mixture of t-butanol (24 mL) and ethyl acetate (2.4 mL). The mixture was filtered, the catalyst was washed with methanol, and the filtrate was evaporated to give 371 mg of the title compound as a pale yellow syrup. R$_f$: 0.2 (5% ethyl acetate in hexane).

$^1$H NMR (500 MHz, CDCl$_3$): δ7.46 (dd, J=9 and 5 Hz, 2 H), 7.12 (t, J=9 Hz, 2 H), 4.18–4.00 (m, 2 H), 2.73–2.61 (m, 2 H), 2.14 (tm, J=16 Hz, 2 H), 1.64 (bd, J=12 Hz, 2 H), 1.46 (s, 9 H), 1.46–1.33 (m, 3 H), 1.08 (qd, J=12 and 4 Hz, 2 H).

Step H: 4-(3,3-Difluoro-3-(4-fluorophenyl)prop-1-yl)piperidine 1-(t-Butoxycarbonyl)-4-(3,3-difluoro-3-(4-fluorophenyl)prop-1-yl)piperidine from Step G (122 mg, 0.34 mmol) was dried by evaporation of a toluene solution at reduced pressure. The residue was dissolved in chloroform (7.6 mL) and iodotrimethylsilane (0.100 mL, 141 mg, 0.70 mmol) was added. After stirring 30 min at rt, the solution was poured into a mixture of saturated aqueous sodium bicarbonate (15 mL) and 2.5 N aq. NaOH (5 mL), and extracted with ether (50 mL). The organic layer was washed with saturated aq. brine (15 mL), dried (sodium sulfate), decanted, and evaporated to give the title compound as 88 mg of colorless oil.

$^1$H NMR (500 MHz, CD$_3$OD): δ7.51 (dd, J=9 and 5 Hz, 2 H), 7.17 (t, J=9 Hz, 2 H), 2.98 (dm, J=12 Hz, 2 H), 2.52 (td, J=12, 3 Hz, 2 H), 2.17 (tm, J=16 Hz, 2 H), 1.65 (bd, J=13 Hz, 2 H), 1.42–1.26 (m, 3 H), 1.07 (qd, J=12 and 4 Hz, 2 H). HPLC/MS (ESI): m/z 258 (M+H); HPLC: 2.64 min.

Procedure 18

4-(2-((4-Fluorophenyl)sulfonyl)eth-1-yl)piperidine trifluoroacetic acid salt

Step A: 4-(2-hydroxyeth-1-yl)piperidine acetic acid salt

Combined 4-(2-hydroxyeth-1-yl)pyridine (25 g, 0.2 mol) and platinum oxide (1 g, 4.4 mmol) in 400 mL acetic acid. Placed under 45 psi hydrogen at 60° C. for 24 h. Decanted, then filtered through Celite and removed the solvent to afford 38 g (100%) of the crude product, which was used without further purification.

Step B: 4-(2-hydroxyeth-1-yl)-1-tert-butoxycarbonylpiperidine

Dissolved sodium bicarbonate (134 g, 1.6 mol) and 4-(2-hydroxyeth-1-yl)piperidine acetic acid salt (38 g, 0.2 mol, from Step A) in 500 mL of 50% tetrahydrofuran in water. Added di-tert-butyl dicarbonate (35 g, 0.2 mol) and stirred at rt overnight. Diluted with ethyl acetate and extracted the aq. layer with 2×300 mL of ethyl acetate. Washed the combined organic layers with 2×300 mL of 1 N HCl and brine. Dried over magnesium sulfate and concentrated to afford 37.4 g (81%) of the title compound.

ESI-MS: 230 (M+H); HPLC A: 2.76 min.

Step C: 4-(2-Iodoeth-1-yl)-1-tert-butoxycarbonylpiperidine

Combined 4-(2-hydroxyeth-1-yl)-1-tert-butoxylcarbonylpiperidine (37.4 g, 0.16 mol, from Step B), triphenylphosphine (55 g, 0.21 mol) and imidazole (14 g, 0.21 mol) in 800 mL of 33% acetonitrile in ether. Cooled to 0° C. and added iodine (56 g, 0.22 mol) portionwise. The iodine is de-colored until the endpoint of the reaction. Diluted with 1 L of ether. Washed organic layer with 2×500 mL each of sat'd. aq. $Na_2S_2O_3$, sat. aq. $CuSO_4$ and brine. Dried over magnesium sulfate, filtered and concentrated. Triphenylphosphine oxide precipitates. Added ether and filtered the slurry through a plug of silica gel. Purified a portion of the crude material by flash chromatography (5% ethyl acetate in hexane eluent) to afford the title compound.

$^1$H-NMR (400 MHz, $CDCl_3$): δ4.10 (br s, 2 H), 3.23 (t, 2 H, J=7.2 Hz), 2.72 (br t, 2 H, 12.3 Hz), 1.79 (q, 2 H, J=7 Hz), 1.67 (br d, 2 H, 14 Hz), 1.61 (m, 1 H), 1.47 (s, 9 H), 1.14 (qd, 2 H, J=4.3, 12 Hz); ESI-MS: 340 (M+H); HPLC A: 3.74 min.

Step D: 4-(2-(4-Fluorophenylthio)eth-1-yl)-1-tert-butoxycarbonylpiperidine

To a slurry of sodium hydride (47 mg, 60% in mineral oil, 1.2 mmol) in tetrahydrofuran at 0° C. was added 4-fluorothiophenol (0.1 mL, 0.94 mmol). The reaction mixture was warmed to rt. for 20 min, followed by addition of 4-(2-iodoeth-1-yl)-1-tert-butoxycarbonylpiperidine (265 mg, 0.78 mmol, from Step C). The reaction was then heated to reflux for 10 min, cooled and diluted with ether. The organic layer was washed with 1 N NaOH, dried over magnesium sulfate and concentrated to provide 252 mg (95%) of the title compound. ESI-MS: 340.0 (M+H); HPLC A: 4.07 min.

Step E: 4-(2-(4-Fluorophenylsulfonyl)eth-1-yl)piperidine trifluoroacetic acid salt Added a solution of oxone (1.14 g, 1.86 mmol) in water to a solution of 4-(2-(4-fluorophenylthio)eth-1-yl)-1-tert-butoxycarbonylpiperidine (252 mg, 0.74 mmol, from Step D) in methanol at 0° C. Warmed to rt. After 90 min., added an additional 0.5 g of oxone. After 3 h, the reaction mixture was diluted with methylene chloride and washed with 1 N NaOH containing sodium bisulfite. The aq. layer was extracted twice with methylene chloride, and the combined organic layers were dried over magnesium sulfate. The solution was concentrated and dissolved in 5% trifluoroacetic acid in methylene chloride for 1 h. The solvent was evaporated to afford 297 mg (100%) of the title compound. ESI-MS: 239.8 (M+H); HPLC A: 2.54 min.

Procedure 19

4-((5-Benzyl)pyrid-3-yl)piperidine di-TFA salt

Step A: N-tert-Butoxycarbonyl-1,2,5,6-tetrahydropyridine-4-trifluoromethane sulfonate.

A dry flask under nitrogen was charged with a solution of sodium hexamethyldisilazide (11 mL, 1.0 M in THF) and was cooled to −78° C. A solution of N-tert-butoxycarbonyl-4-piperidone (2.0 g, 10 mmol) in 10 mL THF was added dropwise via cannula. After 30 min. a solution of 2-(N,N-bis(trifluoromethanesulfonyl)amino-5-chloropyridine (4.7 g, 12 mmol) in 15 mL THF was added. The mixture was warmed to room temperature, quenched with sat'd ammonium chloride and extracted with ethyl acetate. The ethyl acetate layer was separated and washed with sat'd brine then dried over sodium sulfate and concentrated. Flash chromatography (100 g silica, 10/1 Hexane/ethyl acetate) afforded 1.9 g (58%) of the title compound.

$^1$H NMR (400 MHz, $CDCl_3$). δ1.5 (s, 9H), 2.4–2.48 (m, 2H), 3.62–3.68 (t, 2H), 4.05–4.07 (m, 2H), 5.77–5.8 (bs, 1H).

Step B: N-tert-Butoxycarbonyl-4-trimethylstannyl-1,2,5,6-tetrahydropyridine

A dry flask under nitrogen was charged with 20 mL THF, lithium chloride (1.6 g, 37.3 mmol), tetrakistriphenylphosphine palladium(0), (331 mg, 0.28 mmol) and hexamethyldistannane (1.2 mL, 5.7 mmol). N-tert-butoxycarbonyl-1,2,5,6-tetrahydropyridine-4-trifluoromethane sulfonate (1.9 g, 5.7 mmol) was added and the mixture was stirred overnight at 60° C. The mixture was diluted with water and extracted with ethyl acetate (3×150 mL). The combined organic layers were dried over sodium sulfate and concentrated. Flash chromatography (100 g silica, 20/1 Hexane/ethyl acetate) afforded 1.56 g (79%) of the title compound.

$^1$H NMR (300 MHz, $CDCl_3$). δ0.5 (s, 9H), 1.5 (s, 9H), 2.25–2.35 (m, 2H), 3.62–3.68 (t, 2H), 3.95–3.97 (m, 2H), 5.77–5.8 (bs, 1H).

Step C: 3-Bromo-5-benzylpyridine

A dry flask under nitrogen was charged with zinc chloride (16 mL, 0.5 M in THF, 8 mmol), and a solution of phenylmagnesium chloride (4 mL, 2.0 M in THF, 8 mmol). The mixture was heated to 50° C. for 3h then cooled to room temperature and transferred via cannula to a solution of 3,5-dibromopyridine (1.26 g, 5.3 mmol), copper iodide (61 mg, 0.32 mmol), and bis(diphenylphosphino)ferrocene palladium dichloride (218 mg, 0.27 mmol) in 15 mL THF. The resulting mixture was heated to 50° C. overnight. Sat'd ammonium chloride was added and the mixture was extracted with ethyl acetate. The organic portion was dried over sodium sulfate and concentrated. Flash chromatography (8/1 hexanelethyl acetate) afforded 433 mg (33 %) of the title compound. $^1$H NMR (400 MHz, $CDCl_3$), δ4.02 (s, 2H), 7.18–7.4 (m, 8H), 7.65 (s, 1H).

Step D: 4-((5-Benzyl)pyrid-3-yl)piperidine di-TFA

A flask was purged with nitrogen and charged with DMF, 3-bromo-5-benzylpyridine (618 mg, 2.5 mmol, from Step C), tetrakis triphenylphosphine palladium (58 mg, 0.05 mmol), and N-tert-butoxycarbonyl-4-trimethylstannyl-1,2, 5,6-tetrahydropyridine (1.04 g, 3 mmol). The mixture was heated to 100° C. and stirred for 10 h. An additional portion of tetrakis triphenylphosphine palladium (40 mg, 0.03 mmol) was added and stirring was continued for 14 h. The solution was cooled and diluted with ethyl acetate then washed with water, dried over sodium sulfate and concentrated. Flash chromatography (2.5/1 hexane/ethyl acetate) afforded 590 mg (67%) of the coupling product. The product was dissolved in 4 mL methanol and 50 mg 10% Pd/C was added. The mixture was stirred under 1 atm of hydrogen for 3 h. The catalyst was filtered off and the residue was dissolved in 1/1 TFA/methylene chloride. Removal of the solvent and drying under vacuum afforded the title compound as its TFA salt.

$^1$H NMR (500 MHz, $CDCl_3$). δ1.55–1.64 (m, 2H), 1.75–1.8 (d, 2H), 2.57–2.62 (m, 1H), 2.68–2.73 (t, 2H), 3.15–3.2 (d, 2H), 7.14–7.15 (d, 2H), 7.19–7.21 (m, 1H(, 7.26–7.32 (m, 3H), 8.30–8.31 (d, 2H).

Procedure 20

4-(2-(Benzyl)-(2H)-tetrazol-5-yl)piperidine

Step A: 1-(t-Butoxycarbonyl)-4-cyanopiperidine

Isonipecotamide (10.0 g, 78.0 mmol) was added in portions to 25 mL of $POCl_3$ at 0° C. The cooling was removed and the mixture was allowed to reach rt. The mixture was heated at reflux for 2 h, then cooled to rt. The mixture was poured onto 100 g of ice. The pH of the aqueous mixture was adjusted to 11 with solid KOH and extracted with 4×200 mL of methylene chloride. The extracts were combined, dried over magnesium sulfate and concentrated to afford 8.0 g of crude (4-cyano)piperidine.

The crude (4-cyano)piperidine was dissolved in 50 mL of methanol and treated with 17.0 g (78.0 mmol) of di-t-butyl dicarbonate and the resulting mixture was stirred at rt for 1 h. The mixture was concentrated. Flash chromatography on 250 g of silica gel using 1:1 v/v hexanes/ether afforded 13.4 g (80%) of the title compound:

$^1H$ NMR (300 MHz) δ1.46 (s, 9H), 1.76–1.96 (4H), 2.78–2.82 (m, 1H), 3.3—3.37 (m, 2H), 3.63–3.69 (m, 2H).

Step B: 1-(t-Butoxycarbonyl)4-(1H-tetrazol-5-yl)piperidine

A mixture of 2.10 g (10.0 mmol) of 1-(t-butoxycarbonyl)-4-cyanopiperidine (from Step A), 1.95 g (30.0 mmol) of sodium azide and 1.60 g (30.0 mmol) of ammonium chloride in 20 mL of DMF was stirred at 100° C. for 20 h. The mixture was cooled and partitioned between 200 mL of methylene chloride and 200 mL of 1.0 $\underline{N}$ HCl and the layers were separated. The organic layer was washed with 200 mL of water, dried over magnesium sulfate and concentrated. Flash chromatography on 50 g of silica gel using 4:1 v/v methylene chloride/ethyl acetate+1% acetic acid, then 2:1 v/v methylene chloride/ethyl acetate+1% acetic acid as the eluent afforded 1.51 g (60%) of the title compound:

$^1H$ NMR (500 MHz) δ1.49 (s, 9H), 1.83–1.89 (m, 2H), 2.13–2.15 (m, 2H), 2.96–3.04 (m, 2H), 3.13–3.36 (m, 1H), 4.14–4.22 (m, 2H).

Step C: 1-(t-Butoxycarbonyl)-4-((1-benzyl)-(1H)-tetrazol-5-yl)piperidine and 1-(t-Butoxycarbonyl)-4-((2-benzyl)-(2H)-tetrazol-5-yl)piperidine A solution of 438 mg (1.7 mmol) of 1-(t-butoxycarbonyl) 4-(1H-tetrazol-5-yl)piperidine (from Step B) in 2 mL of DMF at 0° C. was treated with 83 mg (0.50 mmol) of sodium hydride (60% in mineral oil) and 0.41 mL (3.4 mmol) of benzyl bromide. The resulting mixture was warmed to rt and stirred for 2.5 h. The mixture was partitioned between 50 mL of ether and 50 mL of water and the layers were separated. The organic layer was washed with 50 mL sat'd brine, dried over magnesium sulfate and concentrated. Flash chromatography using 2:1 v/v methylene chloride/ether, then 1:2 v/v methylene chloride/ether afforded 85 mg (15%) of 1-(t-butoxycarbonyl)-4-(2-(benzyl)-(2H)tetrazol-5-yl) piperidine. Elution with 2:1 v/v ethyl acetate/methylene chloride afforded 95 mg (17%) of 1-(t-butoxycarbonyl)-4-(1-(benzyl)-(1H)-tetrazol-5-yl)piperidine.

For 1-(t-butoxycarbonyl)4-(2-(benzyl)-(2H)-tetrazol-5-yl)piperidine: $^1H$ NMR (500 MHz) δ1.47 (s, 9H), 1.76–1.84 (2H), 2.02–2.05 (2H), 2.91–2.95 (2H), 3.07–3.12 (m, 1H), 4.00–4.20 (2H), 5.71 (s, 2H), 7.35–7.40 (5H). For 1-(t-butoxycarbonyl)-4-(1-(benzyl)-(1H)-tetrazol-5-yl) piperidine: $^1H$ NMR (500 MHz) δ1.45 (s, 9H), 1.59–1.61 (2H), 1.76–1.84 (2H), 2.70–2.80 (2H), 2.85–2.89 (m, 1H), 4.004.20 (2H), 5.55 (s, 2H), 7.17–7.19 (2H), 7.36–7.39 (3H).

Step D: 4-(2-(Benzyl)-(2H)-tetrazol-5-yl)piperidine

A solution of 85 mg (0.25 mmol) of 1-(t-butoxycarbonyl) 4-((2-benzyl)tetrazol-5-yl)piperidine (from Step C) in 2 mL of 1:1 v/v methylene chloride/TFA was stirred at rt for 2 h. The solution was concentrated. Flash chromatography on silica gel using 19:1:0.1 v/v/v methylene chloride/methanol/ $NH_4OH$ as the Eluant afforded 57 mg (94%) of the title compound.

Procedure 21

4-(1-(4-Methylsulfonylbenzyl)-3-ethyl-(1H)-pyrazol-4-yl)piperidine di-TFA salt Step A: N-tert-Butoxycarbonyl-4-piperid-4-ylacetaldehyde A solution of oxalyl chloride (2.4 mL, 27.5 mmol) in 125 mL methylene chloride was cooled to −78° C. and DMSO (3.3 mL, 47.1 mmol) was added slowly. After 10 min a solution of 2-(N-tert-butoxycarbonylpiperidin-4-yl)ethanol (4.5 g, 19.6 mmol) in 10 mL methylene chloride was added. The mixture was stirred for 20 min then triethylamine (13.6 mL, 98.1 mmol) was added and the mixture was warmed to room temperature. After 30 min the mixture was diluted with ethyl acetate and washed with water (3x). The organic portion was dried over sodium sulfate and concentrated. Flash chromatography (3/1 hexane/ethyl acetate) afforded 3.7 g (83%) of the desired aldehyde.

$^1H$ NMR (400 MHz, $CDCl_3$). δ1.13–1.43 (m, 2H), 1.48 (s, 9H), 1.68–1.77 (m, 2H), 2.04–2.11 (m, 1H), 2.38–2.41 (d, 2H), 2.71–2.8 (m, 2H), 4.04–4.14 (m, 2H), 9.8 (s, 1H).

Step B: 3-Ethyl-4-(N-t-butoxycarbonylpiperidin-4-yl)-(1H)-pyrazole

A solution of N-tert-butoxycarbonylpiperidin-4-ylacetaldehyde (4.5 g, 19.8 mmol, from Step A), and morpholine (1.7 mL, 19.8 mmol) in 100 mL benzene was refluxed using a dean-stark apparatus. After refluxing over night the mixture was concentrated to provide the enamine. The crude enamine was dissolved in 40 mL methylene chloride and the solution was cooled to 10° C. Propionyl chloride (1.7 mL, 19.8 mmol) and then triethylamine (1.4 mL, 9.9 mmol) were added. The mixture was gradually warmed to room temperature and stirred for 40 h then concentrated. The residue was dissolved in 60 mL of ethanol and hydrazine (6.2 mL, 198 mmol) was added. The solution was refluxed for 5 h. The solvent was removed and ethyl acetate was added. The organic was washed with water and sat'd sodium chloride then dried over magnesium sulfate and concentrated. Flash chromatography (0.5% methanol/methylene chloride->2% methanol/methylene chloride) afforded 2.1 g (38 %) of the title compound.

$^1H$ NMR (400 MHz, $CDCl_3$). δ1.25–1.31 (t, 3H), 1.44–1.57 (m, 1H), 1.46 (s, 9H), 1.78–1.83 (s, 2H), 2.53–2.6 (m, 1H), 2.62–2.7 (q, 2H), 2.77–2.82 (m, 2H), 4.12–3.23 (m, 2H), 7.32 (s, 1H).

Step C: 4-(1-(4-Methylsulfonylbenzyl)-3-ethyl-(1H)-pyrazol-4-yl)-N-t-butoxylcarbonylpiperidine A dry flask was charged with 5 mL DMF and sodium hydride (224 mg, 60% dispersion in mineral oil, 5.6 mmol). A solution of 3-ethyl-4-(N-t-butoxycarbonylpiperidin-4-yl)-(1H)-pyrazole (1.3 g, 4.7 mmol, from Step B) in 5 mL DMF was added. The mixture was stirred for 1 h at room temperature and a solution of (4-methylsulfonyl)benzyl chloride (1.05 g, 5.2 mmol) in 5 mL DMF was added. After 3 h the solvent was removed and the product was purified by preparative HLC (35% acetonitrile/water ->85% acetonitrile/water, C-18 stationary phase) to give 0.5 g of product as a mixture of isomeric N-alkylation products. The isomers were separated by preparative HPLC using a chiral stationary phase (Chiracel-OJ, 1/1 hexane/ethanol) to provide 210 mg (10%) of the desired isomer along with 70 mg (3%) of the undesired isomer. The substitution pattern of both isomers was determined by NOE difference.

¹H NMR (400 MHz, CDCl₃, desired isomer). δ1.25–1.31 (t, 3H), 1.38–1.47 (m, 1H) 1.46 (s, 9H), 1.8–1.85 (m, 2H), 2.5–2.6 (m, 1H), 2.6–2.66 (q, 2H), 2.75–2.82 (m, 2H), 3.03 (s, 3H), 4.13–4.22 (m, 2H), 5.32 (s, 2H), 7.13 (s, 1H), 7.28–7.31 (d, 2H), 7.89–7.91 (d, 2H).

Step D: 4-(1-(4-Methylsulfonylbenzyl)-3-ethyl-(1H)-pyrazol-4-yl)piperidine di-TFA salt 4-((1-(4-Methylsulfonylbenzyl)-3-ethyl)-(1H)-pyrazol-4-yl)-N-t-butoxylcarbonylpiperidine from Step C was treated with TFA for 1 h and evaporated to afford the title compound as the TFA salt.

Procedure 22

4-(2-Benzylthiazol-5-yl)piperidine di-HCl salt
(Method A)

Step A: 1-t-Butyloxycarbonyl-4-(nitromethylcarbonyl)piperidine

To a solution of 1-t-butyloxycarbonylpiperidine-4-carboxylic acid (22.9 g, 100 mmol) in 200 mL of anhydrous THF was added carbonyl diimidazole (20.0 g, 125 mmol) under nitrogen. Effervescence was observed and the reaction mixture was stirred 1 h at ambient temperature. Freshly distilled nitromethane (7.4 mL, 135 mmol) followed by DBU (21.0 mL, 140 mmol) were added. The resulting reaction mixture was stirred for 1 day at room temperature. After dilution with ethyl acetate, the mixture was washed with 2N HCl and brine. The organic phase was dried over anhydrous magnesium sulfate. Evaporation of the solvent followed by the purification of the residue on silica gel using 1:1 mixture of ethyl acetate -hexane with 1% acetic acid as an eluent gave 25 g of the nitroketone as a semi solid. After removal of last traces of acetic acid by azeotroping with toluene.

¹H NMR (CDCl3) 1.48 (9H,s); 1.65, 1.90, 2.65, 2.80, 4.15 (all multiplets); 5.36 (2H,s).

Step B: 1-t-Butyloxycarbonyl-4-(1-hydroxy-2-nitro)ethyl)piperidine

Sodium borohydride (1.52 g, 40 mmol) was added portionwise to a suspension of 1-t-butyloxycarbonyl-4-(nitromethylcarbonyl) piperidine (10.5 g, 40 mmol) from Step A in methanol (80 mL) at 0° C. After 6.5 h, the solvent was removed in vacuo. The residue was diluted with ethyl acetate and stirred with 2N HCl and the layers were separated. The organic phase was washed with brine and dried over magnesium sulfate. Solvent removal gave 9.1 g of the desired product as amorphous solid.

¹H NMR(CDCl₃) 1.45 (9H,s); 4.45 (2H, m); 1.3, 1.65, 1.85, 2.7, 4.2 (multiplets)

Step C: 1-t-Butyloxycarbonyl-4-(1-hydroxy-2-amino)ethylpiperidine

To a stirred suspension of 1-t-butyloxycarbonyl-4-(1-hydroxy-2-nitro)ethyl)piperidine (9.0 g, 33 mmol) from Step B in anhydrous methanol (100 mL), 10% Pd—C (2.0 g) followed by ammonium formate (12.6 g, 200 mmol) were cautiously added. The reaction mixture was stirred 1.5 days at ambient temperature. The catalyst was filtered through a pad of celite and washed with methanol. The filtrate was concentrated after adding 42 mL of triethylamine to free the product from any formic acid salts. The residue was purified on silica gel using 10:10:1 mixture of ethyl acetate, hexane and NH₄OH as solvent to yield 6.9 g of the desired amino alcohol as white solid after azeotroping with toluene.

¹H NMR (CDCl3): 1.5 (9H,s); 3.6 (2H,s) 1.2, 1.75, 2.6, 3.24, 3.4, 4.15 (all multiplets).

Step D: 1-t-Butyloxycarbonyl-4-(1-hydroxy-2-phenylacetylamino)ethylpiperidine

Phenylacetyl chloride (0.44 mL, 3.3 mmol) was added dropwise to a mixture of 1-t-butyloxycarbonyl-4-(1-hydroxy-2-amino)ethylpiperidine (0.732 g, 3 mmol) from Step C and triethylamine (0,465 mL, 3.3 mmol) in methylene chloride (15 mL) at ice bath temperature and the bath was removed. After stirring for 3 h at room temperature, the reaction mixture was diluted with ethyl acetate and washed with saturated sodium bicarbonate and brine. The organic phase was dried over anhydrous magnesium sulfate. Solvent removal gave a crude product which was used in the next step without further purification.

¹H NMR (CDCl3) 1.45 (9H,s); 3.42 (2H,s); 1.2, 1.75, 2.6, 3.2, 3.42, 4.12 (all multiplets).

Step E: 1-t-Butyloxycarbonyl-4-(2-phenylacetamido)acetylpiperidine

To a stirred solution of 1-t-butyloxycarbonyl-4-(1-hydroxy-2-phenylacetylamino)ethylpiperidine from Step D in acetone at ice bath temperature 8 N Jones reagent was added until the orange color of the reagent persisted. After stirring for 0.5 h, 0.2 mL of isopropanol was added and the stirring was continued for 0.5 h. Solvent was removed in vacuo and the residue was partitioned between water and ethyl acetate. The organic phase was washed with brine and dried over anhydrous magnesium sulfate. Solvent removal gave an oil which was purified on silica gel using 1: ethyl acetate-hexane as solvent to yield 606 mg of the desired ketone as oil.

¹H NMR (CDCl3): 1.46 (9H,s); 3.62 (2H,s); 4.18 (2H, d, J=2); 1.45, 1.8, 2.5, 4.1, 7.35, 7.4 (all multiplets)

Step F: 1-t-Butyloxycarbonyl-4-(2-benzylthiazol-5-yl)piperidine

A mixture of 1-t-butyloxycarbonyl-4-(2-phenylacetamido)acetylpiperidine (595 mg, 1.653 mmol) from Step E and Lawesson's reagent (607 mg, 1.66 mmol) in 5 mL of toluene was heated to 120° C. for 3.5 h. After cooling, 3:1 mixture of ethyl acetate and methylene chloride and saturated sodium bicarbonate solution were added and the mixture was stirred for 0.5 h. The organic phase was separated and washed with brine. Solvent removal gave a crude product which was purified on silica gel using 2:3 mixture of ethyl acetate-hexane as solvent to give 330 mg of the desired product.

¹H NMR (CDCl₃): 1.45 (9H,s); 4.4 (2H,s); 7.46 (1H,s); 1.58, 1.95, 2.85, 2.95, 4.2 multiplets).

Step G: 4-(2-Benzylthiazol-5-yl)piperidine di-hydrochloride

Acetyl chloride (0.3 mL) was added dropwise to a solution 1-t-butyloxycarbonyl-4-(2-benzylthiazol-5-yl)piperidine from Step F in methanol (2 mL) at ice bath temperature. The reaction mixture was stirred 3.5 h as it warmed to room temperature. Solvent removal in vacuo gave the desire amine as glassy solid.

¹H NMR (CD₃OD): 4.58 (2H,s); 8.02 (1H,s); 1.94, 2.24, 3.15, 3.35, 3.45 (all multiplets)

Procedure 23

4-(2-Benzylthiazol-5-yl)piperidine di-HCl salt
(Method B)

Step A: 1-t-Butyloxycarbonyl-4-(2-hydroxyethyl)piperidine

A mixture of 4-(2-hydroxyethyl) piperidine (5.0 g, 40 mmol), di-t-butyl dicarbonate (10.9 g, 50 mmol), and triethylamine (7 mL, 50 mmol) in 100 mL of anhydrous methylene chloride was stirred overnight at room temperature. Volatiles were removed in vacuo and the resulting oil was purified on a silica gel column using 20% ethyl acetate in hexane as eluent to give 7.9 g of the desired product as a colorless oil.

Step B: 1-t-Butyloxycarbonyl-4-formylylmethylpiperidine

Oxalyl chloride (2.2 mL, 25 mmol) was added to 75 mL of anhydrous methylene chloride at −78° C. DMSO (3.5 mL, 50 mmol) was then added dropwise over 5 min, and the resulting mixture was stirred for 15 min. 1-t-Butyloxycarbonyl-4-(2-hydroxyethyl)piperidine (2.29 g, 10 mmol, Step A) was dissolved in 5 mL of anhydrous methylene chloride and added over 10 min to the above mixture. After stirring 30 min, DIEA (17.4 mL, 100 mmol) was added over 10 min. The mixture was then warmed to 0° C. and maintained at that temperature for 1 h. After quenching with water, the reaction mixture was diluted with 75 mL of methylene chloride and the layers were separated. The organic phase was washed with 3×50 mL of water and dried over anhydrous magnesium sulfate. Solvent removal gave an oil, which was purified on silica gel using 20% ethyl acetate in hexane to give 2.05 g of the desired aldehyde which hardened overnight into an oily solid.

NMR: δ2.15 (2H, d, J=3); 9.8 (1H,s); 1.2, 1.5, 1.7, 2.75, 4.1 (all multiplets)

Step C: 1-t-Butyloxycarbonyl4-(α-bromo-formylmethyl)piperidine

A mixture of 1-t-butyloxycarbonyl-4-formylylmethylpiperidine (0.57 g, 2.25 mmol, step B), 3,3-dibromo-Meldrum's acid (0.75 g, 2.5 mmol) in 10 mL of anhydrous ether was stirred for 2 days at room temperature under nitrogen. The reaction mixture was diluted with ethyl acetate and washed with sat'd. sodium bicarbonate solution. The organic phase was dried over anhydrous magnesium sulfate. Solvent removal and purification on silica gel using 20% ethyl acetate in hexane as solvent gave 59% of the pure bromo aldehyde as a colorless oil.

$^1$H NMR: δ(CDCl3): 4.04 (1H,dd; J=1.5; 2); 9.46 (1H,d; J=1.5) 1.35, 1.7, 1.95, 2.1, 2.75, 4.2 (all multiplets)

Step D: 1-t-Butyloxycarbonyl-4-(2-benzylthiazol-5-yl)piperidine

A mixture of 1-t-butyloxycarbonyl-4-(α-bromo-formylmethyl)piperidine (612 mg, 2 mmol), benzyl thioamide (500 mg, 2.55 mmol) in 10 mL of anhydrous toluene was heated to reflux for 6 h. Solvent was then removed and the residue was purified on silica gel using 25% ethyl acetate in hexane as solvent to give 350 mg of the desired thiazole as an oil.

$^1$H NMR (CDCl$_3$): 1.45 (9H,s); 4.4 (2H,s); 7.46 (1H,s); 1.58, 1.95, 2.85, 2.95, 4.2 multiplets).

Step E: 4-(2-Benzylthiazol-5-yl)piperidine di-hydrochloride

The title compound was prepared by removal of the protecting group of 1-t-butyloxycarbonyl-4-(2-benzylthiazol-5-yl)piperidine as described in Example 22, Step G.

Procedure 24

4-(2-Benzyl-4-methylthiazol-5-yl)piperidine

The title thiazole was prepared according to the method of Procedure 22 by substituting nitroethane for nitromethane in Step A.

Procedure 25

4-(2-Benzyl-4-ethylthiazol-5-yl)piperidine

The title compound was obtained by the procedure of Procedure 22 by substituting nitropropane for nitromethane in Step A.

Procedure 26

4-(2-(2-Pyridylmethyl)thiazol-5-yl)piperidine di-HCl salt

Step A: 1-t-Butyloxycarbonyl-4-((1-hydroxy)-2-(2-pyridylmethyl)carbonylamino)ethylpiperidine To 0.361 g (2.08 mmol) of 2-pyridyleacetic acid hydrochloride in 8 mL of methylene chloride, 0.337 g (2.5 mmol) of 1-hydroxybenzotriazole, 0.478 g (2.5 mmol) of EDC and 0.57 mL (5.2 mmol) of N-methylmorpholine were added. After 10 min 0.508 g (2.08 mmol) of 1-t-butyloxycarbonyl-4-(2-amino-1-hydroxy)ethylpiperidine from Procedure 22, Step C was added and the solution was stirred overnight. The reaction was quenched with saturated sodium bicarbonate and extracted with methylene chloride. The combined methylene chloride layer was washed with brine, dried and concentrated. The residue was chromatographed on a flash column using a gradient of 5–10% methanol in ethyl acetate containing 1% triethylamine to isolate 0.68 g of the desired product.

$^1$H NMR (CDCl$_3$): δ1.24 (m, 3H), 1.45 (s, 9H), 1.58 (m, 1H), 1.82 (m, 1H), 2.6 (br, 2H), 3.21 (m, 1H), 3.49 (m, 2H), 3.75 (s, 2H), 4.12 (br, 2H), 7.22 (m, 1H), 7.29 (d, 1H), 7.69 (m, 1H), 852 (m, 1H).

Step B: 1-t-Butyloxycarbonyl-4-(2-(2-pyridylmethyl)carbonylamino)acetylpiperidine To a solution of 0.22 nL (3.2 mmol) of DMSO in 1 mL of methylene chloride cooled in a dry ice-acetone bath, 0.14 mL (1.6 mmol) of oxalyl chloride was added. After 0.5 h, 0.145 g of 1-t-butyloxycarbonyl-4-((1-hydroxy)-2-(2-pyridylmethyl)carbonylamino)ethylpiperidine (Step A) in 1 mL of methylene chloride was added. After 1 h, 0.89 mL (6.38 mmol) of triethylamine was added, the cold bath was removed and the reaction was stirred for 1.5 h. The solution was partitioned between water and methylene chloride. The organic layer was washed with brine, dried and concentrated. The residue was purified on a prep TLC plate using 5% methanol-ethyl acetate as an eluent to furnish 67 mg of the desired product.

$^1$H NMR (CDCl$_3$): δ1.45 (s, 9H),1.5–2.0 (m, 4H), 2.53 9m, 1H), 2.77 (br, 2H), 3.79 (s, 2H), 4.1 (br, 2H), 4.22 (d, 2H), 7.2–8.0 (m, 3H), 8.61 (d, 1H).

Step C: 1-t-Butyloxycarbonyl-4-(2-(2-pyridylmethyl)thiazol-5-yl)piperidine

The title compound was prepared by reacting 1-t-butyloxycarbonyl-4-(2-(2-pyridylmethyl)carbonylamino)acetylpiperidine (Step B) with Lawesson's reagent as described in Procedure 22, Step F.

$^1$H NMR (CDCl$_3$): δ1.47 (s, 9H), 1.6 (m, 2H), 1.99 (m, 2H), 2.82 (br, 2H), 2.94 (m, 1H), 4.17 (br, 2H), 4.48 (s, 2H), 7.2–7.8 (m, 4H), 8.6 (br, 1H).

Step D: 4-(2-(2-Pyridylmethyl)thiazole-5-yl)piperidine di-HCl salt

Removal of the t-butyloxycarbonyl protecting group as described in Procedure 22, Step G furnished the title compound.

Procedure 27

4-(Imidazo[1,2-a]pyridin-3-yl)piperidine di-TFA salt

Step A: 1-(t-Butoxycarbonyl)-4-(imidazo[1,2-a]pyridin-3-yl)piperidine

To a solution of 1.15 g of 1-(t-butoxycarbonyl)-4-(1-bromo-2-oxoethyl)piperidine (from Procedure 23, Step C) in 15 mL ethanol was added 388 mg of 2-aminopyridine. After refluxing for 18 h, the solvent was evaporated. The mixture was partitioned between ethyl acetate and saturated sodium bicarbonate solution. Aqueous layer was extracted with ethyl acetate (3×). The combined organic phase was washed with brine, dried over magnesium sulfate and concentrated. The residue was purified by flash chromatography with 50% ethyl acetate in hexanes, followed by 100% ethyl acetate to give 401 mg of the title compound as a solid.

$^1$H NMR (500 MHz, CDCl$_3$) δ1.48 (s, 9H), 1.70 (m, 2H), 2.06 (d, J=13 Hz, 2H), 2.93–3.02 (m, 3H), 4.26 (br, 2H), 6.87 (t, J=6.8 Hz, 1H). 7.21(m, 1H), 7.44 (s, 1H), 7.69(d, J=9.2 Hz, 1H), 7.99 (d, J=6.9 Hz, 1H).

Step B: 4-Imidazo[1,2-a]pyridin-3-yl)piperidine di-TFA salt

To 100 mg of 1-(t-butoxycarbonyl)-4-(imidazo[1,2-a]pyridin-3-yl)piperidine from Step A was added 2 mL TFA. The reaction was stirred at rt for 1 h. The mixture was concentrated under reduced pressure to afford 180 mg of a viscous oil.

Procedure 28

4-(7-t-Butylimidazo[1,2-a]pyridin-3-yl)piperidine, TFA salt

Step A: 2-Amino-4-t-butylpyridine

To 790 mg of sodium amide were added 20 mL of N,N-dimethylaniline and 2.74 g of 4-t-butyl pyridine at rt. The mixture was stirred at 150° C. for 6 h. During this period, 3 more portions of sodium amide (790 mg each) were added. The reaction was cooled down to rt. The mixture was partitioned between ethyl acetate and water. Aqueous layer was extracted with ethyl acetate (3×). The combined organic phase was washed with brine, dried over magnesium sulfate and concentrated. The residue was purified by flash chromatography with 50% ethyl acetate in hexanes followed by 100% ethyl acetate to give 1.68 g of the title compound as a solid:

$^1$H NMR (500 MHz, CDCl$_3$) δ1.21 (s, 9H), 6.44 (t, 1H), 6.6.62 (dd, J=5.5 Hz and, 1H), 7.94 (d, J=5.5 Hz, 1H).

Step B: 1-(t-Butoxycarbonyl)-4-(7-t-butylimidazo[1,2-a]pyridin-3-yl)piperidine

The title compound was prepared from 470 mg of 1-(t-butoxycarbonyl)-4-(1-bromo-2-oxoethyl)piperidine (from Procedure 23, Step C) and 277 mg of 2-amino-4-t-butyl pyridine (from Step A) in 12 mL ethanol using a procedure analogous to that described in Example 235, Step A to provide 130 mg of the title compound as a solid.

Step C: 4-(7-t-Butylimidazo[1,2-a]pyridin-3-yl)piperidine, TFA salt

The title compound was prepared from 35 mg of 1-(t-butoxycarbonyl)-4-((7-t-butyl)imidazo[1,2-a]pyridin-3-yl)piperidine (from Step B) in 2 mL of TFA, using a procedure analogous to that described in Procedure 27, Step B to provide 60 mg of the title compound as a viscous oil.

Procedure 29

4-(2-Ethyl-5,6,7,8-tetrahydroimidazo[1,2-a]pyridin-3-yl)piperidine, acetic acid salt Step A: 2-Ethyl-imidazo[1,2-a]pyridine The title compound was prepared from 2-aminopyridine and 1-bromo-2-butanone, employing procedures analogous to those described in Procedure 27 Step A.

$^1$H NMR (500 MHz, CDCl$_3$): δ1.34 (t, J=7.3 Hz, 3H), 2.82 (q, J=7.6 Hz, 2H), 6.70 (t, J=6.6 Hz, 1H), 7.10 (m, 1H), 7.32 (s, 3H), 7.51 (d, J=8.9 Hz, 1H), 8.03 (dd, J=6.6, 0.9 Hz, 1H).

Step B: 3-Bromo-2-ethyl-imidazo[1,2-a]pyridine

To a solution of 2-ethyl-imidazo[1,2-a]pyridine (2.17 g, 14.9 mmol) in ethanol (25 mL) was added bromine (2.0 g, 12.5 mmol) in water (5 mL) dropwise at rt. After stirring at rt for 4h, ethanol was evaporated under reduced pressure. The residue was basified with aqueous sodium bicarbonate and extracted with methylene chloride (3×). The organic phase was washed with brine and dried over anhydrous magnesium sulfate. Concentration followed by flash chromatography eluting with 20 % ethyl acetate in hexanes, followed by 50% ethyl acetate in hexanes afforded the title compound (1.88 g) as a viscous oil.

$^1$H NMR (500 MHz, CDCl$_3$): δ1.36 (t, J=7.5 Hz, 3H), 2.83 (q, J=7.6 Hz, 2H), 6.88 (t, J=6.8 Hz, 1H), 7.20 (m, 1H), 7.55 (dd, J=8.9, 0.9 Hz, 1H), 8.05 (dd, J=6.9, 1.2 Hz, 1H).

Step C: 2-Ethyl-3-(4-pyridyl)-imidazo[1,2-a]pyridine

To a solution of 3-bromo-2-ethyl-imidazo[1,2-a]pyridine (1.4 g, 6.28 mmol), 4-tributylstannylpyridine (2.31 g, 6.28 mmol) and Pd (II) (Ph$_3$P)$_2$Cl$_2$ (442 mg, 0.63 mmol) in toluene (5 mL) was added lithium chloride (26.7 mg, 0.63). After refluxing for 18 h, the mixture was partitioned between ethyl acetate and aqueous sodium bicarbonate. The aqueous layer was extracted with ethyl acetate (3×). Combined organic phase was washed with brine and dried over anhydrous magnesium sulfate. Concentration followed by flash chromatography eluting with 100% ethyl acetate, then 10% methanol in methylene chloride afforded the title compound (543 mg) as a viscous oil.

$^1$H NMR (500 MHz, CDCl$_3$): δ1.36 (t, J=7.5 Hz, 3H), 2.84 (q, J=7.5 Hz, 2H), 6.68 (dt, J=6.8, 1.1 Hz, 1H), 7.21 (m, 1H), 7.39 (dd, J=5.9, 1.6 Hz, 2H), 7.61 (dd, J=8.9, 1.0 Hz, 1H), 8.75 (d, J=5.9 Hz, 2H).

Step D: 4-(2-Ethyl-5,6,7,8-tetrahydroimidazo[1,2-a]pyridin-3-yl)piperidine, acetic acid salt A solution of 2-ethyl-3-(4-pyridyl)-imidazo[1,2-a]pyridine (700 mg, 3.13 mmol) in ethanol (12 mL) and acetic acid (4 mL) was hydrogenated using Platinum (IV) oxide (40 mg) under 40 psi of H$_2$ gas in a Parr shaker at rt for 18 h. The mixture was filtered through celite and concentrated to give the title compound (1.47 g) as a viscous oil.

Procedure 30

4-(2-Benzyloxazol-5-yl)piperidine

Step A: 1-Benzoylisonipecotic Acid

To a solution of 10 g of isonipecotic acid in 100 mL of water was added 31 mL of 5 N NaOH at 0° C. The reaction was warmed to room temperature and stirred for 0.5 h. The reaction was again cooled to 0° C. and 11.97 g of benzoyl chloride was added. The reaction was then warmed to room temperature and stirred for 1.5 h. Concentrated HCl was then added until a precipitate formed. The mixture was extracted with 3×150 mL of ethyl acetate and the combined organic layers were dried over magnesium sulfate. The solvent was evaporated under reduced pressure and the residue was dissolved in methylene chloride. Ether was then slowly added to precipitate the product which was filtered to give 8 g of the title compound.

$^1$H NMR (500 MHz) 1.83 (m, 3H), 2.10 (m, 1H), 2.65 (m, 1H), 3.12 (m, 2H), 3.79 (m, 1H), 4.53 (m, 1H), 7.38 (m, 5H).

Step B: 4-hydroxymethyl-1-benzoylpiperidine

To a solution of 2 g of 1-benzoylisonipecotic acid (Step A) in 50 mL THF at 0° C. were added 1.47 g of triethylamine and 1.99 g of isobutyl chloroformate. The reaction was stirred for 1 h at 0° C. To a solution of 1.10 g of sodium borohydride in 30 mL DMF at 0° C. was slowly added the above THF mixture. The reaction was again stirred for 1 h at 0° C. Water (80 mL) was slowly added to the reaction and the mixture was extracted 5×80 mL ethyl acetate and the combined organic layers were dried over magnesium sulfate. The solvent was then evaporated under reduced pressure. The residue was purified by flash chromatography with 1:1 hexane:ethyl acetate followed by hexane: ethyl acetate: methanol, 50:50:5 to give 1.865 g of the title compound.

ESI-MS 219.9 (M+H); HPLC A: 2.34 min. (65148-258)

Step C: 1-Benzoylpiperidine-4-carboxaldehyde

To 1.99 g of dimethyl sulfoxide in 45 mL methylene chloride at −78° C. was added 2.16 g of oxalyl chloride. After 10 min, 1865 g of 4-hydroxymethyl-N- benzoylpiperidine (Step B) in 15 mL of methylene chloride was added at −78° C. and stirred for 30 min. DIEA (5.49 mL) was added and this mixture was stirred for an additional 30 min. at −78° C. and then warmed to room temperature and stirred another 30 min. The reaction was quenched with 50 mL water and extracted with 3×50 mL methylene chloride. The combined organic layers were dried over magnesium sulfate and evaporated under reduced pressure. The residue was chromatographed with 2:1 hexane:ethyl acetate followed by 1:1 hexane:ethyl acetate to give 1.445 g of the title compound.

$^1$H NMR (500 MHz) 1.72 (m, 2H), 1.90 (m, 1H), 2.14 (m, 1H), 2.58 (m, 1H), 3.21 (m, 2H), 3.68 (m, 1H), 4.41 (m, 1H), 7.39 (m, 5H), 9.72 (m, 1H).

Step D: 4-(1-hydroxy-prop-2-enyl)-1-benzoyl piperidine

To a solution of 500 mg of 1-benzoylpiperidine-4-carboxaldehyde (Step C) in 10 mL THF at −78° C., was added 2.99 mmol of vinyl magnesium bromide. The solution was warmed to 0° C. and stirred for 1 h. The reaction was quenched with 15 mL of aq. ammonium chloride and extracted with 3×20 mL ether and the combined organic layers were dried over magnesium sulfate. The solvent was evaporated under reduced pressure and the residue was purified by flash chromatography with 2:1 hexane:ethyl acetate followed by 1:1 hexane:ethyl acetate followed by hexane: ethyl acetate:methanol, 50:50:5 to give 411 mg of the title compound.

$^1$H NMR (500 MHz) 1.31 (m, 2H), 1.74 (m, 5H), 2.69 (m, 1H), 2.92 (m, 1H), 4.80 (m, 1H), 3.68 (m, 1H), 5.22 (dd, 2H), 5.84 (m, 1H), 7.43 (m, 5H).

Step E: 4-(1-Phenylacetyoxy-prop-2-enyl)-1-benzoylpiperidine

To 264 mg of 4-(1-hydroxy-prop-2-enyl)-1-benzoylpiperidine (Step D) in 5 mL DMF was added 220 mg of phenyl acetic acid, 292 mg of 1-hydroxybenzotriazole, 414 mg of EDC, and 419 mg of DIEA. The reaction was stirred at room temperature overnight. The solution was diluted with 50 mL of ether and washed with 2×40 mL water. The aqueous layers were then extracted with 2×50 mL ether and the combined organic layers were dried over magnesium sulfate. The solvent was evaporated under reduced pressure and the residue was purified by flash chromatography with 4:1 hexane:ethyl acetate followed by 2:1 hexane:ethyl acetate to give 123 mg of the title compound.

ESI-MS 364.1 (M+H).

Step F: 1-Benzoyl-4-(2-benzyloxazol-5-yl)piperidine

Ozone was bubbled through a solution of 120 mg of 4-(1-phenylacetyoxy-prop-2-enyl)-1-benzoylpiperidine (Step E) in 8 mL methylene chloride at −78° C. until the reaction turned blue. To this solution 205 mg of methyl sulfide was added and the reaction was stirred at room temperature overnight. The solvent was evaporated under reduced pressure to give 121 mg of the residue. This residue was dissolved in 3 mL of acetic acid and 76 mg of ammonium acetate was added. The reaction was stirred at 110° C. for 2.5 h, 20 mL of water was added and the mixture was extracted with 3×20 mL methylene chloride. The combined organic layers were dried over magnesium sulfate. The solvent was evaporated under reduced pressure and the residue was purified by flash chromatography with 2:1 hexane:ethyl acetate followed by 1:1 hexane:ethyl acetate followed by hexane:ethyl acetate:methanol, 50:50:5 to give 40 mg of the title compound.

ESI-MS 347.0 (M+H); HPLC A: 3.68 min.

Step G: 4-(2-Benzyloxazol-5-yl)piperidine

To 40 mg of 1-benzoyl-4-(2-benzyloxazol-5-yl)piperidine (step F) in 4.5 mL methanol and 0.5 mL water was added 260 mg of potassium hydroxide. The reaction was stirred at 80° C. overnight, 20 mL of water was added and the mixture was extracted with 3×20 mL ethyl acetate. The combined organic layers were dried over magnesium sulfate. The solvent was evaporated under reduced pressure to give 22 mg of the title compound.

ESI-MS 242.9 (M+H); HPLC A: 2.29 min.

Procedure 31

4-(2-Benzyl-1,3-imidazol-5-yl)piperidine

Step A: 4-Bromoacetyl-1-(t-butoxycarbonyl)piperidine

To a freshly prepared solution of LDA (from diisopropylamine (0.61 g, 6.0 mmol) and n-butyl lithium (2.2 mL, 2.5 M sol'n. In hexane) in 10 mL THF at −78° C. was added a solution of 4-acetyl-1-(t-butoxycarbonyl) piperidine (1.0 g, 4.7 mmol) in 2.0 mL THF and the resultant mixture was stirred for 20 min. A mixture of trimethylsilyl chloride and triethylamine (1.37 mL, 10.8 mmol and 2.16 mL, 15.5 mmol) was added and the reaction mixture was gradually warmed to rt and stirred for an additional 1 h. All the volatile were removed and the crude silyl enol ether was dissolved in 10 mL of THF and the mixture was cooled to 0° C. To this mixture was added in succession propylene oxide (1.0 mL) and NBS (1.0 g) and the mixture was stirred for 15 min, quenched with a saturated sodium bicarbonate followed by extraction with methylene chloride. The methylene chloride layer was washed with brine, dried, evaporated and purified by silica column chromatography. Elution with methylene chloride and ether (19:1) gave the title compound (1.11 g) as a yellow solid.

$^1$HNMR (500 MHz, CDCl$_3$): δ4.16 (s, 2H), 4.12 (m, 2H), 2.79–2.84 (m, 3H), 1.47 (s, 3H).

Step B: 4-(2-(2,6-Dichlorobenzyl)-1,3-imidazol-5-yl)-1-(t-butoxycarbonyl)piperidine A mixture of the bromo compound (0.4 g, 1.36 mmol) from Step A and 2,6-dichlorophenylacetamidine (0.55 g, 2.7 mmol) in 30 mL of chloroform was refluxed for 4 h. The reaction mixture was filtered. The filtrate was evaporated and purified by silica column chromatography. Elution with hexane:ethyl acetate:methanol 49:49:2 gave (0.28 g) of the title compound.

$^1$HNMR (500 MHz, CDCl$_3$): δ7.35–7.15 (m, 3H), 6.55 (s, 1H), 4.45 (s, 2H), 4.14 (br, 2H), 2.81–2.69 (m, 3H), 1.46 (s, 3H).

Step C: 4-((2-Benzyl)-1,3-imidazol-5-yl)-1-(t-butoxycarbonyl)piperidine

A mixture of 4-(2-(2,6-dichlorobenzyl)-1,3-imidazol-5-yl)-1-(t-butoxycarbonyl)piperidine (0.51 g, 1.24 mmol) from Step B, Pd/C (0.13 g) and ammonium formate (1.5 g, 24.8 mmol) in 8 mL of methanol was refluxed for 30 min. The reaction mixture was filtered and the filtrate was evaporated. The residue was partitioned between methylene chloride and water (200 mL). The methylene chloride layer was washed with brine, dried, evaporated and purified by silica column chromatography. Elution with 3% methanol-methylene chloride gave (0.35 g) of the title compound.

$^1$HNMR (500 MHz, CDCl$_3$): δ7.34–7.22 (m, 5H), 6.58 (s, 1H), 4.18 (br, 2H), 4.08 (s, 2H), 2.71 (br, 2H), 2.68 (m, 1H), 1.47 (s, 3H).

Step D: 4-(2-Benzyl-1,3-imidazol-5-yl)piperidine hydrochloride

To 4-((2-benzyl)-1,3-imidazol-5-yl)-1-(t-butoxycarbonyl)piperidine (0.16 g) from Step C in 2 mL of ethyl acetate at 0° C. was added a 2 mL saturated solution of HCl in ethyl acetate. The reaction mixture was stirred for 30 min. Evaporation of ethyl acetate followed by trituration of the resultant oil gave (0.15 g) of the title compound.

¹HNMR (500 MHz, CD₃OD): δ7.40–7.29 (m, 6H), 4.32 (s, 2H), 3.49 (m, 2H), 3.31–3.01 (m, 3H), 2.24 (m, 2H), 1.92 (m, 2H).

Procedure 32

4-((2-Benzyl-4-ethyl)-1,3-imidazol-5-yl)piperidine

Step A: 4-((2-Benzyl-4-iodo)-1,3-imidazol-5-yl)-1-(t-butoxycarbonyl)piperidine

To a mixture of 4-((2-benzyl)-1,3-imidazol-5-yl)-1-(t-butoxycarbonyl)piperidine (0.15 g, 0.43 mmol). Iodine (0.16 g, 0.65 mmol) and potassium iodide (0.22 g, 1.3 mmol) in 4 mL THF:water (1:1) was added a solution of sodium hydroxide (0.5 mL) and stirred at rt for 30 min. After confirming the completion of reaction by TLC, the reaction was quenched with a saturated solution of sodium thiosulfate and the pH was adjusted to 7–8. The resultant mixture was extracted with ethyl acetate. The ethyl acetate layer was washed with brine, dried, evaporated and purified by silica column chromatography. Elution with 1% methanol-methylene chloride gave (0.17 g) of the title compound.

¹HNMR (500 MHz, CDCl₃): δ7.32–7.22 (m, 5H), 4.13 (br, 2H), 4.06 (s, 2H), 2.74 (m, 3H), 1.47 (s, 3H).

Step B: 4-((2-Benzyl-4-ethenyl)-1,3-imidazol-5-yl)-1-(t-butoxycarbonyl)piperidine A mixture of 4-((2-benzyl-4-iodo)-1,3-imidazol-5-yl)-1-(t-butoxycarbonyl)piperidine (0.17 g, 0.36 mmol) from Step A, tri-n-butyl vinyltin (0.17 g, 0.54 mmol) and tetrakistriphenylphosphinyl palladium (0.020 g) in 4 mL toluene was stirred at 100–110° C. until the completion of reaction by TLC. Evaporation of the volatiles followed by purification by silica column and elution with 1% methanol-methylene chloride gave (0.061 g) of the title compound.

¹HNMR (500 MHz, CDCl₃): δ7.36–7.26 (m, 5H), 6.61–6.55 (m, 1H), 5.10 (m, 2H), 4.33 (br, 2H), 4.13 (s, 2H), 1.47(s, 3H).

Step C: 4-((2-Benzyl-4-ethyl)-1,3-imidazol-2-yl)-1-(t-butoxycarbonyl)piperidine

A mixture of 4-((2-benzyl-4-ethenyl)-1,3-imidaz-5-yl)-1-(t-butoxycarbonyl)piperidine (0.073 g) from Step B in 3.0 mL methanol was hydrogenated over Pd/C (5 mg) at rt. Evaporation of the volatiles followed by purification by preparative silica chromatography and elution with 1% methanol-methylene chloride gave (0.043 g) of the title compound.

¹HNMR (500 MHz, CDCl₃): δ7.31–7.20 (m, 5H), 4.19 (br, 2H), 4.01 (s, 2H), 2.74–2.66 9 m, 3H), 2.51 (q, 2H), 1.46(s, 3H), 1.15 (t, 3H).

Step D: 4-((2-Benzyl-4-ethyl)-1,3-imidazol-2-yl)piperidine di-hydrochloride

To 4-((2-benzyl-4-ethyl)-1,3-imidazol-2-yl)-1-(t-butoxycarbonyl)piperidine (0.043 g) from Step C in 1.0 mL ethyl acetate at 0° C. was added a 2.0 mL saturated solution of HCl in ethyl acetate. The reaction mixture was stirred for 30 min. Evaporation of ethyl acetate followed by trituration of the resultant oil gave (0.038 g) of the title compound.

Procedure 33

4-(2-Ethyl-4,5,6,7-tetrahydro-(2H)-indazol-3-yl)-1-piperidine

Step A: (1-Benzylpiperidin-4-yl)-(cyclohexanon-2-yl) ketone

To a suspension of 1.60 g 60% sodium hydride in 10 mL dry THF was added a solution of 1.963 g (20 mmole) cyclohexanone and 9.893 g (40 mmole) of 1-benzylpiperidine-4-carboxylic acid ethyl ester in 30 mL THF. This mixture was heated to reflux over night. Work-up followed by silica gel FC (15~50% ethyl acetate in hexanes with 1% triethylamine) provided 4.4 g product containing about 5.7:1 molar ratio of starting 1-benzylpiperidine-4-carboxylic acid ethyl ester and title compound.

ESI-MS 300.3 (M+H), HPLC A: 2.90 and 3.57 min. (for tautomeric forms).

Step B: 4-(2-Ethyl-4,5,6,7-tetrahydro-(2H)-indazol-3-yl)-1-benzylpiperidine

The title compound was prepared from the semi-crude (1-benzylpiperidin-4-yl)-(cyclohexanon-2-yl)ketone from step A and 34% aqueous ethylhydrazine in 4:1 acetonitrile and water at room temperature. This provided 8:1 ratio of isomeric ethyl pyrazoles in favor of the title compound. (Note: Use of ethyl hydrazine oxalate in the presence of DIEA gave about 2:1 ratio of the same isomers.) The 1-benzylpiperidine-4-carboxylic acid ethyl ester present in the starting β-diketone was removed after saponification of the crude product with sodium hydroxide in water ethanol mixture flowed by extractive work-up. The desired ethyl isomer is the higher $R_f$ isomer. It was isolated on silica gel chromatography (60~100% ethyl acetate in hexanes and 5~20% methanol in ethyl acetate, both with 1% triethylamine).

¹H NMR (500 MHz) δ7.33~7.36 (m, 4H), 7.26~7.30 (m, 1H), 4.07 (q, 7.2 Hz, 2H), 3.57 (s, 2H), 3.00~3.03 (m, 2H), 2.64~2.66 (m, 2H), 2.60~2.63 (m, 2H), 2.57~2.63 (m, 1H), 1.96~2.08 (m, 4H), 1.69~1.81 (m, 6H), 1.39 (t, 7.2 Hz, 3H). The identity of the title compound was confirmed by NOE difference spectroscopy.

Step C: 4-(2-Ethyl-4,5,6,7-tetrahydro-(2H)-indazol-3-yl) piperidine

A mixture of 0.273 g 4-(2-ethyl-4,5,6,7-tetrahydro-(2H)-indazol-3-yl)-1-benzylpiperidine from Step B above, 0.789 g ammonium formate, and 35 mg 20% Pd(OH)₂ in 6 mL methanol was heated at 65° C. for 1 h. Basic aqueous work-up with ether extraction provided 0.192 g title compound as a colorless solid (97%).

¹H NMR (500 MHz) δ4.08 (q, 7.2 Hz, 2H), 3.19 (br d, 11.9 Hz, 2H), 2.71~2.77 (m, 1H), 2.68~2.74 (m, 2H), 2.64~2.66 (m, 2H), 2.60~2.62 (m, 2H), 1.82~1.91 (m, 2H), 1.71~1.80 (m, 6H), 1.40 (t, 7.2 Hz, 3H). The identity of the title compound was confirmed again by NOE difference spectroscopy.

Procedure 34

4-(4,5,6,7-Tetrahydro-(2H)-indazol-3-yl)-1-piperidine

Step A: 4-(4,5,6,7-Tetrahydro-(2H)-indazol-3-yl)-1-benzyl piperidine, trifluoroacetic acid salt The title compound was prepared using a procedure similar to that in Procedure 33, Step B with hydrazine instead of ethyl hydrazine. It was further purified on HPLC.

¹H NMR (500 MHz, CD₃OD) δ7.47~7.55 (m, 5H), 4.35 (s, 2H), 3.61 (br d, 12.3 Hz, 2H), 3.13~3.21 (m, 3H), 2.71~2.73 (m, 2H), 2.56~2.58 (m, 2H), 2.17 (br d, 13.3 Hz, 2H), 2.04~2.12 (m, 2H), 1.79~1.89 (m, 4H). ESI-MS 296.3 (M+H), HPLC A: 2.33 min.

Step B: 4-(4,5,6,7-Tetrahydro-(2H)-indazol-3-yl)piperidine

The title compound was prepared using a procedure similar to that in Procedure 33, Step C as a white solid.

¹H NMR (500 MHz) δ3.20 (br d, 12.4 Hz, 2H), 2.72~2.797 (m, 3H), 2.64~2.66 (m, 2H), 2.49~2.52 (m, 2H), 1.87~1.90 (m, 2H), 1.70~1.84 (m, 6H). ESI-MS 206.2 (M+H), HPLC A: 0.80 min.

Procedure 35

3,3-Difluoro-3-(2-pyridyl)propyl)piperidine

Step A: Ethyl oxo(2-pyridyl)acetate

A solution of n-butyl lithium (100 mL, 1.6 M, 160 mmol) in hexanes was added over 2 min. to a stirred solution of 2-bromopyridine (15.0 mL, 24.9 g, 157 mmol) in 500 mL of ether cooled in a dry ice/isopropanol bath, causing a temporary rise in temperature to −47° C. After 25 min., the solution was transferred rapidly to a stirred 0° C. solution of diethyl oxalate (75 mL, 81 g, 550 mmol) in 1000 mL of ether. After 2 h at 0° C., the mixture was washed with saturated aq. sodium bicarbonate (900 mL), water (900 mL), and saturated aq. brine (450 mL). The organic layer was dried (magnesium sulfate), filtered, and evaporated. Distillation gave the title compound as 11.68 g of yellow liquid, B.p. 96–108° C. (0.3 mm Hg pressure). For the title compound:

$^1$H NMR (500 MHz, CDCl$_3$) δ8.78 (d, J=5, 1H), 8.13 (d, J=8, 1H), 7.93 (td, J=8, 2, 1H), 7.56 (ddd, J=8, 5, 1, 1H), 4.51 (q, J=7, 2H), 1.44 (t, J=7, 3H).

Step B: Ethyl difluoro(2-pyridyl)acetate

Ethyl oxo(2-pyridyl)acetate (11.59 g, 64.7 mmol, from Procedure 35, Step A) was added to a flask containing (diethylamino)sulfur trifluoride (18.0 mL, 22.0 g, 136 mmol) and the solution was heated to 45° C. overnight. An additional portion of (diethylamino)sulfur trifluoride (24.9 g, 154 mmol) was added and the solution was heated to 55° C. for 2 days. After cooling to rt, the solution was added carefully to a stirred mixture of ethyl acetate (600 mL), ice (500 g), water (500 mL), and sodium bicarbonate (100 g). After the resulting reaction had subsided, the layers were separated and the organic layer was washed with 250 mL each of saturated aq. sodium bicarbonate, water, and saturated aq. brine. The organic layer was dried (sodium sulfate), decanted, and evaporated. Distillation gave 8.45 g of yellow liquid, B.p. 50–63° C. (0.1 mm Hg), containing a residual impurity. Further purification by flash column chromatography on silica gel, eluting with 80:20 v/v to 75:25 v/v hexanes/ethyl acetate, gave the title compound as 6.54 g of yellow oil. For the title compound:

$^1$H NMR (500 MHz, CDCl$_3$) δ8.68 (d, J=5, 1H), 7.88 (td, J=8, 2, 1H), 7.76 (d, J=8, 1H), 7.44 (dd, J=8, 5, 1H), 4.40 (q, J=7, 2H), 1.35 (t, J=7, 3H).

Step C: 1-(t-Butoxycarbonyl)-4-(3,3-difluoro-3-(2-pyridyl) prop-1-en-1-yl)piperidine Ethyl difluoro(2-pyridyl)acetate (1.00 g, 4.97 mmol, from Procedure 35, Step B) was dissolved in CH$_3$OH (15 mL) in a 3-neck round bottom flask fitted with a mechanical stirrer, and the resulting solution was cooled in a dry ice/ isopropanol bath. Sodium borohydride (114 mg, 3.0 mmol) was added in 2 portions 15 min. apart. After an additional 55 min., the cold reaction was quenched by the addition of saturated aq. ammonium chloride (6.5 mL) over 12 min. After 10 min., the cooling bath was removed and the mixture was stirred for 35 min. before being diluted with saturated aq. brine (100 mL) and extracted with ethyl acetate (4×75 mL). The combined organic layers were dried (sodium sulfate), decanted, and evaporated to give 1.02 g of crude 2,2-difluoro-2-(2-pyridyl)-1-methoxyethanol as an amber oil.

A suspension of ((1-(t-butoxycarbonyl)piperidin-4-yl) methyl)triphenylphosphonium iodide (5.29 g, 9.00 mmol, from Procedure 17, Step C) in THF (70 mL) was stirred at rt for 40 min. A toluene solution of potassium bis (trimethylsilyl)amide (18 mL, 0.5 M, 9.0 mmol) was added, giving an orange suspension. After 40 min., crude 2,2-difluoro-2-(2-pyridyl)-1-methoxyethanol (940 mg, 4.97 mmol) was added in THF (20 mL). After an additional 50 min., the mixture was quenched by the addition of saturated aq. NH$_4$Cl (10 mL). The mixture was partitioned between ethyl acetate (100 mL) and water (100 mL), and the aqueous layer was extracted with ethyl acetate (3×100 mL). The organic layers were washed in succession with saturated aq. brine (100 mL), dried (sodium sulfate), decanted, and evaporated. Purification by flash column chromatography on silica gel, eluting with 90:10 v/v to 80:20 v/v hexanes/ethyl acetate, gave 1.18 mg of the title compound (approximately 95:5 cis/trans mixture) as an oil which solidified upon standing. For the title compound:

$^1$H NMR (500 MHz, CDCl$_3$) δ8.68 (d, J=5, 1H), 7.84 (td, J=8, 2, 1H), 7.70 (d, J=8, 1H), 739 (dd, J=8,5, 1H), 5.93 (td, J=14, 11, 1H), 5.70 (ddt, J=11, 10,2, 1H), 4.17–3.99 (bs, 2H), 2.80–2.62 (m, 3H), 1.58 (d, J=12, 2H), 1.46 (s, 9H), 1.26 (qd, J=12, 4, 2H).

ESI-MS 339 (M+H); HPLC A: 4.28 min.

Step D: 1-(t-Butoxycarbonyl)-4-(3,3-difluoro-3-(2-pyridyl) propyl)piperidine

Potassium azodicarboxylate (246 mg, 1.27 mmol) was added to a stirred solution of 1-(t-butoxycarbonyl)-4-(3,3-difluoro-3-(2-pyridyl)prop-1-enyl)piperidine (143 mg, 0.42 mmol, from Procedure 35, Step C) in methanol (1.4 mL) at rt. A solution (0.58 mL) of 75:25 v/v CH$_3$OH/AcOH was added in three portions at 30-min. intervals. After two h, an additional portion of potassium azodicarboxylate (246 mg, 1.27 mmol) was added, followed by a solution (0.58 mL) of 75:25 v/v CH$_3$OH/AcOH added in three portions at 30-min. intervals. After another two h, a third portion of potassium azodicarboxylate (246 mg, 1.27 mmol) was added, followed by a solution (0.58 mL) of 75:25 v/v CH$_3$OH/AcOH added in the same manner as before. After stirring overnight, the mixture was diluted with ethyl acetate (50 mL) and washed with saturated aq. sodium bicarbonate (30 mL) followed by saturated aq. brine (30 mL). The organic layer was dried (sodium sulfate), decanted, and evaporated to give the crude product containing approximately 30% starting olefin. This material was combined with crude product similarly obtained from 1-(t-butoxycarbonyl)-4-(3,3-difluoro-3-(2-pyridyl)prop-1-enyl)piperidine (20 mg, 0.059 mmol) and purified by preparative HPLC on a 20×250 mm Chiracel OD column, eluting with 98:2 v/v hexanes/isopropanol, to give 105 mg of the title compound:

$^1$H NMR (500 MHz, CDCl$_3$) δ8.68 (d, J=5, 1H), 7.82 (td, J=8, 2, 1H), 7.64 (d, J=8, 1H), 7.38 (dd, J=8, 5, 1H), 4.17–4.00 (bs, 2H), 2.75–2.62 (m, 2H), 2.42–2.30 (m, 2H), 1.67 (d, J=12, 2H), 1.46 (s. 9H), 1.45–1.38 (m, 3H), 1.15–1.04 (m, 2H).

ESI-MS 241 (M+H-100); HP-LC A: 4.36 min.

Step E: 4-(3,3-Difluoro-3-(2-pyridyl)propyl)piperdine

The title compound was prepared using procedures analogous to those described in Procedure 17, Step H,substituting 1-(t-butoxycarbonyl)-4-(3,3-difluoro-3-(2-pyridyl)propyl) piperidine (from Procedure 35, Step D) for 1-(t-butoxycarbonyl)-4-(3,3-difluoro-3-(4-fluorophenyl)propyl) piperidine. For the title compound:

$^1$H NMR (500 MHz, CD$_3$OD) δ8.62 (d, J=5, 1H), 7.95 (td, J=8, 2, 1H), 7.68 (d, J=8, 1H), 7.50 (dd, J=8, 5, 1H), 2.99 (d, J=12, 2H), 2.53 (td, J=12, 3, 2H), 2.37–2.26 (m, 2H), 1.67 (d, J=12, 2H), 1.42–1.28 (m, 3H), 1.08 (dq, J=12, 4, 2H); ESI-MS 241 (M+H); HPLC A: 2.21 min.

Procedure 36

4-(3,3-Difluoro-3-(6-methylpyridazin-3-yl)propyl)piperidine

Step A: 3-Bromo-6-methylpyridazine

A solution (3.0 mL) containing 30% HBr in acetic acid was added to 3-(trifluoromethanesulfonyloxy)-6-methylpyridazine (prepared as described by M. Rohr, et al., *Heterocycles*, 1996, 43, 1459–64) and the mixture was heated in a 100° C. oil bath for 2.5 h. The mixture was cooled in an ice bath, adjusted to pH≧9 (as determined using pH paper) by the careful addition of 20% aqueous NaOH, and extracted with ether (3×20 mL). The organic layers were dried (sodium sulfate), decanted, and evaporated to give title compound as 359 mg of pale tan crystals. For the title compound:

$^1$H NMR (500 MHz, CDCl$_3$) δ7.56 (d, J=9, 1H), 7.22 (d, J=9, 1H), 2.70 (s, 3H).

Step B: Ethyl difluoro(6-methylpyridazin-3-yl)acetate

This procedure is derived from the general method of T. Taguchi, et al. (*Tetrahedron Lett.*, 1986, 27, 6103–6106). Ethyl difluoroiodoacetate (0.355 mL, 651 mg, 2.60 mmol) was added to a rapidly stirred suspension of copper powder (333 mg, 5.24 mmol) in DMSO (6.5 mL) at rt. After 50 min., 3-bromo-6-methylpyridazine (300 mg, 1.73 mmol) was added in DMSO (1.0 mL). After 20 h, the mixture was transferred to a separatory funnel containing water (25 mL) and saturated aq. NH$_4$Cl (25 mL), and extracted with ethyl acetate (2×50 mL). The organic extracts were washed with saturated aq. brine, dried (sodium sulfate), decanted, and evaporated. Purification by flash column chromatography on silica gel, eluting with 70:30 v/v hexanes/ethyl acetate, gave 363 mg of the title compound as an amber liquid. For the title compound:

$^1$H NMR (500 MHz, CDCl$_3$) δ7.79 (d, J=9, 1H), 7.53 (d, J=9, 1H), 4.43 (q, J=7, 2H), 2.82 (s, 3H), 1.38 (t, J=7, 3H).

Steps C–E: 4-(3,3-Difluoro-3-(6-methylpyridazin-3-yl)propyl)piperidine

The title compound was prepared using procedures analogous to those described in Procedure 35, Steps C–E, substituting ethyl difluoro(6-methylpyridazin-3-yl)acetate (from Procedure 36 Step B) for ethyl difluoro(2-pyridyl)acetate in Step C. For the title compound:

$^1$H NMR (500 MHz, CD$_3$OD) δ7.86 (d, J=9, 1H), 7.74 (d, J=9, 1H), 2.99 (dm, J=12, 2H), 2.74 (s, 3H), 2.54 (td, J=12, 3, 2H), 2.51–2.40 (m, 2H), 1.69 (bd, J=12, 2H), 1.47–1.34 (m, 3H), 1.10 (qd, J=12, 4, 2H).

Procedure 37

4-(3,3-Difluoro-3-(5-(trifluoromethyl)pyrid-2-yl)propyl)piperidine

The title compound was prepared using procedures analogous to those described in Procedure 36, substituting 2-bromo-5-(trifluoromethyl)pyridine for 3-bromo-6-methylpyridazine in Step B. For the title compound:

$^1$H NMR (500 MHz, CD$_3$OD) δ8.96 (s, 1H), 8.28 (dd, J=8, 2, 1H), 7.88 (d, J=8, 1H), 2.99 (bd, J=12, 2H), 2.53 (td, J=12, 2, 2H), 2.43–2.31 (m, 2H), 1.68 (bd, J=13, 2H), 1.44–1.28 (m, 3H), 1.09 (qd, J=12, 3, 2H); ESI-MS 309 (M+H); HPLC A: 2.32 min.

Procedure 38

4-(3,3-Difluoro-3-(3-pyridyl)propyl)piperidine

Step A: Dimethyl (2-oxo-2-(3-pyridyl)ethyl)phosphonate

A solution of n-butyl lithium in hexanes (9.0 mL, 1.6 M, 14 mmol) was added over 10 min. to a solution of dimethyl methylphosphonate (1.50 mL, 1.72 g, 13.8 mmol) in THF (60 mL) cooled in a dry ice/isopropanol bath. After 30 min., a solution of methyl nicotinate (757 mg, 5.52 mmol) in THF (6 mL) was added over 2 min. The solution was stirred in the cooling bath for 45 min. before being allowed to warm to 0° C. over 1 h. The reaction was quenched with saturated aq. NH$_4$Cl (50 mL) and then partitioned between saturated aq. brine (50 mL) and methylene chloride (200 mL). The aq. layer was extracted with methylene chloride (2×100 mL). The combined organic layers were dried (sodium sulfate) decanted, and evaporated. Purification by flash column chromatography on silica gel, eluting with ethyl acetate followed by 97:3 v/v methylene chloride/CH$_3$OH, gave material containing some residual impurity. Further purification by flash column chromatography on silica gel, eluting with 50:50:5 v/v/v to 50:50:10 v/v/v toluene/ethyl acetate/CH$_3$OH gave 1.15 g of the title compound. For the title compound: $^1$H NMR (500 MHz, CDCl$_3$) δ9.26–9.20 (bs, 1H), 8.83 (d, J=4, 1H), 8.34 (dt, J=8, 2, 1H), 7.70 (dd, J=8, 4, 1H), 3.82 (d, J=11, 6H), 3.67 (d, J=24, 2H).

Step B: 1-(t-Butoxycarbonyl)-4-(3-oxo-3-(3-pyridyl)prop-1-enyl)piperidine 1,1,1-Triacetoxy-1,1-dihydro-1,2-benzoiodoxol-3(1H)-one (750 mg, 1.77 mmol) was added to a solution of 1-(t-butoxycarbonyl)-4-(hydroxymethyl)piperidine (339 mg, 1.57 mmol, from Procedure 17, Step A) in methylene chloride (10 mL) and the mixture was stirred at rt. After 45 min., and additional portion of 1,1,1-triacetoxy-1,1-dihydro-1,2-benzoiodoxol-3(1H)-one (150 mg, 0.35 mmol) was added. After an additional 30 min., ether (30 mL) and 1.3 N NaOH (10 mL) were added and stirring was continued for 20 min. The mixture was transferred to a separatory funnel with additional ether (30 mL) and 1.3 N NaOH (15 mL). The organic layer was separated, washed with water (20 mL), dried (sodium sulfate), decanted, and evaporated to give 291 mg of 1-(t-butoxycarbonyl)-4-piperidinecarboxaldehyde as a colorless oil.

A solution of dimethyl (2-oxo-2-(3-pyridyl)ethyl)phosphonate (150 mg, 0.65 mmol, from Procedure 38, Step A) in THF (1.8 mL) was added to a stirred suspension of sodium hydride (60% oil dispersion, 15 mg of sodium hydride, 0.63 mmol) in THF (3.0 mL). The resulting suspension was warmed in a 45° C. oil bath for 30 min. After the mixture had cooled to rt, 1-(t-butoxycarbonyl)-4-piperidinecarboxaldehyde (112 mg, 0.53 mmol) was added in THF (1.5 mL). After stirring overnight at rt, the mixture was diluted with ether (20 mL) and washed with 2.5 N NaOH (20 mL) followed by saturated aq. brine (20 mL). The aq. layers were extracted in succession with ether (20 mL), and the combined organic layers were dried (sodium sulfate), decanted, and evaporated. Purification by flash column chromatography on silica gel, eluting with 80:20 v/v to 60:40 v/v hexanes/ethyl acetate, gave 135 mg of the title compound (trans isomer) as a yellow syrup. For the title compound: $^1$H NMR (500 MHz, CDCl$_3$) δ9.17–9.13 (bs, 1H), 8.81 (bd, J=4, 1H), 8.27 (d, J=8, 1H), 7.49 (dd, J=8, 4, 1H), 7.07 (dd, J=15, 7, 1H), 6.85 (dd, J=15, 1, 1H), 4.25–4.13 (bs, 2H), 2.87–2.78 (m, 2H), 2.51–2.41 (m, 1H), 1.83 (d, J=12, 2H), 1.49 (s, 9H), 1.45 (qd, J=12, 4, 2H). ESI-MS 261 (M+H-56), 217 (M+H-100); HPLC A: 1.73 min.

Step C: 1-(t-Butoxycarbonyl)-4-(3-oxo-3-(3-pyridyl)propyl)piperidine 1-(t-Butoxycarbonyl)-4-(3-oxo-3-(3-pyridyl)prop-1-enyl)piperidine (940 mg, 2.97 mmol, from Procedure 38, Step B)

was hydrogenated using 5% Pd/C in 95% ethanol at atmospheric pressure. Purification by flash column chromatography on silica gel, eluting with 90:10 v/v to 50:50 v/v hexanes/ethyl acetate gave 884 mg of the title compound as a colorless syrup. For the title compound:

$^1$H NMR (500 MHz, CDCl$_3$) δ9.23–9.15 (bs, 1H), 8.81 (bd, J=4, 1H), 8.28 (dt, J=8, 1, 1H), 7.48 (dd, J=8, 4, 1H), 4.19–4.04 (bs, 2H), 3.04 (t, J=8, 2H), 2.70 (bt, J=11, 2H), 1.78–1.70 (m, 4H), 1.56–1.45 (m, 1H), 1.47 (s, 9H), 1.17 (qd, J=12, 4, 2H). ESI-MS 263 (M+H-56), 219 (M+H-100); HPLC A: 1.78 min.

Step D: 1-(t-Butoxycarbonyl)-4-(3,3-difluoro-3-(3-pyridyl)propyl)piperidine

A solution of 1-(t-butoxycarbonyl)-4-(3-oxo-3-(3-pyridyl)propyl)piperidine (810 mg, 2.54 mmol, from Procedure 38, Step C) in (diethylamino)sulfur trifluoride (3.30 mL, 3.66 g, 23 mmol) was stirred in a teflon tube at 40° C. for 2 days. The reaction was diluted with methylene chloride (20 mL) and the resulting solution was added in portions to a stirred mixture of water (150 mL), ice (150 g) and sodium bicarbonate (29.3 g). After the resulting reaction had subsided, the mixture was extracted with ethyl acetate (2×200 mL). The organic layers were washed in succession with saturated aq. brine (100 ML), dried (sodium sulfate), decanted, and evaporated. Flash column chromatography on silica gel, eluting with 80:20 v/v to 50:50 v/v toluene/ether, gave material containing some residual impurity. Further purification by preparative BPLC on a 20×250 mm Chiracel OD column, eluting with 80:20 v/v hexanes/isopropanol, gave 395 mg of the title compound:

$^1$H NMR (500 MHz, CD$_3$OD) δ8.69 (s, 1H), 8.64 (d, J=5, 1H), 7.97 (d, J=8, 1H), 7.54 (dd, J=8, 5, 1H), 4.04 (d, J=13, 2H), 2.78–2.62 (bs, 2H), 2.31–2.20 (m, 2H), 1.68 (d, J=12, 2H), 1.50–1.40 (m, 1H), 1.43 (s, 9H), 1.40–1.34 (m, 2H), 1.02 (qd, J=12, 4, 2H). ESI-MS 285 (M+H-56), 241 (M+H-100); HPLC A: 2.10 min.

Step E: 4-(3,3-Difluoro-3-(3-pyridyl)propyl)piperidine

The title compound was prepared using procedures analogous to those described in Procedure 17, Step H, substituting 1-(t-butoxycarbonyl)-4-(3,3-difluoro-3-(3-pyridyl)propyl)piperidine (from Procedure 38, Step D) for 1-(t-butoxycarbonyl)-4-(3,3-difluoro-3-(4-fluorophenyl)propyl)piperidine. For the title compound:

$^1$H NMR (500 MHz, CD$_3$OD) δ8.68 (s, 1H), 8.64 (d, J=4, 1H), 7.97 (d, J=8, 1H), 7.54 (dd, J=8, 4, 1H), 2.98 (bd, J=12, 2H), 2.52 (td, J=12, 3, 2H), 2.30–2.18 (m, 2H), 1.66 (bd, J=13, 2H), 1.44–1.30 (m, 3H), 1.08 (qd, J=12, 3, 2H); ESI-MS 241 (M+H).

Procedure 39

4-(3,3-Difluoro-3-(1-methylpyrazol-4-yl)propyl)piperidine

The title compound was prepared using procedures analogous to those described in Procedure 38, substituting ethyl 1-methyl-4-pyrazolecarboxylate, obtained by methylation of ethyl 4-pyrazolecarboxylate with iodomethane and K$_2$CO$_3$ in CH$_3$CN at rt, for methyl nicotinate in Step A. For the title compound:

$^1$H NMR (500 MHz, CD$_3$OD) δ7.78 (s, 1H), 7.54 (s, 1H), 3.89 (s, 3H), 3.00 (dt, J=12, 3, 2H), 2.55 (td, J=12, 3, 2H), 2.22–2.10 (m, 2H), 1.69 (bd, J=12, 2H), 1.45–1.34 (m, 3H), 1.10 (qd, J=12, 4, 2H). ESI-MS 244 (M+H, 60%), 224 (M-19, 100%); HPLC A: 0.98 min.

Procedure 40

4-(7-Chloroimidazo[1,2-a]pyridin-3-yl)piperidine, TFA salt

The title compound was prepared from 350 mg of 1-(t-butoxycarbonyl)-4-(1-bromo-2-oxoethyl)piperidine (from Procedure, Step C) and 162 mg of 2-amino-4-chloropyridine (prepared using procedures analogous to those described by R. J. Sundberg et al, *Org. Preparations & Procedures Int.* 1997, 29, (1), 117–122) in 10 mL ethanol using a procedure analogous to that described in Procedure 27, Step A–B to provide 240 mg of the BOC intermediate as a solid prior to the final de-BOC to give the title TFA salt.

Procedure 41

4-(7-n-Propylimidazo[1,2-a]pyridin-3-yl)piperidine, TFA salt

The title compound was prepared according to the general procedures of Procedure 27 and 28, employing 2-amino-4-n-propylpyridine (prepared using a procedure analogous to that described in Procedure 28, Step A) in place of 2-aminopyridine in Procedure 27, Step A.

Procedure 42

4-(6-Fluoroimidazo[1,2-a]pyridin-3-yl)piperidine, TFA salt

The title compound was prepared from 1-(t-butoxycarbonyl)-4-(1-bromo-2-oxoethyl)piperidine (from Procedure 23, Step B) and 2-amino-5-fluoropyridine (prepared using procedures analogous to those described by D. C. Baker et al, *Synthesis.* 1989, 905) using a procedures similar to that described in Procedure 27, Step A–C.

For the BOC intermediate: $^1$H NMR (500 MHz, CDCl$_3$): δ1.51 (s, 9H), 1.60–1.80 (m, 2H), 2.07 (br d, 2H), 2.85–3.00 (m, 3H), 4.20–4.40 (br, 2H), 7.11 (m, 1H), 7.47 (s, 3H), 7.60(m, 1H), 7.89 (m, 1H).

Procedure 43

4-(6-Fluoro-7-methylimidazo[1,2-a]pyridin-3-yl)piperidine

The title compound was prepared using procedures analogous to those described in Procedure 27, Step A–C, except 2-amino-5-fluoro-4-methylpyridine (prepared using procedures analogous to those described by D. C. Baker et al, *Synthesis.* 1989, 905) was employed in place of 2-amino-5-fluoropyridine in Step A.

Procedure 44

4-(2-Ethylindazol-3-yl)piperidine, TFA salt

Step A: 2-Ethylindazole

To a solution of indazole (6.2 g, 52.5 mmol) in DMF (30 mL) was added sodium hydride (60% dispersion in mineral oil, 3.0 g, 75.0 mmol) at 0° C.

After stirring at 0° C. for 20 min., ethyl iodide (5 mL, 62.5 mmol) was added dropwise at 0° C. The mixture was stirred at rt for 1 h, and then partitioned between ethyl acetate and water. The aqueous layer was extracted with ethyl acetate (3×). The combined organic phases were washed with brine, and dried over anhydrous magnesium sulfate. TLC indicated that a 2:1 mixture of two isomers was formed. The mixture was purified by flash chromatography (hexanes:ethyl acetate=4:1, then 1:1) to give 2.34 g of the title compound as a viscous oil (slow moving isomer).

Step B: 2-Ethyl-3-bromoindazole

To a solution of 2-ethylindazole (2.32 g, 15.87 mmol) in ethanol (20 mL) was added bromine (2.54 g, 15.87 mmol) in ethanol (1 mL)/water (1 mL) at 0° C. After stirring at 0°

C. for 10 min. and at rt for 1 h, the reaction was quenched with aq. sodium bicarbonate. The mixture was partitioned between ethyl acetate and aq. sodium bicarbonate. The aqueous layer was extracted with ethyl acetate (3x). The combined organic phase was washed with brine, and dried over anhydrous magnesium sulfate. Purification by flash chromatography (hexanes: ethyl acetate =1:1, then 100% ethyl acetate) gave 2.34 g of the title compound as a viscous oil.

Step C: 1-(t-Butoxycarbonyl)-4-hydroxy-4-(2-ethyl-indazol-3-yl)piperidine

To a solution of 2-ethyl-3-bromoindazole (3.4 g, 15.18 mmol) in THF (30 mL) was added t-BuLi (1.7 M in pentane, 10.72 mL, 18.22 mmol) dropwise at −78° C. After stirring at −78° C. for 20 min., was added tert-butyl 4-oxo-1-piperidinecarboxylate (3.03 g, 15.18 mmol) in THF (10 mL) dropwise at −78° C. The mixture was stirred at −78° C. for 10 min. and at rt for 18 h. After the reaction was quenched with aq. $NH_4Cl$, the mixture was partitioned between ethyl acetate and water. The aqueous layer was extracted with ethyl acetate (3x). The combined organic phases were washed with brine, and dried over anhydrous magnesium sulfate. Concentration followed by purification by flash chromatography (hexanes ethyl acetate=4:1, then 1:1) to give 1.18 g of the title compound as a foamy solid.

Step D: 1-(t-Butoxycarbonyl)-4-(2-ethyl-indazol-3-yl)-[1,2,3,6]tetrahydropyridine To a solution of 1-(t-butoxycarbonyl)-4-hydroxy-4-(2-ethyl-indazol-3-yl)piperidine (651 mg, 1.89 mmol) in toluene (5 mL) was added (methoxycarbonylsulfamoyl)-triethylammonium hydroxide inner salt (540 mg, 2.27 mmol). After heating up to ~70° C. for 10 min., was added additional 5 mL of toluene. The mixture was stirred at 70° C. for additional 2 h. The mixture was partitioned between ethyl acetate and aq. sodium bicarbonate. Aqueous layer was extracted with ethyl acetate (3x). The combined organic phases were washed with brine, and dried over anhydrous magnesium sulfate. Concentration followed by purification by flash chromatography (hexanes:ethyl acetate=4:1, then 1:1) gave 514 mg of the title compound as a viscous oil.

Step E: 1-(t-Butoxycarbonyl)-4-(2-ethyl-[5,6,7,8]tetrahydroindazol-3-yl)piperidine A solution of 1-(t-butoxycarbonyl)-4-(2-ethyl-indazol-3-yl)-[1,2,3,6]tetrahydropyridine (500 mg, 1.53 mmol) in methanol (5 mL) was hydrogenated using $Pd(OH)_2$ (100 mg) under atmospheric $H_2$ for 4.5 h. After the addition of Platinum (IV) oxide (100 mg) hydrogenation was continued for additional 4 h. The mixture was filtered through celite and concentrated to give the title compound (461 mg) as a viscous oil. ESI-MS 333 (M+1); HPLC A: 2.45 min.

Step F: 1-(t-Butoxycarbonyl)-4-(2-ethylindazol-3-yl)piperidine

To a solution of 1-(t-butoxycarbonyl)-4-(2-ethyl-[5,6,7,8]tetrahydroindazol-3-yl)piperidine (80 mg, 0.24 mmol) in toluene (3 mL) was added DDQ (115 mg, 0.51 mmol) at rt. After refluxing for 4 h, the mixture was partitioned between ethyl acetate and water. The aqueous layer was extracted with ethyl acetate (3x). The combined organic phases were washed with brine, and dried over anhydrous magnesium sulfate. Concentration gave 25 mg of the title compound as a viscous oil.

ESI-MS 274 (M+1-t-Bu); HPLC A: 3.09 min.

Step G: 4-(2-Ethylindazol-3-yl)piperidine, TFA salt

Using essentially the same method as Procedure 27, Step B, the title compound was obtained as the TFA salt Procedure 45

4-(1,3-Diethyl-4-methyl-(1H)-pyrazol-5-yl)piperidine di-HCl salt

Step A: 1-(t-Butoxycarbonyl)-4-(N-methyl-N-methoxycarboxamido)piperidine

A solution of 1-(t-butoxycarbonyl)isonipecotic acid (13.74 g, 0.06 mol), TEA (14.7 mL, 0.105 mol), 4-DMAP (1.83 g, 0.015 mol), N-ethyl-N'-(3-dimethylaminopropyl)carbodiimide×HCl (11.50 g, 0.06 mol) and O,N-dimethylhydroxylamine×HCl (6.27 g, 0.09 mol) in methylene chloride (250 mL) was stirred at rt for 60 h. The mixture was partitioned between 1 L of ether and 500 mL of water and the layers were separated. The organic layer was washed with 500 mL of 1.0 $\underline{N}$ HCl, 500 mL of 1.0 $\underline{N}$ NaOH, 500 mL of sat'd sodium chloride, dried over magnesium sulfate and concentrated to afford 14.34 g (88%) of the title compound:

$^1$H NMR (500 MHz) δ1.46 (s, 9H), 1.65–1.80 (4H), 2.76–2.86 (3H), 3.19 (s, 3H), 3.71 (s, 3H), 4.15 (2H).

Step B: 1-(t-Butoxycarbonyl)-4-formylpiperidine

A solution of 1-(t-butoxycarbonyl)-4-(N-methyl-N-methoxycarboxamido)piperidine (4.80 g, 17.6 mmol) (from Step A) in methylene chloride (100 mL) at −78° C. was treated with 1.0 $\underline{M}$ DIBALH solution in methylene chloride (25 mL) and stirred cold for 30 min. The reaction was quenched with 1.0 $\underline{N}$ HCl (250 mL) and warmed to rt. The quenched mixture was extracted with 300 mL of ether; the extract was washed with 150 mL of 1.0 $\underline{N}$ NaOH, 150 mL of sat'd sodium chloride, dried over magnesium sulfate and concentrated. Flash chromatography on 125 g of silica gel using 1:1 v/v hexanes/ether as the eluant afforded 3.60 g (95%) of the title compound:

$^1$H NMR (500 MHz) δ1.46 (s, 9H), 1.52–1.59 (m, 2H), 1.85–1.91 (m, 2H), 2.38–2.43 (m, 1H), 2.93 (app t, J=11.0, 2H), 3.95–4.05 (m, 2H), 9.66 (s, 1H).

Step C: 1-(t-Butoxycarbonyl)-4-(1-(RS)-hydroxy-2-(RS)-methyl-3-oxopent-1-yl)piperidine A solution of diisopropylamine (0.63 mL, 4.5 mmol) in THF (16 mL) at 0° C. was treated with 1.6 M n-butyllithium in sol'n in hexanes (2.8 mL). The resulting solution was stirred at 0° C. for 10 min, then cooled to −78° C. 3-Pentanone (0.41 mL, 4.1 mmol) was added and the resulting mixture was stirred cold for 1 h. A solution of 1-(t-butoxycarbonyl)4-formylpiperidine (435 mg, 2.05 mmol) (from Step B) in THF (3 mL) was then added. After 15 min, the reaction was quenched with sat'd ammonium chloride (25 mL) and extracted with ether (100 mL). The extract was dried over magnesium sulfate and concentrated. MPLC (Biotage) on a 40S silica cartridge using 4:1 v/v, then 3:2 v/v hexanes/ethyl acetate as the eluent afforded 517 mg (85%) of the title compound.

Step D: 1-(t-Butoxycarbonyl)-4-(1,3-dioxo-2-(RS)-methylpent-1-yl)piperidine

A solution of oxalyl chloride (0.34 mL, 3.9 mmol) in methylene chloride (12 mL) at −78° C. was treated with DMSO (0.43 mL, 6.0 mmol) and the resulting mixture was stirred cold for 10 min. A solution of 1-(t-butoxycarbonyl)-4-(1-(RS)-hydroxy-2-(RS)-methyl-3-oxopent-1-yl)piperidine (514 mg, 1.7 mmol) (from Step C) was added and the resulting solution was stirred cold for 1 h. N,N-Diisopropylethylamine (2.4 mL, 13.7 mmol) was added and the resulting mixture was warmed to 0° C. The reaction was quenched with 1.0 N HCl (25 mL) and extracted with ether (100 mL). The extract was dried over magnesium sulfate and concentrated. MPLC (Biotage) on a 40S silica cartridge using 2:1 v/v hexanes/ethyl acetate as the eluent afforded 435 mg (85%) of the title compound.

Step E: 1-(t-Butoxycarbonyl)-4-(1,3-diethyl-4-methyl-(1H)-pyrazol-5-yl)piperidine A solution of 1-(t-butoxycarbonyl)-4-(1,3-dioxo-2-(RS)-methylpent-1-yl)piperidine (435 mg, 1.5 mmol) (from Step D) in 2:1 v/v acetonitrile/water (12 mL) was treated with ethylhydrazine (34% sol'n in water, 0.28 mL, 1.6 mmol) and the resulting mixture was stirred at rt for 20 h. The reaction mixture was partitioned between 75 mL of ether and 25 mL of sat'd sodium chloride and the layers were separated. The organic layer was dried over magnesium sulfate and concentrated. MPLC (Biotage) on a 40S silica cartridge using 4:1 v/v, then 1:1 v/v hexanes/ethyl acetate as the eluent afforded 348 mg (74%) of the title compound:

$^1$H NMR (500 MHz) δ1.21 (t, J=7.5, 3H), 1.36 (t, J=7.5, 3H), 1.49 (s, 9H), 1.68–1.72 (m, 2H), 1.86–1.91 (m, 2H), 2.54 (q, J=1.5, 2H), 2.72–2.79 (3H), 4.08 (qd, J=, 2H), 4.20–4.30 (m, 2H).

Step F: 4-(1,3-Diethyl-4-methyl-(1H)-pyrazol-5-yl) piperidine di-HCl salt

A solution of 1-(t-butoxycarbonyl)-4-(1,3-diethyl-4-methyl-(1H)-pyrazol-5-yl)piperidine (348 mg) (from Step E) in 2.5 $\underline{N}$ HCl in methanol was stirred at rt for 16 h. The solution was concentrated and the resulting solid was suspended in ethyl acetate, filtered and dried to afford 293 mg (92%) of the title compound.

Procedure 46

Using essentially the same methods as described in Procedure 45 and substituting the appropriate starting material and/or hydrazine reagent, a variety of other 4-(1,3,4-trialkyl)-(1H)-pyrazol-5-yl)piperidines can be prepared, usually as the di-hydrochloride salts, and utilized in the following Examples as required.

Procedure 47

Using essentially the same methods as described in Procedures 1 and 2 and substituting the appropriate starting material and/or hydrazine reagent, the following representative 4-(3-(substituted)-1-(H or alkyl)-(1H)-pyrazol-5-yl) piperidines can be prepared, usually as the di-hydrochloride salts, and utilized in the following Examples as required.

4-(3-(Benzyl)-1-(methyl)-(1H)-pyrazol-5-yl)piperidine
4-(3-(Benzyl)-1-(n-propyl)-(1H)-pyrazol-5-yl)piperidine
4-(3-(Benzyl)-1-(isopropyl)-(1H)-pyrazol-5-yl)piperidine
4-(3-(2-Fluorobenzyl)-1-(ethyl)-(1H)-pyrazol-5-yl) piperidine
4-(3-(3-Fluorobenzyl)-1-(ethyl)-(1H)-pyrazol-5-yl) piperidine
4-(3-(4-Fluorobenzyl)-1-(ethyl)-(1H)-pyrazol-5-yl) piperidine
4-(3-(4-Fluorobenzyl)-(1H)-pyrazol-5-yl)piperidine
4-(3-(4-Fluorobenzyl)-1-(methyl)-(1H)-pyrazol-5-yl) piperidine
4-(3-(4-Fluorobenzyl)-1-(n-propyl)-(1H)-pyrazol-5-yl) piperidine
4-(3-(3,4-Difluorobenzyl)-1-(ethyl)-(1H)-pyrazol-5-yl) piperidine
4-(3-(3,4-Difluorobenzyl)-1-(methyl)-(1H)-pyrazol-5-yl) piperidine
4-(3-(3,4-Difluorobenzyl)-(1H)-pyrazol-5-yl)piperidine
4-(3-(3,5-Difluorobenzyl)-1-(ethyl)-(1H)-pyrazol-5-yl) piperidine
4-(3-(2,4-Difluorobenzyl)-1-(ethyl)-(1H)-pyrazol-5-yl) piperidine
4-(3-(3-Chlorobenzyl)-1-(ethyl)-(1H)-pyrazol-5-yl) piperidine
4-(3-(4-Chlorobenzyl)-1-(ethyl)-(1H)-pyrazol-5-yl) piperidine
4-(3-(3,4-Dichlorobenzyl)-1-(ethyl)-(1H)-pyrazol-5-yl) piperidine
4-(3-(3-Cyanobenzyl)-1-(ethyl)-(1H)-pyrazol-5-yl) piperidine
4-(3-(4-Cyanobenzyl)-1-(ethyl)-(1H)-pyrazol-5-yl) piperidine
4-(3-(3-Methylsulfonylbenzyl)-1-(ethyl)-(1H)-pyrazol-5-yl) piperidine
4-(3-(4-Methylsulfonylbenzyl)-1-(ethyl)-(1H)-pyrazol-5-yl) piperidine
4-(3-(3-Methoxybenzyl)-1-(ethyl)-(1H)-pyrazol-5-yl) piperidine
4-(3-(4-Methoxybenzyl)-1-(ethyl)-(1H)-pyrazol-5-yl) piperidine
4-(3-(4-Methoxybenzyl)-1-(methyl)-(1H)-pyrazol-5-yl) piperidine
4-(3-(4-Methoxybenzyl)-(1H)-pyrazol-5-yl)piperidine
4-(3-(3-Ethoxybenzyl)-1-(ethyl)-(1H)-pyrazol-5-yl) piperidine
4-(3-(4-Ethoxybenzyl)-1-(ethyl)-(1H)-pyrazol-5-yl) piperidine
4-(3-(4-Ethoxybenzyl)-(1H)-pyrazol-5-yl)piperidine
4-(3-(3-Isopropoxybenzyl)-1-(ethyl)-(1H)-pyrazol-5-yl) piperidine
4-(3-(4-Isopropoxybenzyl)-1-(ethyl)-(1H)-pyrazol-5-yl) piperidine
4-(3-(4-Cyclopropoxybenzyl)-1-(ethyl)-(1H)-pyrazol-5-yl) piperidine
4-(3-(4-Butoxybenzyl)-1-(ethyl)-(1H)-pyrazol-5-yl) piperidine
4-(3-(4-t-Butoxybenzyl)-1-(ethyl)-(1H)-pyrazol-5-yl) piperidine
4-(3-(4-Cyclobutoxybenzyl)-1-(ethyl)-(1H)-pyrazol-5-yl) piperidine
4-(3-(4-Difluoromethoxybenzyl)-1-(ethyl)-(1H)-pyrazol-5-yl)piperidine
4-(3-(4-Trifluoromethoxybenzyl)-1-(ethyl)-(1H)-pyrazol-5-yl)piperidine
4-(3-(4-Trifluoroethoxybenzyl)-1-(ethyl)-(1H)-pyrazol-5-yl)piperidine
4-(3-(3,4-Methylenedioxybenzyl)-1-(ethyl)-(1H)-pyrazol-5-yl) piperidine
4-(3-(3,4-Dimethoxybenzyl)-1-(ethyl)-(1H)-pyrazol-5-yl) piperidine
4-(3-(3,4-Diethoxybenzyl)-1-(ethyl)-(1H)-pyrazol-5-yl) piperidine
4-(3-(3-Fluoro-4-methoxybenzyl)-1-(ethyl)-(1H)-pyrazol-5-yl)piperidine
4-(3-(4-Fluoro-3-methoxybenzyl)-1-(ethyl)-(1H)-pyrazol-5-yl)piperidine
4-(3-(3-Fluoro-4-ethoxybenzyl)-1-(ethyl)-(1H)-pyrazol-5-yl)piperidine
4-(3-(4-Fluoro-3-ethoxybenzyl)-1-(ethyl)-(1H)-pyrazol-5-yl)piperidine
4-(3-(3-Cyano-3-methoxybenzyl)-1-(ethyl)-(1H)-pyrazol-5-yl)piperidine
4-(3-(4-Cyano-3-methoxybenzyl)-1-(ethyl)-(1H)-pyrazol-5-yl)piperidine
4-(3-(3-Cyano-4-ethoxybenzyl)-1-(ethyl)-(1H)-pyrazol-5-yl)piperidine
4-(3-(4-Cyano-3-ethoxybenzyl)-1-(ethyl)-(1H)-pyrazol-5-yl)piperidine
4-(3-(Benzofuran-6-yl)-1-(ethyl)-(1H)-pyrazol-5-yl) piperidine
4-(3-(Benzofuran-5-yl)-1-(ethyl)-(1H)-pyrazol-5-yl) piperidine
4-(3-(2,3-Dihydrobenzofuran-6-yl)-1-(ethyl)-(1H)-pyrazol-5-yl)piperidine
4-(3-(4-Benzyloxybenzyl)-1-(ethyl)-(1H)-pyrazol-5-yl) piperidine
4-(3-(4-hydroxybenzyl)-1-(ethyl)-(1H)-pyrazol-5-yl) piperidine 4-(3-(3-Methylbenzyl)-1-(ethyl)-(1H)-pyrazol-5-yl)piperidine
4-(3-(4-Methylbenzyl)-1-(ethyl)-(1H)-pyrazol-5-yl)piperidine
4-(3-(3-Ethylbenzyl)-1-(ethyl)-(1H)-pyrazol-5-yl)piperidine
4-(3-(4-Ethylbenzyl)-1-(ethyl)-(1H)-pyrazol-5-yl)piperidine
4-(3-(4-Ethylbenzyl)-1-(methyl)-(1H)-pyrazol-5-yl)piperidine
4-(3-(4-Ethylbenzyl)-(1H)-pyrazol-5-yl)piperidine
4-(3-(4-Isopropylbenzyl)-1-(ethyl)-(1H)-pyrazol-5-yl)piperidine
4-(3-(4-t-Butylbenzyl)-1-(ethyl)-(1H)-pyrazol-5-yl)piperidine
4-(3-(4-Trifluoromethylbenzyl)-1-(ethyl)-(1H)-pyrazol-5-yl)piperidine
4-(3-(3-Phenylbenzyl)-1-(ethyl)-(H)-pyrazol-5-yl)piperidine
4-(3-(4-Phenylbenzyl)-1-(ethyl)-(1H)-pyrazol-5-yl)piperidine
4-(3-(4-Naphthyl)-1-(ethyl)-(1H)-pyrazol-5-yl)piperidine
4-(3-(2-Naphthyl)-1-(ethyl)-(1H)-pyrazol-5-yl)piperidine
4-(3-(4-Acetylbenzyl)-1-(ethyl)-(1H)-pyrazol-5-yl)piperidine
4-(3-(4-(1-Methyl-1-hydroxyethylbenzyl)-1-(ethyl)-(1H)-pyrazol-5-yl)piperidine
4-(3-(3-Trifluoromethylbenzyl)-1-(ethyl)-(1H)-pyrazol-5-yl)piperidine
4-(3-(4-Trifluoromethylbenzyl)-1-(ethyl)-(1H)-pyrazol-5-yl)piperidine
4-(3-(Pyridin-3-yl)-1-(ethyl)-(1H)-pyrazol-5-yl)piperidine
4-(3-(Pyridin-3-yl)-(1H)-pyrazol-5-yl) piperidine
4-(3-(Cyclohexylmethyl)-1-(ethyl)-(1H)-pyrazol-5-yl)piperidine
4-(3-(4-Methylcyclohexylmethyl)-1-(ethyl)-(1H)-pyrazol-5-yl)piperidine
4-(3-(Cycloheptylmethyl)-1-(ethyl)-(1H)-pyrazol-5-yl)piperidine
4-(3-(Pyran-4-ylmethyl)-1-(ethyl)-(1H)-pyrazol-5-yl)piperidine
4-(3-(Thiopyran-4-ylmethyl)-1-(ethyl)-(1H)-pyrazol-5-yl)piperidine, S,S-dioxide Procedure 48

Using essentially the same methods as described in Procedures 22–26 and substituting the appropriate starting material and/or reagent, the following representative 4-(2-(substituted)-4-(H or alkyl)thiazol-5-yl)piperidines can be prepared, usually as the di-hydrochloride salts, and utilized in the following Examples as required.
4-(2-(Benzyl)-4-(ethyl)thiazol-5-yl)piperidine
4-(2-(Benzyl)-4-(methyl)thiazol-5-yl)piperidine
4-(2-(Benzyl)thiazol-5-yl)piperidine
4-(2-(2-Fluorobenzyl)-4-(ethyl)thiazol-5-yl)piperidine
4-(2-(2-Fluorobenzyl)-4-(methyl)thiazol-5-yl)piperidine
4-(2-(2-Fluorobenzyl)thiazol-5-yl)piperidine
4-(2-(3-Fluorobenzyl)-4-(ethyl)thiazol-5-yl)piperidine
4-(2-(3-Fluorobenzyl)-4-(methyl)thiazol-5-yl)piperidine
4-(2-(3-Fluorobenzyl)thiazol-5-yl)piperidine
4-(2-(4-Fluorobenzyl)-4-(ethyl)thiazol-5-yl)piperidine
4-(2-(4-Fluorobenzyl)-4-(methyl)thiazol-5-yl)piperidine
4-(2-(4-Fluorobenzyl)thiazol-5-yl)piperidine
4-(2-(2-Chlorobenzyl)-4-(ethyl)thiazol-5-yl)piperidine
4-(2-(2-Chlorobenzyl)-4-(methyl)thiazol-5-yl)piperidine
4-(2-(2-Chlorobenzyl)thiazol-5-yl)piperidine
4-(2-(3-Chlorobenzyl)-4-(ethyl)thiazo-5-y)piperidine
4-(2-(3-Chlorobenzyl)-4-(methyl)thiazol-5-yl)piperidine
4-(2-(3-Chlorobenzyl)thiazol-5-yl)piperidine
4-(2-(4-Chlorobenzyl)-4-(ethyl)thiazol-5-yl)piperidine
4-(2-(4-Chlorobenzyl)-4-(methyl)thiazol-5-yl)piperidine
4-(2-(4-Chlorobenzyl)thiazol-5-yl)piperidine
4-(2-(3-Cyanobenzyl)-4-(ethyl)thiazol-5-yl)piperidine
4-(2-(3-Cyanobenzyl)-4-(methyl)thiazol-5-yl)piperidine
4-(2-(3-Cyanobenzyl)thiazol-5-yl)piperidine
4-(2-(4-Cyanobenzyl)-4-(ethyl)thiazol-5-yl)piperidine
4-(2-(4-Cyanobenzyl)-4-(methyl)thiazol-5-yl)piperidine
4-(2-(4-Cyanobenzyl)thiazol-5-yl)piperidine
4-(2-(3,4-Difluorobenzyl)-4-(ethyl)thiazol-5-yl)piperidine
4-(2-(3,4-Difluorobenzyl)-4-(methyl)thiazol-5-yl)piperidine
4-(2-(3,4-Difluorobenzyl)thiazol-5-yl)piperidine
4-(2-(3,5-Difluorobenzyl)-4-(ethyl)thiazol-5-yl)piperidine
4-(2-(3,5-Difluorobenzyl)-4-(methyl)thiazol-5-yl)piperidine
4-(2-(3,5-Difluorobenzyl)thiazol-5-yl)piperidine
4-(2-(2,4-Difluorobenzyl)-4-(ethyl)thiazol-5-yl)piperidine
4-(2-(2,4-Difluorobenzyl)-4-(methyl)thiazol-5-yl)piperidine
4-(2-(2,4-Difluorobenzyl)thiazol-5-yl)piperidine
4-(2-(3,4-Dichlorobenzyl)-4-(ethyl)thiazol-5-yl)piperidine
4-(2-(3,4-Dichlorobenzyl)-4-(methyl)thiazol-5-yl)piperidine
4-(2-(3,4-Dichlorobenzyl)thiazol-5-yl)piperidine
4-(2-(3,5-Dichlorobenzyl)-4-(ethyl)thiazol-5-yl)piperidine
4-(2-(3,5-Dichlorobenzyl)-4-(methyl)thiazol-5-yl)piperidine
4-(2-(3,5-Dichlorobenzyl)thiazol-5-yl)piperidine
4-(2-(2,4-Dichlorobenzyl)-4-(ethyl)thiazol-5-yl)piperidine
4-(2-(2,4-Dichlorobenzyl)-4-(methyl)thiazol-5-yl)piperidine
4-(2-(2,4-Dichlorobenzyl)thiazol-5-yl)piperidine
4-(2-(3-Methylbenzyl)4-(ethyl)thiazol-5-yl)piperidine
4-(2-(3-Methylbenzyl)-4-(methyl)thiazol-5-yl)piperidine
4-(2-(3-Methylbenzyl)thiazol-5-yl)piperidine
4-(2-(4-Methylbenzyl)-4-(ethyl)thiazol-5-yl)piperidine
4-(2-(4-Methylbenzyl)-4-(methyl)thiazol-5-yl)piperidine
4-(2-(4-Methylbenzyl)thiazol-5-yl) piperidine
4-(2-(3-Ethylbenzyl)-4-(ethyl)thiazol-5-yl)piperidine
4-(2-(3-Ethylbenzyl)-4-(methyl)thiazol-5-yl)piperidine
4-(2-(3-Ethylbenzyl)thiazol-5-yl) piperidine
4-(2-(4-Ethylbenzyl)4-(ethyl)thiazol-5-yl)piperidine
4-(2-(4-Ethylbenzyl)-4-(methyl)thiazol-5-yl)piperidine
4-(2-(4-Ethylbenzyl) thiazol-5-yl) piperidine
4-(2-(4-Isopropylbenzyl)-4-(ethyl)thiazol-5-yl)piperidine
4-(2-(4-Isopropylbenzyl)-4-(methyl)thiazol-5-yl)piperidine
4-(2-(4-Isopropylbenzyl )thiazol-5-yl)piperidine
4-(2-(4-t-Butylbenzyl)4-(ethyl)thiazol-5-yl)piperidine
4-(2-(4-t-Butylbenzyl)-4-(methyl)thiazol-5-yl)piperidine
4-(2-(4-t-Butylbenzyl)thiazol-5-yl)piperidine
4-(2-(3-Trifluoromethylbenzyl)-4-(ethyl)thiazol-5-yl)piperidine
4-(2-(3-Trifluoromethylbenzyl)-4-(methyl)thiazol-5-yl)piperidine
4-(2-(3-Trifluoromethylbenzyl)thiazol-5-yl)piperidine
4-(2-(4-Trifluoromethylbenzyl)-4-(ethyl)thiazol-5-yl)piperidine
4-(2-(4-Trifluoromethylbenzyl)-4-(methyl)thiazol-5-yl)piperidine
4-(2-(4-Trifluoromethylbenzyl)thiazol-5-yl) piperidine
4-(2-(3-Methoxybenzyl)-4-(ethyl)thiazol-5-yl)piperidine
4-(2-(3-Methoxybenzyl)-4-(methyl)thiazol-5-yl)piperidine
4-(2-(3-Methoxybenzyl)thiazol-5-yl)piperidine
4-(2-(4-Methoxybenzyl)-4-(ethyl)thiazol-5-yl)piperidine
4-(2-(4-Methoxybenzyl)-4-(methyl)thiazol-5-yl)piperidine
4-(2-(4-Methoxybenzyl)thiazol-5-yl)piperidine
4-(2-(3-Ethoxybenzyl)4-(ethyl)thiazol-5-yl)piperidine 4-(2-(3-Ethoxybenzyl)-4-(methyl)thiazol-5-yl)piperidine
4-(2-(3-Ethoxybenzyl)thiazol-5-yl)piperidine
4-(2-(4-Ethoxybenzyl)-4-(ethyl)thiazol-5-yl)piperidine
4-(2-(4-Ethoxybenzyl)-4-(methyl)thiazol-5-yl)piperidine
4-(2-(4-Ethoxybenzyl)thiazol-5-yl)piperidine
4-(2-(3-Trifluoromethoxybenzyl)-4-(ethyl)thiazol-5-yl)piperidine
4-(2-(3-Trifluoromethoxybenzyl)-4-(methyl)thiazol-5-yl)piperidine
4-(2-(3-Trifluoromethoxybenzyl)thiazol-5-yl)piperidine
4-(2-(4-Trifluoromethoxybenzyl)-4-(ethyl)thiazol-5-yl)piperidine
4-(2-(4-Trifluoromethoxybenzyl)-4-(methyl)thiazol-5-yl)piperidine
4-(2-(4-Trifluoromethoxybenzyl)thiazol-5-yl)piperidine
4-(2-(4-Methylsulfonylbenzyl)-4-(ethyl)thiazol-5-yl)piperidine
4-(2-(4-Methylsulfonylbenzyl)-4-(methyl)thiazol-5-yl)piperidine
4-(2-(4-Methylsulfonylbenzyl)thiazol-5-yl)piperidine
4-(2-(4-Nitrobenzyl)-4-(ethyl)thiazol-5-yl)piperidine
4-(2-(4-Nitrobenzyl)-4-(methyl)thiazol-5-yl)piperidine
4-(2-(4-Nitrobenzyl)thiazol-5-yl) piperidine Procedure 49

4-(3-Benzyl-1-ethyl-(1-pyrazol-5-yl)piperidine di-HCl salt

Step A: (1-(t-Butoxycarbonyl)piperidin-4-yl)N-methyl-N-methoxycarboxamide

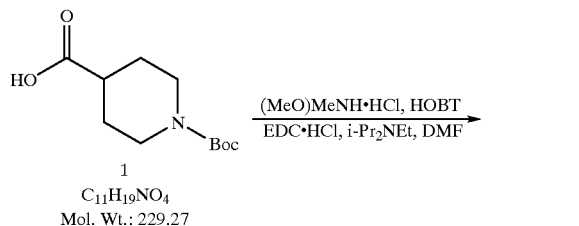

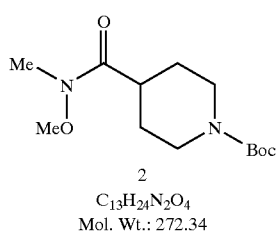

A 100 L round-bottomed-flask equipped with a mechanical stirrer, thermocouple and nitrogen inlet was charged with DMF (51 L), N,O-dimethylhydroxyamine hydrochloride (2.62 Kg, 26.55 mol), HOBT (1.2 Kg, 8.85 mol), and N-Boc isonipecotic acid (4.10 Kg, 17.70 mol). The mixture warmed to 18° C. as the diisopropylethylamine (4.60 Kg, 6.2 L, 35.41 mol) was added over 15 min. The EDC.HCl (5.09 Kg, 26.55 mol) was added in three portions over 3 h maintaining an internal temperature of 18° C. with gentle cooling. The reaction mixture was held at 18° C. for 12 h. HPLC analysis shows no remaining 1. The reaction mixture was pumped into an extractor containing 74 L of water at 5° C. The resulting solution (39.3 g/L of 2) was extracted with ethyl acetate (4×37 L).

The organic phases were combined and washed with 1 N HCl (2×7 L), water (5 L), then brine (10 L then 5 L). The final organic phase was 125.4 Kg (d=0.878) with a concentration of 2 at 36.9 g/L (5.27 Kg).

Step B: 1-(t-Butoxycarbonyl)-4-acetylpiperidine

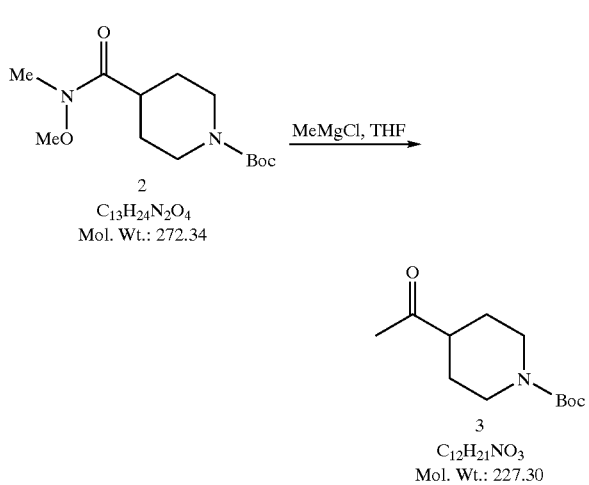

The ethyl acetate solution of (1-(t-butoxycarbonyl)piperidin-4-yl)-N-methyl-N-methoxycarboxamide from Step A (4.44 Kg, 16.29 mol) was dried over anhydrous sodium sulfate (1.6 Kg). The drying agent was removed by filtration then the solvent was removed in vacuo to provide a clear light yellow oil that was held for 16 h under high vacuum to provide a crystalline solid. The solid was dissolved in THF (55 L) then cooled to −20° C. Methyl magnesium chloride (3.12 M in THF, 12.0 L, 37.4 mol) was added over 1.75 h keeping the internal temperature below 0° C. The resulting gray suspension was aged at 0° C. for 2 h then 25° C. for 3 h. An aliquot was drawn and worked up with ethyl acetate, acetic acid and water. The batch was cooled to 9° C., then pumped over 15 min into an extractor charged with a solution of 41 L of water and 4.9 L of acetic acid at 5° C. Ethyl acetate (52 L) was charged to the extractor, the phases were mixed then the lower aqueous phase (44.3 Kg) was cut away. The organic phase was washed with sat'd aq. sodium bicarbonate (2×), 7% aq. sodium chloride (2×) and sat'd aq. sodium chloride. The organic phase (116.2 L, 30.3 g/L of 3) contained 3.52 Kg of the title compound 3 (87.5% yield from 1). The organic phase was dried over anhydrous sodium sulfate (1.5 Kg). The drying agent was removed by filtration, then the solution was batch concentrated to an oil. The compound was diluted with THF and the batch was flushed with 20 L of THF. The residual oil was diluted with THF (5 L).

Step C: 1-(1-(t-Butoxycarbonyl)piperidin-4-phenylbutane-1,3-dione

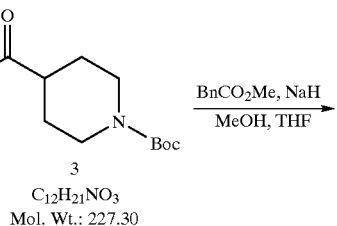

141

-continued

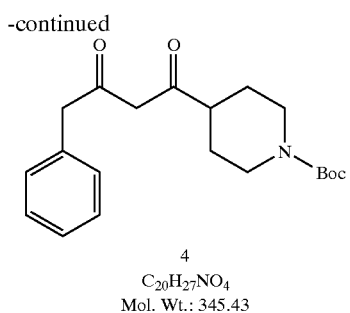

4
C₂₀H₂₇NO₄
Mol. Wt.: 345.43

A 72 L round-bottomed-flask equipped with a mechanical stirrer, nitrogen inlet, thermocouple and 5 L dropping funnel was placed in a temperature control bath. Under a nitrogen sweep, the flask was charged with the NaH (60% in mineral oil, 1.55 Kg, 38.75 mol) and THF (20 L). The batch warmed from 17° C. to 22° C. as methanol (0.10 Kg, 130 mL, 3.09 mol) was added over 45 min (hydrogen evolution!!). The solution of 1-(t-butoxycarbonyl)-4-acetylpiperidine from Step B (3.52 Kg, 15.49 mol) was added over 1 h. To the resulting suspension was added a solution of the methyl phenylacetate 2.46 Kg, 17.04 mol) and THF (5 L) over 8 h maintaining a reaction temperature of about 25° C. by cooling as needed. The mixture was aged at 23° C. for 15 h.

The batch was cooled to 17° C. then pumped into a 100 L extractor containing a solution of concentrated HCl (3.3 L) and water (16 L) at −6° C. (caution, hydrogen evolution!!). The mixture was stirred, allowed to partition then the pH of the aqueous phase was checked (pH=1 to 2). The layers were partitioned and the organic phase was washed with a solution of saturated aqueous sodium bicarbonate (5 L) and brine (1 L) then brine (4 L). MTBE (7.7 L) was added to the extractor along with the acidic first aqueous phase. The mixture was shaken to mix well, allowed to partition then the aqueous was cut away. The sodium bicarbonate phase was added, mixed, allowed to partition then the aqueous was cut away. The brine phase was added to the extractor, the mixture mixed, allowed to partition then the aqueous phase was cut away. The MTBE and THB phases were combined then concentrated to an oil. To the oil was added silica gel 60 (7 Kg) and 5% ethyl acetate/heptanes (10 L) with stirring to provide a slurry. The slurry was poured onto a column containing silica gel 60 (23 Kg) wet with 5% ethyl acetate/heptanes. The column was eluted with 5% etyl acetate/heptanes (200 L) then 20% ethyl acetate/heptanes (200 L) at the rate of 2.2 L/min to obtain the product 4. The rich cut was batch concentrated to provide a slightly yellow slurry that was taken up in DMF (15 L) to provide a clear solution. The batch concentration was continued to remove all residual heptanes and ethyl acetate. To the batch at 18° C. was slowly added water (3.5 L) until the mixture became turbid. The batch was seeded and additional water was added to a total of 8.0 L (final solvent mixture was 35% water and 65% DMF). The batch was cooled to 1° C. The solids were collected on a frit, washed with 5 L of water then dried under a stream of nitrogen to provide 4 (3.57 Kg, 66.7% from 3, 57.8% from 1).

142

Step D: 1-(t-Butoxycarbonyl)-4-(3-benzyl-1-ethyl-(1H)-pyrazol-5-yl)piperidine

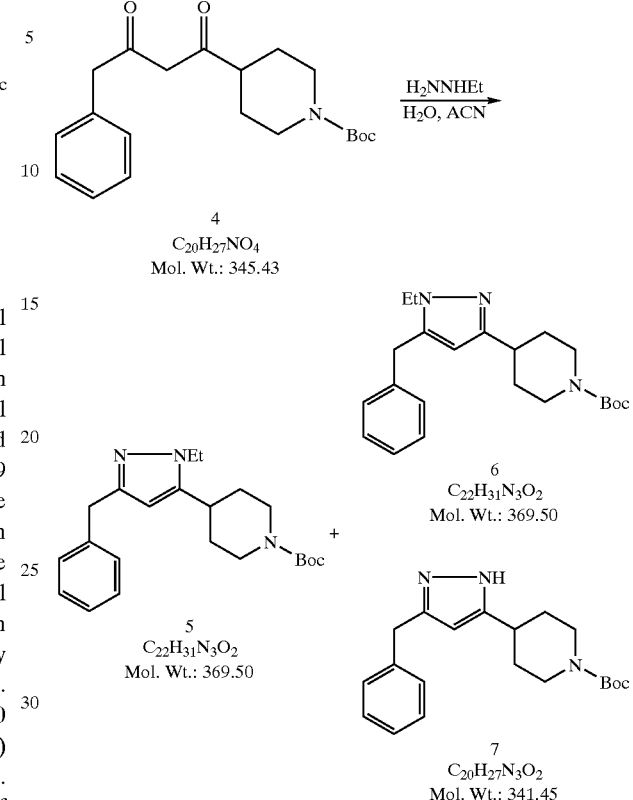

A 100 L cylindrical flask with a bottom valve was equipped with a mechanical stirrer, internal heating coil, 5 L dropping funnel, and thermocouple was charged with the acetonitrile (39 L) and 1-(1-(t-butoxycarbonyl)piperidin-4-yl)-4-phenylbutane-1,3-dione 4 (3.00 Kg, 8.68 mol). To the resulting clear light yellow solution was added water (18.6 l). The mixture was warmed to 19° C. and the mixture became clear. An ethyl hydrazine solution (35% in water, 1.66 Kg, 1.71 L, 9.55 mol) was added via a dropping funnel over 100 min. The batch temperature after the addition was 20° C. The reaction solution was aged for 1 h at 20° C. then checked for completion by HPLC. If any 4 remained, additional ethyl hydrazine was added to complete the reaction. At the end of reaction the ratio of products 5:6:7 is 83.6:14.3:2.1 with complete consumption of 4.

The dropping funnel was removed and a Dean Stark trap was fitted to the flask. To the reaction mixture was added heptanes (5 L) and the acetonitrile was removed by azeotropic distillation at 64° C. During the distillation, the initial reaction volume was maintaining by periodic addition of heptanes. When the internal temperature reached 72° C., the batch was cooled to 60° C. and the heavy aqueous phase was cut away. The distillation was resumed until the internal temperature reached 95° C. and no water droplets were observed in the distillate. The batch was cooled to 50° C., seeded then cooled to 5° C. over 16 h. The resulting solids were collected on a frit, rinsed with heptanes (10 L at 5° C.), then dried under dry nitrogen to provide 2.58 Kg (80.3% yield) of a crystalline solid that was a 98.67:0.49:0.84 mixture of 5:6:7.

Step E: 4-(3-Benzyl-1-ethyl-(1H)-pyrazol-5-yl)piperidine di-HCl salt 1-(t-Butoxycarbonyl)4-(3-benzyl-1-ethyl-(1H)-pyrazol-5-ylpiperidine 5 from Step D (18.5 g, 50 mmol) was added to a solution of HCl (530 mmol) in methanol (300 mL) prepared by the slow addition of acetyl chloride (38 mL, 530 mmol) and aged for 90 min. The reaction was stirred at rt for 16 h and then evaporated to dryness to afford 17.1 g (100%) of the title compound as a hygroscopic white solid.

EXAMPLE 1

N-(1-(SR)-3-(SR)-((4-(3-(Phenyl)prop-1-yl) piperidin-1-yl)methyl)-4-(SR)-phenylcyclopent-1-yl)-1-leucine di-hydrochloride salt and N-(1-(SR)-3-(SR)-((4-(3-(phenyl)prop-1-yl)piperidin-1-yl) piperidin-1-yl)methyl)-4-(SR)-phenylcyclopent-1-yl)-D-leucine di-hydrochloride salt Step A: Methyl (+−)-trans-4-methylene-2-phenylcyclopentanoate A mixture of methyl trans-cinnamate (5.0 g, 31 mmol), tetrakis(triphenylphosphine) palladium(0) (2.6 g, 2.3 mmol), 1,2-bis(diphenylphosphino)ethane (0.70 g, 1.8 mmol) and 2-((trimethylsilyl)methyl)-2-propen-1-yl acetate (6.90 g, 37 mmol) in THF (60 mL) under argon was heated to reflux for 4 h. An additional aliquot of 2-((trimethylsilyl)methyl)-2-propen-1-yl acetate (3.40 g) was added and the reaction was continued for another 16 h. The volatiles were then removed in vacuo and the residue was purified by FC (10% ethyl acetate in hexanes) to afford the title compound (6.2 g).

$^1$H NMR (CDCl$_3$) δ: 2.52 (m, 1H), 2.68 (m, 1H), 2.75–2.9 (m, 2H), 2.95 (ddd, 1 H), 3.45 (ddd, 1 H), 3.57 (s, 3 H), 4.92 (m, 2 H), 7.15–7.3 (m, 5 H).

Step B: (+−)-trans-1-hydroxymethyl-4-methylene-2-phenylcyclopentane

To a solution of methyl (+−)-trans4-methylene-2-phenylcyclopentanoate (26.0 g, 128 mmol) prepared as in Step A in THF (600 mL) under nitrogen and cooled to −10° C. was added dropwise over 15 min 1M lithium aluminum hydride (LAH) in THF (193 mL). After 1 h, the bath was removed and the reaction was stirred at rt for 16 h. The reaction was cooled in an ice/methanol bath and the excess LAH was quenched by dropwise addition of acetone. The reaction was then poured into dilute aq. HCl. The mixture was extracted twice with ether and the organic layers were washed with brine, dried over sodium sulfate, combined and concentrated. The residue was purified by FC (20–30% ethyl acetate in hexanes) to afford the title product (23.8 g).

Step C: (+−)-trans-1-hydroxymethyl-4-oxo-2-phenylcyclopentane

Into a solution of (+−)-trans-1-hydroxymethyl-4-methylene-2-phenylcyclopentane from Step B (22.7 g, 121 mmol) in methanol (300 mL) cooled in a dry ice/acetone bath was bubbled ozone until the blue color persisted. The excess ozone was removed with a stream of nitrogen and then dimethylsulfide (25 mL) was added. After 30 min, the bath was removed and the reaction was allowed to warm to rt over 16 h. The volatiles were removed in vacuo and the residue was purified by FC (15–30% ethyl acetate in hexanes) to give the title compound (22.1 g).

$^1$H NMR (CDCl$_3$) δ: 2.2–2.5 (m, 4 H), 2.71 (dd, 1 H), 3.28 (m, 1 H), 3.55 (dABq, 2 H), 7.23 (m, 3 H), 7.34 (m, 2 H).

Step D: 1-(SR)-Benzylamino-3-(SR)-hydroxymethyl-4-(SR)-phenylcyclopentane and 1-(RS)-benzylamino-3-(SR)-hydroxymethyl-4-(SR)-phenylcyclopentane To a solution of (+−)-trans-1-hydroxymethyl-4-oxo-2-phenylcyclopentane from Step C (9.8 g, 52 mmol) in 1,2-dichloroethane (200 mL) was added benzylamine (11.3 mL, 103 mmol) and acetic acid (6.2 mL, 103 mmol). After 10 min, sodium triacetoxyborohydride (33 g, 155 mmol) was added in portions and the reaction was stirred at rt for 3 h. The reaction was quenched into dilute aq. sodium carbonate and the mixture was extracted twice with ethyl acetate. The organic layers were washed with brine, dried over sodium sulfate, combined and concentrated. The residue was purified by FC (1–5% methanol in ether) to obtain the title products (13.1 g) as a mixture of C-1 isomers.

Step E: 1-(SR)-Benzyloxycarbonylamino-3-(SR)-hydroxymethyl-4-(SR)-phenylcyclopentane (Higher R$_f$ isomer) and 1-(RS)-benzyloxycarbonylamino-3-(SR)-hydroxymethyl-4-(SR)-phenylcyclopentane (Lower R$_f$ isomer)

To a solution of 1-(SR)-benzylamino-3-(SR)-hydroxymethyl-4-(SR)-phenylcyclopentane and 1-(RS)-benzylamino-3-(SR)-hydroxymethyl-4-(SR)-phenylcyclopentane (13 g, 46 mmol) from Step D was added 20% palladium hydroxide (2.5 g, 50% by wt water), ammonium formate (60 g, 930 mmol) and an additional 200 mL of methanol. The reaction was heated at 60° C. for 6 h. The reaction was filtered and concentrated. The residue was taken up in water and extracted twice with methylene chloride to remove any remaining benzylamine intermediate. The aqueous layer was made basic with 2N sodium hydroxide and extracted twice with methylene chloride. The organic layers were washed with brine, dried over sodium sulfate, combined and concentrated to afford 8.1 g of crude amino-alcohol.

The above product (8.1 g, 42 mmol) was taken up in methylene chloride (200 mL), cooled in an ice bath and DIPEA (22 mL, 126 mmol) and benzyl chloroformate (6.33 mL, 44 mmol) were added. After 2.5 h at rt, the reaction was poured into dilute aq. HCl and extracted twice with methylene chloride. The organic layers were washed with brine, dried over sodium sulfate, combined and concentrated. The residue was purified by Prep LC (30–75% ethyl acetate in hexanes) to afford the title compounds (4.0 g higher, 6.6 g lower).

Step F: 1-(SR)-Benzyloxycarbonylamino-3-(SR)-formyl-4-(SR)-phenylcyclopentane (Higher R$_f$ isomer) and 1-(SS)-benzyloxycarbonylamino-3-(SR)-formyl-4-(SR)-phenylcyclopentane (Lower R$_f$ isomer)

To a solution of oxalyl chloride (0.350 mL, 3.85 mmol) in methylene chloride (10 mL) at −70° C. was added dropwise DMSO (0.550 mL, 7.65 mmol). After 15 min, a solution of 1-(SR)-benzyloxycarbonylamino-3-(SR)-hydroxymethyl4-(SR)-phenylcyclopentane (Higher R$_f$ isomer from Step E) (500 mg, 1.53 mmol) in methylene chloride (10 mL) was added. The reaction was stirred at −70° C. for 1 h and then DIPEA (2.7 mL, 15 mmol) in methylene chloride (5 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20–30% ethyl acetate in hexanes) to give the title product (465 mg) as an oil.

$^1$H NMR (CDCl$_3$) δ: 1.9–2.0 (m, 1 H, 2b-H), 2.05–2.15 (m, 2 H, both 5-H's), 2.3–2.45 (m, 1 H, 2a-H), 3.06 (q, 1 H, 3-H), 3.47 (q, 1 H, 4-H), 4.32 (br m, 1 H, 1-H), 4.94 (br s, 1 H, NH), 5.08 (s, 2 H, CH$_2$O), 7.1–7.4 (m, 10 H), 9.74 (s, 1 H, COH). The assignment of cis stereochemistry between C-1 and C-3 and trans between C-1 and C-4 were confirmed by 2-D NOESY NMR.

Using essentially the same procedure as above, material derived from the lower isomer from Step E (500 mg, 1.5 mmol) was also converted to the lower R$_f$ title compound (457 mg).

$^1$H NMR (CDCl$_3$) δ: 1.71 (q, 1 H, 5a-H), 1.8–1.95 (m, 1 H, 2a-H), 2.48 (p, 1 H, 2b-H), 2.5–2.6 (m, 1 H, 5b-H), 3.0–3.1 (m, 1 H, 3-H), 3.3–3.4 (m, 1 H, 4-H), 4-H), 4.0–4.2 (m, 1 H, 1-H), 4.82 (br s, 1H, NH), 5.08 (s, 2H, OCH$_2$), 7.2–7.4 (m, 10 H), 9.63 (d, 1 H, COH). The assignment of trans stereochemistry between C-1 and C-3 and cis between C-1 and C-4 were confirmed by 2-D NOESY NMR.

Step G: 1-(SR)-(Benzyloxycarbonylamino)-3-(SR)-((4-(3-phenylprop-1-yl)piperidin-1-yl)methyl)-4-(SR)-phenylcyclopentane (Higher R$_f$ isomer)

To a solution of 1-((SR)-(benzyloxycarbonylamino)-3-(SR)-(carbonyl)-4-(SR)-phenylcyclopentane (from Step F, derived from Higher R$_f$ isomer in Step E) (450 mg, 0.1.4 mmol) in 1,2-dichloroethane (10 mL) was added 4-(3-phenylprop-1-yl)piperidine (424 mg, 2.1 mmol) and acetic acid (0.125 mL, 2.1 mmol). After 15 min, sodium triacetoxyborohydride (890 mg, 4.2 mmol) was added in portions over 30 min and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC (30–40% ethyl acetate in hexanes) to give the title product (698 mg) as the free amine.

MS (NH$_3$/ESI): m/z 511 (M+1).

Step H: 1-(SR)-(Amino)-3-(SR)-((4-(3-phenylprop-1-yl)piperidin-1-yl)methyl)-4-(SR)-phenylcyclopentane (Higher R$_f$ isomer)

To a solution of 1-(SR)-(benzyloxycarbonylamino)-3-(SR)-((4-(3-phenylprop-1-yl)piperidin-1-yl)methyl)-4-(SR)-phenylcyclopentane (from Step G, derived from the Higher R$_f$ isomer from Step E) (500 mg, 1.0 mmol) in methanol (10 mL) was added 10% Pd/C (100 mg). The mixture was hydrogenated on a Parr shaker at 40 psi for 2 h and was then filtered and concentrated to afford the crude title compound (350 mg) as an oil.

Step I: N-(1-(SR)-3-(SR)-((4-(3-(Phenyl)prop-1-yl)piperidin-1-yl)methyl)-4-(SR)-phenylcyclopent-1-yl)-1-leucine di-hydrochloride salt and N-(1-(SR)-3-(SR)-((4-(3-(phenyl)prop-1-yl)piperidin-1-yl)piperidin-1-yl)methyl)-4-(SR)-phenylcyclopent-1-yl)-D-leucine di-hydrochloride salt To a solution of 1-(SR)-(amino)-3-(SR)-((4-(3-phenylprop-1-yl)piperidin-1-yl)methyl)-4-(SR)-phenylcyclopentane (from Step H, derived from the Higher R$_f$ isomer from Step E) (25 mg, 0.067 mmol), 4-methyl-2-oxovaleric acid (17 mg, 0.13 mmol) and acetic acid (0.008 mL, 0.13 mmol) in 1,2-dichloroethane (2 mL) was added sodium triacetoxyborohydride (42 mg, 0.20 mmol). The reaction was stirred at rt for 24 h and was then quenched into dilute aq. sodium carbonate solution and was extracted three times with ethyl acetate. The organic layers were washed with brine, dried over sodium sulfate, combined and evaporated. The residue was purified by Prep TLC (5% methanol in methylene chloride) to afford separation of the 2 title compounds. The hydrochlorides were prepared by taking up in methylene chloride, addition of excess 1M HCl in ether, and evaporation to dryness.

Higher: MS (NH$_3$/ESI): m/z 491 (M+1). Lower: MS (NH$_3$/ESI): m/z 491 (M+1).

EXAMPLE 2

N-(1-(RS)-3-(SR)-((4-(3-(Phenyl)prop-1-yl)piperidin-1-yl)methyl)4-(SR)-phenylcyclopent-1-yl)-1-yl)-L-leucine di-hydrochloride salt and N-(1-(RS)-3-(SR)-((4-(3-(phenyl)prop-1-yl)piperidin-1-yl)piperidin-1-yl)methyl)-4-(SR)-phenylcyclopent-1-yl)-D-leucine di-hydrochloride salt Using essentially the same procedures as in Example 1, Steps G–I, but substituting the lower R$_f$ product from Steps E and F, the 2 title compounds were obtained after Prep TLC separation.

Higher: MS (NH$_3$/ESI): m/z 491 (M+1). Lower: MS (NH$_3$/ESI): m/z 491 (M+1).

EXAMPLE 3

N-(1-(SR)-3-(SR)-((4-(3-(Phenyl)prop-1-yl)piperidin-1-yl)methyl)-4-(SR)-phenylcyclopent-1-yl)-1-norvaline di-hydrochloride salt and N-(1-(SR)-3-(SR)-((4-(3-(phenyl)prop-1-yl)piperidin-1-yl)piperidin-1-yl)methyl)-4-(SR)-phenylcyclopent-1-yl)-D-norvaline di-hydrochloride salt Using essentially the same procedure as in Example 1, Step I, but substituting 2-oxovaleric acid in Step I, the 2 title compounds were obtained as a mixture after Prep TLC purification (no separation of the diastereomers was seen in this case).

MS (NH$_3$/ESI): m/z 477 (M+1).

EXAMPLE 4

N-(1-(RS)-3-(SR)-((4-(3-(Phenyl)prop-1-yl)piperidin-1-yl)methyl)-4-(SR)-phenylcyclopent-1-yl)-1-norvaline di-hydrochloride salt and N-(1-(RS)-3-(SR)-((4-(3-(phenyl)prop-1-yl)piperidin-1-yl)piperidin-1-yl)methyl)-4-(SR)-phenylcyclopent-1-yl)-D-norvaline di-hydrochloride salt Using essentially the same procedures as in Example 1, Steps G–I, but substituting the lower R$_f$ product from Steps E and F and 2-oxovaleric acid in Step I the 2 title compounds were obtained as a mixture after Prep TLC purification (no separation of the diastereomers was seen in this case).

MS (NH3/ESI): m/z 477 (M+1).

EXAMPLE 5

N-(1-(RS)-3-(SR)-((4-(3-(Phenyl)prop-1-yl)piperidin-1-yl)methyl)-4-(SR)-phenylcyclopent-1-yl)-1-phenylglycine di-hydrochloride salt and N-(1-(RS)-3-(SR)-((4-(3-(phenyl)prop-1-yl)piperidin-1-yl)piperidin-1-yl)methyl)-4-(SR)-phenylcyclopent-1-yl)-D-phenylglycine di-hydrochloride salt Using essentially the same procedures as in Example 1, Steps G–I, but substituting the lower R$_f$ product from Steps E and F and 2-oxophenylacetic acid in Step I the 2 title compounds were obtained as a mixture after Prep TLC purification (no separation of the diastereomers was seen in this case).

HPLC/MS (ESI): m/z 511 (M+1).

Examples 6–9 illustrate the chemistry described in Schemes X–Y of the general chemistry section and were used to determine the absolute stereochemistry at the C-1, 3 and 4 positions of the cyclopentyl scaffold for the intermediates and final products. This was then applied to the preparation and assignment of stereochemistry for the subsequent Examples in this patent.

EXAMPLE 6

N-(1-(S)-3-(R)-((4-(N-(4-Nitrobenzyloxycarbonyl)-N-(allyl)amino)piperidin-1-yl)methyl)-4-(R)-phenylcyclopent-1-yl)-1-leucine (Isomer 6A), N-(1-(S)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6B), N-(1-(R)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucine (Isomer 6D) di-TFA salts Step A: (+–)-trans-4-Methylene-2-phenylcyclopentanoic Acid To a solution of methyl (+–)-trans-4-methylene-2-phenylcyclopentanoate prepared as in Example 1, Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+−)-trans-1-hydroxymethyl-4-methylene-2-phenylcyclopentane

To a solution of (+−)-trans-4-methylene-2-phenylcyclopentanoic acid (26 g, 129 mmol) from Step A in THF (600 mL) under nitrogen at −10° C. was added dropwise over 15 min 1M lithium aluminum hydride (LAH) in THF (193 mL, 193 mmol). After 16 h at rt, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title product (23.8 g) as an oil.

Step C: (+−)-trans-1-hydroxymethyl-4-oxo-2-phenylcyclopentane

Into a solution of (+−)-trans-1-hydroxymethyl-4-methylene-2-phenylcyclopentane from Step B (22.7 g, 121 mmol) in methanol (200 mL) cooled in a dry ice/acetone bath was bubbled ozone until the blue color persisted. The excess ozone was removed with a stream of nitrogen and then dimethylsulfide (20 mL) was added. After 10 min, the bath was removed and the reaction was allowed to warm to rt over 16 h. The volatiles were removed iii vacuo and the residue was purified by FC (15–30% ethyl acetate in hexanes) to give the title compound (22.1 g).

Step D: (+−)-trans-4-Oxo-2-phenylcyclopentanecarboxaldehyde

To a solution of oxalyl chloride (1.15 mL, 13.1 mmol) in methylene chloride (30 mL) at −70° C. was added dropwise DMSO (1.87 mL, 26.3 mmol). After 15 min, a solution of (+−)-trans-1-hydroxymethyl-4-oxo-2-phenylcyclopentane from Step C (1.0 g, 5.26 mmol) in methylene chloride (10 mL) was added. The reaction was stirred at −70° C. for 1.5 h and then DIPEA (9.25 mL, 53 mmol) in methylene chloride (10 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (30% ethyl acetate in hexanes) to give the title product (0.9 g) after vacuum drying.

Step E: 3-(SR)-((4-(N-(4-Nitrobenzyloxycarbonyl)-N-(allyl)amino)piperidin-1-yl)methyl)-4-(SR)-phenylcyclopentan-1-one di-hydrochloride salt To a solution of (+−)-trans-4-oxo-2-phenylcyclopentanecarboxaldehyde from Step D (327 mg, 1.74 mmol) in 1,2-dichloroethane (20 mL) was added 4-(N-(4-nitrobenzyloxycarbonyl)(N-allyl)amino)piperidine hydrochloride (667 mg, 1.9 mmol) and DIPEA (0.36 mL, 2.1 mmol). After 5 min, sodium triacetoxyborohydride (740 mg, 3.5 mmol) was added and the reaction was stirred at rt for 4 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with a gradient of 35 to 75% ethyl acetate in hexanes to give the title product (365 mg) as the free amine. This was taken up in ether and 1M hydrogen chloride in ether (0.5 mL) was added to form the di-hydrochloride salt. The volatiles were removed in vacuo to give the title salt.

MS (NH$_3$/ESI): m/z 492 (M+1).

Step F: N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-leucine t-butyl ester (Isomer A), N-(1-(S)-3-(S)-((4-(N-(4-nitrobenzyloxycarbonyl)-N-(allyl)amino)piperidin-1-yl)methyl)-4-(S)-phenylcyclopent-1-yl)-L-leucine t-butyl ester (Isomer B), N-(1-(R)-3-(S)-((4-(N-(4-nitrobenzyloxycarbonyl)-N-(allyl)amino)piperidin-1-yl)methyl)4-(S)-phenylcyclopent-1-yl)-L-leucine t-butyl Ester (Isomer C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucine t-butyl Ester (Isomer D)

To a solution of 3-(SR)-((4-(N-(4-nitrobenzyloxycarbonyl)-N-(allyl)amino)piperidin-1-yl)methyl)4-(SR)-phenylcyclopentan-1-one (52 mg, 0.10 mmol) from Step E, L-leucine t-butyl ester hydrochloride (65 mg, 0.29 mmol) and DIPEA (0.069 mL, 0.40 mmol) in 1,2-dichloroethane (2 mL) at rt was added sodium triacetoxyborohydride (41 mg, 0.20 mmol). The reaction was stirred at rt for 16 h and was then diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting first with 75% ethyl acetate in hexanes to give partial separation of the four diastereomeric title products. Prep TLC was repeated with 40% ethyl acetate in hexanes for each band to give clean highest R$_f$ product (Isomer A), a mixture of the middle R$_f$ products (Isomers B and C), and clean lowest R$_f$ product (Isomer D) as the free amines. (higher R$_f$): HPLC/MS (ESI): m/z 663 (M+1). (middle R$_f$): HPLC/MS (ESI): m/z 663 (M+1) (2 isomers seen). (lower R$_f$): HPLC/MS (ESI): m/z 663 (M+1).

Step G: N-(1-(S)-3-(R)-((4-(N-(4-Nitrobenzyloxycarbonyl)-N-(allyl)amino)piperidin-1-yl)methyl)-4-(R)-phenylcyclopent-1-yl)-L-leucine (Isomer 6A), N-(1-(S)-3-(S)-((4-(N-(4-nitrobenzyloxycarbonyl)-N-(allyl)amino)piperidin-1-yl)methyl)-4-(S)-phenylcyclopent-1-yl)-L-leucine (Isomer 6B), N-(1-(R)-3-(S)-((4-(N-(4-nitrobenzyloxycarbonyl)-N-(allyl)amino)piperdin-1-yl)methyl)-4-(S)-phenylcyclopent-1-yl)-L-leucine (Isomer 6C) and N-(1-(R)-3-(R)-((4-(N-(4-nitrobenzyloxycarbonyl)-N-(allyl)amino)piperidin-1-yl)methyl)-4-(R)-phenylcyclopent-1-yl)-L-leucinc (Isomer 6D) di-TFA salts The 2 individual diastereomers and the mixed diastereomers from Step F were each taken up in 1:1 methylene chloride:ether (2 mL) and 1M hydrogen chloride in ether (1 mL) was added. After 3 days at rt the volatiles were removed under nitrogen to give the title compounds as white solids. These were analyzed by HPLC (Advantage 4.6×150 mm C-18 column, using a gradient of 10% A:90% B to 35% A:65% B over 30 min; A=0.5% TFA in water, B=0.5% TFA in acetonitrile) and purified by Prep HPLC (Combi Prep 20×50 mm C-18). Evaporation of the clean fractions to dryness afforded the title compounds as their di-TFA salts.

Isomer A (from highest R$_f$): HPLC/MS (ESI): m/z 607 (M+1), R$_t$=25.5 min Isomer B (from middle R$_f$): BPLC/MS (ESI): m/z 607 (M+1), R$_t$=25.2 min. Isomer C (from middle R$_f$): HPLC/MS (ESI): m/z 607 (M+1), R$_t$=25.9 min. Isomer D (from lowest R$_f$): BPLC/MS (ESI): m/z 607 (M+1), R$_t$=25.2 min.

EXAMPLE 7

N-(1-(R)-3-(S)-((4-(N-(4-Nitrobenzyloxycarbonyl)-N-(allyl)amino)piperidin-1-yl)methyl)-4-(S)-phenylcyclopent-1-yl)-D-leucine (Isomer 7E), N-(1-(R)-3-(R)-((4-(N-(4-nitrobenzyloxycarbonyl)-N-(allyl)amino)piperidin-1-yl)methyl)-4-(R)-phenylcyclopent-1-yl)-D-leucine (Isomer 7F), N-(1-(S)-3-(R)-((4-(N-(4-nitrobenzyloxycarbonyl)-N-(allyl)amino)piperidin-1-yl)methyl)-4-(R)-phenylcyclopent-1-yl)-D-leucine (Isomer 7G) and N-(1-(S)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 7H) di-TFA salts Using essentially the same procedures as in Example 6, Step F and G, but substituting D-leucine t-butyl ester hydrochloride in Step F, the four title diastereomers were obtained which were enantiomeric to those of Example 6.

Isomer E (from highest $R_f$): HPLC/MS (ESI): m/z 607 (M+1), $R_t$=25.5 min Isomer F (from middle $R_f$): HPLC/MS (ESI): m/z 607 (M+1), $R_t$=25.2 min. Isomer G (from middle $R_f$): HPLC/MS (ESI): m/z 607 (M+1), $R_t$=25.9 min. Isomer H (from lowest $R_f$): HPLC/MS (ESI): m/z 607 (M+1), $R_t$=25.2 min.

EXAMPLE 8

N-(1-(S )-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 6B) and N-(1-(S)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 7H) di-TFA salts Step A: (+−)-trans-4-Methylene-2-phenylcyclopentanoic acid To a solution of methyl (+−)-trans-4-methylene-2-phenylcyclopentanoate prepared as in Example 1, Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+)-trans-4-Methylene-2-phenylcyclopentanoic acid, (S)-(−)-α-methylbenzylamine salt and (−)-trans-4-methylene-2-phenylcyclopentanoic Acid, (R)-(+)-α-methylbenzylamine salt The crude (+−)-trans-4-methylene-2-phenylcyclopentanoic acid from Step A (assumed 131 mmol) was taken up in 2-propanol (400 mL), warmed to 80° C. and treated with (S)-(−)-α-methylbenzylamine (8.45 mL, 66 mmol). The mixture was stirred while allowed to cool to rt over 16 h and was then cooled to −10° C. for 1 h. The salt was filtered, washed with a small amount of ether to remove 2-propanol and air dried to give 6.442 g of salt. This was recrystallized twice from 2-propanol to give the title salt (4.713 g), $[\alpha]_D$=+56 (MeOH, c=0.20).

The combined mother liquors from above were concentrated and the residue was taken up in water, acidified with 2M hydrochloric acid and extracted twice with methylene chloride. The organic layers were each washed with brine, dried over sodium sulfate, combined and concentrated in vacuo. The residue was taken up in 2-propanol (400 mL), warmed to 80° C. and treated with (R)-(+)-α-methylbenzylamine (9.1 mL, 70 mmol). The mixture was stirred while allowed to cool to rt over 16 h and was then cooled to −10° C. for 1 h. The salt was filtered, washed with a small amount of ether to remove 2-propanol and air dried to give 8.22 g of salt. This was recrystallized from 2-propanol to give the title salt (6.31 g), $[\alpha]_D$=−55 (MeOH, c=0.21).

Step C: (+)-trans-4-Methylene-2-phenylcyclopentanoic Acid and (−)-trans-4-methylene-2-phenylcyclopentanoic acid Method A:

The (+)-trans-4-methylene-2-phenylcyclopentanoic acid, (S)-(−)-α-methylbenzylamine salt from Step B (4.7 g) was suspended in methylene chloride and water and acidified with 2M hydrochloric acid and extracted twice with methylene chloride. The organic layers were each washed with brine, dried over sodium sulfate, combined and concentrated in vacuo to give the title (+) acid (3.1 g), $[\alpha]_D$=+101 (MeOH, c=0.135).

Similarly, the (−)-trans-4-methylene-2-phenylcyclopentanoic acid, (R)-(+)-α-methylbenzylamine salt (6.3 g) was converted to the free (−)-title acid (4.23 g), $[\alpha]_D$=−103 (MeOH, c=0.23).

Method B:

Step B1: 1-(S)-(((S)-(−)-4-Benzyl-2-oxazolidin-1-yl)carbonyl)-3-methylene-2-(S)-phenylcyclopentane (Higher $R_f$) and 1-(R)-(((S)-(−)-4-benzyl-2-oxazolidin-1-yl)carbonyl)-3-methylene-2-(R)-phenylcyclopentane (Lower $R_f$)

A solution of (+−)-trans-4-methylene-2-phenylcyclopentanoic acid (47.5 g, 235 mmol) in ether (1 L) and TEA (36 mL, 260 mmol) was cooled to −10° C. Trimethylacetyl chloride (31.8 mL, 260 mmol) was then added slowly and after stirring at −10° C. for 10 min, the reaction was allowed to warm to 10° C. over 1 h. The reaction was then recooled to −60° C.

To the above solution at −60° C. was added via a cannula a solution of (S)-(−)-4-benzyl-2-oxazolidinone (45.8 g, 260 mmol) in THF (500 mL) which had been treated at −50° C. with 2.5 M n-butyl lithium (103 mL, 257 mmol) and aged at −50° C. for 45 min. The reaction was allowed to warm to rt over 16 h. The reaction was diluted with ether (1 L) and quenched with sat'd aqueous ammonium chloride (1 L). The layers were separated and the aqueous layer was reextracted with a second portion of ether. The organic layers were each washed twice with 2N hydrochloric acid, twice with 1N sodium hydroxide and brine, dried over sodium sulfate, combined and concentrated. The residue was purified by chromatography (20% ethyl acetate in hexanes) to give the two diastereomeric products, higher $R_f$ (18.4 g) and lower $R_f$ (17.7 g).

Step B2: (+)-trans-4-Methylene-2-phenylcyclopentanoic acid

A solution of 1-(S)-(((S)-(−)4-benzyl-2-oxazolidin-1-yl)carbonyl)-3-methylene-2-(S)-phenylcyclopentane (higher $R_f$ product from Step B1) (20.9 g, 58 mmol) in a 3:1 mixture of THF:water (1 L) was cooled to 5° C. hydrogen peroxide (30%, 39.5 mL, 350 mmol) and lithium hydroxide (4.85 g, 106 mmol) were added and the reaction was stirred for 3.5 h. The excess peroxide was quenched by dropwise addition of sodium sulfite (60 g) in water (1 L) over 1.5 h while maintaining the temperature below 5° C. After stirring for 2 additional hours, most of the THF was removed in vacuo and the aqueous layer was washed 3 times with methylene chloride. The aqueous layer was acidified to pH=2 with conc. HCl and reextracted twice with methylene chloride. The organic layers were washed with brine, dried and concentrated to give the (+) title product, $[\alpha]_D$=+100.5 (MeOH, c=0.207).

Step D: (+)-trans-1-hydroxymethyl-4-methylene-2-phenylcyclopentane and (−)-trans-1-hydroxymethyl-4-methylene-2-phenylcyclopentane Method A:

A solution of (+)-trans-4-methylene-2-phenylcyclopentanoic acid from Step C (4.15 g, 20.5 mmol) in THF (100 mL) under nitrogen was cooled to −7° C. and 1M LAH in THF (31 mL, 31 mmol) was added dropwise over 15. The reaction was allowed to warm to rt over 16 h. The excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title (+) product (3.93 g), $[\alpha]_D$=+50 (MeOH, c=0.20).

Similarly, the (−)-trans-4-methylene-2-phenylcyclopentanoic acid from Step C (4.23 g) was converted to the title (−) alcohol (3.75 g), $[\alpha]_D$=−51 (MeOH, c=0.2).

Method B:

Prep-HPLC of (+−)-trans-4-methylene-2-phenylcyclopentanoic from example 1, Step B using a Chiracel OD column (5–10% isopropanol in hexanes) affords good separation of the title (−) enantiomer as the first eluting band and the (+) enantiomer as the second eluting band.

Step E: (+)-trails-1-t-Butyldimethylsilyloxymethyl-4-methylene-2-phenylcyclopentane and (−)-trans-1-t-butyldimethylsilyloxymethyl-4-methylene-2-phenylcyclopentane To a solution of (+)-trans-1-hydroxymethyl-4-methylene-2-phenylcyclopentane from Step D (3.9 g, 21 mmol) in methylene chloride (50 mL) was added t-butyldimethylsilyl chloride (4.7 g, 31 mmol) and DIPEA (7.3 mL, 42 mmol). The reaction was stirred at rt for 16 h, poured into dilute aq. HCl and extracted twice with ether. The organic layers were washed with brine, dried over sodium sulfate, combined and concentrated. The residue was purified by FC (100% hexanes) to afford the title product (5.6 g) as a oil, $[\alpha]_D$=+42.3 (MeOH, c=0.18).

Similarly, (−)-trans-1-hydroxymethyl-4-methylene-2-phenylcyclopentane from Step D (3.75 g) was converted to the title (−) silylether (5.5 g), $[\alpha]_D$=−44.4 (MeOH, c=0.18).

Step F: (+)-trans-1-hydroxymethyl-4-oxo-2-phenylcyclopentane and (−)-trans-1-hydroxymethyl-4-oxo-2-phenylcyclopentane Method A:

A solution of (+)-trans-1-t-butyldimethylsilyloxymethyl-4-methylene-2-phenylcyclopentane from Step E (4.6 g, 15 mmol) in methanol (100 mL) was cooled to −70° C. in a dry-ice acetone bath and ozone was bubbled through until a blue color persisted which was discharged with a stream of nitrogen. Dimethylsulfide (10 mL) was added and after 15 min, the reaction was allowed to warm to rt over 16 h. Since by TLC (20% ethyl acetate in hexanes) indicated that there was significant loss of the silyl as well as dimethylketal formation, the methanol was mostly remove in vacuo. The residue was diluted with water and treated with sulfuric acid (6 mL) and stirred for 2 h. The mixture was extracted twice with ethyl acetate and the organic layers were washed with brine (containing some sodium bicarbonate), dried over sodium sulfate, combined and concentrated. The residue was purified by FC (15–30% ethyl acetate in hexanes) to give the (+) title ketone/alcohol (2.87 g), $[\alpha]_D$=−96 (MeOH, c=0.2).

Similarly, (−)-trans-1-t-butyldimethylsilyloxymethyl-4-methylene-2-phenylcyclopentane from Step E (4.4 g) was converted to the title (−) ketone/alcohol (2.8 g), $[\alpha]_D$=+97 (MeOH, c=0.2).

Method B:

The title compounds can also be obtained directly from (+)-trans-1-hydroxymethyl-4-methylene-2-phenylcyclopentane and (−)-trans-1-hydroxymethyl-4-methylene-2-phenylcyclopentane by ozonolysis as above. Thus, (+)-trans-1-hydroxymethyl-4-methylene-2-phenylcyclopentane (3.7 gm, 20 mmol) afforded from (+)-trans-1-hydroxymethyl-4-oxo-2-phenylcyclopentane (3.5 g).

Step G: 1-(S)-Benzylamino-3-(S)-hydroxymethyl-4-(S)-phenylcyclopentane and 1-(R)-benzylamino-3-(S)-hydroxymethyl-4-(S)-phenylcyclopentane To a solution of (+)-trans-1-hydroxymethyl-4-oxo-2-phenylcyclopentane from Step F (1.19 g, 6.3 mmol) in 1,2-dichloroethane (25 mL) was added benzylamine (1.3 mL, 12 mmol) and acetic acid (0.75 mL, 13 mmol). After 10 min, sodium triacetoxyborohydride (2.65 g, 12.5 mmol) was added in portions and the reaction was stirred at rt for 16 h. The reaction was quenched into dilute aq. sodium carbonate and the mixture was extracted twice with ethyl acetate. The organic layers were washed with brine, dried over sodium sulfate, combined and concentrated. The residue was purified by FC (5–10% methanol in methylene chloride) to separate the title products (1.6 g) as a mixture of C-1 isomers.

Step H: 1-(S)-t-Butoxycarbonylamino-3-(S)-hydroxymethyl-4-(S)-phenylcyclopentane (Higher $R_f$ isomer) and 1-(R)-t-butoxycarbonylamino-3-(S)-hydroxymethyl-4-(S)-phenylcyclopentane (Lower $R_f$ isomer)

To a solution of 1-(S)-benzylamino-3-(S)-hydroxymethyl-4-(S)-phenylcyclopentane and 1-(R)-benzylamino-3-(S)-hydroxymethyl-4-(S)-phenylcyclopentane from Step G (1.6 g, 5.6 mmol) in methanol (40 mL) was added 20% palladium hydroxide (300 mg, 50% by wt water) and ammonium formate (7.0 g, 111 mmol). The reaction was heated at 60° C. for 6 h and rt for 16 h. The reaction was filtered and concentrated. The residue was taken up in water and the aqueous layer was made basic with 2N sodium hydroxide and extracted twice with methylene chloride. The organic layers were washed with brine, dried over sodium sulfate, combined and concentrated to afford crude amino-alcohol.

The above product was taken up in methylene chloride (25 mL), cooled in an ice bath and DIPEA (2.9 mL, 17 mmol) and di-t-butyl dicarbonate (1.28 g, 5.8 mmol) were added. After 16 h, the reaction was poured into dilute aq. HCl and extracted twice with methylene chloride. The organic layers were washed with brine, dried over sodium sulfate, combined and concentrated. The residue was purified by FC (30–40% ethyl acetate in hexanes) to afford separation of the two title compounds.

Higher $R_f$: $^1$H NMR (CDCl$_3$) δ: 1.43 (s, 9 H), 1.45 (m, 1 H), 1.9–2.1 (m, 2 H), 2.17 (m, 1 H), 2.40 (m, 1 H), 3.01 (q, 1 H), 3.59 (dABq, 2 H), 4.20 (br m, 1 H), 5.00 (br s, 1 H), 7.15–7.3 (m, 5 H). Lower $R_f$: $^1$H NMR (CDCl$_3$) δ: 1.43 (s, 9 H), 1.58 (ddd, 1H), 1.78.1 (ddd, 1H), 2.02 (m, 1 H), 2.29 (m, 1 H), 2.47 (ddd, 1 H), 2.76 (ddd, 1 H), 3.54 (dABq, 2 H), 4.06 (br m, 1 H), 4.62 (br s, 1 H), 7.15–7.3 (m, 5 H).

Step I: 1-(S)-t-Butoxycarbonylamino-3-(S)-formyl-4-(S)-phenylcyclopentane (Higher $R_f$ isomer) and 1-(R)-t-butoxycarbonylamino-3-(S)-formyl-4-(S)-phenylcyclopentane (Lower $R_f$ isomer)

To a solution of oxalyl chloride (0.145 mL, 1.67 mmol) in methylene chloride (10 mL) at −70° C. was added dropwise DMSO (0.24 mL, 3.3 mmol). After 15 min, a solution of 1-(S)-t-butoxycarbonylamino-3-(S)-hydroxymethyl-4-(S)-phenylcyclopentane (Higher $R_f$ isomer from Step H) (194 mg, 0.66 mmol) in methylene chloride (5 mL) was added. The reaction was stirred at −70° C. for 1.5 h and then DIPEA (1.2 mL, 6.6 mmol) in methylene chloride (5 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (15% ethyl acetate in hexanes) to give the title product (155 mg) after vacuum drying.

Using essentially the same procedure as above, material derived from the lower isomer from Step H (0.189 g, 0.6 mmol) was also converted to the lower $R_f$ title compound (175 mg).

Step J: 1-(S)-(t-Butoxycarbonylamino)-3-(S)-((4-(N-(4-nitrobenzyloxycarbonyl)-N-(allyl)amino)piperidin-1-yl)methyl)-4-(S)-phenylcyclopentane (Higher $R_f$ isomer) and 1-(R)-(t-butoxycarbonylamino)-3-(S)-((4-(N-(4-nitrobenzyloxycarbonyl)-N-(allyl)amino)piperidin-1-yl)methyl)-4-(S)-phenylcyclopentane (Lower $R_f$ isomer)

To a solution of 1-((S)-(t-butoxycarbonylamino)-3-(S)-(carbonyl)-4-(S)-phenylcyclopentane (from Step I, derived from Higher $R_f$ isomer in Step H) (155 mg, 0.54 mmol) in 1,2-dichloroethane (5 mL) was added 4-(N-(4-nitrobenzyloxycarbonyl)(N-allyl)amino)piperidine hydrochloride (210 mg, 0.59 mmol) and DIPEA (0.12 mL, 0.64 mmol). After 15 min, sodium triacetoxyborohydride (230 mg, 1.1 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product (280 mg) as the free amine.

MS (NH$_3$/ESI): m/z 593 (M+1).

Using essentially the same procedure as above, material derived from the lower isomer from Step H-I (0.175 g, 0.6 mmol) was also converted to the lower $R_f$ title compound (275 mg).

Step K: 1-(S)-(Amino)-3-(S)-((4-(N-(4-nitrobenzyloxycarbonyl)-N-(allyl)amino)piperidin-1-yl)methyl)-4-(S)-phenylcyclopentane di-hydrochloride salt (Higher $R_f$ isomer) and 1-(R)-(amino)-3-(S)-((4-(N-(4-nitrobenzyloxycarbonyl)-N-(allyl)amino)piperidin-1-yl)methyl)-4-(S)-phenylcyclopentane di-hydrochloride salt (Lower $R_f$ isomer)

A solution of hydrogen chloride (4.6 mmol) in methanol was prepared by addition of acetyl chloride (0.325 mL, 4.6 mmol) to methanol (10 mL) and aging for 15 min. To this was added 1-(S)-(t-butoxycarbonylamino)-3-(S)-((4-(N-(4-nitrobenzyloxycarbonyl)-N-(allyl)amino)piperidin-1-yl)methyl)-4-(S)-phenylcyclopentane (Higher $R_f$ isomer from Step J) (270 mg, 0.46 mmol). After 16 h, the volatiles were removed in vacuo to dryness to give the title compound as the di-hydrochloride salt (248 mg).

Using essentially the same procedure as above, material derived from the lower isomer from Step H-J (0.250 g, 0.42 mmol) was also converted to the lower $R_f$ title compound (235 mg).

Step L: N-(1-(S)-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 6B) and N-(1-(S)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 7H) di-TFA salts To a solution of 1-(S)-(amino)-3-(S)-((4-(N-(4-nitrobenzyloxycarbonyl)-N-(allyl)amino)piperidin-1-yl)methyl)-4-(S)-phenylcyclopentane di-hydrochloride salt (derived from the higher $R_f$ isomer in Steps H-K) (20 mg, 0.045 mmol), 4-methyl-2-oxo-valeric acid (15 mg, 0.11 mmol) and DIPEA (0.016 mL, 0.09 mmol) in 1,2-dichloroethane (2 mL) was added sodium triacetoxyborohydride (29 mg, 0.135 mmol). The reaction was stirred at 50° C. for 10 h and then at rt for another 16 h. It was then quenched with aq sodium carbonate and extracted three times with ethyl acetate. The organic layers were each washed with brine, dried over sodium sulfate, combined and concentrated in vacuo. The residue was purified by Prep TLC eluting with 10% methanol in methylene chloride to give the title products (8 mg) as a mixture of the free amines. HPLC analysis as in Example 6 and 7 gave only a single band corresponding to Isomers B (and enantiomeric Isomer F) and H (and enantiomeric Isomer D) which co-elute.

HPLC/MS (ESI): m/z 593 (M+1).

EXAMPLE 9

N-(1-(R)-3-(S)-((4-(N-(4-Nitrobenzyloxycarbonyl)-N-(allyl)amino)piperidin-1-yl)methyl)-4-(S)-phenylcyclopent-1-yl)-L-leucine (Isomer 7E) and N-(1-(R)-3-(S)-((4-(N-(4-nitrobenzyloxycarbonyl)-N-(allyl)amino)piperidin-1-yl)methyl)-4-(S)-phenylcyclopent-1-yl)-D-leucine (Isomer 6C) di-TFA salts Using essentially the same procedure as in Example 8, Step L, but substituting 1-(R)-(amino)-3-(S)-((4-(N-(4-nitrobenzyloxycarbonyl)-N-(allyl)amino)piperidin-1-yl)methyl)-4-(S)-phenylcyclopentane di-hydrochloride salt (derived from the lower $R_f$ isomer in Steps H-K) (20 mg, 0.045 mmol), the two title compounds were prepared. HPLC analysis of the crude products as in Example 6 and 7 indicated two peaks. In this case the diastereomers were separable on Prep TLC (10% methanol in methylene chloride). HPLC analysis as in Example 6 and 7 now gave only a single peak for each sample from the Prep TLC. The higher band corresponded to Isomer E (and enantiomeric Isomer A) and the lower band corresponded to Isomer C (and enantiomeric Isomer G) which are distinct in the HPLC. The di-TFA salts were prepared by evaporation from 0.5% TFA in acetonitrile.

Higher Isomer E: HPLC/MS (ESI): m/z 593 (M+1).
Lower Isomer C: HPLC/MS (ESI): m/z 593 (M+1).

EXAMPLE 10

Using essentially the same procedure as in Example 6, Steps E to G, but substituting 4-(3-(4-fluorophenyl)prop-1-yl)piperidine hydrochloride in Step E and L-valine t-butyl ester hydrochloride in Step F, the following diastereomers can be obtained after a combination of Prep TLC and HPLC separation.

N-(1-(S)-3-(R)-((4-(3-(4-fluorophenyl)prop-1-yl)piperidin-1-yl)methyl)-4-(R)-phenylcyclopent-1-yl)-L-valine di-TFA salt (Isomer A), N-(1-(S)-3-(S)-((4-(3-(4-fluorophenyl)prop-1-yl)piperidin-1-yl)methyl)-4-(S)-phenylcyclopent-1-yl)-L-valine di-TFA salt (Isomer B), N-(1-(R)-3-(S)-((4-(3-(4-fluorophenyl)prop-1-yl)piperidin-1-yl)methyl)-4-(S)-phenylcyclopent-1-yl)-L-valine di-TFA salt (Isomer C)

N-(1-(R)-3-(R)-((4-(3-(4-fluorophenyl)prop-1-yl)piperidin-1-yl)methyl)-4-(R)-phenylcyclopent-1-yl)-L-valine di-TFA salt (Isomer D)

EXAMPLE 11

Using essentially the same procedure as in Example 6, Steps E to G, but substituting 4-(3-(4-fluorophenyl)prop-1-yl)piperidine hydrochloride (from Procedure 9) in Step E and L-leucine t-butyl ester hydrochloride in Step F, the following diastereomers can be obtained after a combination of Prep TLC and HPLC separation.

N-(1-(S)-3-(R)-((4-(3-(4-fluorophenyl)prop-1-yl)piperidin-1-yl)methyl)-4-(R)-phenylcyclopent-1-yl)-L-leucine di-TFA salt (Isomer A), N-(1-(S)-3-(S)-((4-(3-(4-fluorophenyl)prop-1-yl)piperidin-1-yl)methyl)-4-(S)-phenylcyclopent-1-yl)-L-leucine di-TFA salt (Isomer B), N-(1-(R)-3-(S)-((4-(3-(4-fluorophenyl)prop-1-yl)piperidin-1-yl)methyl)-4-(S)-phenylcyclopent-1-yl)-L-isoleucine di-TFA salt (Isomer C)

N-(1-(R)-3-(R)-((4-(3-(4-fluorophenyl)prop-1-yl)piperidin-1-yl)methyl)-4-(R)-phenylcyclopent-1-yl)-L-leucine di-TFA salt (Isomer D)

EXAMPLE 12

Using essentially the same procedure as in Example 6, Steps E to G, but substituting 4-(3-(4-fluorophenyl)prop-1-yl)piperidine hydrochloride (from Procedure 9) in Step E and L-phenylglycine t-butyl ester hydrochloride in Step F, the following diastereomers can be obtained after a combination of Prep TLC and HPLC separation.

N-(1-(S)-3-(R)-((4-(3-(4-fluorophenyl)prop-1-yl)piperidin-1-yl)methyl)-4-(R)-phenylcyclopent-1-yl)-L-phenylglycine di-TFA salt (Isomer A), N-(1-(S)-3-(S)-((4-(3-(4-fluorophenyl)prop-1-yl)piperidin-1-yl)methyl)-4-(S)-phenylcyclopent-1-yl)-L-phenylglycine di-TFA salt (Isomer B), N-(1-(R)-3-(S)-((4-(3-(4-fluorophenyl)prop-1-yl)piperidin-1-yl)methyl)-4-(S)-phenylcyclopent-1-yl)-L-phenylglycine di-TFA salt (Isomer C)

N-(1-(R)-3-(R)-((4-(3-(4-fluorophenyl)prop-1-yl)piperidin-1-yl)methyl)-4-(R)-phenylcyclopent-1-yl)-L-phenylglycine di-TFA salt (Isomer D)

EXAMPLE 13

Using essentially the same procedure as in Example 6, Steps E to G, but substituting 4-(3-(4-fluorophenyl)prop-1-yl)piperidine hydrochloride (from Procedure 9) in Step E and L-cyclohexylglycine t-butyl ester hydrochloride in Step F, the following diastereomers can be obtained after a combination of Prep TLC and HPLC separation.

N-(1-(S)-3-(R)-((4-(3-(4-fluorophenyl)prop-1-yl)piperidin-1-yl)methyl)-4-(R)-phenylcyclopent-1-yl)-1-cyclohexylglycine di-TFA salt (Isomer A), HPLC/MS (ESI): m/z 633 (M+1).

N-(1-(S)-3-(S)-((4-(3-(4-fluorophenyl)prop-1-yl)piperidin-1-yl)methyl)-4-(S)-phenylcyclopent-1-yl)-L-cyclohexylglycine di-TFA salt (Isomer B), HPLC/MS (ESI): m/z 633 (M+1).

N-(1-(R)-3-(S)-((4-(3-(4-fluorophenyl)prop-1-yl)piperidin-1-yl)methyl)-4-(S)-phenylcyclopent-1-yl)-L-cyclohexylglycine di-TFA salt (Isomer C) HPLC/MS (ESI): m/z 633 (M+1).

N-(1-(R)-3-(R)-((4-(3-(4-fluorophenyl)prop-1-yl)piperidin-1-yl)methyl)-4-(R)-phenylcyclopent-1-yl)-L-cyclohexylglycine di-TFA salt (Isomer D) HPLC/MS (ESI): m/z 633 (M+1).

EXAMPLE 14

Using essentially the same procedures as in Example 6, Steps E to G, but substituting 4-(3-benzyl-1-ethyl-1H-pyrazol-5-yl)piperidine hydrochloride (from Procedure 1) in Step E and L-cyclohexylglycine t-butyl ester hydrochloride in Step F and TFA in place of HCl in ether in Step G, the following diastereomers can be obtained after a combination of Prep TLC and HPLC separation.

N-(1-(S)-3-(R)-((4-(3-benzyl-1-ethyl-1H-pyrazol-5-yl)piperidin-1-yl)methyl)-4-(R)-phenylcyclopent-1-yl)-L-cyclohexylglycine di-TFA salt (Isomer A), N-(1-(S)-3-(S)-((4-(3-benzyl-1-ethyl-H-pyrazol-5-yl)piperidin-1-yl)methyl)-4-(S)-phenylcyclopent-1-yl)-L-cyclohexylglycine di-TFA salt (Isomer B), N-(1-(R)-3-(S)-((4-(3-benzyl-1-ethyl-1H-pyrazol-5-yl)piperidin-1-yl)methyl)-4-(S )-phenylcyclopent-1-yl)-L-cyclohexylglycine di-TFA salt (Isomer C)

N-(1-(R)-3-(R)-((4-(3-benzyl-1-ethyl-1H-pyrazol-5-yl)piperidin-1-yl)methyl)-4-(R)-phenylcyclopent-1-yl)-L-cyclohexylglycine di-TFA salt (Isomer D)

EXAMPLE 15

Using essentially the same procedures as in Example 6, Steps E to G, but substituting 4-(4-fluorophenyl)piperidine hydrochloride (from Procedure 9) in Step E and L-cyclohexylglycine t-butyl ester hydrochloride in Step F and TFA in place of HCl in ether in Step G, the following diastereomers can be obtained after a combination of Prep TLC and HPLC separation.

N-(1-(S)-3-(R)-((4-(4-fluorophenyl)piperidin-1-yl)methyl)-4-(R)-phenylcyclopent-1-yl)-L-cyclohexylglycine di-TFA salt (Isomer A), N-(1-(S)-3-(S)-((4-(4-fluorophenyl)piperidin-1-yl)methyl)-4-(S)-phenylcyclopent-1-yl)-L-cyclohexylglycine di-TFA salt (Isomer B), N-(1-(R)-3-(S)-((4-(4-fluorophenyl)piperidin-1-yl)methyl)-4-(S)-phenylcyclopent-1-yl)-L-cyclohexylglycine di-TFA salt (Isomer C)

N-(1-(R)-3-(R)-((4-(4-fluorophenyl)piperidin-1-yl)methyl)-4-(R)-phenylcyclopent-1-y])-L-cyclohexylglycine di-TFA salt (Isomer D)

EXAMPLE 16

N-(1-(R)-3-(S)-((4-(3-(4-Fluorophenyl)prop-1-yl)piperidin-1-yl)methyl)-4-(S)-phenylcyclopent-1-yl)-D-leucine di-TFA salt and N-(1-(S)-3-(S)-((4-(3-(4-fluorophenyl)prop-1-yl)piperidin-1-yl)methyl)-4-(S)-phenylcyclopent-1-yl)-D-leucine di-TFA salt Step A: (1-(R)-3-(S)-(hydroxymethyl)-4-(S)-phenylcyclopent-1-yl)-D-leucine (Higher $R_f$) and (1-(S)-3-(S)-(hydroxymethyl)-4-(S)-phenylcyclopent-1-yl)-D-leucine (Lower $R_f$)

Method A:

To a solution of (+)-trans-1-hydroxymethyl-4-oxo-2-phenylcyclopentane from Example 8, Step F (250 mg, 1.32 mmol), D-leucine t-butyl ester hydrochloride (370 mg, 2.0 mmol) and DIPEA (0.36 mL, 2.0 mmol) in 1,2-dichloroethane (10 mL) was added sodium triacetoxyborohydride (840 mg, 4.0 mmol). The reaction was stirred at rt for 4 h and was then quenched with aq sodium carbonate and extracted three times with ethyl acetate. The organic layers were each washed with brine, dried over sodium sulfate, combined and concentrated in vacuo. The residue was purified by FC eluting with a gradient of 5–25% ethyl acetate in hexanes to give the higher $R_f$ 1-(R) title compound as the major product (280 mg) and the lower $R_f$ 1-(S) as the minor product (160 mg mixed fractions).

Method B:

To a solution of (+)-trans-1-hydroxymethyl-4-oxo-2-phenylcyclopentane from Example 8, Step F (3.3 g, 16 mmol) in methylene chloride (100 mL) was added t-butyldimethylsilyl chloride (11 g, 49 mmol) and DIPEA (22 mL, 74 mmol). The reaction was stirred at rt for 16 h, poured into dilute aq. HCl and extracted twice with ether. The organic layers were washed with brine, dried over sodium sulfate, combined and concentrated. The residue was purified by FC (5% ethyl acetate in hexanes) to afford of (+)-trans-1-t-butyldimethylsilyloxymethyl-4-oxo-2-phenylcyclopentane (6.3 g) as a oil, $[\alpha]_D=+97$ (MeOH, c=0.2).

To a solution of (+)-trans-1-t-butyldimethylsilyloxymethyl-4-oxo-2-phenylcyclopentane from above (1.0 g, 3.28 mmol), D-leucine t-butyl ester hydrochloride (2,2 g, 3.0 mmol) and DIPEA (1.8 mL, 10.2 mmol) in 1,2-dichloroethane (20 mL) was added sodium triacetoxyborohydride (2.1 g, 10 mmol). The reaction was stirred at rt for 5 h and was then quenched with aq sodium carbonate and extracted three times with ethyl acetate. The organic layers were each washed with brine, dried over sodium sulfate, combined and concentrated in vacuo. The residue was purified by FC eluting with 5% ethyl acetate in hexanes to give the higher $R_f$ 1-(R) title compound as the minor product and the lower $R_f$ 1-(S) as the major product (1.35 g as a mixture).

To a solution of the above product (1.35 g, 2.85 mmol) in THF (10 mL) was added 1M TBAF in THF (4.3 mL, 4.3 mmol). The reaction was stirred at rt for 16 h and the concentrated. The residue was purified by FC eluting with 20–25% ethyl acetate in hexanes to give the higher $R_f$ 1-(R) title compound as the minor product (33 mg pure) and the lower $R_f$ 1-(S) as the major product (202 mg pure, 0.70 g as a mixture).

Step B: (1-(R)-3-(S)-(Formyl)-4-(S)-phenylcyclopent-1-yl)-D-leucine (Higher $R_f$) and (1-(S)-3-(S)-(carbonyl)-4-(S)-phenylcyclopent-1-yl)-D-leucine (Lower $R_f$)

Method A:

To a solution of oxalyl chloride (0.100 mL, 1.1 mmol) in methylene chloride (20 mL) at −70° C. was added dropwise DMSO (2.2 mL, 5.0 mmol). After 15 min, a solution of (1-(R)-3-(S)-(hydroxymethyl)-4-(S)-phenylcyclopent-1-yl)-D-leucine (Higher $R_f$ from Step A, Method A) (160 mg, 0.44 mmol) containing 1 eq. of 1M HCl in ether in methylene chloride (5 mL) was added. The reaction was stirred at −70° C. for 1.5 h and then DPEA (0.77 mL, 4.5 mmol) in methylene chloride (5 mL) was added dropwise over 5 min. After a further 10 min, the mixture was allowed to warm to rt for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20% ethyl acetate in hexanes) to give the higher $R_f$ title product (38 mg) after vacuum drying.

Method B:

To a solution of (1-(R)-3-(S)-(hydroxymethyl)4-(S)-phenylcyclopent-1-yl)-D-leucine (mixture of higher and lower $R_f$ from Step A, Method A) (142 mg, 0.39 mmol) in methylene chloride (10 mL) was added TPAP (6.9 mg, 0.020 mmol) and N-methylmorholine (70 mg, 0.60 mmol). The reaction was stirred under nitrogen at rt for 1 h and was then concentrated. The residue was purified by FC (25% ethyl acetate in hexanes) to give the title products (108 mg) after vacuum drying.

Step C: N-(1-(R)-3-(S)-((4-(3-(4-Fluorophenyl)prop-1-yl)piperidin-1-yl)methyl)-4-(S)-phenylcyclopent-1-yl)-D-leucine t-butyl Ester (Higher $R_f$) and N-(1-(S)-3-(S)-((4-(3-(4-fluorophenyl)prop-1-yl)piperidin-1-yl)methyl)-4-(S)-phenylcyclopent-1-yl)-D-leucine t-butyl Ester (Lower $R_f$)

To a solution of (1-(R)-3-(S)-(formyl)-4-(S)-phenylcyclopent-1-yl)-D-leucine (higher $R_f$) and (1-(S)-3-(S)-(formyl)-4-(S)-phenylcyclopent-1-yl)-D-leucine (lower $R_f$) (from Step B, Method B) (9 mg, 0.025 mmol) in 1,2-dichloroethane (1 mL) was added 4-(3-(4-fluorophenyl)prop-1-yl)piperidine hydrochloride (from Procedure 9) (8 mg, 0.032 mmol) and DIPEA (0.006 mL, 0.033 mmol). After 15 min, sodium triacetoxyborohydride (11 mg, 0.051 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 60% ethyl acetate in hexanes to give the title products as the free amines.

(Each isomer): HPLC/MS (ES): m/z 565 (M+1).

Step D: N-(1-(R)-3-(S)-((4-(3-(4-Fluorophenyl)prop-1-yl)piperidin-1-yl)methyl)-4-(S)-phenylcyclopent-1-yl)-D-leucine di-TFA salt (Derived from Higher $R_f$) and N-(1-(S)-3-(S)-((4-(3-(4-fluorophenyl)prop-1-yl)piperidin-1-yl)methyl)-4-(S)-phenylcyclopent-1-yl)-D-leucine di-TFA salt (Derived from Lower $R_f$)

Each the products from Step C were taken up in TFA (5 mL) and aged at rt for 16 h. The volatiles were removed under a stream of nitrogen to afford the title products as the di-TFA salts (4 mg and 6 mg).

(Each isomer): HPLC/MS (ES): m/z 509 (M+1).

EXAMPLE 17

N-(1-(R)-3-(S)-((4-(3-(Benzofurazan-5-yl)prop-1-yl)piperidin-1-yl)methyl)-4-(S)-phenylcyclopent-1-yl)-D-leucine di-TFA salt and N-(1-(S)-3-(S)-((4-(benzofurazan-5-yl)piperidin-1-yl)methyl)-4-(S)-phenylcyclopent-1-yl)-D-leucine di-TFA salt Using essentially the same procedures as in Example 16, Step C and D, but substituting 4-(3-(benzofurazan-5-yl)prop-1-yl)piperidine hydrochloride (from Procedure 6) in Step C, the two diastereomeric title compounds were prepared.

(Each isomer): HPLC/MS (ESI): m/z 533 (M+1).

EXAMPLE 18

N-(1-(R)-3-(S)-((4-(3-(4-Cyano-3-fluorophenyl)prop-1-yl)piperidin-1-yl)methyl)-4-(S)-phenylcyclopent-1-yl)-D-leucine di-TFA salt and N-(1-(S)-3-(S)-((4-(3-(4-cyano-3-fluorophenyl)prop-1-yl)piperidin-1-yl)methyl)-4-(S)-phenylcyclopent-1-yl)-D-leucine di-TFA salt Using essentially the same procedures as in Example 16, Step C and D, but substituting 4-(3-(4-cyano-3- fluorophenyl)prop-1-yl)piperidine hydrochloride (from Procedure 8) in Step C, the title compounds can be prepared.

EXAMPLE 19

N-(1-(R)-3-(S)-((4-(3-Benzyl-1-ethyl-1H-pyrazol-5-yl)piperidin-1-yl)methyl)-4-(S)-phenylcyclopent1-yl)-D-leucine di-TFA salt and N-(1-(S)-3-(S)-((4-(3-benzyl-1-ethyl-1H-pyrazol-5-yl)piperidin-1-yl)methyl)-4-(S)-phenylcyclopent-1-yl)-D-leucine di-TFA salt D-leucine Using essentially the same procedures as in Example 16, Step C and D, but substituting 4-(3-benzyl-1-ethyl-1H-pyrazol-5-yl)piperidine hydrochloride (from Procedure 1) in Step C, the title compounds can be prepared.

EXAMPLE 20

N-(1-(R)-3-(S)-((4-(N-(Propyl)-N-(pyrrimidin-2-yl)amino)piperidin-1-yl)methyl)-4-(S)-phenylcyclopent-1-yl)-D-leucine di-TFA salt and N-(1-(S)-3-(S)-((4-(N-(propyl)-N-(pyrrimidin-2-yl)amino)piperidin-1-yl)methyl)-4-(S)-phenylcyclopent-1-yl)-D-leucine di-TFA salt Using essentially the same procedures as in Example 16, Step C and D, but substituting 4-(N-(propyl)-N-(pyrimidin-2-yl)amino)piperidine hydrochloride (from Procedure 13) in Step C, the title compounds can be prepared.

EXAMPLE 21

N-(1-(R)-3-(S)-((4-(4-Fluorophenyl)piperidin-1-yl)methyl)-4-(S)-phenylcyclopent-1-yl)-D-leucine di-TFA salt and N-(1-(S)-3-(S)-((4-(4-fluorophenyl)piperidin-1-yl)methyl)-4-(S)-phenylcyclopent-1-yl)-D-leucine di-TFA salt Using essentially the same procedures as in Example 16, Step C and D, but substituting 4-(4-fluorophenyl)piperidine hydrochloride in Step C, the title compounds can be prepared.

EXAMPLE 22

N-(1-(R)-3-(S)-((4-(3-(4-Fluorophenyl)prop-1-yl)piperidin-1-yl)methyl)-4-(S)-phenylcyclopent-1-yl)-D-cyclohexylglycine di-TFA salt and N-(1-(S)-3-(S)-((4-(3-(4-fluorophenyl)prop-1-yl)piperidin-1-yl)methyl)-4-(S)-phenylcyclopent-1-yl)-D-cyclohexylglycine di-TFA salt Using essentially the same procedures as in Example 16, Step A to D, but substituting D-cyclohexylglycine t-butyl ester hydrochloride in Step A and 4-(3-(4-fluorophenyl)prop-1-yl)piperidine hydrochloride (from Procedure 9) in Step C, the title compounds were prepared.

(Each isomer): HPLC/MS (ESI): m/z 535 (M+1).

EXAMPLE 23

N-(1-(R)-3-(S)-((4-(3-(4-Cyano-3-fluorophenyl)prop-1-yl)piperidin-1-yl)methyl)-4-(S)-phenylcyclopent-1-yl)-D-cyclohexylglycine di-TFA salt and N-(1-(S)-3-(S)-((4-(3-(4-cyano-3-fluorophenyl)prop-1-yl)piperidin-1-yl)methyl)-4-(S)-phenylcyclopent-1-yl)-D-cyclohexylglycine di-TFA salt Using essentially the same procedures as in Example 16, Step A to D, but substituting D-cyclohexylglycine t-butyl ester hydrochloride in Step A and 4-(3-(4-cyano-3-fluorophenyl)prop-1-yl)piperidine hydrochloride (from Procedure 8) in Step C, the title compounds were prepared.

(Each isomer): HPLC/MS (ESI): m/z 560 (M+1).

EXAMPLE 24

N-(1-(R)-3-(S)-((4-(3-Benzyl-1-ethyl-1H-pyrazol-5-yl)piperidin-1-yl)methyl)-4-(S)-phenylcyclopent-1-yl)-D-cyclohexylglycine di-TFA salt and N-(1-(S)-3-(S)-((4-(3-benzyl-1-ethyl-1H-pyrazol-5-yl)piperidin-1-yl)methyl)-4-(S)-phenylcyclopent-1-yl)-D-cyclohexylglycine di-TFA salt Using essentially the same procedures as in Example 16, Step A to D, but substituting D-cyclohexylglycine t-butyl ester hydrochloride in Step A and 4-(3-benzyl-1-ethyl-1H-pyrazol-5-yl)piperidine hydrochloride (from Procedure 1) in Step C, the title compounds were prepared.

(Each isomer): HPLC/MS (ESI): m/z 583 (M+1).

EXAMPLE 25

N-(1-(R)-3-(S)-((4-(N-(Propyl)-N-(pyrrimidin-2-yl)amino)piperidin-1-yl)methyl)-4-(S)-phenylcyclopent-1-yl)-D-cyclohexylglycine di-TFA salt and N-(1-(S)-3-(S)-((4-(N-(propyl)-N-(pyrrimidin-2-yl)amino)piperidin-1-yl)methyl)-4-(S)-phenylcyclopent-1-yl)-D-cyclohexylglycine di-TFA salt Using essentially the same procedures as in Example 16, Step A to D, but substituting D-cyclohexylglycine t-butyl ester hydrochloride in Step A and 4-(N-(propyl)-N-(pyrrimidin-2-yl)amino)piperidine hydrochloride (from Procedure 13) in Step C, the title compounds were prepared.

(Each isomer): HPLC/MS (ESI): m/z 534 (M+1).

EXAMPLE 26

N-(1-(R)-3-(S)-((4-(4-Fluorophenyl)piperidin-1-yl)methyl)-4-(S)-phenylcyclopent-1-yl)-D-cyclohexylglycine di-TFA salt and N-(1-(S)-3-(S)-((4-(4-fluorophenyl)piperidin-1-yl)methyl)-4-(S)-phenylcyclopent-1-yl)-D-cyclohexylglycine di-TFA salt Using essentially the same procedures as in Example 16, Step A to D, but substituting D-cyclohexylglycine t-butyl ester hydrochloride in Step A and 4-(4-fluorophenyl)piperidine hydrochloride in Step C, the title compounds were prepared.

(Each isomer): HPLC/MS (ESI): m/z 493 (M+1).

EXAMPLE 27

N-(1-(R)-3-(S)-((4-(3-(4-Fluorophenyl)prop-1-yl)piperidin-1-yl)methyl)-4-(S)-phenylcyclopent1-yl)-D-cyclobutylalanine di-TFA salt and N-(1-(S)-3-(S)-((4-(3-(4-fluorophenyl)prop-1-yl)piperidin-1-yl)methyl)-4-(S)-phenylcyclopent-1-yl)-D-cyclobutylalanine di-TFA salt Using essentially the same procedures as in Example 16, Step A to D, but substituting D/L-cyclobutylalanine t-butyl ester hydrochloride in Step A and 4-(3-(4-fluorophenyl)prop-1-yl)piperidine hydrochloride (from Procedure 9) in Step C, the title compounds can be prepared.

EXAMPLE 28

N-(1-(R)-3-(S)-((4-(3-(4-Cyano-3-fluorophenyl)prop-1-yl)piperidin-1-yl)methyl)-4-(S)-phenylcyclopent-1-yl)-D/L-cyclobutylalanine di-TFA salt and N-(1-(S)-3-(S)-((4-(3-(4-cyano-3-fluorophenyl)prop-1-yl)piperidin-1-yl)methyl)-4-(S)-phenylcyclopent-1-yl)-D/L-cyclobutylalanine di-TFA salt Using essentially the same procedures as in Example 16, Step A to D, but substituting D/L-cyclobutylalanine t-butyl ester hydrochloride in Step A and 4-(3-(4-cyano-3-fluorophenyl)prop-1-yl)piperidine hydrochloride (from Procedure 8) in Step C, the title compounds can be prepared.

EXAMPLE 29

N-(1-(R)-3-(S)-((4-(3-Benzyl-1-ethyl-1H-pyrazol-5-yl)piperidin-1-yl)methyl)-4-(S)-phenylcyclopent-1-yl)-D/L-cyclobutylalanine di-TFA salt and N-(1-(S)-3-(S)-((4-(3-benzyl-1-ethyl-1H-pyrazol-5-yl)piperidin-1-yl)methyl)-4-(S)-phenylcyclopent-1-yl)-D/L-cyclobutylalanine di-TFA salt Using essentially the same procedures as in Example 16, Step A to D, but substituting D/L-cyclobutylalanine t-butyl ester hydrochloride in Step A and 4-(3-benzyl-1-ethyl-1H-pyrazol-5-yl)piperidine hydrochloride (from Procedure 1) in Step C, the title compounds were prepared.

EXAMPLE 30

N-(1-(R)-3-(S)-((4-(N-(Propyl)-N-(pyrrimidin-2-yl)amino)piperidin-1-yl)methyl)-4-(S)-phenylcyclopent-1-yl)-D/L-cyclobutylalanine di-TFA salt and N-(1-(S)-3-(S)-((4-(N-(propyl)-N-(pyrrimidin-2-yl)amino)piperidin-1-yl)methyl)-4-(S)-phenylcyclopent-1-yl)-D/L-cyclobutylalanine di-TFA salt Using essentially the same procedures as in Example 16, Step A to D, but substituting D/L-cyclobutylalanine t-butyl ester hydrochloride in Step A and 4-(N-(propyl)-N-(pyrrimidin-2-yl)amino)piperidin-1-yl)piperidine hydrochloride (from Procedure 13) in Step C, the title compounds can be prepared.

EXAMPLE 31

N-(1-(R)-3-(S)-((4-(3-(4-Fluorophenyl)prop-1-yl)piperidin-1-yl)methyl)-4-(S)-phenylcyclopent-1-yl)-D-cyclopropylalanine di-TFA salt and N-(1-(S)-3-(S)-((4-(3-(4-fluorophenyl)prop-1-yl)piperidin-1-yl)methyl)-4-(S)-phenylcyclopent-1-yl)-D-cyclopropylalanine di-TFA salt Using essentially the same procedures as in Example 16, Step A to D, but substituting D-cyclopropylalanine t-butyl ester hydrochloride in Step A and 4-(3-(4-fluorophenyl)prop-1-yl)piperidine hydrochloride in Step C, the title compounds can be prepared.

EXAMPLE 32

N-(1-(R)-3-(S)-((4-(3-Benzyl-1-ethyl-1H-pyrazol-5-yl)piperidin-1-yl)methyl)-4-(S)-phenylcyclopent-1-yl)-D-cyclopropylalanine di-TFA salt and N-(1-(S)-3-(S)-((4-(3-benzyl-1-ethyl-1H-pyrazol-5-yl)piperidin-1-yl)methyl)-4-(S)-phenylcyclopent-1-yl)-D-cyclopropylalanine di-TFA salt Using essentially the same procedures as in Example 16, Step A to D, but substituting D-cyclopropylalanine t-butyl ester hydrochloride in Step A and 4-(3-benzyl-1-ethyl-1H-pyrazol-5-yl)piperidine hydrochloride (from Procedure 1) in Step C, the title compounds were prepared.

EXAMPLE 33

N-(1-(R)-3-(S)-((4-(3-(Benzofurazan-5-yl)prop-1-yl)piperidin-1-yl)methyl)-4-(S)-phenylcyclopent-1-yl)-D-cyclohexylglycine di-hydrochloride salt Using essentially the same procedure as in Example , Steps A to D, but substituting D-cyclohexylglycine t-butyl ester hydrochloride in Step A and 4-(3-(benzofurazan-5-yl)prop-1-yl)piperidine (from Procedure 5) in Step C, the title compound was prepared.

HPLC/MS (ESI): m/z 559 (M+1).

EXAMPLE 34

N-(1-(R)-3-(S)-((4-(3-(4-Flurophenyl)prop-1-yl)piperidin-1-yl)methyl)-4-(S)-phenylcyclopent-1-yl)-L-leucine di-hydrochloride salt Using essentially the same procedure as in Example 16, Steps A to D, but substituting L-leucine t-butyl ester hydrochloride in Step A and 4-(3-(4-flurophenyl)prop-1-yl)piperidine in Step F, the title compound was prepared.

HPLC/MS (ESI): m/z 509 (M+1).

EXAMPLE 35

N-(1-(R)-3-(S)-((4-(3-Benzyl-1-ethyl-1H-pyrazol-5-yl)piperidin-1-yl)methyl)-4-(S)-(3-fluorophenyl)cyclopent-1-yl)-D-cyclohexylglycine Tri-hydrochloride salt Step A: Methyl (+–)-trans-4-methylene-2-(3-fluorophenyl)cyclopentanoate A mixture of methyl trans-3-fluorocinnamate (41.25 g, 229 mmol), tetrakis(triphenylphosphine) palladium(0) (18.5 g, 16 mmol), 1,2-bis(diphenylphosphino)ethane (5.5 g, 13.7 mmol) and 2-((trimethylsilyl)methyl)-2-propen-1-yl acetate (42.66 g, 229 mmol) in THF (300 mL) under nitrogen was heated to reflux for 6 h and then stirred at rt for 16 h. The reaction was diluted with hexane and filtered to remove yellow precipitate. The volatiles were then removed in vacuo and the residue was purified by FC (3 to 5% ethyl acetate in hexanes) to afford the title compound (45 g).

$^1$H NMR (CDCl$_3$) δ: 2.52 (m, 1 H), 2.68 (m, 1 H), 2.8–2.9 (m, 2 H), 2.95 (ddd, 1 H), 3.45 (ddd, 1 H), 3.63 (s, 3 H), 4.96 (m, 2 H), 6.9–7.0 (m, 2 H), 7.03 (d, 1 H), 7.2–7.3 (m, 1 H).

Step B: (+–)-trans-4-Methylene-2-(3-fluorophenyl)cyclopentanoic acid

To a solution of methyl (+–)-trans-4-methylene-2-(3-fluoro)phenylcyclopentanoate prepared as in Example 35, Step A (47 g, 200 mmol) in methanol (500 mL) was added 5N sodium hydroxide (200 mL, 1000 mmol). The reaction was stirred at rt for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

Step C: (+)-trans-1-hydroxymethyl-4-methylene-2-(3-fluorophenyl)cyclopentane and (–)-trans-1-hydroxymethyl-4-methylene-2-(3-fluorophenyl)cyclopentane A solution of (+–)-trans-4-methylene-2-(3-fluorophenyl)cyclopentanoate (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at rt for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (−)-enantiomer, $[\alpha]_D=$−45.5 (MeOH, c=0.9), as the first eluting peak ($R_t$=17.5 min) and the (+)-enantiomer (1.87 g), $[\alpha]_D$=+45.0 (MeOH, c=1.0), as the second peak ($R_t$=22.0 min).

$^1$H NMR (CDCl$_3$) δ: 2.2–2.35 (m, 2 H), 2.5 (m, 1 H), 2.65–2.85 (m, 2 H), 2.9 (m, 1H), 3.51 and 3.68 (dABq, 2 H), 4.93 (m, 2 H), 6.9–7.0 (m, 2 H), 7.06 (d, 1 H), 7.3–7.4 (m, 1 H).

Step D: (+)-trans-3-hydroxymethyl-4-(3-fluorophenyl) cyclopentanone

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g) ), $[\alpha]_D$=+132 (MeOH, c=1.2),.

$^1$H NMR (CDCl$_3$) δ: 2.3–2.45 (m, 2 H), 2.5 (m, 1 H), 2.61 and 2.77 (dABq, 2 H), 2.28 (ddd, 1 H), 3.61 and 3.75 (dABq, 2 H), 6.9–7.0 (m, 2 H), 7.06 (d, 1 H), 7.3–7.4 (m, 1 H).

Step E: N-(1-(R)-3-(S)-hydroxymethyl-4-(S)-phenylcyclopent-1-yl)-D-cyclohexylglycine t-butyl Ester To a solution of (+)-trans-3-hydroxymethyl-4-(3-fluorophenyl)cyclopentanone from Step D (500 mg, 2.4 mmol) in 1,2-dichloroethane (25 mL) was added D-cyclohexylglycine t-butyl ester (0.61 g, 2.88 mmol) and acetic acid (0.15 mL, 2.64 mmol). After 15 min, sodium triacetoxyborohydride (1.0 g, 4.8 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 30% ethyl acetate in hexanes to give the product (936 mg) as clean major higher $R_f$ title compound (425 mg) plus a mixture of C-1 isomers (511 mg) as the free amines.

Step F: N-(1-(R)-3-(S)-Formyl-4-(S)-phenylcyclopent-1-yl)-D-cyclohexylglycine t-butyl Ester To a solution of (1-(R)-3-(S)-(hydroxymethyl)-4-(S)-phenylcyclopent-1-yl)-D-cyclohexylglycine (higher $R_f$ from Step E) (162 mg, 0.4 mmol) in methylene chloride (5 mL) was added TPAP (7 mg, 0.020 mmol) and N-methylmorholine (70 mg, 0.60 mmol). The reaction was stirred under nitrogen at rt for 1 h and was then concentrated. The residue was purified by FC (15% ethyl acetate in hexanes) to give the title product (115 mg) after vacuum drying.

Step G: N-(1-(R)-3-(S)-((4-(3-Benzyl-1-ethyl-1H-pyrazol-5-yl)piperidin-1-yl)methyl)-4-(S)-(3-fluorophenyl) cyclopent-1-yl)-D-cyclohexylglycine t-butyl Ester To a solution of N-(1-(R)-3-(S)-formyl-4-(S)-phenylcyclopent-1-yl)-D-cyclohexylglycine t-butyl ester (13 mg, 0.032 mmol) from Step F in 1,2-dichloroethane (2 mL) was added 4-(3-benzyl-1-ethyl-1H-pyrazol-5-yl) piperidine hydrochloride (from Procedure 1) (15 mg, 0.035 mmol) and DIPEA (0.012 mL, 0.069 mmol). After 15 min, sodium triacetoxyborohydride (14 mg, 0.064 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product as the free amine.

Step H: N-(1-(R)-3-(S)-((4-(3-Benzyl-1-ethyl-1H-pyrazol-5-yl)piperidin-1-yl)methyl)-4-(S)-(3-fluorophenyl) cyclopent-1-yl)-D-cyclohexylglycine Tri-hydrochloride salt The N-(1-(R)-3-(S)-((4-(3-benzyl-1-ethyl-1H-pyrazol-5-yl)piperidin-1-yl)methyl)-4-(S)-(3-fluorophenyl)cyclopent-1-yl)-D-cyclohexylglycine t-butyl ester from Step F was taken up in TFA (2 mL) and aged at rt for 16 h. The volatiles were evaporated under a stream of nitrogen. The residue was taken up in methanol and adsorbed onto a 500 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, addition of excess 1M hydrogen chloride in ether and evaporation to dryness.

HPLC/MS (ESI): m/z 601 (M+1).

EXAMPLE 36

N-(1-(R)-3-(S)-((4-(3-(4-Cyano-3-flurophenyl)prop-1-yl)piperidin-1-yl)methyl)-4-(S)-( 3-fluorophenyl) cyclopent-1-yl)-D-cyclohexylglycine di-hydrochloride salt Using essentially the same procedure as in Example 35, Steps G and H, but substituting 4-(3-(4-cyano-3-flurophenyl)prop-1-yl)piperidine (from Procedure 8) in Step G, the title compound was prepared.

HPLC/MS (ESI): m/z 578 (M+1).

EXAMPLE 37

N-(1-(R)-3-(S)-((4-(5-Benzylpyrazol-3-yl)piperidin-1-yl)methyl)-4-(S)-(3-fluorophenyl)cyclopent-1-yl)-D-cyclohex-ylglycine di-hydrochloride salt Using essentially the same procedure as in Example 35, Steps G and H, but substituting 4-(5-benzylpyrazol-3-yl) piperidine (from Procedure 2) in Step G, the title compound can be prepared.

EXAMPLE 38

N-(1-(R)-3-(S)-((4-(3-Benzyl-1-propyl-1H-pyrazol-5-yl)piperidin-1-yl)methyl)-4-(S)-(3-fluorophenyl) cyclopent-1-yl)-D-cyclohexylglycine Tri-hydrochloride salt Using essentially the same procedure as in Example 35, Steps G and H, but substituting 4-(5-benzyl-2-propylpyrazol-3-yl)piperidine (from Procedure 15) in Step G, the title compound can be prepared.

EXAMPLE 39

Using essentially the same procedure as in Example 35, Steps E to G, but substituting the appropriate L- and/or D-aminoacid t-butyl ester in Step E, the following compounds A–D can be prepared.

EXAMPLE 39A

N-(1-(R)-3-(S)-((4-(3-Benzyl-1-ethyl-1H-pyrazol-5-yl)piperidin-1-yl)methyl)-4-(S)-(3-fluorophenyl)cyclopent-1-yl)-D-cyclobutylalanine Tri-hydrochloride salt

EXAMPLE 39B

N-(1-(R)-3-(S)-((4-(3-Benzyl-1-ethyl-1H-pyrazol-5-yl)piperidin-1-yl)methyl)-4-(S)-(3-fluorophenyl)cyclopent-1-yl)-D-cyclopropylalanine Tri-hydrochloride salt

EXAMPLE 39C

N-(1-(R)-3-(S)-((4-(3-Benzyl-1-ethyl-1H-pyrazol-5-yl)piperidin-1-yl)methyl)-4-(S)-(3-fluorophenyl)cyclopent-1-yl)-D-leucine Tri-hydrochloride salt

EXAMPLE 39D

N-(1-(R)-3-(S)-((4-(3-Benzyl-1-ethyl-1H-pyrazol-5-yl)piperidin-1-yl)methyl)-4-(S)-(3-fluorophenyl)cyclopent-1-yl)-D-valine Tri-hydrochloride salt

EXAMPLE 40

N-(2-Methylprop-1-yl)-N-(1-(SR)-3-(SR)-((4-(3-(phenyl)prop-1-yl)piperidin-1-yl)methyl)-4-(SR)-phenylcyclopent-1-yl)glycine di-hydrochloride salt Step A: 1-(SR)-Benzyloxycarbonylamino-3-(SR)-hydroxymethyl-4-(SR)-phenylcyclopentane (Higher $R_f$ isomer) and 1-(RS)-benzyloxycarbonylamino-3-(SR)-hydroxymethyl-4-(SR)-phenylcyclopentane (Lower $R_f$ isomer)

Using essentially the same procedure as in Example 1, Step E, 1-(SR and RS)-benzylamino-3-(SR)-hydroxymethyl-4-(SR)-phenylcyclopentane (13 g) was converted to the title compounds. Prep LC (30% ethyl acetate in hexanes) afforded pure minor, higher $R_f$ product (4.0 g), then a mixture and finally pure major, lower $R_f$ product (6.6 g).

Step B: 1-(SR)-Benzyloxycarbonylamino-3-(SR)-t-butyldimethylsilyloxymethyl-4-(SR)-phenylcyclopentane (Higher $R_f$ isomer) and 1-(RS)-benzyloxycarbonylamino-3-(SR)-t-butyldimethylsilyloxymethyl-4-(SR)-phenylcyclopentane (Lower $R_f$ isomer)

To a solution of 1-(SR)-benzyloxycarbonylamino-3-(SR)-hydroxymethyl-4-(SR)-phenylcyclopentane (Higher $R_f$ isomer from Step A) (3.96 g, 12.2 mmol) in methylene chloride (100 mL) was added DIPEA (6.4 mL, 37 mmol) and t-butyldimethylsilyl chloride (2.0 g, 13.4 mmol). The reaction was stirred at rt for 16 h when a second portion of t-butyldimethylsilyl chloride (1.0 g, 6.7 mmol) was added. After a further 24 h, the reaction was diluted with methylene chloride and poured into dilute hydrochloric acid. The layers were separated and the organic layer was washed with brine containing sodium bicarbonate, dried over sodium sulfate and concentrated. The residue was purified by FC (5 to 40% ethyl acetate in hexanes) to give the title compound (4.7 g). After eluting with 75% ethyl acetate in hexanes, recovered starting material was obtained.

In a similar way, 1-(RS)-benzyloxycarbonylamino-3-(SR)-hydroxymethyl-4-(SR)-phenylcyclopentane (lower $R_f$ isomer from Step A) (6.6 g, 20.3 mmol) was converted to the lower $R_f$ title compound (7.7 g) and recovered starting material.

Step C: 1-(SR)-N-(2-Methylprop-2-en-1-yl)-N-(benzyloxycarbonyl)amino-3-(SR)-t-butyldimethylsilyloxymethyl-4-(SR)-phenylcyclopentane (Higher $R_f$ isomer) and 1-(RS)-N-(2-methylprop-2-en-1-yl)-N-(benzyloxycarbonyl)amino-3-(SR)-t-butyldimethylsilyloxymethyl-4-(SR)-phenylcyclopentane (Lower $R_f$ isomer)

To a solution of 1-(SR)-benzyloxycarbonylamino-3-(SR)-t-butyldimethylsilyloxymethyl-4-(SR)-phenylcyclopentane (Higher $R_f$ isomer from Steps A–B) (500 mg, 1.14 mmol) and 1-bromo-2-methylprop-2-ene (0.175 mL, 1.7 mmol) in DMF (10 mL) was added at rt in portions over 10 min 60% sodium hydride in mineral oil (68 mg, 1.7 mmol). After 3 h, the reaction was diluted with ether and quenched into water. The layers were separated and the organic layer was washed with brine containing sodium bicarbonate, dried over sodium sulfate and concentrated. The residue was purified by FC (5 to 10% ethyl acetate in hexanes) to give the title compound (0.32 g).

$^1$H NMR (CDCl$_3$): δ –0.06 (s, 3 H), –0.05 (s, 3 H), 0.84 (s, 9 H), 1.54 (s, 3 H), 1.65–1.8 (m, 3 H), 1.95–2.2 (m, 3 H), 2.8–3.0 (M, 1 H), 3.3–3.45 (m, 1 H), 3.45–3.55 (m, 1H), 3.7–3.9 (m, 2 H), 4.80 (d, 2 H), 5.14 (br s, 2 H), 7.15 (m, 2 H), 7.25 (m, 5H 7.34 (m, 3 H).

In a similar way, 1-(RS)-benzyloxycarbonylamino-3-(SR)-t-butyldimethylsilyloxymethyl-4-(SR)-phenylcyclopentane (lower $R_f$ isomer from Step A–B) (1.0 g, 2.3 mmol) was converted to the lower $R_f$ title compound (0.55 g).

Step D: 1-(SR)-N-(2-Methylprop-1-yl)amino-3-(SR)-t-butyldimethylsilyloxymethyl-4-(SR)-phenylcyclopentane (Higher $R_f$ isomer) and 1-(RS)-N-(2-methylprop-1-yl)amino-3-(SR)-t-butyldimethylsilyloxymethyl-4-(SR)-phenylcyclopentane (Lower $R_f$ isomer)

To a solution of 1-(SR)-N-(2-methylprop-2-en-1-yl)-N-(benzyloxycarbonyl)amino-3-(SR)-t-butyldimethylsilyloxymethyl-4-(SR)-phenylcyclopentane (Higher $R_f$ isomer from Steps A–C) (320 mg, 0.65 mmol) in methanol (5 mL) was added 10% Pd/C (50 mg) and a drop of DIPEA. The mixture was hydrogenated at 40 psi for 2 h. The reaction was filtered and the filtrate was concentrated. The residue of title compound was used directly in Step E.

$^1$H NMR (CDCl$_3$): δ –0.05 (s, 3 H), –0.04 (s, 3 H), 0.84 (s, 9 H), 0.89 (s, 3 H), 0.91 (s, 3 H), 1.35 (ddd, 1 H), 1.73 (hept, 1 H), 1.93 (m, 2 H), 2.15 (m, 1 H), 2.25 (m, 1 H), 2.38 (d, 2 H), 2.96 (q, 1 H), 3.28 (m, 1 H), 3.49 (dABq, 2 H), 7.15 (m, 3 H), 7.24 (m, 2 H).

In a similar way, 1-(RS)-N-(2-methylprop-2-en-1-yl)-N-(benzyloxycarbonyl)amino-3-(SR)-t-butyldimethylsilyloxymethyl-4-(SR)-phenylcyclopentane (lower $R_f$ isomer from Step A–C) (0.55 g, 1.1 mmol) was converted to the lower $R_f$ title compound (0.475 g).

Step E: N-(2-Methylprop-1-yl)-N-(1-(SR)-3-(SR)-t-butyldimethylsilyloxymethyl-4-(SR)-phenylcyclopent-1-yl)-glycine (Higher $R_f$ Isomer) and N-(2-methylprop-1-yl)-N-(1-(RS)-3-(SR)-t-butyldimethylsilyloxymethyl-4-(SR)-phenylcyclopent-1-yl)-glycine (Lower $R_f$ Isomer)

A solution of 1-(SR)-N-(2-methylprop-1-yl)amino-3-(SR)-t-butyldimethylsilyloxymethyl-4-(SR)-phenylcyclopentane (Higher $R_f$ isomer from Steps A–D)

(0.65 mmol), t-butyl bromoacetate (125 mg, 0.65 mmol) and DIPEA (1.1 mL, 6.5 mmol) in acetonitrile (15 mL) was stirred at rt for 16 h. The reaction was diluted with aqueous sodium carbonate and extracted three times with ethyl acetate. The organic layers were washed with brine containing sodium bicarbonate, dried over sodium sulfate, combined and concentrated. The residue was purified by FC (50% ethyl acetate in hexanes) to give impure product and recovered starting material (135 mg). The impure product fractions were repurified by FC (5% ethyl acetate in hexanes) to afford the title higher $R_f$ compound (0.13 g). The recovered starting material was recycled using the same procedure but doing the reaction at 50° C. for 16 h to afford additional title compound (140 mg).

$^1$H NMR (CDCl$_3$): δ −0.05 (s, 3 H), −0.04 (s, 3 H), 0.84 (s, 9 H), 0.86 (d, 3 H), 0.88 (d, 3 H), 1.44 (s, 9 H), 1.70 (hept, 1 H), 1.95 (m, 1 H), 2.00 (m, 1 H), 2.08 (m, 2 H), 2.38 (dABq, 2 H), 2.90 (m, 1 H), 3.26 (ABq, 2 H), 3.49 (dABq, 2 H), 3.5–3.6 (m, 1 H), 7.15 (m, 3 H), 7.24 (m, 2 H).

In a similar way, but doing the reaction at 50° C. for 20 h, 1-(RS)-N-(2-methylprop-1-yl)amino-3-(SR)-t-butyldimethylsilyloxymethyl-4-(SR)-phenylcyclopentane (lower $R_f$ isomer from Steps A–D) (0.375 mg) was converted to the lower $R_f$ title compound (0.435 g).

Step F: N-(2-Methylprop-1-yl)-N-(1-(SR)-3-(SR)-hydroxymethyl-4-(SR)-phenylcyclopent-1-yl)-glycine (Higher $R_f$ isomer) and N-(2-methylprop-1-yl)-N-(1-(RS)-3-(SR)-hydroxymethyl-4-(SR)-phenylcyclopent-1-yl)-glycine (Lower $R_f$ isomer)

A solution of N-(2-methylprop-1-yl)-N-(1-(SR)-3-(SR)-t-butyldimethylsilyloxymethyl-4-(SR)-phenylcyclopent-1-yl)-glycine (Higher $R_f$ isomer from Steps A–E) (270 mg, 0.57 mmol) and 1M TBAF in THF (0.85 mL, 0.85 mmol) in THF (5 mL) was stirred at rt for 1 h. The reaction was concentrated and the residue was purified by FC (20% ethyl acetate in hexanes) to give the title higher $R_f$ product (140 mg).

In a similar way, N-(2-methylprop-1-yl)-N-(1-(RS)-3-(SR)-t-butyldimethylsilyloxymethyl-4-(SR)-phenylcyclopent-1-yl)-glycine (Lower $R_f$ isomer from Steps A–E) (0.435 mg) was converted to the lower $R_f$ title compound (0.300 mg).

Step G: N-(2-Methylprop-1-yl)-N-(1-(SR)-3-(SR)-formyl-4-(SR)-phenylcyclopent-1-yl)-glycine-(Higher $R_f$ isomer) and N-(2-methylprop-1-yl)-N-(1-(RS)-3-(SR)-formyl-4-(SR)-phenylcyclopent-1-yl)-glycine (Lower $R_f$ Isomer)

Using essentially the same procedure as in Example 1, Step C, N-(2-methylprop-1-yl)-N-(1-(SR)-3-(SR)-hydroxymethyl-4-(SR)-phenylcyclopent-1-yl)-glycine (Higher $R_f$ isomer from Steps A–F) (140 mg, 0.39 mmol) was oxidized to the title compound (100 mg).

In a similar way, N-(2-methylprop-1-yl)-N-(1-(RS)-3-(SR)-hydroxymethyl-4-(SR)-phenylcyclopent-1-yl)-glycine (Lower $R_f$ isomer from Steps A–F) (0.150 mg) was converted to the lower $R_f$ title compound (0.140 mg).

Step H: N-(2-Methylprop-1-yl)-N-(1-(SR)-3-(SR)-((4-(3-(phenyl)prop-1-yl)piperidin-1-yl)methyl)-4-(SR)-phenylcyclopent-1-yl)glycine t-butyl Ester (Higher $R_f$ Isomer)

To a solution of N-(2-methylprop-1-yl)-N-(1-(SR)-3-(SR)-formyl-4-(SR)-phenylcyclopent-1-yl)-glycine (Higher $R_f$ isomer from Steps A–G) (25 mg, 0.070 mmol) in 1,2-dichloroethane (2 mL) was added 4-(3-(phenyl)prop-1-yl)piperidine (22 mg, 0.11 mmol) and acetic acid (0.006 mL, 0.11 mmol). After 15 min, sodium triacetoxyborohydride (45 mg, 0.21 mmol) was added and the reaction was stirred at rt for 4 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product (38 mg) as the free amine.

Step I: N-(2-Methylprop-1-yl)-N-(1-(SR)-3-(SR)-((4-(3-(phenyl)prop-1-yl)piperidin-1-yl)methyl)-4-(SR)-phenylcyclopent-1-yl)glycine di-TFA salt A solution of N-(2-methylprop-1-yl)-N-(1-(SR)-3-(SR)-((4-(3-(phenyl)prop-1-yl)piperidin-1-yl)methyl)-4-(SR)-phenylcyclopent-1-yl)glycine t-butyl ester (higher $R_f$ isomer from Steps A–H) (33 mg) in TFA (4 mL) was heated at 50° C. for 4 h and then the volatiles were removed under a stream of nitrogen. An additional 2×3 mL of methylene chloride were evaporated to dryness to afford the title compound as the di-TFA salt (50 mg).

HPLC/MS (ESI): m/z 491 (M+1).

EXAMPLE 41

N-(2-Methylprop-1-yl)-N-(1-(SR)-3-(SR)-((4-(3-(4-cyanophenyl)prop-1-yl)piperidin-1-yl)methyl)-4-(SR)-phenylcyclopent-1-yl)glycine di-TFA salt Using essentially the same procedure as in Example 40, Steps H and I, but substituting 4-(3-(4-cyanophenyl)prop-1-yl)piperidine (from Procedure 7) in Step H, the title compound was prepared.

HPLC/MS (ESI): m/z 516 (M+1).

EXAMPLE 42

N-(2-Methylprop-1-yl)-N-(1-(SR)-3-(SR)-((4-(3-(4-fluorophenyl)prop-1-yl)piperidin-1-yl)methyl)-4-(SR)-phenylcyclopent-1-yl)glycine di-TFA salt Using essentially the same procedure as in Example 40, Steps H and I, but substituting 4-(3-(4-fluorophenyl)prop-1-yl)piperidine (from Procedure 9) in Step H, the title compound can be prepared.

EXAMPLE 43

N-(2-Methylprop-1-yl)-N-(1-(RS)-3-(SR)-((4-(3-(4-cyanophenyl)prop-1-yl)piperidin-1-yl)methyl)-4-(SR)-phenylcyclopent-1-yl)glycine di-TFA salt Using essentially the same procedure as in Example 40, Steps H and I, but substituting the lower $R_f$ aldehyde from Steps A–G and 4-(3-(4-cyanophenyl)prop-1-yl)piperidine (from Procedure 7) in Step H, the title compound was prepared.

HPLC/MS (ESI): m/z 594 (M+1).

EXAMPLE 44

N-(2-Methylprop-1-yl)-N-(1-(RS)-3-(SR)-((4-(3-(4-fluorophenyl)prop-1-yl)piperidin-1-yl)methyl)-4-(SR)-phenylcyclopent-1-yl)glycine di-TFA salt Using essentially the same procedure as in Example 40, Steps H and I, but substituting the lower $R_f$ aldehyde from Steps A–G and 4-(3-(4-fluorophenyl)prop-1-yl)piperidine (from Procedure 9) in Step H, the title compound can be prepared.

EXAMPLE 45

N-(2-Methylprop-1-yl)-N-(1-(RS)-3-(SR)-((4-(3-benzyl-1-ethyl-1H-pyrazol-5-yl)piperidin-1-yl)methyl)-4-(SR)-phenylcyclopent-1-yl)-glycine di-TFA salt Using essentially the same procedure as in Example 40, Steps H and I, but substituting the lower $R_f$ aldehyde from Steps A–G and 4-(3-benzyl-1-ethyl-1H-pyrazol-5-yl) piperidine (from Procedure 1) in Step H, the title compound can be prepared.

EXAMPLE 46

N-(Cyclobutylmethyl)-N-(1-(R)-3-(S)-((4-(3-(4-fluorophenyl)prop-1-yl)piperidin-1-yl)methyl)-4-(S)-phenylcyclopent-1-yl)glycine di-HCl salt Step A: N-(1-(R)-3-(S)-(Hydroxymethyl)-4-(S)-phenylcyclopent-1-yl)glycine and N-(1-(S)-3-(S)-Hydroxymethyl)-4-(S)-phenylcyclopent-1-yl)glycine To a solution of (+)-trans-3-hydroxymethyl-4-phenylcyclopentan-1-one from Example 8, Step F, Method B (180 mg, 0.96 mmol), glycine t-butyl ester hydrochloride (241 mg, 1.44 mmol) and DIPEA (0.25 mL, 1.44 mmol) in 1,2-dichloroethane (6 mL) was added sodium triacetoxyborohydride (284 mg, 1.92 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by FC (50–100% ethyl acetate in hexanes) to give the title product (196 mg) as a 2:1 mixture of C-1 free amine isomers.

$^1$H NMR (CDCl$_3$): δ1.48 (s, 9H), 1.6–1.7 (m, 1.3H), 1.8–2.0 (2 m, 1.7H), 2.23 (ddd. 0.3H), 2.3–2.45 (m, 2H), 2.68 (ddd, 0.7H), 3.2–3.4 (2 m and 2 s, 3H), 3.45–3.65 (dABq (major) and d (minor), 2H), 3.96 (d, 1H), 7.2–7.35 (m, 5H).

Step B: N-(Cyclobutylmethyl)-N-(1-(R)-3-(S)-(hydroxymethyl)-4-(S)-phenylcyclopent-1-yl)glycine (Major, Higher R$_f$) and N-(cyclobutylmethyl)-N-(1-(S)-3-(S)-(hydroxymethyl)-4-(S)-phenylcyclopent-1-yl) glycine (Minor, Lower R$_f$)

To a solution of N-(1-(R and S)-3-(S)-(hydroxymethyl)-4-(S)-phenylcyclopent-1-yl)glycine from Step A (180 mg, 0.59 mmol), cyclobutylaldehyde (27 mg, 0.32 mmol) and DIPEA (0.25 mL, 1.5 mmol) in 1,2-dichloroethane (6 mL) was added sodium triacetoxyborohydride (175 mg, 1.2 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by Prep TLC (30% ethyl acetate in hexanes) to give the title 1-(R) product (45 mg pure, 31 mg mixture with the 1-(S) diastereomer) as the higher R$_f$ C-1 isomer. (Major, higher isomer): $^1$H NMR (CDCl$_3$): δ1.49 (s, 9H), 1.6–1.85 (m, 4H), 1.85-1.95 (m, 2H), 2.0–2.15 (m, 2H), 2.24 (p, 1H), 2.2.33 (m, 1H), 2.53 (hept, 1H), 2.7-2.8 (m, 3H), 3.31 (s, 2H), 3.4–3.5 (m, 1H), 3.48 and 3.61 (dABq, 2H), 7.24 (tt, 1H), 7.25–7.35 (m, 4H).

Repurification of the mixture on Prep TLC afforded a sample of pure 1-(S) minor, lower R$_f$ isomer.

(Minor, lower isomer): $^1$H NMR (CDCl$_3$): δ1.47 (s, 9H), 1.6–1.75 (m, 3H), 1.75-1.85 (m, 1H), 1.9–2.0 (m, 1H), 2.05–2.25 (m, 4H), 2.3 (m, 1H), 2.54 (hept, 1H), 2.78 (ddd, 2H), 3.09 (q, 1H), 3.35 (ABq, 2H), 3.55 (m, 1H), 3.61 (dABq, 2H), 7.24 (tt, 1H), 7.25–7.35 (m, 4H).

Step C: N-(Cyclobutylmethyl)-N-(1-(R)-3-(S)-(formyl)-4-(S)-phenylcyclopent-1-yl)glycine Using essentially the same procedure as in Example 1, Step F, N-(cyclobutylmethyl)-N-(1-(R)-3-(S)-(hydroxymethyl)-4-(S)-phenylcyclopent-1-yl)glycine (higher R$_f$ isomer from Steps B) (45 mg, 0.12 mmol) was oxidized to the title compound (56 mg crude without purification).

Step D: N-(Cyclobutylmethyl)-N-(1-(R)-3-(S)-((4-(3-(4-fluorophenyl)prop-1-yl)piperidin-1-yl)methyl)-4-(S)-phenylcyclopent-1-yl)glycine t-butyl Ester To a solution of N-(cyclobutylmethyl)-N-(1-(R)-3-(S)-(formyl)-4-(S)-phenylcyclopent-1-yl)glycine (higher R$_f$ isomer from Steps B-C) (22 mg, 0.059 mmol) in 1,2-dichloroethane (1 mL) was added 4-(3-(4-fluorophenyl) prop-1-yl)piperidine hydrochloride (from Procedure 9) (23 mg, 0.089 mmol) and DIPEA (0.016 mL, 0.089 mmol). After 15 min, sodium triacetoxyborohydride (18 mg, 0.12 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 30% ethyl acetate in hexanes to give the title product (26 mg) as the free amine.

Step E: N-(Cyclobutylmethyl)-N-(1-(R)-3-(S)-((4-(3-(4-fluorophenyl)prop-1-yl)piperidin-1-yl)methyl)-4-(S)-phenylcyclopent-1-yl)glycine di-HCl salt A solution of N-(cyclobutylmethyl)-N-(1-(R)-3-(S)-((4-(3-(4-fluorophenyl)prop-1-yl)piperidin-1-yl)methyl)-4-(S)-phenylcyclopent-1-yl)glycine t-butyl ester (higher R$_f$ isomer from Steps B-D) in TFA (4 ML) was stirred at rt for 16 h and then the volatiles were removed under a stream of nitrogen. An additional 2×3 mL of toluene were evaporated and the residue was purified by Prep TLC (95:5:1:1 methylene chloride:methanol:water:NH$_4$OH). The free amine (5 mg) was taken up in methylene chloride and excess 1M hydrogen chloride in ether was added. The mixture was evaporated to dryness to afford the title compound as the di-HCl salt (7.3 HPLC/MS (ESI): m/z 521 (M+1).

EXAMPLE 47

N-(Cyclopropylmethyl)-N-(1-(R)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting cyclopropylaldehyde in Step B, the title compound was prepared.
HPLC/MS (ESI): m/z 507 (M+1).

EXAMPLE 48

N-(Cyclohexyl)-N-(1-(R)-3-(S)-((4-(3-(4-fluorophenyl)prop-1-yl)piperidin-1-yl)methyl)4-(S)-phenylcyclopent-1-yl)glycine di-HCl salt Using essentially the same procedure as in Example 46, Steps B–E, but substituting cyclohexanone in Step B, the title compound was prepared.
HPLC/MS (ESI): m/z 535 (M+1).

EXAMPLE 49

N-(Cyclopentylmethyl)-N-(1-(R)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting cyclopentylaldehyde in Step B, the title compound was prepared.
HPLC/MS (ESI): m/z 535 (M+1).

EXAMPLE 50

N-(Cyclobutylmethyl)-N-(1-(S)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting the lower R$_f$ product from Step B in Steps C–E, the title compound could be prepared.
HPLC/MS (ESI): m/z 521 (M+1).

EXAMPLE 51

N-(Cyclohexyl)-N-(1-(S)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting cyclohexanone in Step B and using the lower $R_f$ product from Step B in Steps C–E, the title compound was prepared.

HPLC/MS (ESI): m/z 535 (M+1).

EXAMPLE 52

N-(Cyclopropylmethyl)-N-(-(S)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting cyclopropyl aldehyde in Step B and using the lower $R_f$ product from Step B in Steps C–E, the title compound was prepared.

HPLC/MS (ESI): m/z 507 (M+1).

EXAMPLE 53

N-(Cyclopentylmethyl)-N-(1-(S)-3-(S)-((4-(3-(4-fluorophenyl)prop-1-yl)piperidin-1-yl)methyl)-4-(S)-phenylcyclopent-1-yl)glycine di-HCl salt Using essentially the same procedure as in Example 46, Steps B–E, but substituting cyclopentyl aldehyde in Step B and using the lower $R_f$ product from Step B in Steps C–E, the title compound was prepared.

HPLC/MS (ESI): m/z 507 (M+1).

EXAMPLE 54

N-(Cyclohexyl)-N-(1-(S)-3-(S)-((4-(3-(3,4-difluorophenyl)prop-1-yl)piperidin-1-yl)methyl)-4-(S)-phenylcyclopent-1-yl)glycine di-HCl salt Step A: N-(1-(S)-3-(S)-(t-Butyldimethylsilyloxymethyl)-4-(S)-phenylcyclopent-1-yl)glycine (major, higher $R_f$) and N-(1-(R)-3-(S)-(t-butyldimethylsilyloxymethyl)-4-(S)-phenylcyclopent-1-yl)glycine (minor, lower $R_f$)

To a solution of (+)-trans-3-t-butyldimethylsilyloxymethyl-4-phenylcyclopentan-1-one from Example 16, Step A, Method B (332 mg, 1.1 mmol), glycine t-butyl ester hydrochloride (275 mg, 1.64 mmol) and DIPEA (0.285 mL, 1.64 mmol) in 1,2-dichloroethane (13 mL) was added sodium triacetoxyborohydride (323 mg, 2.18 mmol). The reaction was stirred at rt for 16 h and was then diluted with aq. sodium bicarbonate and extracted three times with methylene chloride. The organic layers were each washed with brine, dried over sodium sulfate, combined and concentrated in vacuo. The residue was purified by FC (10% ethyl acetate in hexanes) to give the title product (437 mg) as a 2.6:1 mixture of C-1 free amine isomers. (Note: The product C-1 isomer ratio here with the silyl ether is opposite to that of example 46 with the free alcohol. Also, note that the relative retention on TLC of the NH intermediates are opposite that of the N-alkylation products of Step B.) Careful FC (5% ethyl acetate in hexanes) of an initial sample afforded the separated isomers.

(Major, higher isomer): $^1$H NMR (CDCl$_3$): δ–0.05 (s, 3H), –0.04 (s, 3H), 0.87 (s, 9 H), 1.42 (m, 1H), 1.50 (s, 9H), 1.98 (dd, 2H), 2.17 (m, 1H), 2.27 (dt, 1H), 3.00 (q, 1H), 3.3–3.4 (m and s, 3H), 3.45 and 3.60 (dABq, 2H), 7.15–7.25 (m, 3H), 7.25–7.35(m, 2H). (Minor, lower isomer): $^1$H NMR (CDCl$_3$): δ–0.05 (s, 3H), –0.04 (s, 3H), 0.87 (s, 9 H), 1.50 (s, 9H), 1.62 (dt, 1H), 1.75 (ddd, 1H), 1.95 (dt, 1H), 2.25–2.4 (2 m, 2H), 2.85 (m, 1H), 3.22 (m, 1H), 3.34 (s, 2H), 3.42 and 3.54 (dABq, 2H), 7.24 (tt, 1H), 7.25–7.35 (m, 4H).

Step B: N-(Cyclohexyl)-N-(1-(S)-3-(S)-(hydroxymethyl)-4-(S)-phenylcyclopent-1-yl)glycine (lower, major $R_f$) and N-(cyclohexyl)-N-(1-(R)-3-(S)-(hydroxymethyl)-4-(S)-phenylcyclopent-1-yl)glycine (Higher, Minor $R_f$)

To a solution of N-(1-(R and S)-3-(S)-(t-butyldimethylsilyloxymethyl)-4-(S)-phenylcyclopent-1-yl) glycine from Step A (437 mg, 1.04 mmol), cyclohexanone (0.650 mL, 6.24 mmol) and DIPEA (0.272 mL, 1.56 mmol) in 1,2-dichloroethane (10 mL) was added sodium triacetoxyborohydride (693 mg, 0.68 mmol). The reaction was stirred at rt for 16 h when additional cyclohexanone (0.600 mL) and sodium triacetoxyborohydride (300 mg) were added. After a further 48 h, the reaction was complete by HPLC/MS and was diluted with aq. sodium bicarbonate and extracted three times with methylene chloride. The organic layers were each washed with brine, dried over sodium sulfate, combined and concentrated in vacuo. The residue (2 g) was used directly in the following desilylation.

The residue from above was taken up in THF (10 mL) and 1M TBAF in THF (5 mL, 5.0 mmol) was added. The reaction was stirred at rt for 6 h and was then poured into aq. sodium bicarbonate and extracted three times with ethyl acetate. The organic layers were each washed with brine, dried over sodium sulfate, combined and concentrated in vacuo. The residue was purified by FC and Prep TLC (40% ethyl acetate in hexanes) to give the title (R) product (114 mg) as the minor, higher $R_f$ band and the title (S) product (235 mg) as the major, lower $R_f$ band.

(Major, higher isomer): $^1$H NMR (CDCl$_3$): δ1.1–1.4 (m, 5H), 1.48 (s, 9H), 1.5–1.7 (m, 2H), 1.7–2.0 (m, 5H), 2.17 (m, 1H), 2.31 (m, 1H), 2.65–2.8 (m, 2H), 3.24 (Abq, 2H), 3.45–3.55 (m, 2H), 3.6–3.7 (m, 2H), 7.24 (tt, 1H), 7.25–7.35 (m, 4H). (Minor, lower isomer): $^1$H NMR (CDCl$_3$): δ1.1–1.4 (m, 5H), 1.48 (s, 9H), 1.6–1.7 (m, 2H), 1.7–2.0 (m, 5H), 2.17 (m, 2H), 2.25 (m, 1H), 2.75 (m, 1H), 3.10 (q, 1H), 3.25 (Abq, 2H), 3.55–3.65 (m and ABq, 3H), 7.24 (tt, 1H), 7.25–7.35 (m, 4H).

Step C: N-(Cyclohexyl)-N-(1-(S)-3-(S)-(formyl)-4-(S)-phenylcyclopent-1-yl)glycine Using essentially the same procedure as in Example 1, Step C, N-(cyclohexyl)-N-(1-(S)-3-(S)-(hydroxymethyl)-4-(S)-phenylcyclopent-1-yl)glycine (lower $R_f$ isomer from Step B) (75 mg, 0.19 mmol) was oxidized to the title compound (84 mg crude without purification).

Step D: N-(Cyclohexyl)-N-(1-(R)-3-(S)-((4-(3-(3,4-difluorophenyl)prop-1-yl)amino)piperidin-1-yl)methyl)-4-(S)-phenylcyclopent-1-yl)glycine t-butyl Ester To a solution of N-(cyclohexyl)-N-(1-(S)-3-(S)-(formyl)-4-(S)-phenylcyclopent-1-yl)glycine (lower $R_f$ isomer from Steps B-C) (19 mg, 0.050 mmol) in 1,2-dichloroethane (1 mL) was added 4-(3-(3,4-difluorophenyl)prop-1-yl) piperidine hydrochloride (from Procedure 14) (15 mg, 0.054 mmol) and DIPEA (0.013 mL, 0.074 mmol). After 15 min, sodium triacetoxyborohydride (15 mg, 0.10 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 80% ethyl acetate in hexanes to give the title product (20 mg) as the free amine.

Step E: N-(Cyclohexyl)-N-(1-(R)-3-(S)-((4-(3-(3,4-difluorophenyl)prop-1-yl)piperidin-1-yl)methyl)-4-(S)-phenylcyclopent-1-yl)glycine di-HCl salt A solution of N-(cyclohexyl)-N-(1-(R)-3-(S)-((4-(3-(3,4-difluorophenyl)prop-1-yl)piperidin-1-yl)methyl)-4-(S)-phenylcyclopent-1-yl)glycine t-butyl ester (lower $R_f$ isomer from Steps B-D) (20 mg) in TFA (1 mL) was stirred at rt for 16 h and then the volatiles were removed under a stream of nitrogen. The residue was taken up in methanol and adsorbed onto a 500 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, addition of excess 1M hydrogen chloride in ether and evaporation to dryness.

HPLC/MS (ESI): m/z 553 (M+1).

EXAMPLE 55

N-(Cyclohexyl)-N-(1-(S)-3-(S)-((4-(3-(4-cyanophenyl)prop-1-yl)piperidin-1-yl)methyl)-4-(S)-phenylcyclopent-1-yl)glycine di-HCl salt Using essentially the same procedure as in Example 54, Steps D and E, but substituting 4-(3-(4-cyanophenyl)prop-1-yl)piperidine (from Procedure 7) in Step D and using the lower $R_f$ product from Step B in Steps C–E, the title compound was prepared.

HPLC/MS (ESI): m/z 542 (M+1).

EXAMPLE 56

N-(Cyclohexyl)-N-(1-(S)-3-(S)-((4-(3-benzyl-1-ethyl-1H-pyrazol-5-yl)piperidin-1-yl)methyl)-4-(S)-phenylcyclopent-1-yl)glycine di-HCl salt Using essentially the same procedure as in Example 54, Steps D and E, but substituting 4-(3-benzyl-1-ethyl-1H-pyrazol-5-yl)piperidine (from Procedure 1) in Step D and using the lower $R_f$ product from Step B in Steps C–E, the title compound was prepared.

HPLC/MS (ESI): m/z 583 (M+1).

EXAMPLE 57

N-(Cyclohexyl)-N-(1-(S)-3-(S)-((4-(N-propyl-N-(pyrrimidin-2-yl)amino)piperidin-1-yl)methyl)-4-(S)-phenylcyclopent-1-yl)glycine di-HCl salt Using essentially the same procedure as in Example 54, Steps D and E, but substituting 4-(N-propyl-N-(pyrrimidin-2-yl)amino)piperidine (from Procedure 13) in Step D and using the lower $R_f$ product from Step B in Steps C–E, the title compound was prepared.

HPLC/MS (ESI): m/z 534 (M+1).

EXAMPLE 58

N-(Cyclohexyl)-N-(1-(S)-3-(S)-((4-(3-(quinolin-3-yl)prop-1-yl)piperidin-1-yl)methyl)-4-(S)-phenylcyclopent-1-yl)glycine di-HCl salt Using essentially the same procedure as in Example 54, Steps D and E, but substituting 4-(3-(quinolin-3-yl)prop-1-yl)amino)piperidine (from Procedure 10) in Step D and using the lower $R_f$ product from Step B in Steps C–E, the title compound was prepared.

HPLC/MS (ESI): m/z 568 (M+1).

EXAMPLE 59

N-(Cyclohexyl)-N-(1-(S)-3-(S)-((4-(4-fluorophenyl)piperidin-1-yl)methyl)-4-(S)-phenylcyclopent-1-yl)glycine di-HCl salt Using essentially the same procedure as in Example 54, Steps D and E, but substituting 4-(4-fluorophenyl)piperidine in Step D and using the lower $R_f$ product from Step B in Steps C–E, the title compound was prepared.

HPLC/MS (ESI): m/z 493 (M+1).

EXAMPLE 60

N-(1-(R)-3-(S)-((4-(3-(4-Fluorophenyl)prop-1-yl)piperidin-1-yl)methyl)-4-(S)-phenylcyclopen1-yl)-D-proline di-HCl salt Using essentially the same procedure as in Example 46, but substituting D-proline t-butyl ester in Step A, omitting Step B, and using the higher $R_f$ product from Step A in Steps C–E, the title compound was prepared.

HPLC/MS (ESI): m/z 493 (M+1).

EXAMPLE 61

N-(1-(S)-3-(S)-((4-(3-(4-Fluorophenyl)prop-1-yl)piperidin-1-yl)methyl)-4-(S)-phenylcyclopen 1-yl)-D-proline di-HCl salt Using essentially the same procedure as in Example 46, but substituting D-proline t-butyl ester in Step A, omitting Step B, and using the lower $R_f$ product from Step A in Steps C–E, the title compound was prepared.

HPLC/MS (ESI): m/z 493 (M+1).

EXAMPLE 62

N-(1-(R)-3-(S)-((4-(3-(4-Fluorophenyl)prop-1-yl)piperidin-1-yl)methyl)-4-(S)-phenylcyclopen-1-yl)-1-proline di-HCl salt Using essentially the same procedure as in Example 46, but substituting L-proline t-butyl ester in Step A, omitting Step B, and using the higher $R_f$ product from Step A in Steps C–E, the title compound was prepared.

HPLC/MS (ESI): m/z 493 (M+1).

EXAMPLE 63

N-(1-(S)-3-(S)-((4-(3-(4-Fluorophenyl)prop-1-yl)piperidin-1-yl)methyl)-4-(S)-phenylcyclopen 1-yl)-D-proline di-HCl salt Using essentially the same procedure as in Example 46, but substituting L-proline t-butyl ester in Step A, omitting Step B, and using the lower $R_f$ product from Step A in Steps C–E, the title compound was prepared.

HPLC/MS (ESI): m/z 493 (M+1).

EXAMPLE 64

N-(1-(S)-3-(S)-((4-(3-Benzyl-1-ethyl-1H-pyrazol-5-yl)piperidin-1-yl)methyl)-4-(S)-(3-fluorophenyl)cyclopent-1-yl)-D-proline di-HCl salt Using essentially the same procedure as in Example 54, but substituting (+)-trans-3-hydroxymethyl-4-(3- fluorophenyl)cyclopentan-1-one from example 35, Step D and L-proline t-butyl ester in Step A, omitting Step B, using the lower $R_f$ product from Step A in Steps C–E and substituting 4-(3-benzyl-1-ethyl-1H-pyrazol-5-yl)piperidine in Step F, the title compound was prepared.

HPLC/MS (ESI): m/z 559 (M+1).

EXAMPLE 65

N-Methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine tri-hydrochloride salt Step A: Methyl (+−)-trans-4-methylene-2-(3-fluorophenyl) cyclopentanoate A mixture of methyl trans-3-fluorocinnamate (4–1.25 g, 229 mmol), tetrakis(triphenylphosphine) palladium(0) (18.5 g, 16 mmol), 1,2-bis(diphenylphosphino)ethane (5.5 g, 13.7 mmol) and 2-((trimethylsilyl)methyl)-2-propen-1-yl acetate (42.66 g, 229 mmol) in THF (300 mL) under nitrogen was heated to reflux for 6 h and then stirred at rt for 16 h. The reaction was diluted with hexane and filtered to remove yellow precipitate. The volatiles were then removed in vacuo and the residue was purified by FC (3 to 5% ethyl acetate in hexanes) to afford the title compound (45 g).

$^1$H NMR (CDCl$_3$) δ: 2.52 (m, 1H), 2.68 (m, 1H), 2.8–2.9 (m, 2H), 2.95 (ddd, 1H), 3.45 (ddd, 1H), 3.63 (s, 3H), 4.96 (m, 2H), 6.9–7.0 (m, 2H), 7.03 (d, 1H), 7.2–7.3 (m, 1H).

Step B: (+−)-trans-4-Methylene-2-(3-fluorophenyl) cyclopentanoic Acid

To a solution of methyl (+−)-trans-4-methylene-2-(3-fluoro)phenylcyclopentanoate prepared as in Step A (47 g, 200 mmol) in methanol (500 mL) was added 5N sodium hydroxide (200 mL, 1000 mmol). The reaction was stirred at rt for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

(Note: The title compound can also be prepared in non-racemic form using essentially the same procedures as Example 8, Steps A–D using the chiral oxazolidine intermediate, $[α]_D$=+93 (MeOH, c=1).)

Step C: (+)-trans-1-Hydroxymethyl-4-methylene-2-(3-fluorophenyl)cyclopentane and (−)-trans-1-hydroxymethyl-4-methylene-2-(3-fluorophenyl) cyclopentane A solution of (+−)-trans-4-methylene-2-(3-fluorophenyl) cyclopentanoate (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at rt for 16 h, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (−)-enantiomer, $[α]_D$=−45.5 (MeOH, c=0.9), as the first eluting peak ($R_t$=17.5 min) and the (+)-enantiomer (1.87 g), $[α]_D$=+45.0 (MeOH, c=1.0), as the second peak ($R_t$=22.0 min).

$^1$H NMR (CDCl$_3$) δ: 2.2–2.35 (m, 2H), 2.5 (m, 1H), 2.65–2.85 (m, 2H), 2.9 (m, 1H), 3.51 and 3.68 (dABq, 2H), 4.93 (m, 2H), 6.9–7.0 (m, 2H), 7.06 (d, 1H), 7.3–7.4 (m, 1H).

Step D: (+)-trans-3-Hydroxymethyl-4-(3-fluorophenyl) cyclopentanone

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g), $[α]_D$=+132 (MeOH, c=1.2).

$^1$H NMR (CDCl$_3$) δ: 2.3–2.45 (m, 2H), 2.5 (m, 1H), 2.61 and 2.77 (dABq, 2H), 2.28 (ddd, 1H), 3.61 and 3.75 (dABq, 2H), 6.9–7.0 (m, 2H), 7.06 (d, 1H), 7.3–7.4 (m, 1H).

(Note: The (+)-non-racemic title compound was also prepared by essentially the same reduction of non-racemic acid from Step B.)

Step E: N-(1-(R)-3-(S)-Hydroxymethyl-4-(S)-(3-fluorophenyl)cyclopent-1-yl)-D-valine t-butyl Ester To a solution of (+)-trans-3-hydroxymethyl-4-(3-fluorophenyl)cyclopentanone from Step D (1.0 g, 4.8 mmol) in 1,2-dichloroethane (50 ml) was added D-valine t-butyl ester (0.90 g, 5.2 mmol) and acetic acid (0.330 mL, 5.8 mmol). After 15 min, sodium triacetoxyborohydride (2.0 g, 5.6 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by FC eluting with 30% ethyl acetate in hexanes to give the product (1.62 g) as a mixture of the higher $R_f$ title compound and the C-1 isomer as the free amines.

Step F: N-Methyl-N-(1-(R)-3-(S)-hydroxymethyl-4-(S)-(3-fluorophenyl)cyclopent-1-yl)-D-valine t-butyl Ester To a solution of N-(1-(R)-3-(S)-hydroxymethyl-4-(S)-(3-fluorophenyl)cyclopent-1-yl)-D-valine t-butyl ester from Step E (1.62, 4.44 mmol) and 37 wt % formaldehyde in water (2.1 mL, 27 mmol) in methanol (35 mL) was added 10% Pd/C (200 mg). After 10 min, the mixture was placed under hydrogen and stirred at atmospheric pressure for 60 h. The catalyst was removed by filtration and the filtrate was evaporated. The residue was purified by FC eluting with a gradient of 15 to 50% ethyl acetate in hexanes to give the higher $R_f$ title product (1.44 g) and the lower C-1 isomer (0.17 g) as the free amines.

Step G: N-Methyl-N-(1-(R)-3-(S)-formyl-4-(S)-(3-fluorophenyl)cyclopent-1-yl)-D-valine t-butyl Ester To a solution of oxalyl chloride (0.235 mL, 2.65 mmol) in methylene chloride (10 mL) at −70° C. was added dropwise DMSO (0.385 mL, 5.3 mmol). After 15 min, a solution of N-methyl-N-(1-(R)-3-(S)-hydroxymethyl-4-(S)-(3-fluorophenyl)cyclopent-1-yl)-D-valine t-butyl ester (higher $R_f$ isomer from Step F) (400 mg, 1.05 mmol) in methylene chloride (10 mL) was added. The reaction was stirred at −70° C. for 1 h and then DIPEA (1.8 mL, 11 mmol) in methylene chloride (5 mL) was added dropwise over 5 min. After a further 10 min, the mixture was allowed to warm to rt for 1 h and then diluted with methylene chloride. The layers were separated. The aq. layer was reextracted with a second portion of methylene chloride and the organic layers were each washed with brine, dried over sodium sulfate, combined and concentrated in vacuo. The residue was purified by FC (15% ethyl acetate in hexanes) to give the title product (378 mg) as an oil.

Step H: N-Methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine t-butyl Ester To a solution of N-methyl-N-(1-(R)-3-(S)-formyl-4-(S)-(3-fluorophenyl)cyclopent-1-yl)-D-valine t-butyl ester (250 mg, 0.66 mmol) from Step G in 1,2-dichloroethane (20 mL) was added 4-(3-benzyl-1-ethyl-(1H)-pyrazol-5-yl) piperidine di-hydrochloride (from Procedure 1) (250 mg, 0.73 mmol) and DIPEA (0.25 mL, 1.46 mmol). After 15 min, sodium triacetoxyborohydride (280 mg, 1.33 mmol) was added and the reaction was stirred at rt for 16 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 50% ethyl acetate in hexanes to give the title product as the free amine.

HPLC/MS (ESI): m/z 631 (M+1).

Step I: N-Methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine tri-hydrochloride salt The N-methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine t-butyl ester from Step H was taken up in TFA (2 mL) and aged at rt for 16 h. The volatiles were evaporated under a stream of nitrogen. The residue was taken up in methanol and adsorbed onto a 500 mg Varian SCX ion-exchange resin cartridge. The resin was eluted with 2×3 mL of methanol, then the product was eluted with 2×3 mL of 2M ammonia in methanol. The product solution was concentrated under nitrogen, then 2 volumes of methylene chloride were evaporated to remove methanol and ammonia to give the free amine. The hydrochloride salt was prepared by dissolving the free amine in methylene chloride, adding excess (>3-fold) 1M hydrogen chloride in ether and evaporating to dryness.

HPLC/MS (ESI): m/z 575 (M+1).

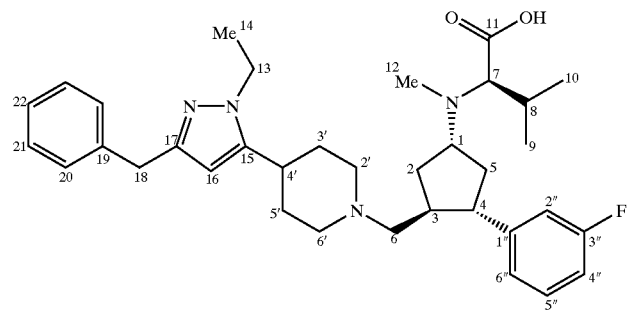

Carbon-13 and Proton Assignments

| Position | Carbon-13 | Proton(mult, \i J [Hz]) |
|---|---|---|
| 1 | 64.0 | 3.46 |
| 2a | 33.8 | 2.08 |
| 2b | | 1.83 — |
| 3 | 42.8 | 2.33 |
| 4 | 49.6 | 2.69 |
| 5a | 40.1 | 1.82 |
| 5b | | 2.22 — |
| 6a | 63.6 | 2.33 |
| 6b | | 2.19 — |
| 7 | 73.5 | 3.11 (d, J = 7.3) |
| 8 | 27.2 | 2.07 |
| 9 | 20.5 | 1.03 (d, J = 6.6) |
| 10 | 19.3 | 0.90 (d, J = 6.7) |
| 11 | 172.2 | — |
| 12 | 34.5 | 2.51 (s) |
| 13 | 43.8 | 3.93 (q, J = 7.3) |
| 14 | 16.1 | 1.26 (t, J = 7.3) |
| 15 | 148.1 | — |
| 16 | 101.8 | 5.71 (s) |
| 17 | 151.3 | — |
| 18 | 35.1 | 3.79 (s) |
| 19 | 41.5 | — |
| 20 | 129.7 | 7.21 |
| 21 | 129.3 | 7.25 |
| 22 | 126.9 | 7.16 |
| 2'ax | 54.6 | 1.97 |
| 2'eq | | 2.76 — |
| 3'ax | 32.3 | 1.33 (dq, J = 3.9, 12.6) |
| 3'eq | | 1.59 — |

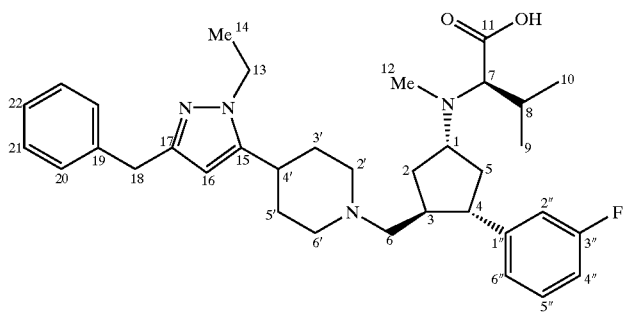

Carbon-13 and Proton Assignments

| Position | Carbon-13 | Proton(mult, \i J [Hz]) |
|---|---|---|
| 4' | 33.2 | 2.48 |
| 5'ax | 32.6 | 1.49 (dq, J = 4.0, 12.6) |
| 5'eq | 1.68 | — |
| 6'ax | 53.6 | 1.88 |
| 6'eq | 2.92 | — |
| 1" | 148.1 | — |
| 2" | 115.2 | 7.05 (br d, J = 10.8) |
| 3" | 163.9 | — |
| 4" | 113.8 | 6.90 (dt, J = 2.5, 8.4) |
| 5" | 130.9 | 7.27 (m) |
| 6" | 124.7 | 7.08 (d, J = 7.5) |

EXAMPLE 66A

N-Methyl-N-(1-(R)-3-(S)-((4-(3-(4-fluorobenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(4-fluorobenzyl)-1-ethyl-(1H)-pyrazol-5-yl)piperidine di-hydrochloride in Step H, the title compound was prepared.

HPLC/MS (ESI): m/z 593 (M+1).

EXAMPLE 66B

N-Methyl -N-(1-(R)-3-(S)-((4-(3-(3,4-difluorobenzyl)-1-methyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(3,4-difluorobenzyl)-1-methyl-(1H)-pyrazol-5-yl)piperidine di-hydrochloride in Step H, the title compound was prepared.

HPLC/MS (ESI): m/z 597 (M+1).

EXAMPLE 66C

N-Methyl-N-(1-(R)-3-(S)-((4-(3-(benzyl)-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(benzyl)-(1H)-pyrazol-5-yl)piperidine di-hydrochloride in Step H, the title compound was prepared.

HPLC/MS (ESI): m/z 547 (M+1).

EXAMPLE 66D

N-Methyl -N-(1-(R)-3-(S)-((4-(2-(4-fluorophenyl)sulfonyleth-1-yl)piperidin-1-yl)methyl)-4-(S)-(3-fluorophenyl)cyclopent-1-yl)-D-valine di-hydrochloride salt Using essentially the same procedures as in Example 65, Steps H and I, but substituting 4-(2-(4-fluorophenyl)sulfonyleth-1-yl)piperidine hydrochloride in Step H, the title compound was prepared.

HPLC/MS (ESI): m/z 577 (M+1).

EXAMPLE 66E

N-Methyl-N-(1-(R)-3-(S)-((4-(2-benzylthiazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(2-(benzyl)thiazol-5-yl)piperidine di-hydrochloride in Step H, the title compound was prepared.

HPLC/MS (ESI): m/z 564 (M+1).

EXAMPLE 66F

N-Methyl-N-(-(R)-3-(S)-((4-(2-benzyl-4-methylthiazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(2-benzyl-4-methylthiazol-5-yl)piperidine di-hydrochloride in Step H, the title compound was prepared.

HPLC/MS (ESI): m/z 578 (M+1).

EXAMPLE 66G

N-Methyl-N-(1-(R)-3-(S)-((4-(2-benzyl-4-ethylthiazol-5-yl)piperidin-1-yl)methyl)-4-(S)-(3-fluorophenyl)cyclopent-1-yl)-D-valine tri-hydrochloride Salt Using essentially the same procedures as in Example 65, Steps H and I, but substituting 4-(2-benzyl-4-ethylthiazol-5-yl)piperidine di-hydrochloride in Step H, the title compound was prepared.

HPLC/MS (ESI): m/z 592 (M+1).

EXAMPLE 66H

N-Methyl-N-(1-(R)-3-(S)-((4-(3-(4-methoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(4-methoxybenzyl)-1-ethyl-(1H)-pyrazol-5-yl)piperidine di-hydrochloride in Step H, the title compound was prepared.

HPLC/MS (ESI): m/z 605 (M+1).

EXAMPLE 66I

N-Methyl-N-(1-(R)-3-(S)-((4-(3-(4-trifluoromethylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(4-trifluoromethylbenzyl)-1-ethyl-(1H)-pyrazol-5-yl)piperidine di-hydrochloride in Step H, the title compound was prepared.

HPLC/MS (ESI): m/z 643 (M+1).

EXAMPLE 66J

N-Methyl-N-(1-(R)-3-(S)-((4-(3-(pyridin-3-ylmethyl)-1-ethyl-(1H)-pyrazol-5-yl)piperidin-1-yl)methyl)-4-(S)-(3-fluorophenyl)cyclopent-1-yl)-D-valine Tetra-Hydrochloride salt Using essentially the same procedures as in Example 65, Steps H and I, but substituting 4-(3-(pyridin-3-ylmethyl)-1-ethyl-(1H)-pyrazol-5-yl)piperidine tri-hydrochloride in Step H, the title compound was prepared.

HPLC/MS (ESI): m/z 576 (M+1).

EXAMPLE 66K

N-Methyl-N-(1-(R)-3-(S)-((4-(3-(pyridin-3-ylmethyl)-(1H)-pyrazol-5-yl)piperidin-1-yl)methyl)-4-(S)-(3-fluorophenyl)cyclopent-1-yl)-D-valine Tetra-Hydrochloride salt Using essentially the same procedures as in Example 6–5, Steps H and I, but substituting 4-(3-(pyridin-3-ylmethyl)-(1H)-pyrazol-5-yl)piperidine tri-hydrochloride in Step H, the title compound was prepared.

HPLC/MS (ESI): m/z 548 (M+1).

EXAMPLE 66L

N-Methyl-N-(1-(R)-3-(S)-((4-(3-(4-chlorobenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(4-chlorobenzyl)-1-ethyl-(1H)-pyrazol-5-yl)piperidine di-hydrochloride in Step H, the title compound was prepared.

HPLC/MS (ESI): m/z 609 (M+1), 611 (M+3).

EXAMPLE 66M

N-Methyl-N-(1-(R)-3-(S)-((4-(3-(3-fluorobenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(3-fluorobenzyl)-1-ethyl-(1H)-pyrazol-5-yl)piperidine di-hydrochloride in Step H, the title compound was prepared.

HPLC/MS (ESI): m/z 593 (M+1).

EXAMPLE 66N

N-Methyl-N-(1-(R)-3-(S)-((4-(3-(3,5-difluorobenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(3,5-difluorobenzyl)-1-ethyl-(1H)-pyrazol-5-yl)piperidine di-hydrochloride in Step H, the title compound was prepared.

HPLC/MS (ESI): m/z 611 (M+1).

EXAMPLE 66O

N-Methyl-N-(1-(R)-3-(S)-((4-(3-benzylpyridin-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-benzylpyridin-5-yl)piperidine di-hydrochloride in Step H, the title compound was prepared.

HPLC/MS (ESI): m/z 558 (M+1).

EXAMPLE 66P

N-Methyl-N-(1-(R)-3-(S)-((4-(3-(4-cyanobenzyl)-1-ethyl-(1H)-pyrazol-5-yl)piperidin-1-yl)methyl)4-(S)-(3-fluorophenyl)cyclopent-1-yl)-D-valine tri-hydrochloride salt Using essentially the same procedures as in Example 65, Steps H and I, but substituting 4-(3-(4-cyanobenzyl)-1-ethyl-(1H)-pyrazol-5-yl)piperidine di-hydrochloride in Step H, the title compound was prepared.

HPLC/MS (ESI): m/z 600 (M+1).

EXAMPLE 66Q

N-Methyl-N-(1-(R)-3-(S)-((4-(3-(cyclohexylmethyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(cyclohexylmethyl)-1-ethyl-(1H)-pyrazol-5-yl)piperidine di-hydrochloride in Step H, the title compound was prepared.

HPLC/MS (ESI): m/z 581 (M+1).

EXAMPLE 66R

N-Methyl-N-(1-(R)-3-(S)-((4-(3-(4-ethoxybenzyl)-1-ethyl-(1H)-pyrazol-5-yl )piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(3-(4-ethoxybenzyl)-1- ethyl-(1H)-pyrazol-5-yl)piperidine di-hydrochloride in Step H, the title compound was prepared.

HPLC/MS (ESI): m/z 619 (M+1).

EXAMPLE 66S

N-Methyl-N-(1-(R)-3-(S)-((4-(3-(4-trifluoromethoxybenzyl)-1-ethyl -(1H)-pyrazol-5-yl) piperidin-1-yl)methyl)-4-(S)-(3-fluorophenyl) cyclopent-1-yl)-D-valine tri-hydrochloride salt Using essentially the same procedures as in Example 65, Steps H and I, but substituting 4-(3-(4-trifluoromethoxybenzyl)-1-ethyl -(1H)-pyrazol-5-yl) piperidine di-hydrochloride in Step H, the title compound was prepared.

HPLC/MS (ESI): m/z 659 (M+1).

EXAMPLE 66T

N-Methyl -N-(1-(R)-3-(S)-((4-((4-benzyl)-2-ethyl-(1H)-imidazol-1-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-((4-benzyl)-2-ethyl-(1H)-imidazol-1-yl))piperidine di-hydrochloride in Step H, the title compound was prepared.

HPLC/MS (ESI): m/z 575 (M+1).

EXAMPLE 66U

N-Methyl-N-(1-(R)-3-(S)-((4-((3-benzyl)-1,2,4-oxadiazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-((3-benzyl)-1,2,4-oxadiazol-1-yl))piperidine di-hydrochloride in Step H, the title compound was prepared.

HPLC/MS (ESI): m/z 549 (M+1).

EXAMPLE 66V

N-Methyl-N-(1-(R)-3-(S)-((4-((2-benzyl)-4-ethyl-oxazol-5-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-((2-benzyl)4-ethyl-oxazol-5-yl))piperidine di-hydrochloride in Step H, the title compound was prepared.

HPLC/MS (ESI): m/z 576 (M+1).

EXAMPLE 66W

N-Methyl-N-(1-(R)-3-(S)-((4-(imidazo[1,2-A] pyridin-3-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(imidazo[1,2-A]pyridin-3-yl))piperidine di-hydrochloride in Step H, the title compound was prepared.

HPLC/MS (ESI): m/z 507 (M+1).

EXAMPLE 66X

N-Methyl-N-(1-(R)-3-(S)-((4-(6-trifluoromethylimidazo[1,2-A]pyridin-3-yl) piperidin-1-yl)methyl)-4-(S)-(3-fluorophenyl) cyclopent-1-yl)-D-valine tri-hydrochloride salt Using essentially the same procedures as in Example 65, Steps H and I, but substituting 4-(6-trifluoromethylimidazo [1,2-A]pyridin-3-yl))piperidine di-hydrochloride in Step H, the title compound was prepared.

HPLC/MS (ESI): m/z 575 (M+1).

EXAMPLE 66Y

N-Methyl-N-(1-(R)-3-(S)-((4-(6-ethylimidazo[1,2-A]pyridin-3-yl)piperidin-1-yl)methyl)-4-(S)-(3-fluorophenyl)cyclopent-1-yl)-D-valine tri-hydrochloride salt Using essentially the same procedures as in Example 65, Steps H and I, but substituting 4-(6-ethylimidazo[ 1 ,2-A] pyridin-3-yl))piperidine di-hydrochloride in Step H, the title compound was prepared.

HPLC/MS (ESI): m/z 535 (M+1).

EXAMPLE 66Z

N-Methyl -N-(1-(R)-3-(S)-((4-(3-(4-methylsulfonylbenzyl)-1-ethyl-(1H)-pyrazol-5-yl) piperidin-1-yl)methyl)-4-(S)-(3-fluorophenyl) cyclopent-1-yl)-D-valine tri-hydrochloride salt Using essentially the same procedures as in Example 65, Steps H and I, but substituting 4-(3-(4-methylsulfonylbenzyl)-1-ethyl-(1H)-pyrazol-5-yl) piperidine di-hydrochloride in Step H, the title compound was prepared.

HPLC/MS (ESI): m/z 653 (M+1).

EXAMPLE 66AA

N-Methyl-N-(1-(R)-3-(S)-((4-(3-(4-methylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 589.4 (M+1), $R_t$=1.62 min.

EXAMPLE 66BB

N-Methyl-N-(1-(R)-3-(S)-((4-(3-(4-ethylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 603.5 (M+1), $R_t$=1.68 min.

EXAMPLE 66CC

N-Methyl-N-(1-(R)-3-(S)-((4-(3-(4-isopropylbenzyl)-1-ethyl-(1H)-pyrazol-5-yl) piperidin-1-yl)methyl)-4-(S)-(3-fluorophenyl) cyclopent-1-yl)-D-valine tri-hydrochloride salt HPLC/MS (ESI): m/z 617.4 (M+1), $R_t$=1.82 min.

EXAMPLE 66DD

N-Methyl-N-(1-(R)-3-(S)-((4-(3-(4-t-butylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 631.7 (M+1), $R_t$=1.93 min.

EXAMPLE 66EE

N-Methyl-N-(1-(R)-3-(S)-((4-(3-(3-methoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 605.7 (M+1), $R_t$=1.51 min.

EXAMPLE 66FF

N-Methyl-N-(1-(R)-3-(S)-((4-(3-(4-difluoromethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 641.5 (M+1), $R_t$=1.68 min.

EXAMPLE 66GG

N-Methyl-N-(1-(R)-3-(S)-((4-(3-(4-isopropoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 633.4 (M+1), $R_t$=1.66 min.

EXAMPLE 66HH

N-Methyl-N-(1-(R)-3-(S)-((4-(3-(3,4-methylenedioxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 619.5 (M+1), $R_t$=1.51 min.

EXAMPLE 66II

N-Methyl-N-(1-(R)-3-(S)-((4-(3-(3,4-dimethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 635.5 (M+1), $R_t$=1.46 min.

EXAMPLE 66JJ

N-Methyl-N-(1-(R)-3-(S)-((4-(3-(3-ethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 619.6 (M+1), $R_t$=1.60 min.

EXAMPLE 66KK

N-Methyl-N-(1-(R)-3-(S)-((4-(3-(2-naphthyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 625.6 (M+1), $R_t$=1.75 min.

EXAMPLE 66LL

N-Methyl-N-(1-(R)-3-(S)-((4-(3-(1-naphthyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 625.6 (M+1), $R_t$=1.71 min.

EXAMPLE 66MM

N-Methyl-N-(1-(R)-3-(S)-((4-(3-(3-fluoro-4-methoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 623.7 (M+1), $R_t$=1.58 min.

EXAMPLE 66NN

N-Methyl-N-(1-(R)-3-(S)-((4-(3-(3-fluoro-4-ethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 637.6 (M+1), $R_t$=1.68 min.

EXAMPLE 66OO

N-Methyl-N-(1-(R)-3-(S)-((4-(3-(3-cyano-4-methoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 630.7 (M+1), $R_t$=1.53 min.

EXAMPLE 66PP

N-Methyl-N-(1-(R)-3-(S)-((4-(3-(4-cyclobutoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 645.5 (M+1), $R_t$=1.79 min.

EXAMPLE 66QQ

N-Methyl-N-(1-(R)-3-(S)-((4-(3-(benzofuran-6-ylmethyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 615.5 (M+1), $R_t$=1.55 min.

EXAMPLE 66RR

N-Methyl-N-(1-(R)-3-(S)-((4-(3-(2,3-dihydrobenzofuran-6-ylmethyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 617.5 (M+1), $R_t$=1.47 min.

EXAMPLE 66SS

N-Methyl-N-(1-(R)-3-(S)-((4-(3-(4-benzyloxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 681.5 (M+1), $R_t$=1.64 min.

EXAMPLE 66TT

N-Methyl-N-(1-(R)-3-(S)-((4-(3-(4-hydroxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 591.6 (M+1), $R_t$=1.29 min.

EXAMPLE 66UU

N-Methyl-N-(1-(R)-3-(S)-((4-(3-(4-ethoxybenzyl)-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 591.6 (M+1), $R_t$=1.53 min.

EXAMPLE 66VV

N-Methyl-N-(1-(R)-3-(S)-((4-(3-(4-ethoxybenzyl)-1-(2-fluoroeth-1-yl)-(1H)-pyrazol-5-yl)piperidin-1-yl)methyl)4-(S)-(3-fluorophenyl)cyclopent-1-yl)-D-valine tri-hydrochloride salt HPLC/MS (ESI): m/z 637 (M+1), $R_t$=1.60 min.

EXAMPLE 66WW

N-Methyl-N-(1-(R)-3-(S)-((4-(3-(4-cyclopropoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 631 (M+1), $R_t$=1.62 min.

EXAMPLE 66XX

N-Methyl-N-(1-(R)-3-(S)-((4-(3-(4-phenylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 651 (M+1), $R_t$=1.80 min.

EXAMPLE 66YY

N-Methyl-N-(1-(R)-3-(S)-((4-(3-(4-(2,2,2-trifluoroeth-1-yloxy)benzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 673 (M+), $R_t$=1.69 min.

EXAMPLE 66ZZ

N-Methyl-N-(1-(R)-3-(S)-((4-(3-(4-acetylbenzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 617.5 (M+1), $R_t$=1.44 min.

EXAMPLE 66AAA

N-Methyl-N-(1-(R)-3-(S)-((4-(3-(4-(1-methyl-1-hydroxyeth-1-yl)benzyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 633.5 (M+1), $R_t$=1.97 min.

EXAMPLE 66BBB

N-Methyl-N-(1-(R)-3-(S)-((4-(2-ethyl-(2H)-4,5,6,7-tetrahydroindazol-3-yl)piperidin-1-yl)methyl)-4-(S)-(3-fluorophenyl)cyclopent-1-yl)-D-valine tri-hydrochloride salt HPLC/MS (ESI): m/z 539.5 (M+1), $R_t$=1.22 min.

EXAMPLE 66CCC

N-Methyl-N-(1-(R)-$^3$-(S)-((4-(3-(4-methylcyclohexylmethyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 595.5 (M+1), $R_t$=1.77 min.

EXAMPLE 66DDD

N-Methyl-N-(1-(R)-$^3$-(S)-((4-(3-(pyran-4-ylmethyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 583.7 (M+1), $R_t$=1.25 min.

EXAMPLE 66EEE

N-Methyl-N-(1-(R)-$^3$-(S)-((4-(3-(cycloheptylmethyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 595.7 (M+1), $R_t$=1.68 min.

EXAMPLE 66FFF

N-Methyl-N-(1-(R)-3-(S)-((4-(3-((1,1-dioxothiopyran-4-yl)methyl)-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 631.5 (M+1), $R_t$=1.33 min.

EXAMPLE 66GGG

N-Methyl-N-(1-(R)-3-(S)-((4-(2-(4-fluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 582 (M+1).

EXAMPLE 66HHH

N-Methyl-N-(1-(R)-3-(S)-((4-(2-(4-fluorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 596 (M+1).

EXAMPLE 66III

N-Methyl-N-(1-(R)-3-(S)-((4-(2-(4-fluorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 610 (M+1).

EXAMPLE 66JJJ

N-Methyl-N-(1-(R)-3-(S)-((4-(2-(4-chlorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 598, 600 (M+1, M+3).

EXAMPLE 66KKK

N-Methyl-N-(1-(R)-3-(S)-((4-(2-(4-chlorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 612, 614 (M+1, M+1).

EXAMPLE 66LLL

N-Methyl-N-(1-(R)-3-(S)-((4-(2-(4-chlorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 626, 628 (M+1, M+1).

EXAMPLE 66MMM

N-Methyl-N-(1-(R)-3-(S)-((4-(2-(4-trifluoromethylbenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 632 (M+1).

EXAMPLE 66NNN

N-Methyl-N-(1-(R)-3-(S)-((4-(2-(4-trifluoromethylbenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 646 (M+1).

EXAMPLE 66OOO

N-Methyl-N-(1-(R)-3-(S)-((4-(2-(4-trifluoromethylbenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 660 (M+1).

EXAMPLE 66PPP

N-Methyl-N-(1-(R)-3-(S)-((4-(2-(2,4-difluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 600 (M+1).

EXAMPLE-66OQQQ

N-Methyl-N-(1-(R)-3-(S)-((4-(2-(2,4-difluorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 614 (M+1).

EXAMPLE 66RRR

N-Methyl-N-(1-(R)-3-(S)-((4-(2-(2,4-difluorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 628 (M+1).

EXAMPLE 66SSS

N-Methyl-N-(1-(R)-3-(S)-((4-(2-(2,4-dichlorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 630,632,634 (M+1, M+3, M+5).

EXAMPLE 66TTT

N-Methyl-N-(1-(R)-3-(S)-((4-(2-(2,4-dichlorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 644, 646, 648 (M+1, M+3, M+5).

EXAMPLE 66UUU

N-Methyl -N-(1-(R)-3-(S)-((4-(2-(2,4-dichlorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 658, 660, 662 (M+1, M+3, M+5).

EXAMPLE 66VVV

N-Methyl -N-(1-(R)-3-(S)-((4-(2-(3-trifluoromethylbenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 632 (M+1).

EXAMPLE 66WWW

N-Methyl-N-(1-(R)-3-(S)-((4-(2-(3-trifluoromethylbenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 646 (M+1).

EXAMPLE 66XXX

N-Methyl-N-(1-(R)-3-(S)-((4-(2-(3-trifluoromethylbenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 660 (M+1).

EXAMPLE 66YYY

N-Methyl-N-(1-(R)-3-(S)-((4-(2-(3,4-difluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 600 (M+1).

EXAMPLE 66ZZZ

N-Methyl-N-(1-(R)-3-(S)-((4-(2-(3,4-difluorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 614 (M+1).

EXAMPLE 66AAAA

N-Methyl-N-(1-(R)-3-(S)-((4-(2-(3,4-difluorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 628 (M+1).

EXAMPLE 66BBBB

N-Methyl-N-(1-(R)-3-(S)-((4-(2-(3,4-dichlorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 630, 632, 634 (M+1, M+3, M+5).

EXAMPLE 66CCCC

N-Methyl-N-(1-(R)-3-(S)-((4-(2-(3,4-dichlorobenzyl)-4-methylthiazol-5-yl)piperidin-1-yl)methyl)-4-(S)-(3-fluorophenyl)cyclopent-1-yl)-D-valine tri-hydrochloride salt HPLC/MS (ESI): m/z 644, 646, 648 (M+1, M+3, M+5).

EXAMPLE 66DDDD

N-Methyl-N-(1-(R)-3-(S)-((4-(2-(3,4-dichlorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 658, 660, 662 (M+1, M+3, M+5).

EXAMPLE 66EEEE

N-Methyl-N-(1-(R)-3-(S)-((4-(2-(3,5-difluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/l 600 (M+1).

EXAMPLE 66FFFF

N-Methyl-N-(1-(R)-3(S)-((4-(2-(3,5-difluorobenzyl)-4-methylthiazol-5-yl)piperidin-1-methyl)-4-(S)-(3-fluorophenyl)cyclopent-1-yl)-D-valine tri-hydrochloride salt HPLC/MS (ESI): m/z 614 (M+1).

EXAMPLE 66GGGG

N-Methyl-N-(1-(R)-3-(S)-((4-(2-(3,5-difluorobenzyl)-4ethylthiazol-5yl)piperidin-1-yl)methyl)-4-(S)-(3-fluorophenyl)cyclopent-1-yl)-D-valine tri-hydrochloride salt HPLC/MS (ESI): m/z 628 (M+1).

EXAMPLE 66HHHH

N-Methyl-N-(1-(R)-3-(S)-((4-(2-(cyclohexylmethyl)thiazol-5-yl)piperidin-1-yl)methyl)-4-(S)-(3-fluorophenyl)cyclopent-1-yl)-D-valine tri-hydrochloride salt HPLC/MS (ESI): m/z 570 (M+1).

EXAMPLE 66IIII

N-Methyl-N-(1-(R)-3-(S)-((4-(2-(cyclohexylmethyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 598 (M+1).

EXAMPLE 66JJJJ

N-Methyl-N-(1-(R)-3-(S)-((4-(2-(2-chlorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 598, 600 (M+1, M+3).

EXAMPLE 66KKKK

N-Methyl-N-(1-(R)-3-(S)-((4-(2-(2-chlorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 626, 628 (M+1, M+1).

EXAMPLE 66LLLL

N-Methyl-N-(1-(R)-3-(S)-((4-(2-(3-chlorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 598, 600 (M+1, M+3).

EXAMPLE 66MMMM

N-Methyl-N-(1-(R)-3-(S)-((4-(2-(3-chlorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 626,–628 (M+1, M+1).

EXAMPLE 66NNNN

N-Methyl-N-(1-(R)-3-(S)-((4-(2-(3-fluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 582 (M+1).

EXAMPLE 66OOOO

N-Methyl-N-(1-(R)-3-(S)-((4-(2-(3-fluorobenzyl)-4-ethylthiazol-5-yl)piperidin-1-yl)methyl)-4-(S )-(3-fluorophenyl)cyclopent-1-yl)-D-valine tri-hydrochloride salt HPLC/MS (ESI): m/z 610 (M+1).

EXAMPLE 66PPPP

N-Methyl-N-(1-(R)-3-(S)-((4-(2-(2-fluorobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 582 (M+1).

EXAMPLE 66OOOO

N-Methyl-N-(1-(R)-3-(S)-((4-(2-(2-fluorobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 610 (M+1).

EXAMPLE 66RRRR

N-Methyl-N-(1-(R)-3-(S)-((4-(2-(2-trifluoromethylbenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 632 (M+1).

EXAMPLE 66SSSS

N-Methyl-N-(1-(R)-3-(S)-((4-(2-(2-trifluoromethylbenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 660 (M+1).

EXAMPLE 66TTTT

N-Methyl-N-(1-(R)-3-(S)-((4-(2-(4-trifluoromethoxybenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 648 (M+1).

EXAMPLE 66UUUU

N-Methyl-N-(1-(R)-3-(S)-((4-(2-(4-trifluoromethoxybenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 676 (M+1).

EXAMPLE 66VVVV

N-Methyl-N-(-(R)-3-(S)-((4-(2-(4-methylsulfonylbenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 642 (M+1).

EXAMPLE 66WWWW

N-Methyl-N-(1-(R)-3-(S)-((4-(2-(4-methylsulfonylbenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 670 (M+1).

EXAMPLE 66XXXX

N-Methyl-N-(1-(R)-3-(S)-((4-(2-(4-nitrobenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 609 (M+1).

EXAMPLE 66YYYY

N-Methyl-N-(1-(R)-3-(S)-((4-(2-(4-nitrobenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 637 (M+1).

EXAMPLE 66ZZZZ

N-Methyl-N-(1-(R)-3-(S)-((4-(2-(4-ethoxybenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 608 (M+1).

EXAMPLE 66AAAAA

N-Methyl-N-(1-(R)-3-(S)-((4-(2-(4-ethoxybenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 636 (M+1).

EXAMPLE 66BBBBB

N-Methyl-N-(1-(R)-3-(S)-((4-(2-(4-isopropylbenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 606 (M+1).

EXAMPLE 66CCCCC

N-Methyl-N-(1-(R)-3-(S)-((4-(2-(4-isopropylbenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 634 (M+1).

EXAMPLE 66DDDDD

N-Methyl-N-(1-(R)-3-(S)-((4-(2-(4-methoxybenzyl)thiazol-5-yl)piperidin-1-yl)methyl)-4-(S)-(3-fluorophenyl)cyclopent-1-yl)-D-valine tri-hydrochloride salt HPLC/MS (ESI): m/z 594 (M+1).

EXAMPLE 66EEEEE

N-Methyl-N-(1-(R)-3-(S)-((4-(2-(4-methoxybenzyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 622 (M+1).

EXAMPLE 66FFFFF

N-Methyl-N-(1-(R)-3-(S)-((4-(7-propylimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 549 (M+1).

EXAMPLE 66GGGGG

N-Methyl-N-(1-(R)-3-(S)-((4-(7-t-butylimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 563 (M+1).

EXAMPLE 66HHHHH

N-Methyl-N-(1-(R)-3-(S)-((4-(6-chloroimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 541, 543 (M+1, M+3).

EXAMPLE 66IIIII

N-Methyl-N-(1-(R)-3-(S)-((4-(2-ethyl-5,6,7,8-tetrahydroimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 539 (M+1).

EXAMPLE 66JJJJJ

N-Methyl-N-(1-(R)-3-(S)-((4-(6-fluoroimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 525 (M+1).

EXAMPLE 66KKKKK

N-Methyl-N-(1 (R)-3-(S)-((4-(6-fluoro-7-methylimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 539 (M+1).

EXAMPLE 66LLLLL

N-Methyl-N-(1-(R)-3-(S)-((4-(2-ethylimidazo[1,2-A]pyridin-3-yl)piperidin-1-yl)methyl)-4-(S)-(3-fluorophenyl)cyclopent-1-yl)-D-valine tri-hydrochloride salt HPLC/MS (ESI): m/z 535 (M+1).

EXAMPLE 66MMMMM

N-Methyl-N-(1-(R)-3-(S)-((4-(2-(2-thienyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 598 (M+1).

EXAMPLE 66NNNNN

N-Methyl-N-(1-(R)-3-(S)-((4-(2-(3-thienyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 598 (M+1).

EXAMPLE 66OOOOO

N-Methyl-N-(1-(R)-3-(S)-((4-(2-(3-pyridyl)-4-ethylthiazol-5-yl)piperidin-1-yl)methyl)-4-(S)-(3-fluorophenyl)cyclopent-1-yl)-D-valine tri-hydrochloride salt HPLC/MS (ESI): m/z 593 (M+1).

EXAMPLE 66PPPPP

N-Methyl-N-(1-(R)-3-(S)-((4-(2-benzyl-(2H)
tetrazol-5-yl)piperidin-1-yl)methyl)-4-(S)-(3-
fluorophenyl)cyclopent-1-yl)-D-valine tri-
hydrochloride salt HPLC/MS (ESI): m/z 549 (M+1).

EXAMPLE 66QQQQQ

N-Methyl-N-(1-(R)-3-(S)-((4-(1,3-diethyl-4-methyl-
(1H)-pyrazol-5-yl)piperidin-1-yl)methyl)-4-(S)-(3-
fluorophenyl)cyclopent-1-yl)-D-valine tri-
hydrochloride salt HPLC/MS (ESI): m/z 527 (M+1).

EXAMPLE 66RRRRR

N-Methyl-N-(1-(R)-3-(S)-((4-(1-ethyl-3,4-dimethyl-
(1H)-pyrazol-5-yl)piperidin-1-yl)methyl)-4-(S)-(3-
fluorophenyl)cyclopent-1-yl)-D-valine tri-
hydrochloride salt HPLC/MS (ESI): m/z 513 (M+1).

EXAMPLE 66SSSSS

N-Methyl-N-(1-(R)-3-(S)-((4-(1,3-dimethyl-3-ethyl-
(1H)-pyrazol-5-yl)piperidin-1-yl)methyl)-4-(S)-(3-
fluorophenyl)cyclopent-1-yl)-D-valine tri-
hydrochloride salt HPLC/MS (ESI): m/z 513 (M+1).

EXAMPLE 66TTTTT

N-Methyl-N-(1-(R)-3-(S)-((4-(3-(4-
trifluoromethysulfonylbenzyl)-1-ethyl-(1H)-pyrazol-
5-yl)piperidin-1-yl)methyl)-4-(S)-(3-fluorophenyl)
cyclopent-1-yl)-D-valine tri-hydrochloride salt HPLC/MS (ESI): m/z 707 (M+1).

EXAMPLE 66UUUUU

N-Methyl-N-(1-(R)-3-(S)-((4-(1,3-dimethyl-3-ethyl-
(1H)-pyrazol-5-yl)piperidin-1-yl)methyl)-4-(S)-(3-
fluorophenyl)cyclopent-1-yl)-D-valine tri-
hydrochloride salt HPLC/MS (ESI): m/z 513 (M+1).

EXAMPLE 67

N-Methyl-N-(1-(S)-3-(S)-((4-(3-(benzyl)-1-ethyl -
(1H)-pyrazol-5-yl)piperidin-1-yl)methyl)-4-(S)-(3-
fluorophenyl)cyclopent-1-yl)-D-valine tri-
hydrochloride salt Using essentially the same procedures as in Example 65, Steps G, H and I, but substituting N-methyl-N-(1-(S)-3-(S)-hydroxymethyl4-(S)-(3-fluorophenyl)cyclopent-1-yl)-D-valine t-butyl ester (lower $R_f$ isomer from Step F), the title compound was prepared.

HPLC/MS (ESI): m/z 575 (M+1).

EXAMPLE 67A

N-Methyl-N-(1-(S)-3-(S)-((4-(3-(3,4-
difluorobenzyl)-1-ethyl-(1H)-pyrazol-5-yl)piperidin-
1-yl)methyl)-4-(S)-(3-fluorophenyl)cyclopent-1-yl)-
D-valine tri-hydrochloride salt Using essentially the same procedures as in Example 67, but substituting 4-(3-(3,4-difluorobenzyl)-1-ethyl-(1H)-pyrazol-5-yl)piperidine di-hydrochloride in Step H, the title compound was prepared. HPLC/MS (ESI): m/z 597 (M+1).

EXAMPLE 67B

N-Methyl-N-(1-(S)-3-(S)-((4-(2-(4-
fluorophenylsulfonyl)eth-1-yl)piperidin-1-yl)
methyl)-4-(S)-(3-fluorophenyl)cyclopent-1-yl)-D-
valine tri-hydrochloride salt Using essentially the same procedures as in Example 67, but substituting 4-(3-(2-(4-fluorophenylsulfonyl)eth-1-yl) piperidine di-hydrochloride in Step H, the title compound was prepared.

HPLC/MS (ESI): m/z 577 (M+1).

EXAMPLE 68

N-Methyl-N-(1-(R)-3-(S)-((4-(3-(benzyl)-1-ethyl-
(1H)-pyrazol-5-yl)piperidin-1-yl)methyl)-4-(S)-(3-
fluorophenyl)cyclopent-1-yl)-(R)-ethylglycine tri-
hydrochloride salt Using essentially the same procedures as in Example 65, Steps E–I, but substituting (R)-ethylglycine-t-butyl ester in Step E and using the higher $R_f$ isomer from Step F, the title compound was prepared.

HPLC/MS (ESI): m/z 561 (M+1).

EXAMPLE 69

N-Methyl-N-(1-(R)-3-(S)-((4-(3-(benzyl)-1-ethyl-
(1H)-pyrazol-5-yl)piperidin-1-yl)methyl)-4-(S)-(3-
fluorophenyl)cyclopent-1-yl)-D-norvaline tri-
hydrochloride salt Using essentially the same procedures as in Example 65, Steps E–I, but substituting D-norvaline-t-butyl ester in Step E and using the higher $R_f$ isomer from Step F, the title compound was prepared.

HPLC/MS (ESI): m/z 575 (M+1).

EXAMPLE 70

N-Methyl-N-(1-(R)-3-(S)-((4-(3-(benzyl)-1-ethyl-
(1H)-pyrazol-5-yl)piperidin-1-yl)methyl)-4-(S)-(3-
fluorophenyl)cyclopent-1-yl)-D-leucine tri-
hydrochloride salt Using essentially the same procedures as in Example 65, Steps E–I, but substituting D-leucine-t-butyl ester in Step E and using the higher $R_f$ isomer from Step F, the title compound was prepared.

HPLC/MS (ESI): m/z 589 (M+1).

EXAMPLE 71

Using essentially the same procedures as in Example 65, Steps E–I, but substituting D-leucine-t-butyl ester in Step E, using the higher $R_f$ isomer from Step F, and substituting the appropriate piperidine in Step H, the following title compounds were prepared.

EXAMPLE 71A

N-Methyl-N-(1-(R)-3-(S)-((4-(3-(4-
methylsulfonylbenzyl)-1-ethyl-(1H)-pyrazol-5-yl)
piperidin-1-yl)methyl)-4-(S)-(3-fluorophenyl)
cyclopent-1-yl)-D-leucine tri-hydrochloride salt HPLC/MS (ESI): m/z 667 (M+1).

EXAMPLE 71B

N-Methyl-N-(1-(R)-3-(S)-((4-(3-(4-trifluoromethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 673 (M+1).

EXAMPLE 71C

N-Methyl-N-(1-(R)-3-(S)-((4-(3-(cyclohexylmethyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 595 (M+1).

EXAMPLE 71D

N-Methyl-N-(1-(R)-3-(S)-((4-(2-(benzyl)-4-ethyl-thiazol-5-yl)piperidin-1-yl)methyl)-4-(S)-(3-fluorophenyl)cyclopent-1-yl)-D-leucine tri-hydrochloride salt HPLC/MS (ESI): m/z 606 (M+1).

EXAMPLE 71E

N-Methyl-N-(1-(R)-3-(S)-((4-(2-(4-fluorobenzyl)-4-ethyl-thiazol-5-yl)piperidin-1-yl)methyl)-4-(S)-(3-fluorophenyl)cyclopent-1-yl)-D-leucine tri-hydrochloride salt HPLC/MS (ESI): m/z 624 (M+1).

EXAMPLE 71F

N-Methyl-N-(1-(R)-3-(S)-((4-(2-(4-trifluoromethylbenzyl)-4-ethyl-thiazol-5-yl)piperidin-1-yl)methyl)-4-(S)-(3-fluorophenyl)cyclopent-1-yl)-D-leucine tri-hydrochloride salt HPLC/MS (ESI): m/z 674 (M+1).

EXAMPLE 71G

N-Methyl-N-(1-(R)-3-(S)-((4-(2-(cyclohexylsulfonyl)eth-1-yl)piperidin-1-yl)methyl)-4-(S)-(3-fluorophenyl)cyclopent-1-yl)-D-leucine tri-hydrochloride salt HPLC/MS (ESI): m/z 579 (M+1).

EXAMPLE 71H

N-Methyl-N-(1-(R)-3-(S)-((4-(3-(4-methoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 619 (M+1).

EXAMPLE 71I

N-Methyl-N-(1-(R)-3-(S)-((4-(3-(3-methoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 619.4 (M+1), $R_t$=1.57 min.

EXAMPLE 71J

N-Methyl-N-(1-(R)-3-(S)-((4-(3-(4-ethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 633.6 (M+1).

EXAMPLE 71K

N-Methyl-N-(1-(R)-3-(S)-((4-(3-(3-ethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 633.7 (M+1), $R_t$=1.66 min.

EXAMPLE 71L

N-Methyl-N-(1-(R)-3-(S)-((4-(3-(4-isopropoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 647.9 (M+1), $R_t$=1.69 min.

EXAMPLE 71M

N-Methyl-N-(1-(R)-3-(S)-((4-(3-(4-cyclopropoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 645.9 (M+1), $R_t$=1.66 min.

EXAMPLE 71N

N-Methyl-N-(1-(R)-3-(S)-((4-(3-(4-difluoromethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 655.4 (M+1), $R_t$=1.66 min.

EXAMPLE 71O

N-Methyl-N-(1-(R)-3-(S)-((4-(3-(4-cyclobutoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 659 (M+1), $R_t$=1.29 min.

EXAMPLE 71P

N-Methyl-N-(1-(R)-3-(S)-((4-(3-(4-benzyloxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 695 (M+1), $R_t$=1.68 min.

EXAMPLE 71Q

N-Methyl-N-(1-(R)-3-(S)-((4-(3-(4-hydroxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 605 (M+1), $R_t$=1.35 min.

EXAMPLE 71R

N-Methyl-N-(1-(R)-3-(S)-((4-(3-(4-ethoxybenzyl)-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 605.6 (M+1), $R_t$=1.57 min.

EXAMPLE 71S

N-Methyl-N-(1-(R)-$^3$-(S)-((4-(3-(4-(2,2,2-trifluoroethoxy)benzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 687 (M+1), $R_t$=1.73 min.

EXAMPLE 71T

N-Methyl-N-(1-(R)-3-(S)-((4-(3-(3,4-methylenedioxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 633.8 (M+1), $R_t$=1.60 min.

EXAMPLE 71U

N-Methyl-N-(1-(R)-3-(S)-((4-(3-(3,4-dimethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 649.6 (M+1), $R_t$=1.47 min.

EXAMPLE 71V

N-Methyl -N-(1-(R)-3-(S)-((4-(3-(3-fluoro-4-methoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 637 (M+1), $R_t$=1.64 min.

EXAMPLE 71W

N-Methyl-N-(1-(R)-3-(S)-((4-(3-(3-fluoro-4-ethoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 651 (M+1), $R_t$=1.75 min.

EXAMPLE 71X

N-Methyl-N-(1-(R)-3-(S)-((4-(3-(3-cyano-4-methoxybenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): n/z 644.7 (M+1), $R_t$=1.60 min.

EXAMPLE 71Y

N-Methyl-N-(1-(R)-3-(S)-((4-(3-(benzofuran-6-yl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 629 (M+1), $R_t$=1.60 min.

EXAMPLE 71Z

N-Methyl-N-(1-(R)-3-(S)-((4-(3-(2,3-dihydrobenzofuran-6-yl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 631 (M+1), $R_t$=1.53 min.

EXAMPLE 71AA

N-Methyl-N-(1 -(R)-3-(S)-((4-(3-(4-methylbenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 603.6 (M+1), $R_t$=1.68 min.

EXAMPLE 71BB

N-Methyl -N-(1-(R)-3-(S)-((4-(3-(4-ethylbenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 617 (M+1), $R_t$=1.73 min.

EXAMPLE 71CC

N-Methyl-N-(1-(R)-3-(S)-((4-(3-(4-iospropylbenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 631.7 (M+1), $R_t$=1.90 min.

EXAMPLE 71DD

N-Methyl-N-(1-(R)-3-(S)-((4-(3-(4-t-butylbenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 645.7 (M+1), $R_t$=1.95 min.

EXAMPLE 71EE

N-Methyl-N-(1-(R)-3-(S)-((4-(3-(1-naphthyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 639.7 (M+1), $R_t$=1.77 min.

EXAMPLE 71FF

N-Methyl-N-(1-(R)-3-(S)-((4-(3-(2-naphthyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 639.7 (M+1), $R_t$=1.86 min.

EXAMPLE 71GG

N-Methyl-N-(1-(R)-3-(S)-((4-(3-(4-phenylbenzyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 665 (M+1), $R_t$=1.84 min.

EXAMPLE 71HH

N-Methyl-N-(1-(R)-3-(S)-((4-(3-(pyran-4-ylmethyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 597.7 (M+1), $R_t$=1.33 min.

EXAMPLE 71II

N-Methyl-N-(1-(R)-3-(S)-((4-(3-(cycloheptylmethyl)-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 609.7 (M+1), $R_t$=1.71 min.

EXAMPLE 72

N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt Using essentially the same procedures as in Example 65, Steps E–I, but substituting (R)-t-butylglycine t-butyl ester in Step E, skipping Step F and using the higher $R_f$ isomer from Step E, the title compound was prepared.

HPLC/MS (ESI): m/z 575 (M+1).

EXAMPLE 73

Using essentially the same procedures as in Example 72 and Example 65, Steps E–I, but substituting (R)-t-butylglycine t-butyl ester in Step E and skipping Step F, using the higher $R_f$ isomer from Step E (as in Example 72), and substituting the appropriate piperidine in Step H, the following title compounds were prepared.

EXAMPLE 73A

N-(1-(R)-3-(S)-((4-(3-(4-trifluoromethylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 643 (M+1).

EXAMPLE 73B

N-(1-(R)-3-(S)-((4-(3-(4-fluorobenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 593 (M+1).

EXAMPLE 73C

N-(1-(R)-3-(S)-((4-(3-(benzyl)-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 547 (M+1).

EXAMPLE 73D

N-(1-(R)-3-(S)-((4-(2-(benzyl)-4-ethyl-thiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 592 (M+1).

EXAMPLE 73E

N-(1-(R)-3-(S)-((4-(3-(cyclohexylmethyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 581 (M+1).

EXAMPLE 73F

N-(1-(R)-3-(S)-((4-(3-(4-methylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 589 (M+1).

EXAMPLE 73G

N-(1-(R)-3-(S)-((4-(3-(4-isopropylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 617 (M+1).

EXAMPLE 73H

N-(1-(R)-3-(S)-((4-(3-(4-t-butylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 631 (M+1).

EXAMPLE 73I

N-(1-(R)-3-(S)-((4-(3-(3-ethoxybenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 619 (M+1).

EXAMPLE 73J

N-(1-(R)-3-(S)-((4-(3-(4-ethoxybenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 619 (M+1).

EXAMPLE 73K

N-(1-(R)-3-(S)-((4-(3-(4-isopropyloxybenzyl)-1-ethyl-(1H)-pyrazol-5-yl)piperidin-1-yl)methyl)4-(S)-(3-fluorophenyl)cyclopent-1-yl)-(R)-t-butylglycine tri-hydrochloride salt HPLC/MS (ESI): m/z 633 (M+1).

EXAMPLE 73L

N-(1-(R)-3-(S)-((4-(3-(4-difluoromethoxybenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 641 (M+1).

EXAMPLE 73M

N-(1-(R)-3-(S)-((4-(3-(2-naphthylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 625 (M+1).

EXAMPLE 74

N-Methyl-N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-(R)-t-butyl-lycine tri-hydrochloride salt Using essentially the same procedures as in Example 65, Steps E–I, but substituting (R)-t-butylglycine t-butyl ester in Step E and using the higher $R_f$ isomer from Step F, the title compound was prepared.

HPLC/MS (ESI): m/z 589 (M+1).

EXAMPLE 75

Using essentially the same procedures as in Example 74 and Example 65, Steps E–I, but substituting (R)-t-butylglycine t-butyl ester in Step E, using the higher $R_f$ isomer from Step F, and substituting the appropriate piperidine in Step H, the following title compounds were prepared.

EXAMPLE 75A

N-Methyl-N-(1-(R)-3-(S)-((4-(3-(4-trifluoromethylbenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 657 (M+1).

EXAMPLE 75B

N-Methyl-N-(1-(R)-3-(S)-((4-(3-(4-fluorobenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 607 (M+1).

EXAMPLE 75C

N-Methyl-N-(1-(R)-3-(S)-((4-(3-(3,4-difluorobenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 625 (M+1).

EXAMPLE 75D

N-Methyl-N-(1-(R)-3-(S)-((4-(3-(4-methoxybenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 619 (M+1).

EXAMPLE 75E

N-Methyl-N-(1-(R)-3-(S)-((4-(3-(cyclohexylmethyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 595 (M+1).

EXAMPLE 75F

N-Methyl-N-(1-(R)-3-(S)-((4-(3-(benzyl)-(1H)-pyrazol-5-yl)piperidin-1-yl)methyl)4-(S)-(3-fluorophenyl)cyclopent-1-yl)-(R)-t-butylglycine tri-hydrochloride salt HPLC/MS (ESI): m/z 561 (M+1).

EXAMPLE 75G

N-Methyl-N-(1-(R)-3-(S)-((4-(3-(4-ethoxybenzyl)-1-ethyl-(1H)-pyrazol-5-yl)piperidin-1-yl)methyl)-4-(S)-(3-fluorophenyl)cyclopent-1-yl)-(R)-t-butylglycine tri-hydrochloride salt HPLC/MS (ESI): n/z 633 (M+1).

EXAMPLE 75H

N-Methyl-N-(1-(R)-3-(S)-((4-(2-(benzyl)-4-ethyl-thiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 606 (M+1).

EXAMPLE 75I

N-Methyl-N-(1-(R)-3-(S)-((4-(2-(4-fluorobenzyl)-4-ethyl-thiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 624 (M+1).

EXAMPLE 75J

N-Methyl-N-(1-(R)-3-(S)-((4-(2-(4-trifluoromethylbenzyl)thiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 646 (M+1).

EXAMPLE 75K

N-Methyl-N-(1-(R)-3-(S)-((4-(2-(3-trifluoromethylbenzyl)-4-ethylthiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 674 (M+1).

EXAMPLE 75L

N-Methyl-N-(1-(R)-3-(S)-((4-(2-(3,4-dichlorobenzyl)-4-ethylthiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 673, 675, 677 (M+1, M+3, M+4).

EXAMPLE 75M

N-Methyl-N-(1-(R)-3-(S)-((4-(2-(4-chlorobenzyl)-4-ethyloxazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 624, 626 (M+1, M+3).

EXAMPLE 75N

N-Methyl-N-(1-(R)-3-(S)-((4-(2-(2,4-difluorobenzyl)-4-ethylthiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 642 (M+1).

EXAMPLE 75O

N-Methyl-N-(1-(R)-3-(S)-((4-(2-(3,4-difluorobenzyl)-4-ethylthiazol-5-yl)piperidin-1-yl)methyl)-4-(S)-(3-fluorophenyl)cyclopent-1-yl)-(R)-t-butylglycine tri-hydrochloride salt HPLC/MS (ESI): m/z 642 (M+1).

EXAMPLE 76

N-Methyl-N-(1-(R)-3-(S)-((4-(3-(benzyl)-1-ethyl-(1H)-pyrazol-5-yl)piperidin-1-yl)methyl)-4-(S)-(phenyl)cyclopent-1-yl)-D-valine tri-hydrochloride salt Using essentially the same procedures as in Example 65, Steps A–I, but substituting methyl trans-cinnamate in Step A

EXAMPLE 77

N-Methyl-N-(1-(S)-3-(R)-((4-(3-(benzyl)-1-ethyl-(1H)-pyrazol-5-yl)piperidin-1-yl)methyl)-4-(R)-(3-fluorophenyl)cyclopent-1-yl)-1-valine tri-hydrochloride salt Using essentially the same procedures as in Example 65, Steps D–I, but substituting the faster (−)-enantiomer from Step C in Step D, L-valine in Step E and using the higher $R_f$ isomer from Step F, the title compound was prepared.

HPLC/MS (ESI): m/z 575 (M+1).

EXAMPLE 78

N-Methyl-N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentanecarboxylic Acid tri-hydrochloride salt Step A: 3-(S)-(Benzyloxymethyl)-4-(R)-(3-fluorophenyl)-1-methylenecyclopentane To a solution of 3-(S)-(hydroxymethyl)-4-(R)-(3-fluorophenyl)-1-methylenecyclopentane (3.11 g, 16.5 mmol) from Example 65, Step C in DMF (100 mL) was added benzyl bromide (4.24 g, 24.8 mmol) and then sodium hydride (60% in mineral oil, 0.73 g, 18.2 mmol) portionwise over 5 min. The reaction was stirred at rt for 16 h, then diluted with ether (100 mL) and quenched slowly into aq. sodium bicarbonate (200 mL). The layers were separated and the aqueous was extracted with ether. The organic layers were washed 3× with water, then brine, dried over sodium sulfate and concentrated. The residue (7 g) was purified by FC using 0.5–1% ethyl acetate in hexanes to afford the title compound (2.32 g).

Step B: 3-(S)-(Benzyloxymethyl)-4-(S)-(3-fluorophenyl)cyclopentanone

A solution of 3-(S)-(benzyloxymethyl)-4-(R)-(3-fluorophenyl)-1-methylenecyclopentane (0.77 g, 2.75 mmol) from Step A in methanol (30 mL) was cooled to −70° C. and ozone was bubbled through the solution until a blue color persisted. The excess ozone was removed with a stream of nitrogen and then di methyl sulfide (5 mL) was added and the reaction was allowed to warm to rt over 16 h. Several drops of 2N HCl were added and the solution was stirred for 15 min to convert any methyl ketal to the desired ketone. The methanol was removed in vacuo and the was residue diluted with water, aq. sodium bicarbonate and ether.). The layers were separated and the aqueous was extracted with ether. The organic layers were washed with water, then brine, dried over sodium sulfate and concentrated. The residue was purified by FC using 10% ethyl acetate in hexanes to afford the title compound (0.88 g).

Step C: t-Butyl N-(1-(R and S)-3-(S)-(benzyloxymethyl)-4-(S)-(3-fluorophenyl)cyclopent-1-yl)-1-aminocyclopentanecarboxylate To a mixture of 3-(S)-(benzyloxymethyl)-4-(R)-(3-fluorophenyl)cyclopentanone (365 mg, 1.3 mmol) from Step B and t-butyl 1-aminocyclopentanecarboxylate (349 mg, 1.8 mmol) was added 5 mL of titanium tetra-t-butoxide at rt. After 2 h the reaction was diluted with methanol (2 mL) and sodium borohydride (48 mg, 1.3 mmol) was added. The reaction was stirred for 0.5 h, diluted with water, filtered and concentrated. The residue was taken up in water and extracted twice with ethyl acetate. The organic layers were washed with brine,-dried over sodium sulfate and concentrated. The residue was purified by FC using 1% TEA in 20% ethyl acetate in hexanes to afford the title compound (275 mg) as a mixture of C-1 isomers.

(Note: The reaction is faster using titanium tetra-isopropoxide, especially with more hindered amines, however, trans esterification to the isopropyl ester can occur in the above reaction, especially with less hindered amines.)

Step D: t-Butyl N-methyl-N-(1-(R and S)-3-(S)-(benzyloxymethyl)-4-(S)-(3-fluorophenyl)cyclopent-1-yl)-1-aminocyclopentanecarboxylate To a solution of t-butyl N-(1-(R and S)-3-(S)-(benzyloxymethyl)-4-(S)-(3-fluorophenyl)cyclopent-1-yl)-1-aminocyclopentanecarboxylate (635 mg, 1.4 mmol) from Step C in DCE (25 mL) was added acetic acid (0.117 mL 2.0 mmol), 37% aq. formaldehyde (0.22 mL, 2.7 mmol) and then sodium triacetoxyborohydride (576 mg, 2.7 mmol). After 1.5 h, the reaction was diluted with aq. sodium bicarbonate solution, extracted 3× with DCM, washed with brine, dried over sodium sulfate and concentrated. The residue was purified by FC using 15% ethyl acetate in hexanes to afford the title compound (678 mg) as a mixture of C-1 isomers).

Step E: t-Butyl N-methyl-N-(1-(R and S)-3-(S)-(hydroxymethyl)-4-(S)-(3-fluorophenyl)cyclopent-1-yl)-1-aminocyclopentanecarboxylate A mixture of t-butyl N-(1-(R and S)-3-(S)-(benzyloxymethyl)-4-(S)-(3-fluorophenyl)cyclopent-1-yl)-1-aminocyclopentanecarboxylate (678 mg, 0.1.4 mmol) from Step D, acetic acid (0.080 mL, 0.1.4 mmol) and 20% palladium hydroxide on carbon (200 mg) in methanol (6 mL) was shaken under 50 psi hydrogen for 4 days. The reaction was filtered, washed with methanol and concentrated. The residue was taken up in water and extracted 3× with DCM. The organic layers were washed with brine, dried over sodium sulfate and concentrated. The residue was purified by FC using in 50–60% ethyl acetate in hexanes to afford separation of the C-1 title compound isomers, higher Rf (145 mg) and lower Rf (275 mg).

Step F: t-Butyl N-methyl-N-(1-(R)-3-(S)-(formyl)-4-(S)-(3-fluorophenyl)cyclopent-1-yl)-1-aminocyclopentanecarboxylate Using essentially the same procedure as in Example 65, Step G, t-butyl N-methyl-N-(1-(R)-3-(S)-(hydroxymethyl)-4-(S)-(3-fluorophenyl)cyclopent-1-yl)-1-aminocyclopentanecarboxylate (100 mg) from Step E (higher Rf product) was converted to the title compound (100 mg crude).

Step G: t-Butyl N-methyl-N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentanecarboxylate Using essentially the same procedure as in Example 65, Step H, t-butyl N-methyl-N-(1-(R)-3-(S)-(formyl)-4-(S)-(3-fluorophenyl)cyclopent-1-yl)-1-aminocyclopentanecarboxylate (50 mg) from Step F (derived from the higher Rf product from Step E) was converted to the title compound (113 mg).

Step H: N-Methyl-N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentanecarboxylic Acid tri-hydrochloric acid salt Using essentially the same procedure as in Example 65, Step I, t-butyl N-methyl-N-(1-(R)-3-(S)-((4-(3-(benzyl)-1- ethyl-(1H)-pyrazol-5-yl)piperidin-1-yl)methyl)-4-(S)-(3-fluorophenyl)cyclopent-1-yl)-1-aminocyclopentanecarboxylate (113 mg) from Step G (derived from the higher Rf product from Step E) was converted to the title compound (30 mg) as a single isomer. HPLC/MS (ESI): m/z 587.5 (M+1), $R_t$=1.51 min.

EXAMPLE 79

N-Methyl-N-(1-(S)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, but substituting lower $R_f$ isomer from Step E, the title compound was prepared. HPLC/MS (ESI): m/z 587.5 (M+1), $R_t$=1.53 min.

EXAMPLE 80

N-Methyl-N-(1-(R)-3-(S)-((4-(3-(benzyl)-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, using the higher $R_f$ isomer from Step E, and substituting (4-(3-(benzyl)-(1H)-pyrazol-5-yl)piperidine in Step G, the title compound was prepared.

HPLC/MS (ESI): m/z 559.5 (M+1), $R_t$=1.46 min.

EXAMPLE 81

N-Methyl-N-(1-(S)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, using the lower $R_f$ isomer from Step E, and substituting (4-(3-(benzyl)-(1H)-pyrazol-5-yl)piperidine in Step G, the title compound was prepared.

HPLC/MS (ESI): m/z 559.5 (M+1), $R_t$=1.46 min.

EXAMPLE 82

N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, skipping Step D, using the higher $R_f$ isomer from Step E, the title compound was prepared. HPLC/MS (ESI): m/z 573.5 (M+1), $R_t$=1.58 min.

EXAMPLE 83

N-(1-(S)-3-(S)-((4-(3-(benzyl)-1-ethyl-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, skipping Step D, using the lower $R_f$ isomer from Step E, the title compound was prepared. HPLC/MS (ESI): m/z 573.5 (M+1), $R_t$=1.58 min.

EXAMPLE 84

N-(1-(S or R)-3-(R)-((4-(3-(benzyl)-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, skipping Step D, using the higher $R_f$ isomer from Step E, and substituting (4-(3-(benzyl)-(1H)-pyrazol-5-yl)piperidine in Step G, the title compound was prepared.

HPLC/MS (ESI): m/z 545.5 (M+1), $R_t$=1.55 min.

EXAMPLE 85

N-(1-(R or S)-3-(S)-((4-(3-(benzyl)-(1H)-pyrazol-5-yl)piperidin-1-yl)methyl)-4-(S)-(3-fluorophenyl)cyclopent-1-yl)-1-aminocyclopentane Carboxylic Acid tri-hydrochloride salt Using essentially the same procedures as in Example 78, skipping Step D, using the lower $R_f$ isomer from Step E, and substituting (4-(3-(benzyl)-(1H)-pyrazol-5-yl)piperidine in Step G, the title compound was prepared.

HPLC/MS (ESI): m/z 545.5 (M+1), $R_t$=1.64 min.

EXAMPLE 86

N-Methyl-N-(1-(R)-3-(S)-((4-(3-(benzyl)-1-ethyl-(1H)-pyrazol-5-yl)piperidin-1-yl)methyl)-4-(S)-(3-fluorophenyl)cyclopent-1-yl)-α,α-dimethylglycine tri-hydrochloride salt Using essentially the same procedures as in Example 78, but substituting α,α-dimethylglycine t-butyl ester in Step C and using the higher Rf isomer from Step E, the title compound was prepared.

HPLC/MS (ESI): m/z 561.5 (M+1), $R_t$=1.46 min.

EXAMPLE 87

N-Methyl-N-(1-(S)-3-(S)-((4-(3-(benzyl)-1-ethyl-(1H)-pyrazol-5-yl)piperidin-1-yl)methyl)-4-(S)-(3-fluorophenyl)cyclopent-1-yl)-α,α-dimethylglycine tri-hydrochloride salt Using essentially the same procedures as in Example 78, but substituting α,α-dimethylglycine t-butyl ester in Step C and using the lower Rf isomer from Step E, the title compound was prepared.

HPLC/MS (ESI): m/z 561.5 (M+1), $R_t$=1.46 min.

EXAMPLE 88

N-Methyl-N-(1-(R and S)-3-(S)-((4-(3-(benzyl)-1-ethyl-(1H)-pyrazol-5-yl)piperidin-1-yl)methyl)-4-(S)-(3-fluorophenyl)cyclopent-1-yl)-D and L-α-methylleucine tri-hydrochloride salt Using essentially the same procedures as in Example 78, but substituting D/L-α-methylleucine t-butyl ester in Step C, all four of the title compound isomers were prepared.

HPLC/MS (ESI): m/z 589.5 (M+1), $R_t$=1.64 min.
HPLC/MS (ESI): m/z 589.6 (M+1), $R_t$=1.68 min.
HPLC/MS (ESI): m/z 589.5 (M+1), $R_t$=1.73 min.
HPLC/MS (ESI): m/z 589.5 (M+1), $R_t$=1.62 min.

EXAMPLE 89

N-(1-(R and S)-3-(S)-((4-(3-(benzyl)-1-ethyl-(1H)-pyrazol-5-yl)piperidin-1-yl)methyl)-4-(S)-(3-fluorophenyl)cyclopent-1-yl)-D and L-α-methylleucine tri-hydrochloride salt Using essentially the same procedures as in Example 78, but substituting D/L-α-methylleucine t-butyl ester in Step C and skipping Step D, all four of the title compound isomers were prepared as single diastereomers at either Step D or E, but the stereochemical assignments were not made.

HPLC/MS (ESI): m/z 575.5 (M+1), $R_t$=1.52 min.
HPLC/MS (ESI): m/z 575.5 (M+1), $R_t$=1.53 min.
HPLC/MS (ESI): m/z 575.5 (M+1), $R_t$=1.55 min.
HPLC/MS (ESI): m/z 575.5 (M+1), $R_t$=1.58 min.

EXAMPLE 90

N-Isopropyl-N-(1-(R)-3-(S)-((4-(3-(phenyl)prop-1-yl)piperidin-1-yl)methyl)-4-(S)-(3-fluorophenyl)cyclopent-1-yl)glycine tri-hydrochloride salt Using essentially the same procedures as in Example 46, but substituting acetone in Step B and using the higher isomer from Step B, the title compound was prepared.
HPLC/MS (ESI): m/z 495 (M+1).

EXAMPLE 91

N-Isopropyl-N-(1-(S)-3-(S)-((4-(3-(phenyl)prop-1-yl)piperidin-1-yl)methyl)-4-(S)-(3-fluorophenyl)cyclopent-1-yl)glycine tri-hydrochloride salt Using essentially the same procedures as in Example 46, but substituting acetone in Step B and using the lower isomer from Step B, the title compound was prepared.
HPLC/MS (ESI): m/z 495 (M+1).

EXAMPLE 92

N-Methyl-N-(1-(R)-3-(S)-((4-(3,3-difluoro-3-(4-fluorophenyl)prop-1-yl)piperidin-1-yl)methyl)-4-(S)-(3-fluorophenyl)cyclopent-1-yl)-D-valine tri-hydrochloride salt Step A: N-Methyl-N-(1-(R)-3-(S)-((4-(3,3-difluoro-3-(4-fluorophenyl)prop-1-yl)piperidin-1-yl)methyl)-4-(S)-(3-fluorophenyl)cyclopent-1-yl)-D-valine benzyl ester The title compound was prepared using procedures analogous to those described in EXAMPLE 65, Steps D–H, substituting D-valine benzyl ester for D-valine t-butyl ester in Step D and using 4-(3,3-difluoro-3-(4-fluorophenyl)propyl)piperdine (from PROCEDURE 17) in Step H. For the title compound:
ESI-MS 653 (M+H); HPLC A: 1.98 min.

Step B: N-Methyl-N-(1-(R)-3-(S)-((4-(3,3-difluoro-3-(4-fluorophenyl)prop-1-yl)piperidin-1-yl)methyl)-4-(S)-(3-fluorophenyl)cyclopent-1-yl)-D-valine tri-hydrochloride salt N-Methyl-N-(1-(R)-3-(S)-((4-(3,3-difluoro-3-(4-fluorophenyl)prop-1-yl)piperidin-1-yl)methyl)-4-(S)-(3-fluorophenyl)cyclopent-1-yl)-D-valine (40 mg, 0.061 mmol) from EXAMPLE 92, Step A, in 95% ethanol (4.0 ml) was hydrogenated at atmospheric pressure using 10% palladium on carbon (10 mg). After 2 h, the mixture was filtered, the catalyst was washed with 95% ethanol, and the filtrate was evaporated. The crude product was purified by flash column chromatography on silica gel packed in $CH_2Cl_2$. Elution with 95:5:1 v/v/v $CH_2Cl_2/CH_3OH/NH_4OH$ followed by 90:10:2 v/v/v $CH_2Cl_2/CH_3OH/NH_4OH$ gave 28 mg of the title compound:
ESI-MS 563 (M+H); HPLC A: 1.69 min.

EXAMPLE 93

N-Methyl-N-(1-(R)-3-(S)-((4-(3,3-difluoro-3-(6-methylpyridazin-3-yl)prop-1-yl)piperidin-1-yl)methyl)-4-(S)-(3-fluorophenyl)cyclopent-1-yl)-D-valine tri-hydrochloride salt The title compound was prepared using procedures analogous to those described in EXAMPLE 92, using 4-(3,3-difluoro-3-(6-methylpyridazin-3-yl)propyl)piperidine (from PROCEDURE 36). For the title compound:
ESI-MS 561 (M+H); HPLC A: 1.30 min.

EXAMPLE 94

N-Methyl-N-(1-(R)-3-(S)-((4-(3,3-difluoro-3-(4-trifluoromethyl-2-pyridyl)prop-1-yl)piperidin-1-yl)methyl)-4-(S)-(3-fluorophenyl)cyclopent-1-yl)-D-valine tri-hydrochloride salt The title compound was prepared using procedures analogous to those described in EXAMPLE 92, using 4-(3,3-difluoro-3-(5-(trifluoromethyl)pyrid-2-yl)propyl)piperidine (from PROCEDURE 37). For the title compound:
ESI-MS 614 (M+H); HPLC A: 1.68 min.

EXAMPLE 95

N-Methyl-N-(1-(R)-3-(S)-((4-(3,3-difluoro-3-(2-pyridyl)prop-1-yl)piperidin-1-yl)methyl)-4-(S)-(3-fluorophenyl)cyclopent-1-yl)-D-valine tri-hydrochloride salt The title compound was prepared using procedures analogous to those described in EXAMPLE 92, using 4-(3,3-difluoro-3-(3-pyridyl)propyl)piperidine (from PROCEDURE 38). For the title compound: ESI-MS 546 (M+H); HPLC A: 1.18 min.

EXAMPLE 96

N-Methyl-N-(1-(R)-3-(S)-((4-(3,3-difluoro-3-(1-methyl-pyrazol-4-yl)prop-1-yl)piperidin-1-yl)methyl)-4-(S)-(3-fluorophenyl)cyclopent-1-yl)-D-valine tri-hydrochloride salt The title compound was prepared using procedures analogous to those described in EXAMPLE 92, using 4-(3,3-difluoro-3-(1-methylpyrazol4-yl)propyl)piperidine (from PROCEDURE 39). For the title compound:
ESI-MS 549 (M+H); HPLC A: 1.36 min.

EXAMPLE 97

Using essentially the same procedure as in Example 35, Steps E to H, but substituting the appropriate L- and/or D-aminoacid t-butyl ester in Step E and the appropriate piperidine in Step G, the following compounds A–F were prepared.

EXAMPLE 97A

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-cyclohexylglycine di-hydrochloride salt HPLC/MS (ESI): m/z 603 (M+1).

EXAMPLE 97B

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-isoleucine di-hydrochloride salt HPLC/MS (ESI): m/z 577 (M+1).

EXAMPLE 97C

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-cyclobutylmethylglycine di-hydrochloride salt HPLC/MS (ESI): m/z 589 (M+1).

EXAMPLE 97D

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-valine di-hydrochloride salt HPLC/MS (ESI): m/z 563 (M+1).

EXAMPLE 97E

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-alloleucine Di-Hydrochloride salt HPLC/MS (ESI): m/z 577 (M+1).

EXAMPLE 97F

N-(1-(R)-3-(S)-((4-(2-(4-Fluorophenylsulfonyl)eth-1-yl)piperidin-1-yl)methyl)-4-(S)-(3-fluorophenyl)cyclopent-1-yl)-D-leucine Di-Hydrochloride salt HPLC/MS (ESI): m/z 577 (M+1).

EXAMPLE 98

Using essentially the same procedure as in Example 35, Steps E to H, but substituting the appropriate L- and/or D-aminoacid t-butyl ester in Step E, the following compounds A–E were prepared.

EXAMPLE 98A

N-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-D-cyclobutylalanine tri-hydrochloride salt HPLC/MS (ESI): m/z 587 (M+1).

EXAMPLE 98B

N-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-D-alloleucine tri-hydrochloride salt HPLC/MS (ESI): m/z 575 (M+1).

EXAMPLE 98C

N-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-D-leucine tri-hydrochloride salt HPLC/MS (ESI): m/z 575 (M+1).

EXAMPLE 98D

N-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-D-valine tri-hydrochloride salt HPLC/MS (ESI): m/z 561 (M+1).

EXAMPLE 98E

N-(1-(R)-3-(S)-((4-(3-Benzyl-1-ethyl-(1H)-pyrazol-5-yl)piperidin-1-yl)methyl)-4-(S)-(3-fluorophenyl)cyclopent-1-yl)-D-isoleucine tri-hydrochloride salt HPLC/MS (ESI): m/z 575 (M+1).

EXAMPLE 99

N-Ethyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedure as in Example 65, Steps F to H, but substituting acetaldehyde in Step F, the title compound was prepared.

HPLC/MS (ESI): m/z 589 (M+1).

EXAMPLE 100

N-Ethyl-N-(1-(R)-3-(S)-((4-(3-(4-ethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedure as in Example 65, Steps F to H, but substituting acetaldehyde in Step F, the title compound was prepared.

HPLC/MS (ESI): m/z 633 (M+1).

EXAMPLE 101

N-Ethyl-N-(1-(R)-3-(S)-((4-(3-(3,4-dimethoxybenzyl)-1-ethyl-(1H)-pyrazol-5-yl)piperidin-1-yl)methyl)-4-(S)-(3-fluorophenyl)cyclopent-1-yl)-D-valine tri-hydrochloride salt Using essentially the same procedure as in Example 65, Steps F to H, but substituting acetaldehyde in Step F, the title compound was prepared.

HPLC/MS (ESI): m/z 649 (M+1).

EXAMPLE 102

N-Ethyl-N-(1-(R)-3-(S)-((4-(1,3-diethyl-4-methyl-(1H)-pyrazol-5-yl)piperidin-1-yl)methyl)-4-(S)-(3-fluorophenyl)cyclopent-1-yl)-D-valine tri-hydrochloride salt Using essentially the same procedure as in Example 65, Steps F to H, but substituting acetaldehyde in Step F, the title compound was prepared.

HPLC/MS (ESI): m/z 541 (M+1).

EXAMPLE 103

N-Methyl-N-(1-(R)-3-(S)-(1-(R and S)-(4-(3-benzyl-1-ethyl-(1H)-pyrazol-5-yl)piperidin-1-yl)eth-1-yl)-4-(S)-(3-fluorophenyl)cyclopent-1-yl)-D-valine tri-hydrochloride salt Using essentially the same procedures as Example 65, Step G-I, but substituting, N-methyl-N-(1-(R)-3-(S)-(1-(R and S)-hydroxyeth-1-yl)-4-(S)-(3-fluorophenyl)cyclopent-1-yl)-D-valine t-butyl ester (obtained by addition at 0° C. in THF for 1 h of methyl magnesium bromide to the aldehyde from Example 65, Step G), the title compounds were obtained as a mixture of isomers.

HPLC/MS (ESI): m/z 589 (M+1).

EXAMPLE 104

N-Methyl -N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine Step A: (1RS)-1-(3-Fluorophenyl)prop-2-en-1-yl acetate

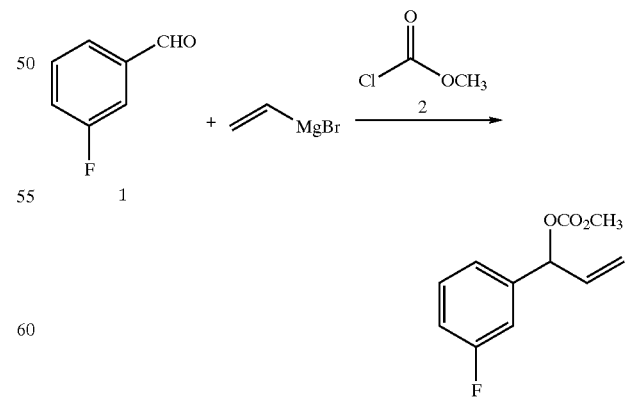

A 100-L flask equipped with mechanic stirrer, thermocouple, nitrogen inlet, and addition funnel was charged with nitrogen and then with toluene (60 L) and 3-fluorobenzaldehyde (1, 4 Kg, 97%, 31.2 mol). After the solution was cooled to −5° C., vinyl Grignard (20.6 L, 1.6 M in THF, 32.8 mol) was added dropwise over a period of 1.5 h while maintaining the temperature below 0° C. The reaction was stirred for an additional 60 min at −5 to 0° C., at which point HPLC assay indicated ~0.4 area % of starting material vs. product. Methyl chloroformate (2, 2.74 L, d=1.223, 35.4 mol) was added via an addition funnel over 30 min while maintaining the temperature below 0° C. After stirring for 60 min, 0.5 N HCl (40 L) was added, while maintaining the temperature <20° C. The organic layer was separated, and filtered through silica gel (4 Kg). The filtrates containing the product was concentrated to remove solvents. The weight of the concentrated material was 8.88 Kg. $^1$H NMR of the solution showed the material was 56.7 wt %, yielding 5.01 Kg of allyl carbonate 3 as a light yellow oil.

$^1$H-NMR(400 MHz, CDCl$_3$) δ7.34 (q, 1H), 7.16 (d, 1H), 7.09 (d, 1H), 7.02 (m, 1H), 6.02 (m, 2H), 5.36 (m, 2H), 3.85 (s, 3H).

$^{13}$C-NMR (400 MHz, CDCl$_3$) δ164.1, 161.6, 154.9, 140.8, 135.2, 103.2, 122.5, 118.1. 114.6 (dd), 79.3, 54.9.

Step B: Sodium dimethyl malonate

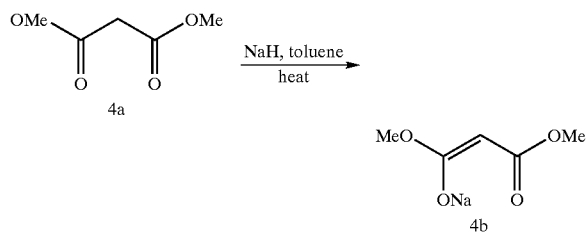

A 100 L round bottom flask was charged with dimethyl malonate (4a, 4.25 kg, 31.52 mol) and toluene (50 L), and was then flushed with nitrogen followed by the addition of sodium hydride (60% dispersion in mineral oil, 1.197 Kg, 29.94 mol) in roughly four equal portions over 20 min. The resulting mixture was heated at 70° C. for 45 min and then cooled to 5° C. The thick slurry was filtered and flushed with heptane to give the product 4b as a white fluffy solid (6.063 Kg, 81% pure, remainder toluene, quantitative yield).

Step C: (1S,2S)-N-N'-Dipicolinoyl-1,2-diaminocyclohexane

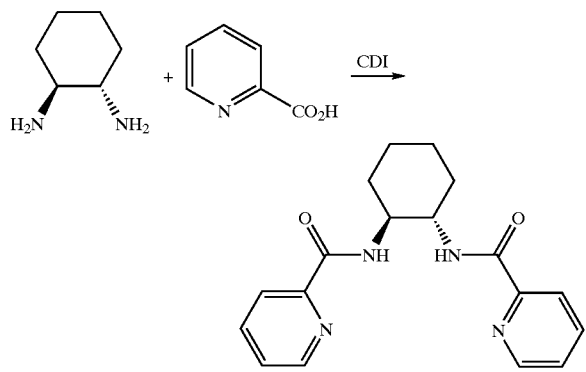

A 22 L flask was charged with 1,1'-carbonyldiimidazole (1.7 Kg, 10.48 mol) and THF (7.5 L). Solid picolinic acid (1.36 Kg, 11 mol) was added to the slurry at room temperature. The reaction was endothermic causing the mixture to cool from 18° C. to 12° C. The reaction mixture was then warmed to 18–19° C. The resulting clear solution was stirred for 1 h and molten (1S,2S)-(+)-1,2-diaminocyclohexane (0.5 Kg, 4.38 mol) was added while keeping the temperature below 50° C. The beaker and funnel were rinsed with 2.5 L of THF. The reaction was stirred at rt for 15 h. Water (0.5 L) was added to the thin slurry giving a clear solution and the reaction mixture was stirred for 1 h. The reaction mixture was concentrated to an orange semi-solid by rotary evaporation. The reaction product was slurried in 5 L of ethanol and concentrated by rotary evaporation. The reaction product was dissolved in ethanol (5 L) at 64–65° C. The solution was allowed to cool. The solution turned hazy around 58° C. At this temperature, the hazy solution was seeded (10 g) and cooled to −8° C. The resulting white crystals were isolated by filtration on a sintered glass funnel, washed with 5 L of cold ethanol (−8 to −10° C.), dried under house vacuum with nitrogen sweep, and then dried in a vacuum oven (35° C.). This resulted in the isolation of 1.23 Kg (86.3%) of white crystalline solid.

$^1$H NMR (400 MHz, CDCl$_3$) δ8.50–8.49 (m, 2H), 8.23 (d, J=6.47 Hz, 2H), 8.02–7.99 (m, 2H), 7.69–7.64 (m, 2H), 7.29–7.24 (m, 2H), 4.03 (bs, 2H), 2.18–2.15 (m, 2H), 1.79 (bs, 2H), 1.42–1.41 (m, 4H).

$^{13}$C NMR (CDCl$_3$) δ164.5, 149.8, 148.1, 136.9, 125.8, 122.0, 53.2, 32.6, 24.8

Step D: Dimethyl 2-(1-(R)-(3-fluorophenyl)prop-2-en-1-yl) malonate

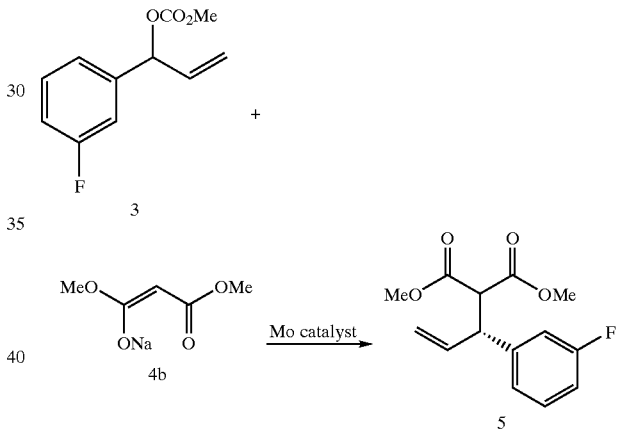

A 2 L round bottom flask equipped with a mechanical stirrer, vacuum inlet, argon inlet and a septa was charged with MO(CO)$_6$ (218.8 g, 0.828 mol; 0.1 eq.) and (1S,2S)-N,N'-dipicolinoyl-1,2-diaminocyclohexane (402 g, 1.242 mol; 0.15 eq.), and then evacuated and back filled with argon (3 cycles). To this mixture was added toluene (4.36 L) and the resulting solution was evacuated and back filled with argon (3 cycles). The solution was heated to 85° C. for 4.0 h. Separately, a 50 L flask was charged with sodium dimethyl malonate 4b (2.36 kg; 1.5 eq) and toluene (30.6 L). The heterogeneous solution was heated to 50–55° C. followed by the addition of the carbonate 3 (87.1%; 2 kg; 8.28 mol; 1 eq.) in toluene (3 L) and the molybdenum/ligand solution. The mixture was heated at 85° C. for 15 h, and then cooled to 25–30° C. Water (20 L) was added to the mixture, and the resulting mixture was transferred to an extractor. The organic layer was separated, concentrated to approximately 5 L, filtered through SiO$_2$, concentrated under vacuum, to afford an oil containing 2.077 Kg (94.3% yield, ee=96.1%) of the desired product. Ratio of regioisomers was 19:1 trans to cis.

$^1$H-NMR (400 MHz, CDCl$_3$) δ7.28 (m, 1H), 7.02 (d, 1H, J=7.8 Hz), 6.95(m, 2H), 6.71 (m, 1H), 5.14 (dd, 2H), 4.12 (t,

1H, J=8.3 Hz)), 3.85 (d, 1H, J=1.0 Hz), 3.76 (s, 3H), 3.54 (s, 3H). $^{13}$C-NMR (400 MHz, CDCl$_3$) δ167.9, 167.6, 164.0, 161.6, 142.6, 137.1, 130.1, 123.6, 117.2, 114.9(d), 114.1 (d), 57.1, 52.6, 49.3

Step E: (3S)-3-(3-Fluorophenyl)pent-4-enoic acid

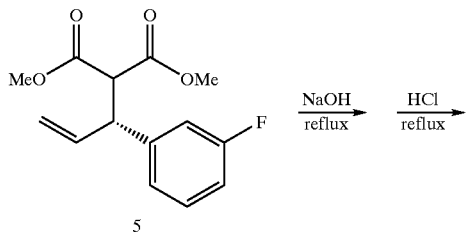

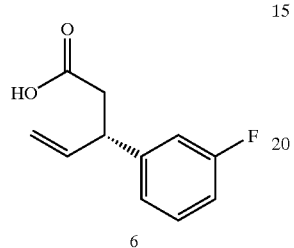

A solution of dimethyl 2-(1-(R)-(3-fluorophenyl)prop-2-en-1-yl)malonate e 5 (2.256 kg, 8.47 mol; 36.1% by wt in MTBE, total wt 6.251 kg) was charged to a 50 L, 4-necked round bottom flask, equipped with mechanical stirrer, stopper, thermocouple, and batch concentrator. The solution was concentrated at 29" vacuum until no more distillate was obtained at an internal temperature of 15° C. To the orange oil was added water (11 L) and 5 N NaOH (5 L), and the resulting mixture was refluxed for 30 min. The mixture was allowed to cool to 18–23° C. and the volatiles were removed by distillation at atmospheric pressure. The distillation was stopped when the level of methanol reached 3 mole percent. A total of 6.7 L of distillate was collected. The pH of the aqueous phase was adjusted to 0.81 using conc. HCl (1.9 L). The mixture was refluxed for 12 h. The reaction mixture was cooled to 46° C. and extracted twice with toluene (once with 5.5 L and once with 3.5 L). The toluene extracts were combined and extracted once with 5% sodium chloride (aq) (3 L). The toluene solution was dried with sodium sulfate (1 kg) and filtered. The solution was assayed by HPLC. The yield was 1.429 kg (86.9%).

$^1$H NMR (CDCl$_3$) δ2.77 (m, 2H), 3.87 (m, 1H), 5.12 (m, 2H), 5.96 (m, 1H), 6.93 (m, 2H), 7.01 (m, 1H), 7.28

A 72 L, 4-necked flask, equipped with mechanical stirrer, thermocouple, reflux condenser with nitrogen inlet, addition funnel, and steam pot, was charged with a toluene solution of the monoacid 6 (10.6 kg of solution, 1.3 kg of monoacid, 6.69 mol). To the solution was added acetonitrile (29.3 L), and the resulting mixture was heated to reflux. When the solution began to reflux (about 78° C.), (S)-α-methylbenzylamine (779 g) was added over 5 min. The solution was allowed to cool. At 64° C., the salt began to crystallize. At 58° C., ice bath cooling was applied. The temperature dropped to 10° C., and the mixture was stirred at that temperature for 45 min. The mixture was filtered, and the cake was washed with an ice-cold 3:1 mixture of acetonitrile and toluene (9 L). The monoacid salt wet cake was placed under positive nitrogen pressure using a plastic bag over the filter pot.

A 50 L extractor was charged with the monoacid salt wet cake (13.91 moles). To the extractor were added water (20 L), 50% NaOH (820 mL), and methylene chloride (12 L). The contents were mixed thoroughly, allowed to settle, and the layers were separated. The aqueous phase was extracted again with methylene chloride (12 L). To the aqueous phase was added toluene (19 L) and conc. HCl (1.5 L). The layers were separated, and the aqueous phase was extracted again with toluene (4 L). The toluene extracts were combined and extracted with 5% sodium chloride solution (10 L). The toluene layer was dried with sodium sulfate (1 kg). The mixture was filtered, the cake was washed with toluene (2 L), and the combined filtrate and wash was assayed by HPLC. The yield was 2522 g (93.4% overall for salt formation and salt break).

Step F: Methyl (5S)-5-(3-fluorophenyl)-3-oxohept-6-enoate

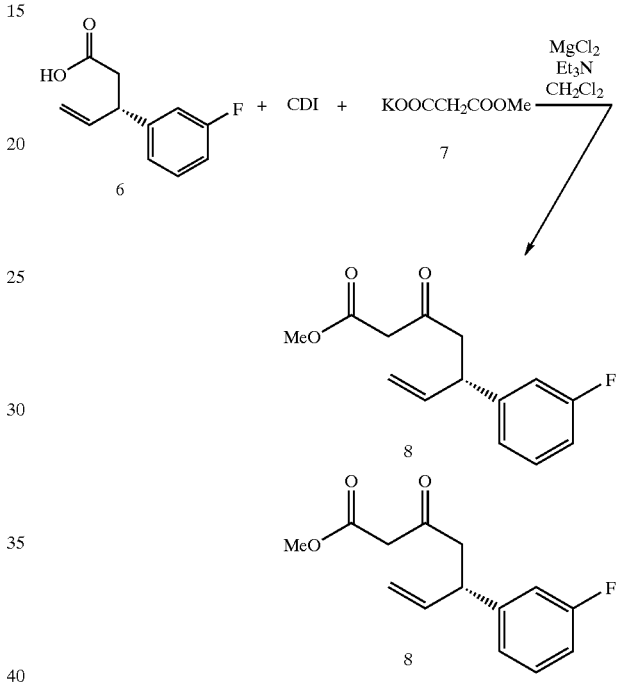

The toluene solution of (3S)-3-(3-fluorophenyl)pent-4-enoic acid from Step E (11,230 g of a solution containing 1158 g of acid and 1043 g of a second solution containing 102 g of acid) was concentrated to an oil using a Buchi rotary evaporator. The oil was dissolved in methylene chloride (0.5 L). The KF was 36 μg/mL. A 50 L, 4-necked round bottom flask, equipped with mechanical stirrer, thermocouple, reflux condenser with nitrogen inlet, addition funnel, and steam pot, was charged sequentially with methylene chloride (5.5 L), monomethylmalonate potassium salt (7, 1.52 kg), and magnesium chloride (618 g). The mixture was cooled to 0–5° C. Triethylamine (2.71 L) was charged to the addition funnel and added to the mixture over 2–5 min. The addition was slightly exothermic; the temperature rose 2° C. The mixture was aged for 30 min at 0–5° C., then warmed to 20° C. and aged for 30 min. A 22 L, 4-necked round bottom flask, equipped with mechanical stirrer, thermocouple, nitrogen inlet, dry ice condenser, and addition funnel, was charged with methylene chloride (4 L) and 1,1'-carbonyldiimidazole (1.10 kg). The monoacid solution from above was charged to the addition funnel and added to the 22 L flask over 30–40 min to give a solution. Gas (CO$_2$) vigorously evolved, which entrained methylene chloride, hence the need for the dry ice condenser. The resulting solution of activated monoacid was pumped into the 50 L flask. The dry ice condenser was moved from the 22 L flask to the top of the water condenser on the 50 L flask. The reaction mixture was heated to 41° C. During the addition of activated monoacid, the temperature rose from 20.1° C. to 20.7° C. The temperature continued to slowly rise to 28° C., at which point steam was intermittently applied to the 50 L flask. The progress of the reaction was followed by HPLC. When the reaction was complete (about 1.5 h), the mixture was cooled to 0–5° C. To the cold mixture was added cold 2 N HCl (19 L). The pH of the aqueous phase was 2.9. The addition was exothermic; the temperature increased to 20° C. The two phase mixture was transferred to a 50 L extractor, and the layers were separated. The aqueous phase was extracted with methylene chloride (3 L). The methylene chloride extracts were combined and dried with anhydrous sodium sulfate (1 kg). The mixture was filtered and the cake was washed with methylene chloride (1 L). The filtrate and washes were combined. Final yield was >95%.

$^1$H NMR (CD$_3$Cl) δ2.98 (m, 2H), 3.39 (d, J=1.2 Hz, 2H), 3.70 (s, 3H), 3.94 (m, 1H), 5.06 (m, 2H), 5.93, (m, 1H), 6.90 (m, 1H), 6.92 (m, 1H), 6.99 (m, 1H), 7.26 (m, 1H). $^{13}$C NMR (CD$_3$Cl) δ43.6, 47.8, 49.3, 52.2, 113.5 (d, J=20.9 Hz), 114.4 (d, J=21.7 Hz), 115.3, 123.3 (d, J=3.2 Hz), 130.0 (d, J=8.0 Hz), 139.5, 145.0 (d, J=7.2 Hz), 162.8 (d, J=Hz), 167.2, 200.2.

Step G: Methyl (5S)-5-(3-fluorophenyl)-2-diazo-3-oxohept-6-enoate

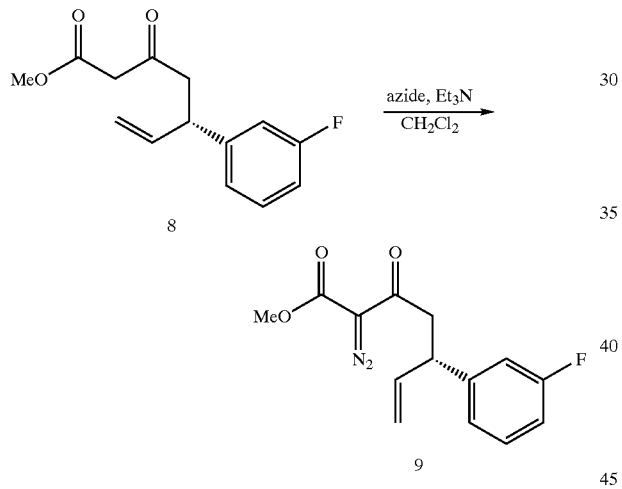

A 50 L, 4-necked round bottom flask, equipped with mechanical stirrer, thermocouple, addition funnel, nitrogen inlet, and steam pot, was charged with a solution of methyl (5S)-5-(3-fluorophenyl)-3-oxohept-6-enoate 8 (8823 g of solution, 1300 g of ketoester in 1,2-dichloroethane). Additional 1,2-dichloroethane (7 L) was charged to the flask, followed by 4-acetamidobenzenesulfonyl azide (1.25 kg). The solution was heated from about 18° C. to 21° C. with steam. (Note: the dissolution of azide was endothermic.) Triethylamine (2.17 L) was added over 40 min with water bath cooling to maintain a temperature of 19–23° C. The reaction was stirred at 18–23° C. for approximately 9 h. The reaction was mildly exothermic. The reagent product, 4-acetamidobenzenesulfonyl amide, began to precipitate from the reaction during the addition of triethylamine and eventually formed a thick slurry. The reaction was followed by HPLC and was judged complete when the amount of starting material was <0.5%. When completed, the reaction mixture was filtered, and the cake was washed four times with 1,2-dichloroethane (3×2 L displacement washes, 1×1 L slurry wash). The filtrate and washes were combined and extracted with cold (5–10° C.) 2N HCl (7.4 L). The extraction was exothermic and was done in a 50 L extractor with cooling to maintain a temperature of 20–22° C. The pH of the aqueous phase was 1.0. The organic layer was extracted twice with water (2×7 L). The organic extract was charged to a 50 L, 4-necked round bottom flask, equipped with mechanical stirrer, thermocouple, nitrogen inlet, and stopper. The solution was dried for 4 h with sodium sulfate (1 kg). The organic solution was passed through a 5 μ inline filter. The final weight of organic solution was 25.6 kg. Final yield of 9 was >95%.

$^1$H NMR (CDCl$_3$) δ3.32 (d, J=7.6 Hz, 2H), 3.84 (s, 3H), 4.02 (m, 1H), 5.08 (m, 2H), 5.97 (m, 1H), 6.90 (m, 1H), 6.96 (m, 1H), 7.04 (m, 1H), 7.26 (m, 1H).

Step G: (1S,5R)-4-(S)-(3-Fluorophenyl)-1-methoxycarbonyl-2-oxo[3,10]bicyclohexane (10) and (1R,5S)-4(S)-(3-Fluorophenyl)-1-methoxycarbonyl-2-oxo[3.1.0]bicyclohexane(10')

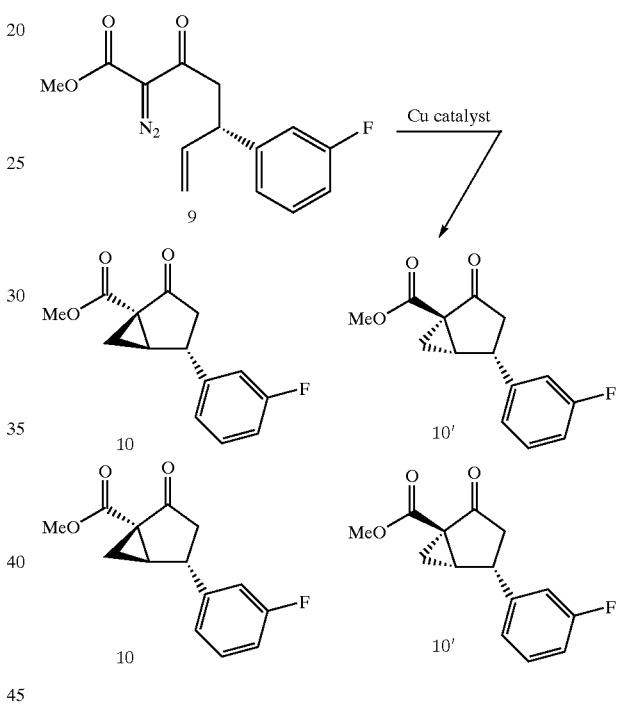

A 100 L flask equipped with a 5 L addition funnel, reflux condenser, temperature probe, stopper, and air-driven overhead stirrer was charged with 1,2-dichloroethane (11 L) and (CH$_3$CN)$_4$CuPF$_6$ (55.41 g, 0.149 mol). The temperature-controlled water bath was set to 77° C., and the starting methyl (5S)-5-(3-fluorophenyl)-2-diazo-3-oxohept-6-enoate 9 (1373 g in DCE solution, 4.97 mol) was added to the reaction vessel over a period of 8 h, with the reaction temperature maintaining at 77–81° C. After finishing addition, reaction was stirred for 1 additional h, steam was turned off, and ice was added to the water bath. After cooling for 2 h the flask contents were pumped into a 100 L extractor, and the reaction flask was rinsed with 2 L methylene chloride. Brine (30 L) was pumped into the extractor and the mixture stirred for 10 min, then settled for 30 min. The layers were separated and the organic layers were dried over magnesium sulfate in a cold room overnight. The mixture was filtered and the organic layers were concentrated, yielding 96.5% of the trans and cis mixture 10 and 10', 77.5% of trans only (4.47:1 trans:cis).

$^1$H-NMR (400 MHz, CDCl$_3$) δ7.31 (m, 2H), 6.95 (m, 2H), 3.82 (s, 3H), 3.49 (d, 1H, J=8.5 Hz), 2.76 (m, 1H), 2.64(dd, 1H, J=8.2 Hz), 2.28 (d, 1H, J=19.1 Hz), 2.15 (m, 1H), 1.54 (t, 1H, J=5.3 Hz). $^{13}$C-NMR (400 MHz, CDCl$_3$) δ205.4, 168.3, 163.1 (d, J=2.4 Hz), 147.1, 130.8, 122.0, 114.1(d), 113.6(d), 52.6, 42.4, 39.1,39.0, 38.0, 21.5.

Step H: (+)-trans-3-Hydroxymethyl-4-(3-fluorophenyl) cyclopentanone

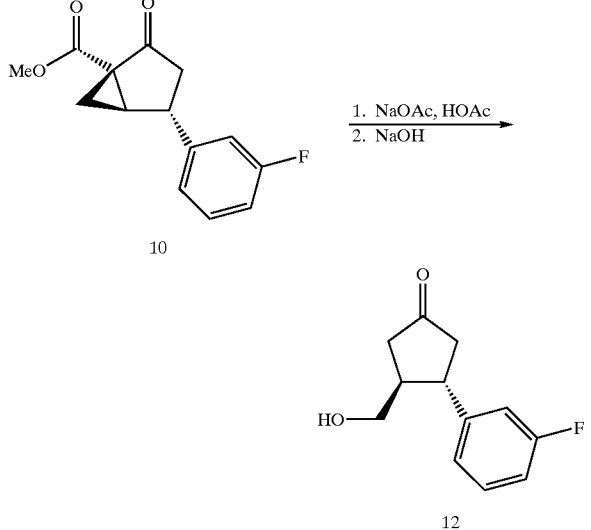

A 72 L round bottom flask equipped with a temperature probe, overhead stirrer, nitrogen and vacuum inlet was charged with the mixture of (1S,5R)-4-(S)-(3-fluorophenyl)-1-methoxycarbonyl-2-oxo[3.1.0]bicyclohexane (10) and (1R,5S)-4-(S)-(3-fluorophenyl)-1-methoxycarbonyl-2-oxo [3.1.0]bicyclohexane (10') (6.45 Kg of 10 starting material, 3.4 mol) from Step G, sodium acetate (2.77 Kg, 33.8 mol), and acetic acid (14 L, 244 mol). The mixture was evacuated and back filled with nitrogen (3 cycles) and heated to 105° C. for 15 h followed by distillation of 12–13 L of acetic acid. The mixture is cooled to 50° C. followed by the addition of DMF (15 L). To the solution was added 3N NaOH until pH=>12 (keeping solution temp <35° C.) followed by heating to 70° C. for 30 min. The solution was cooled to room temperature and transferred into an extractor. To the extractor was added 30 L of MTBE, and the aqueous layer separated and back extracted with 30 L of MTBE. The organic layers were combined, washed with 30 L of 10% sodium chloride in water, dried over magnesium sulfate, filtered, and concentrated to yield 2.23 Kg of material containing 698 g of product 12 (98% yield based on 10) with the remainder MTBE. This material was identical that that made in Example 65, Step D.

$^1$H NMR (CDCl$_3$) δ2.3–2.45 (m, 2H), 2.5 (m, 1H), 2.61 and 2.77 (dABq, 2H), 2,28 (ddd, 1H), 3.61 and 3.75 (dABq, 2H), 6.9–7.0 (m, 2H), 7.06 (d, 1H), 7.3–7.4 (m, 1H).

Step I: N-Methyl-N-(1-(R)-3-(S)-((4-(3-benzyl-1-ethyl-(1H)-pyrazol-5-yl)piperidin-1-yl)methyl)-4-(S)-(3-fluorophenyl)cyclopent-1-yl)-D-valine Using essentially the same procedures as described in Example 65, Steps E–I, (+)-trans-3-hydroxymethyl-4-(3-fluorophenyl)cyclopentanone from Step I was converted to the title compound. The free amine in the final step can be crystallized from ethanol or other appropriate solvents to afford the crystalline free amine title compound rather than the salt.

EXAMPLE 105

Using essentially the same procedures as in Examples 35 or 65, but substituting the appropriate L- and/or D-amino-acid t-butyl ester, with or without a subsequent alkylation with formaldehyde or acetaldehyde, and employing one of the appropriate piperidines as listed in Procedures 1–46, a variety of other final compounds can also prepared besides those described in the above Examples.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of treating graft rejection, reperfusion injury, or cytokine-induced toxicity which comprises administering to a subject in need of such treatment a therapeutically effective amount of a compound of the formula I, or a pharmaceutically acceptable salt or individual diastereomer thereof:

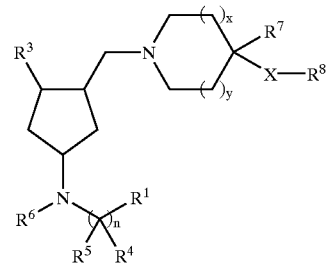

I wherein:
X is selected from:
—(C$_{0-6}$ alkyl)-Y-(C$_{0-6}$ alkyl)-, —(C$_{0-6}$ alkyl)-C$_{3-8}$ cycloalkyl-(C$_{0-6}$ alkyl)-, C$_{2-10}$ alkenyl, and C$_{2-10}$ alkynyl,
where the alkyl is unsubstituted or substituted with 1–7 substituents where the substituents are independently selected from:
(a) halo,
(b) hydroxy,
(c) —O—C$_{1-3}$ alkyl, and
(d) trifluoromethyl,
and where Y is selected from:
a single bond, —O—, —SO$_2$—, —NR$^{10}$—, —NR$^{10}$—, —SO$_2$—SO$_2$—NR$^{10}$—, —S—, and —SO—,
and where R$^{10}$ is independently selected from:
hydrogen, C$_{1-6}$ alkyl, C$_{2-6}$ alkenyl, C$_{2-6}$ alkynyl, C$_{5-6}$ cycloalkyl, benzyl, phenyl, and C$_{1-6}$ alkyl-C$_{3-6}$ cycloalkyl,
which is unsubstituted or substituted with 1–3 substituents where the substituents are independently selected from:
halo, C$_{1-3}$ alkyl, C$_{1-3}$ alkoxy and trifluoromethyl;

$R^1$ is selected from:
(1) —$CO_2H$,
(2) —$NO_2$,
(3) -tetrazolyl,
(4) -hydroxyisoxazole,
(5) —$SO_2NHCO$—($C_{0-3}$ alkyl)-$R^9$, wherein $R^9$ is independently selected from:
hydrogen, $C_{1-6}$ alkyl, $C_{5-6}$ cycloalkyl, benzyl or phenyl, which is unsubstituted or substituted with 1–3 substituents where the substituents are independently selected from:
halo, $C_{1-3}$ alkyl, $C_{1-3}$ alkoxy and trifluoromethyl, and
(6) —$P(O)(OH)_2$;

$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$, $R^5$ and $R^6$ are independently selected from:
hydrogen, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)-$C_{3-8}$ cycloalkyl, naphthyl, biphenyl, and heterocycle,
which is unsubstituted or substituted with 1–7 of $R^{11}$ where $R^{11}$ is independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a 3–8 membered saturated ring which may be unsubstituted or substituted with 1–7 of $R^{11}$,
or where $R^5$ and $R^6$ may be joined together to form a 3–8 membered saturated ring which may be unsubstituted or substituted with 1–7 of $R^{11}$;

$R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy, and
(4) halo;

$R^8$ is selected from:
hydrogen, $C_{3-8}$ cycloalkyl, phenyl, naphthyl, biphenyl, and heterocycle,
which is unsubstituted or substituted with 1–7 of $R^{12}$ where $R^{12}$ is independently selected from:
(a) halo,
(b) cyano,
(c) hydroxy,
(d) $C_{1-6}$ alkyl, which is unsubstituted or substituted with 1–5 of $R^{13}$ where $R^{13}$ is independently selected from:

halo, cyano, hydroxy, $C_{1-6}$ alkoxy, —$CO_2H$, —$CO_2(C_{1-6}$ alkyl), trifluoromethyl, and —$NR^9R^{10}$,
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) $C_{0-6}$ alkyl-phenyl or $C_{0-6}$ alkyl-heterocycle, which is unsubstituted or substituted with 1–7 substituents where the substituents are independently selected from:
(i) halo,
(ii) hydroxy,
(iii) $C_{1-6}$ alkyl, unsubstituted or substituted with 1–5 substituents, each of which is independently selected from halo, cyano, hydroxy, $C_{1-6}$ alkoxy, —$CO_2H$, —$CO_2(C_{1-6}$ alkyl), trifluoromethyl, and —$NR^9R^{10}$,
(iv) —O—$C_{1-6}$ alkyl,
(v) —$CF_3$,
(vi) —$OCF_3$,
(vii) —$NO_2$,
(viii) —CN,
(ix) —$SO_2$—$C_{1-6}$ alkyl,
(x) —$CO_2R^9$,
(xi) —$NR^9R^{10}$,
(xii) —$CONR^9R^{10}$,
(xiii) —$SO_2$—$NR^9R^{10}$,
(xiv) —$NR^9$—$SO_2$—$R^{10}$,
(xv) —$C_{3-8}$ cycloalkyl,
(xvi) —$C_{3-8}$ cycloalkyl, and
(xvii) phenyl;
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$,
(v) —$NR^9S(O)_2$—$NR^9R^{10}$,
(w) $C_{1-6}$ alkyl substituted with —$C_{3-8}$ cycloalkyl, and
(x) —$C_{3-8}$ cycloalkyl;

n is an integer selected from 1, 2, 3 and 4;
x is an integer selected from 0, 1 and 2, and y is an integer selected from 0, 1 and 2, with the proviso that the sum of x and y is 2.

2. The method according to claim 1, wherein $R^1$ in the compound of Formula I is selected from:
(1) —$CO_2H$, and
(2) -tetrazolyl.

3. The method according to claim 1, wherein $R^1$ in the compound of Formula I is —$CO_2H$.

4. The method according to claim 1, wherein $R^3$ in the compound of Formula I is selected from the group consisting of:
phenyl and thienyl,
which may be unsubstituted or substituted with 1–5 substituents where the substituents are independently selected from:

(a) halo,
(b) trifluoromethyl,
(c) hydroxy,
(d) $C_{1-3}$ alkyl, and
(e) —O—$C_{1-3}$ alkyl.

5. The method according to claim 1, wherein $R^3$ in the compound of Formula I is selected from the group consisting of:
phenyl, which may be unsubstituted or substituted with 1–5 substituents where the substituents are independently selected from:
(a) fluoro, and
(b) chloro; and
unsubstituted thienyl.

6. The method according to claim 1, wherein $R^3$ in the compound of Formula I is unsubstituted phenyl, (3-fluoro) phenyl or 3-thienyl.

7. The method according to claim 1, wherein $R^4$ in the compound of Formula I is hydrogen.

8. The method according to claim 1, wherein $R^5$ in the compound of Formula I is selected from: hydrogen, $C_{1-6}$ alkyl, $C_{3-8}$ cycloalkyl, $C_{1-6}$ alkyl-$C_{3-8}$ cycloalkyl, and phenyl.

9. The method according to claim 1, wherein $R^5$ in the compound of Formula I is selected from: isopropyl, isobutyl, sec-butyl, and cyclohexyl.

10. The method according to claim 1, wherein $R^6$ in the compound of Formula I is selected from: hydrogen, $C_{1-6}$ alkyl, $C_{3-8}$ cycloalkyl, $C_{1-6}$ alkyl-$C_{3-8}$ cycloalkyl, and phenyl.

11. The method according to claim 1, wherein $R^6$ in the compound of Formula I is selected from: hydrogen, methyl, —$CH_2$-cyclopropyl, —$CH_2$-cyclobutyl, and cyclohexyl.

12. The method according to claim 1, wherein $R^7$ in the compound of Formula I is hydrogen.

13. The method according to claim 1, wherein X in the compound of Formula I is:
—($C_{0-4}$ alkyl)-Y-($C_{0-4}$ alkyl)-,
where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl,
and where Y is selected from:
a single bond, —O—, —$SO_2$—, —$NR^{10}$—, —S—, and —SO—,
and where $R^{10}$ is independently selected from:
hydrogen, $C_{1-6}$ alkyl, $C_{2-6}$ alkenyl, $C_{2-6}$ alkynyl, benzyl, phenyl, and $C_{1-6}$ alkyl-$C_{3-6}$ cycloalkyl, which is unsubstituted or substituted with 1–3 substituents where the substituents are independently selected from:
halo, $C_{1-3}$ alkyl, $C_{1-3}$ alkoxy and trifluoromethyl.

14. The method according to claim 1, wherein X in the compound of Formula I is selected from:
(1) a single bond,
(2) —$CH_2CH_2$—,
(3) —$CH_2CH_2CH_2$—,
(4) —$CH_2CH_2$—$CF_2$—,
(5) —$CH_2CH_2$—$SO_2$—, and
(6) —$CH_2CH_2$—SO—.

15. The method according to claim 1, wherein $R^8$ in the compound of Formula I is selected from:
phenyl, naphthyl, cyclohexyl, benzoimidazolyl, benzofurazanyl, imidazopyridyl, imidazolyl, isoxazolyl, oxazolyl, pyrazinyl, pyridazinyl, pyridyl, pyrimidyl, thiazolyl, tetrazolopyridyl, and pyrazolyl;
which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{13}$ where $R^{13}$ is independently selected from:
halo, cyano, hydroxy, $C_{1-6}$ alkoxy, —$CO_2H$, —$CO_2$($C_{1-6}$ alkyl), trifluoromethyl, and —$NR^9R^{10}$, wherein $R^9$ and $R^{10}$ are independently selected from:
hydrogen, $C_{1-6}$ alkyl, $C_{5-6}$ cycloalkyl, benzyl or phenyl, which is unsubstituted or substituted with 1–3 substituents where the substituents are independently selected from:
halo, $C_{1-3}$ alkyl, $C_{1-3}$ alkoxy and trifluoromethyl;
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) $C_{0-6}$ alkyl-phenyl or $C_{0-6}$ alkyl-heterocycle, which is unsubstituted or substituted with 1–7 substituents where the substituents are independently selected from:
(i) halo,
(ii) hydroxy,
(iii) $C_{1-6}$ alkyl,
(iv) —O—$C_{1-6}$ alkyl,
(v) —$CF_3$,
(vi) —$OCF_3$,
(vii) —$NO_2$,
(viii) —CN,
(ix) —$SO_2$—$C_{1-6}$ alkyl,
(x) —$CO_2R^9$,
(xi) —$NR^9R^{10}$,
(xii) —$CONR^9R^{10}$,
(xiii) —$SO_2$—$NR^9R^{10}$, and
(xiv) —$NR^9$—$SO_2$—$R^{10}$;
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

16. The method according to claim 1, wherein $R^8$ in the compound of Formula I is selected from:
imidazolyl, oxazolyl, pyrazolyl, and thiazolyl; which is unsubstituted or substituted with 1–3 substituents where the substituents are independently selected from:
(a) fluoro,
(b) cyano,
(c) $C_{1-3}$ alkyl,
(d) —$CH_2$-phenyl, which is unsubstituted or substituted with 1–4 substituents where the substituents are independently selected from:

(i) fluoro,
(ii) chloro,
(iii) —O—CH₃,
(iv) —CF₃,
(v) —CN, and
(e) —CF₃.

17. A method of treating graft rejection, reperfusion injury, or cytokine-induced toxicity which comprises administering to a subject in need of such treatment a therapeutically effective amount of a compound of formula (II):

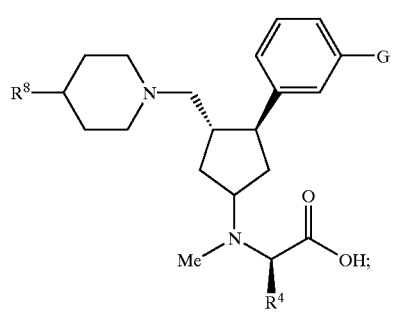
(II)

wherein
R⁴ is

R⁴ is

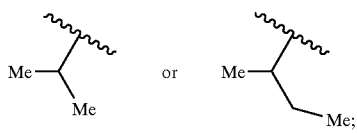

R⁸ is selected from the group consisting of

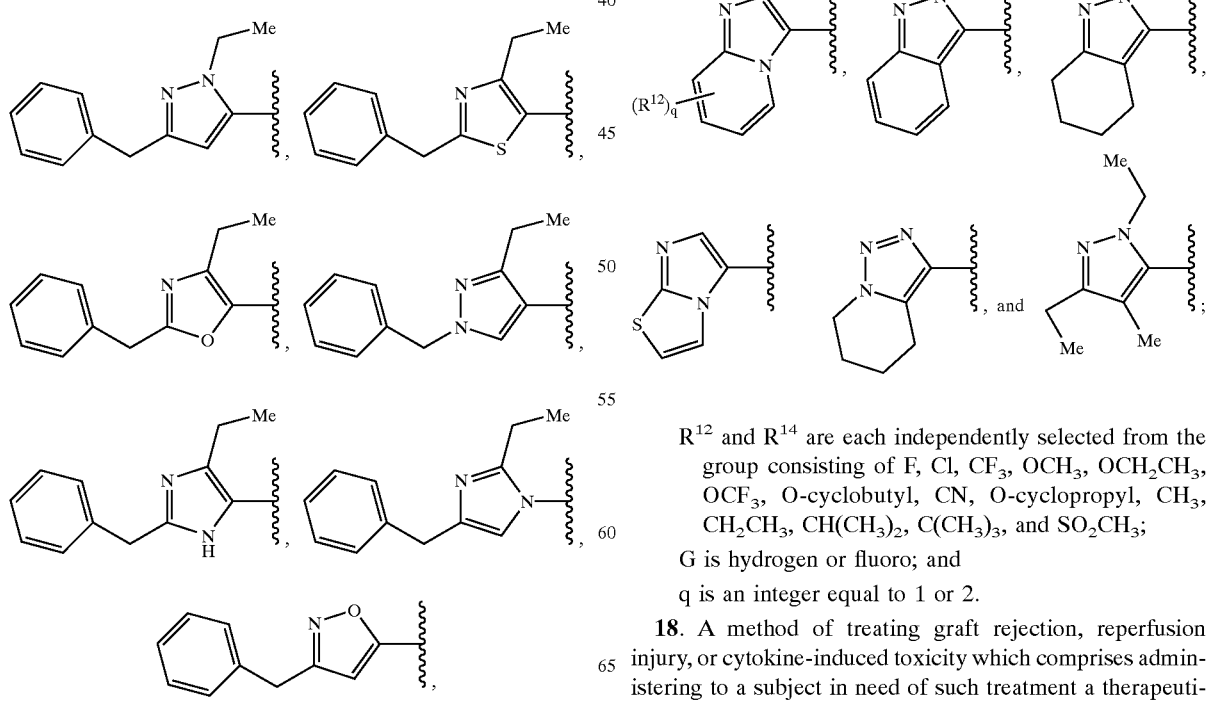

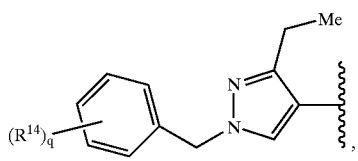

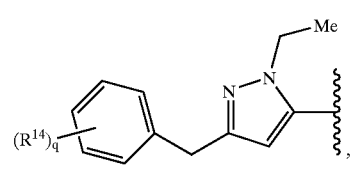

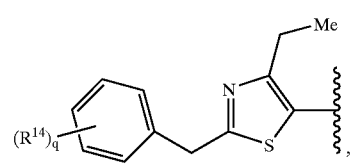

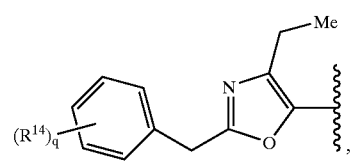

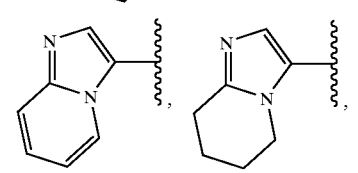

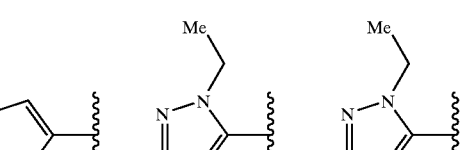

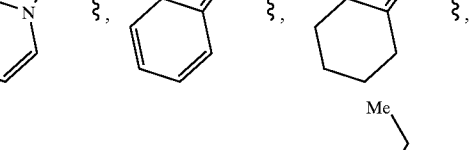

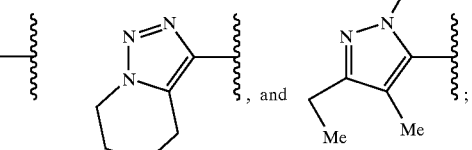

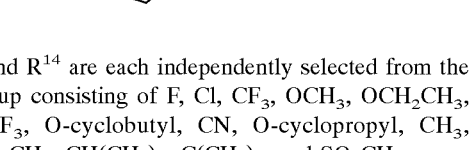

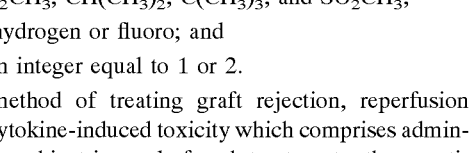

R¹² and R¹⁴ are each independently selected from the group consisting of F, Cl, CF₃, OCH₃, OCH₂CH₃, OCF₃, O-cyclobutyl, CN, O-cyclopropyl, CH₃, CH₂CH₃, CH(CH₃)₂, C(CH₃)₃, and SO₂CH₃;

G is hydrogen or fluoro; and q is an integer equal to 1 or 2.

18. A method of treating graft rejection, reperfusion injury, or cytokine-induced toxicity which comprises administering to a subject in need of such treatment a therapeutically effective amount of

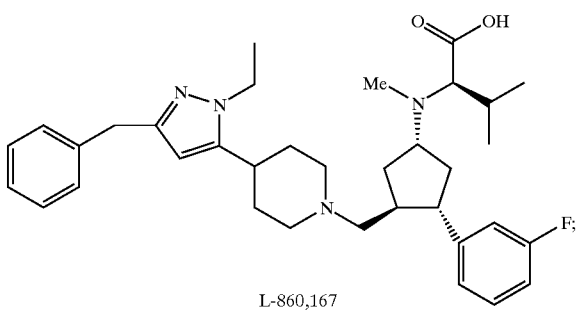

L-860,167 or a pharmaceutically acceptable salt thereof.

19. The method according to claim 1, which is a method of treating graft rejection.

20. The method according to claim 1, which is a method of treating reperfusion injury.

21. The method according to claim 1, which is a method of treating cytokine-induced toxicity.

22. The method according to claim 17, which is a method of treating graft rejection.

23. The method according to claim 17, which is a method of treating reperfusion injury.

24. The method according to claim 17, which is a method of treating cytokine-induced toxicity.

25. The method according to claim 18, which is a method of treating graft rejection.

26. The method according to claim 18, which is a method of treating reperfusion injury.

27. The method according to claim 18, which is a methos of treating cytokine-induced toxicity.

* * * * *